US009133154B2

(12) United States Patent
Kuksa et al.

(10) Patent No.: US 9,133,154 B2
(45) Date of Patent: Sep. 15, 2015

(54) SUBSTITUTED 3-PHENYLPROPYLAMINE DERIVATIVES FOR THE TREATMENT OF OPHTHALMIC DISEASES AND DISORDERS

(71) Applicant: Acucela Inc., Seattle, WA (US)

(72) Inventors: Vladimir A. Kuksa, Bothell, WA (US); Mark W. Orme, Seattle, WA (US); Feng Hong, Bellevue, WA (US); Ryo Kubota, Seattle, WA (US)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 14/205,117

(22) Filed: Mar. 11, 2014

(65) Prior Publication Data

US 2014/0275043 A1 Sep. 18, 2014

Related U.S. Application Data

(60) Provisional application No. 61/777,903, filed on Mar. 12, 2013.

(51) Int. Cl.
| | |
|---|---|
| *C07D 309/06* | (2006.01) |
| *C07D 213/38* | (2006.01) |
| *C07D 335/02* | (2006.01) |
| *C07D 211/26* | (2006.01) |
| *C07D 211/76* | (2006.01) |
| *C07D 307/81* | (2006.01) |
| *C07D 307/14* | (2006.01) |
| *C07D 279/02* | (2006.01) |
| *C07D 311/58* | (2006.01) |
| *C07D 207/09* | (2006.01) |
| *C07D 239/26* | (2006.01) |
| *C07D 333/20* | (2006.01) |
| *C07D 209/14* | (2006.01) |

(52) U.S. Cl.
CPC ............ *C07D 309/06* (2013.01); *C07D 207/09* (2013.01); *C07D 209/14* (2013.01); *C07D 211/26* (2013.01); *C07D 211/76* (2013.01); *C07D 213/38* (2013.01); *C07D 239/26* (2013.01); *C07D 279/02* (2013.01); *C07D 307/14* (2013.01); *C07D 307/81* (2013.01); *C07D 311/58* (2013.01); *C07D 333/20* (2013.01); *C07D 335/02* (2013.01)

(58) Field of Classification Search
CPC .. C07D 309/06; C07D 213/38; C07D 335/02; C07D 211/26; C07D 211/76; C07D 307/81; C07D 307/14; C07D 279/02; C07D 311/58; C07D 207/09
See application file for complete search history.

(56) References Cited

U.S. PATENT DOCUMENTS

| | | | |
|---|---|---|---|
| 4,305,960 A | 12/1981 | Haynes | |
| 5,641,750 A | 6/1997 | Louis | |
| 5,736,516 A | 4/1998 | Louis | |
| 6,090,624 A | 7/2000 | Greenwood et al. | |
| 6,117,675 A | 9/2000 | van der Kooy et al. | |
| 6,183,735 B1 | 2/2001 | Greenwood et al. | |
| 6,406,840 B1 | 6/2002 | Li et al. | |
| 6,713,300 B1 | 3/2004 | Allikmets et al. | |
| 7,982,071 B2 * | 7/2011 | Scott et al. | 564/323 |
| 8,076,516 B2 | 12/2011 | Scott et al. | |
| 2002/0009713 A1 | 1/2002 | Miller et al. | |
| 2003/0032078 A1 | 2/2003 | Travis | |
| 2003/0050283 A1 | 3/2003 | Richter et al. | |
| 2004/0116403 A1 | 6/2004 | Klimko et al. | |
| 2004/0147019 A1 | 7/2004 | Kubota et al. | |
| 2005/0059148 A1 | 3/2005 | Kubota | |
| 2005/0159662 A1 | 7/2005 | Imanishi et al. | |
| 2007/0002275 A1 | 1/2007 | Yan et al. | |
| 2009/0326074 A1 | 12/2009 | Scott et al. | |
| 2010/0113539 A1 | 5/2010 | Scott et al. | |
| 2011/0003895 A1 | 1/2011 | Kubota et al. | |

FOREIGN PATENT DOCUMENTS

| | | |
|---|---|---|
| WO | WO 98/12303 | 3/1998 |
| WO | WO 99/29279 | 6/1999 |
| WO | WO 00/40699 | 7/2000 |
| WO | WO 01/09327 | 2/2001 |
| WO | WO 01/42784 | 6/2001 |
| WO | WO 01/81551 | 11/2001 |
| WO | WO 01/83714 | 11/2001 |
| WO | WO2013/109991 | 7/2013 |

OTHER PUBLICATIONS

Allikmets et al., A photoreceptor cell-specific ATP-binding transporter gene (ABCR) is mutated in recessive Stargardt macular dystrophy, Nat. Genet. 15:236-246 (1997).

Ambati et al., An animal model of age-related macular degeneration in senescent Ccl-2- or Ccr-2-deficient mice, Nat. Med. 9:1390-1397 (2003); Epub Oct. 19, 2003.

Berge S.M. et al., Pharmaceutical Salts, Journal of Pharmaceutical Science, 66:1-19 (1997).

(Continued)

*Primary Examiner* — Sun Jae Yoo
(74) *Attorney, Agent, or Firm* — Wilson Sonsini Goodrich Rosati

(57) ABSTRACT

The present invention relates generally to compositions and methods for treating neurodegenerative diseases and disorders, particularly ophthalmic diseases and disorders. Provided herein are substituted 3-phenylpropylamine derivative compounds and pharmaceutical compositions comprising said compounds. The subject compositions are useful for treating and preventing ophthalmic diseases and disorders, including age-related macular degeneration (AMD) and Stargardt's Disease.

12 Claims, 4 Drawing Sheets

(56) References Cited

OTHER PUBLICATIONS

Bundgard, Design of Prodrugs (1985), pp. 7-9, 21-24.
Chen et al., RPE65 gene delivery restores isomerohydrolase activity and prevents early cone loss in Rpe65-/- mice, Invest. Ophthalmol. Vis. Sci. 47:1177-1184 (2006).
Crabb et al., Cloning of the cDNAs encoding the cellular retinaldehyde-binding protein from bovine and human retina and comparison of the protein structures, J. Biol. Chem. 263:18688-18692 (1988).
Crabb et al., Structural and functional characterization of recombinant human cellular retinaldehyde-binding protein, Protein Science 7:746-757 (1998).
De Laey et al., Hyperlipofuscinosis and subretinal fibrosis in Stargardt's disease, Retina 15:399-406 (1995).
Deigner et al., Membranes as the energy source in the endergonic transformation of vitamin A to 11-cis-retinol, Science, 244: 968-971 (1989).
Eldred et al., Retinal age pigments generated by self-assembling lysosomotropic detergents, Nature 361:724-726 (1993).
Filipek et al., G protein-coupled receptor rhodopsin: a prospectus, Annu. Rev. Physiol. 65:851-879 (2003).
Finneman et al., The lipofuscin component A2E selectively inhibits phagolysosomal degradation of photoreceptor phospholipid by the retinal pigment epithelium, Proc. Natl. Acad. Sci. USA 99:3842-3847 (2002).
Glazer et al., Understanding the etiology of Stargardt's disease, Ophthalmol. Clin. North Am. 15:93-100 (2002).
Golczak et al., Positively charged retinoids are potent and selective inhibitors of the trans-cis isomerization in the retinoid (visual) cycle, Proc. Natl. Acad. Sci. USA 102:8162-8167 (2005).
Gollapalli et al., Specific inactivation of isomerohydrolase activity by 11-cis-retinoids, Biochim Biophys Acta. 1651: 93-101 (2003).
Gollapalli et al., The specific binding of retinoic acid to RPE65 and approaches to the treatment of macular degeneration, Proc. Natl. Acad. Sci. USA 101:10030-10035 (2004).
Gorin et al., The genetics of age-related macular degeneration, Mol. Vis. 5:29 (1999).
Groenendijk et al., Quantitative Determination of Retinals with Complete Retention of Their Geometric Configuration, Biochim. Biophys. Acta. 617:430-438 (1980).
Haeseleer et al., Essential role of Ca2+-binding protein 4, a Cav1.4 channel regulator, in photoreceptor synaptic function, Nat. Neurosci. 7:1079-1087 (2004).
Holz et al., Inhibition of lysosomal degradative functions in RPE cells by a retinoid component of lipofuscin, Invest. Ophthalmol. Vis. Sci. 40:737-43 (1999).
Imanishi, et al., Noninvasive two-photon imaging reveals retinyl ester storage structures in the eye, J. Cell Biol. (2004), 164:373-383.
Intres et al., Molecular cloning and structural analysis of the human gene encoding cellular retinaldehyde-binding protein, J. Biol. Chem. 269:25411-25418 (1994).
Iyengar et al., Dissection of genomewide-scan data in extended families reveals a major locus and oligogenic susceptibility for age-related macular degeneration, Am. J. Hum. Genet. 74:20-39 (2004) (Epub Dec. 19, 2003).
Jaakson et al., Genotyping microarray (gene chip) for the ABCR (ABCA4) gene, Hum. Mutat. 22:395-403 (2003).
Karan et al., Lipofuscin accumulation, abnormal electrophysiology, and photoreceptor degeneration in mutant ELOVL4 transgenic mice: a model for macular degeneration, Proc. Natl. Acad. Sci. USA 102:4164-4169 (2005).
Keating et al., Technical Aspects of multifocal ERG recording, Documenta Ophthalmologica 100:77-92 (2000).
Kenealy et al., Linkage analysis for age-related macular degeneration supports a gene on chromosome 10q26, Mol. Vis. 10:57-61 (2004).
Kermani et al., Refined genetic and physical positioning of the gene for Doyne honeycomb retinal dystrophy (DHRD)., Hum. Genet. 104:77-82 (1999).
Koenig, Synthesis of R- and S- Fluoxetine, Norfluoxetine and Related Compounds from Styrene Oxide, Synthetic Communications, 1995, 25(8):1231-1238.
Koevary, Pharmacokinetics of topical ocular drug delivery: potential uses for the treatment of diseases of the posterior segment and beyond, Curr. Drug Metab. 4:213-222 (2003).
Lamb et al., Dark adaptation and the retinoid cycle of vision, Progress in Retinal and Eye Research, 23:307-380 (2004).
Law et al., The molecular basis of retinoic acid induced night blindness, Biochem. Biophys. Res. Commun 161:82582-82589 (1989).
Lee et al., Review on the systemic delivery of insulin via the ocular route, Int. J. Pharm. 233:1-18 (2002).
Maeda et al., Evaluation of the role of the retinal G protein-coupled receptor (RGR) in the vertebrate retina in vivo, J. Neurochem. 85:944-956 (2003).
Mata et al., Biosynthesis of a major lipofuscin fluorophore in mice and humans with ABCR-mediated retinal and macular degeneration, Proc. Natl. Acad. Sci. USA 97:7154-7159 (2000).
Mata et al., Delayed dark-adaptation and lipofuscin accumulation in abcr+/− mice: implications for involvement of ABCR in age-related macular degeneration, Invest. Ophthalmol. Sci. 42:1685-1690 (2001).
Mata et al., Isomerization and oxidation of vitamin a in cone-dominant retinas: a novel pathway for visual-pigment regeneration in daylight., Neuron 36:69-80 (2002).
McBee et al., Confronting complexity: the interlink of phototransduction and retinoid metabolism in the vertebrate retina, Prog. Retin. Eye Res. 20:469-472 (2001).
Moiseyev et al., RPE65 is the isomerohydrolase in the retinoid visual cycle, Proc. Natl. Acad. Sci. USA 102:12413-12418 (2004).
Oglivie et al., Growth Factors in Combinatino, but Not Individually, Rescue rd Mouse Photoreceptors in Organ Culture, Exp. Neurol. 161:675-685 (2000).
Okajima et al., Retinol kinetics in the isolated retina determined by retinoid extraction and HPLC, Exp. Eye Res. 65:331-340 (1997).
Parish et al., Isolation and one-step preparation of A2E and iso-A2E, fluorophores from human retinal pigment epithelium, Proc. Natl. Acad. Sci. USA 95:14609-14613 (1998).
Radu et al., Light exposure stimulates formation of A2E oxiranes in a mouse model of Stargardt's macular degeneration, Proc Natl Acad Sci USA 101:5928-5933 (2004).
Radu et al., Treatment with isotretinoin inhibits lipofuscin accumulation in a mouse model of recessive Stargardt's macular degeneration, Proc. Natl. Acad. Sci. USA 100:4742-4747 (2003).
Seddon et al., Assessment of mutations in the Best macular dystrophy (VMD2) gene in patients with adult-onset foveomacular vitelliform dystrophy, age-related maculopathy, and bull's-eye maculopathy, Ophthalmology 108:2060-2067 (2001).
Sparrow et al., A2E, a lipofuscin fluorophore, in human retinal pigmented epithelial cells in culture, Invest. Ophthalmol. Vis. Sci. 40:2988-2995 (1999).
Sparrow et al., A2E-epoxides damage DNA in retinal pigment epithelial cells. Vitamin E and other antioxidants inhibit A2E-epoxide formation, J. Biol. Chem. 278(20):18207-18213 (2003).
Sparrow et al., Involvement of oxidative mechanisms in blue-light-induced damage to A2E-laden RPE, Invest. Ophthalmol. Vis. Sci. 43:1222-1227 (2002).
Sparrow, Proc. Therapy for macular degeneration: insights from acne, Natl. Acad. Sci. USA 100:4353-4354 (2003).
Stecher et al., Preferential release of 11-cis-retinol from retinal pigment epithelial cells in the presence of cellular retinaldehyde-binding protein, J Biol Chem 274:8577-8585 (1999).
Sugitomo et al., A procedure for electroretinogram (ERG) recording in mice—effect of monoiodoacetic acid on the ERG in pigmented mice, J. Toxicol. Sci. 22 Suppl 2:315-325 (1997).
Suter et al., Age-related macular degeneration. The lipofusion component N-retinyl-N-retinylidene ethanolamine detaches proapoptotic proteins from mitochondria and induces apoptosis in mammalian retinal pigment epithelial cells, J. Biol. Chem. 275:39625-39630 (2000).
Suzuki et al., Retinyl and 3-dehydroretinyl esters in the crayfish retina, Vis. Res. 28:1061-1070 (1988).

(56) References Cited

OTHER PUBLICATIONS

Trevino et al., Retinoid cycles in the cone-dominated chicken retina, J. Exp. Biol. 208:4151-4157 (2005).
Van Hooser et al., Recovery of visual functions in a mouse model of Leber congenital amaurosis, J Biol Chem 277:19173-19182, 2002.
Weng et al., Insights into the function of Rim protein in photoreceptors and etiology of Stargardt's disease from the phenotype in abcr knockout mice, Cell 98:13-23 (1999).
Wenzel et al., Molecular mechanisms of light-induced photoreceptor apoptosis and neuroprotection for retinal degeneration, Prog. Retin. Eye Res. 24:275-306 (2005).
Woodruff et al., Spontaneous activity of opsin apoprotein is a cause of Leber congenital amaurosis, Nat. Genet. 35:158-164 (2003).
Yates et al., Genetic susceptibility to age related macular degeneration, J. Med. Genet. 37:83-87 (2000).
PCT/US2014/023751 International Search Report and Written Opinion dated Jul. 28, 2014.

* cited by examiner

SUBSTITUTED 3-PHENYLPROPYLAMINE DERIVATIVES FOR THE TREATMENT OF OPHTHALMIC DISEASES AND DISORDERS

CROSS REFERENCE

This application claims the benefit of U.S. Provisional Application No. 61/777,903, filed Mar. 12, 2013, the content of which is hereby incorporated by reference in its entirety.

BACKGROUND

Neurodegenerative diseases, such as glaucoma, macular degeneration, and Alzheimer's disease, affect millions of patients throughout the world. Because the loss of quality of life associated with these diseases is considerable, drug research and development in this area is of great importance.

BRIEF SUMMARY OF THE INVENTION

We have identified a need for effective therapies for treating ophthalmic diseases or disorders resulting in ophthalmic dysfunction including those described above. In particular, we have identified a pressing need for compositions and methods for treating Stargardt's disease and age-related macular degeneration (AMD) without causing further unwanted side effects such as progressive retinal degeneration, LCA-like conditions, night blindness, or systemic vitamin A deficiency. We have also identified a need for effective treatments for other ophthalmic diseases and disorders that adversely affect the retina.

One embodiment provides a compound of Formula (C), or a pharmaceutically acceptable salt thereof:

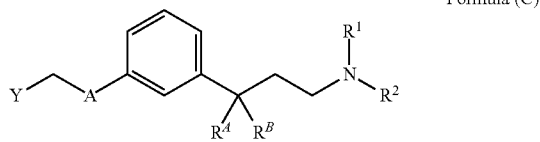

Formula (C)

wherein,
A is selected from —O— or —CH$_2$—;
Y is

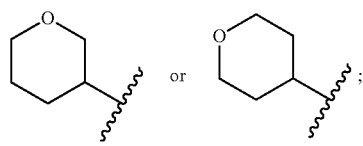 [SMILES: *C1CCCOC1 ; *C1CCOCC1]

or

;

$R^A$ is OH, $R^B$ is H; or optionally, $R^A$ and $R^B$ together form an oxo;
$R^1$ and $R^2$ are each independently selected from hydrogen, $C_1$-$C_4$ alkyl, —C(=O)$R^3$; and
$R^3$ is selected from alkyl, alkoxy, or —OCH$_2$OC(O)$R^4$, wherein $R^4$ is an alkyl or alkoxy.

In a further embodiment is a compound, or a pharmaceutically acceptable salt thereof, selected from the group consisting of:
(R)-3-Amino-1-(3-((tetrahydro-2H-pyran-4-yl)methoxy)phenyl)propan-1-ol;
3-Amino-1-(3-((tetrahydro-2H-pyran-4-yl)methoxy)phenyl)propan-1-ol;
(1R)-3-Amino-1-(3-((tetrahydro-2H-pyran-3-yl)methoxy)phenyl)propan-1-ol;
(R)-3-Amino-1-(3-(pyridin-4-ylmethoxy)phenyl)propan-1-ol;
(R)-3-Amino-1-(3-(pyridin-3-ylmethoxy)phenyl)propan-1-ol;
(R)-3-Amino-1-(3-(pyridin-2-ylmethoxy)phenyl)propan-1-ol;
(1R)-3-amino-1-(3-((tetrahydro-2H-thiopyran-3-yl)methoxy)phenyl)propan-1-ol;
(R)-3-Amino-1-(3-((tetrahydro-2H-thiopyran-4-yl)methoxy)phenyl)propan-1-ol;
(R)-4-((3-(3-Amino-1-hydroxypropyl)phenoxy)methyl)tetrahydro-2H-thiopyran 1,1-dioxide;
3-((3-((R)-3-Amino-1-hydroxypropyl)phenoxy)methyl)tetrahydro-2H-thiopyran 1,1-dioxide;
(R)-1-(4-((3-(3-amino-1-hydroxypropyl)phenoxy)methyl)piperidin-1-yl)ethanone;
(R)-3-Amino-1-(3-((6-methylpyridin-2-yl)methoxy)phenyl)propan-1-ol;
(1R)-3-Amino-1-(3-((2,3-dihydrobenzofuran-2-yl)methoxy)phenyl)propan-1-ol;
(1R)-3-Amino-1-(3-((tetrahydrofuran-2-yl)methoxy)phenyl)propan-1-ol;
(R)-3-Amino-1-(3-(piperidin-4-ylmethoxy)phenyl)propan-1-ol;
(R)-3-Amino-1-(3-((1-methylpiperidin-4-yl)methoxy)phenyl)propan-1-ol;
(R)-Methyl 4-((3-(3-amino-1-hydroxypropyl)phenoxy)methyl)piperidine-1-carboxylate;
(R)-3-Amino-1-(3-(pyrimidin-5-ylmethoxy)phenyl)propan-1-ol;
(1R)-3-Amino-1-(3-(chroman-3-ylmethoxy)phenyl)propan-1-ol;
(R)-4-((3-(3-Amino-1-hydroxypropyl)phenoxy)methyl)tetrahydro-2H-thiopyran 1-oxide;
(R)-3-Amino-1-(3-(((S)-1-methylpyrrolidin-2-yl)methoxy)phenyl)propan-1-ol;
(R)-3-Amino-1-(3-((S)-pyrrolidin-2-ylmethoxy)phenyl)propan-1-ol;
(R)-3-Amino-1-(3-(((tetrahydro-2H-pyran-4-yl)methyl)amino)phenyl)propan-1-ol;
3-Amino-1-(3-(((1,1-dioxidotetrahydro-2H-thiopyran-4-yl)methyl)sulfonyl)phenyl)propan-1-one;
3-Amino-1-(3-(((tetrahydro-2H-pyran-3-yl)methyl)sulfonyl)phenyl)propan-1-one;
3-Amino-1-(3-(((tetrahydro-2H-pyran-4-yl)methyl) sulfonyl)phenyl)propan-1-one;
3-((3-((R)-3-Amino-1-hydroxypropyl)phenoxy)methyl)piperidin-2-one;
(R)-3-Amino-1-(3-(thiophen-2-ylmethoxy)phenyl)propan-1-ol;
(R)-3-Amino-1-(3-(thiophen-3-ylmethoxy)phenyl)propan-1-ol;
(R)-tert-Butyl 4-((3-(3-amino-1-hydroxypropyl)phenoxy)methyl)piperidine-1-carboxylate;
(E)-3-(3-((Tetrahydro-2H-pyran-4-yl)methoxy)phenyl)prop-2-en-1-amine;
3-(3-((Tetrahydro-2H-pyran-4-yl)methoxy)phenyl)propan-1-amine;
(R)-3-(Methylamino)-1-(3-((tetrahydro-2H-pyran-4-yl)methoxy)phenyl)propan-1-ol;
1-((S)-2-((3-((R)-3-Amino-1-hydroxypropyl)phenoxy)methyl)pyrrolidin-1-yl)ethanone;
5-((3-((R)-3-Amino-1-hydroxypropyl)phenoxy)methyl)piperidin-2-one;

4-((3-((R)-3-Amino-1-hydroxypropyl)phenoxy)methyl)piperidin-2-one;
6-((3-((R)-3-Amino-1-hydroxypropyl)phenoxy)methyl)-1-methylpiperidin-2-one;
5-((3-((R)-3-Amino-1-hydroxypropyl)phenoxy)methyl)pyrrolidin-2-one;
5-((3-((R)-3-Amino-1-hydroxypropyl)phenoxy)methyl)-1-methylpyrrolidin-2-one;
N-(3-(3-Amino-1-hydroxypropyl)phenyl)-6-oxopiperidine-3-carboxamide;
3-((3-((R)-3-Amino-1-hydroxypropyl)phenoxy)methyl)-1,2-thiazinane 1,1-dioxide;
(R)-1-(3-((1H-Pyrrol-2-yl)methoxy)phenyl)-3-aminopropan-1-ol;
(R)-3-Amino-1-(3-(furan-2-ylmethoxy)phenyl)propan-1-ol;
(R)-3-Amino-1-(3-((1-(methylsulfonyl)piperidin-4-yl)methoxy)phenyl)propan-1-ol;
(R)-1-(3-(((1H-Indol-6-yl)methyl)amino)phenyl)-3-aminopropan-1-ol;
(R)-1-(3-((1H-Indol-6-yl)methoxy)phenyl)-3-aminopropan-1-ol;
(R)-3-Amino-1-(3-(benzofuran-2-ylmethoxy)phenyl)propan-1-ol;
3-(3-((Tetrahydro-2H-pyran-4-yl)methoxy)phenyl)prop-2-yn-1-amine;
3-Amino-1-(3-(((tetrahydro-2H-pyran-4-yl)methyl)thio)phenyl)propan-1-ol;
3-Amino-1-(3-(((tetrahydro-2H-pyran-4-yl)methyl)sulfonyl)phenyl)propan-1-ol;
3-Amino-1-(3-(2-(tetrahydro-2H-pyran-4-yl)ethyl)phenyl)propan-1-ol;
3-Amino-1-(3-(2-(pyridin-3-yl)ethyl)phenyl)propan-1-ol;
3-Amino-1-(3-(2-(thiophen-3-yl)ethyl)phenyl)propan-1-ol;
(E)-1-(3-(3-Amino-1-hydroxypropyl)styryl)pyrrolidin-2-one;
1-(3-(3-Amino-1-hydroxypropyl)phenethyl)pyrrolidin-2-one;
3-Amino-1-(3-(2-(pyrrolidin-1-yl)ethyl)phenyl)propan-1-ol;
(E)-1-(3-(2-(1H-Imidazol-1-yl)vinyl)phenyl)-3-aminopropan-1-ol;
1-(3-(2-(1H-Imidazol-1-yl)ethyl)phenyl)-3-aminopropan-1-ol;
(E)-3-Amino-1-(3-(2-(pyridin-2-yl)vinyl)phenyl)propan-1-ol;
3-Amino-1-(3-(2-(pyridin-2-yl)ethyl)phenyl)propan-1-ol;
(E)-3-Amino-1-(3-(2-(tetrahydro-2H-pyran-4-yl)vinyl)phenyl)propan-1-ol; and
3-Amino-1-(3-(2-(tetrahydro-2H-pyran-4-yl)ethyl)phenyl)propan-1-ol.

One embodiment provides a pharmaceutical composition comprising a pharmaceutically acceptable carrier and a compound of Formula (C), or a pharmaceutically acceptable salt thereof.

One embodiment provides a pharmaceutical composition comprising a pharmaceutically acceptable carrier and a compound described in Table 1, or a pharmaceutically acceptable salt thereof.

One embodiment provides a method for treating an ophthalmic disease or disorder in a subject, comprising administering to the subject a pharmaceutical composition comprising a compound of Formula (C), or a pharmaceutically acceptable salt thereof. Another embodiment provides the method for treating an ophthalmic disease or disorder in a subject, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a pharmaceutical composition comprising a compound disclosed in Table 1, or a pharmaceutically acceptable salt thereof. Another embodiment provides the method for treating an ophthalmic disease or disorder in a subject, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
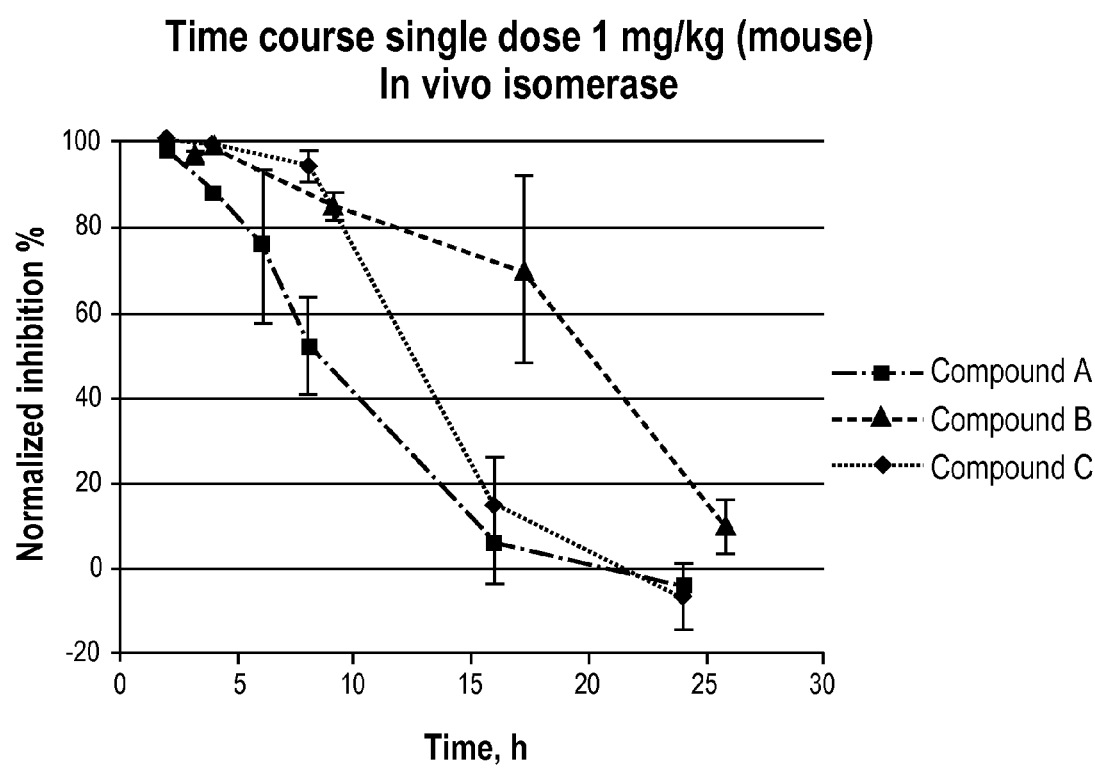
FIG. 1 provides a summary of an illustrative time course experiment for in vivo isomerase inhibition as described in biological evaluation example 2.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

DEFINITIONS

As used in the specification and appended claims, unless specified to the contrary, the following terms have the meaning indicated below.

As used herein and in the appended claims, the singular forms "a," "and," and "the" include plural referents unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Hydrazino" refers to the =N—NH$_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —$N(R^a)$C(O)$R^a$, —$N(R^a)$S(O)$_t R^a$ (where t is 1 or 2), —S(O)$_t OR^a$ (where t is 1 or 2) and —S(O)$_t N(R^a)_2$ (where t is 1 or 2) where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—$N(R^a)_2$, —$R^b$—C(O)$R^a$, —$R^b$C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_t R^a$ (where t is 1 or 2), —$R^b$—S(O)$_t OR^a$ (where t is 1 or 2) and —$R^b$—S(O)$_t N(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_t R^a$ (where t is 1 or 2), —$R^b$—S(O)$_t OR^a$ (where t is 1 or 2) and —$R^b$—S(O)$_t N(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-SR^a$, $-R^b-OC(O)-R^a$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-SR^a$, $-R^b-OC(O)-R^a$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)— or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

The compounds presented herein may exist as tautomers. A "tautomer" refers to a proton shift from one atom of a molecule to another atom of the same molecule, accompanied by an isomerization of an adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the 3-phenylpropylamine derivative compound as described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, ben-

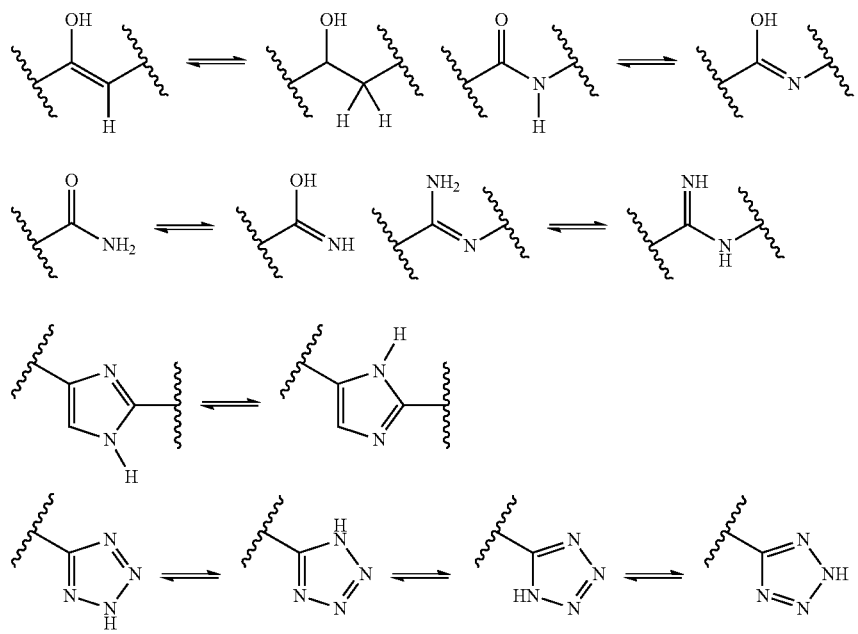

zenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Non-retinoid compound" refers to any compound that is not a retinoid. A retinoid is a compound that has a diterpene skeleton possessing a trimethylcyclohexenyl ring and a polyene chain that terminates in a polar end group. Examples of retinoids include retinaldehyde and derived imine/hydrazide/oxime, retinol and any derived ester, retinyl amine and any derived amide, retinoic acid and any derived ester or amide. A non-retinoid compound can comprise though not require an internal cyclic group (e.g., aromatic group). A non-retinoid compound can contain though not require an alkoxyphenyl-linked amine group.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions are optionally administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, are optionally prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted 3-phenylpropylamine derivative compounds are described herein that inhibit an isomerization step of the retinoid cycle. These compounds and compositions comprising these compounds are useful for inhibiting degeneration of retinal cells or for enhancing retinal cell survival. The compounds described herein are, therefore, be useful for treating ophthalmic diseases and disorders, including retinal diseases or disorders, such as age related macular degeneration and Stargardt's disease.

Substituted 3-Phenylpropylamine Derivative Compounds

In one embodiment is a compound of Formula (A), or a pharmaceutically acceptable salt thereof:

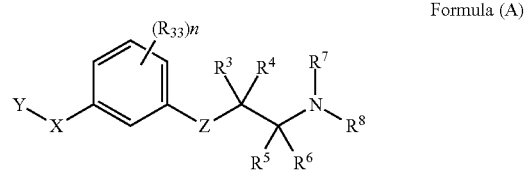

Formula (A)

wherein,
X is selected from *—O—C($R^9$)$_2$—, *—O—C(=O)—, *—S—C($R^9$)$_2$—, *—S(O)—C($R^9$)$_2$—, *—S(O)$_2$—C($R^9$)$_2$—, *—SO$_2$(N$R^9$)—, *—N$R^9$—C($R^9$)$_2$—, *—N$R^9$—C(=O)—, *—N$R^9$—S(O)$_2$—, —C($R^9$)$_2$—C($R^9$)$_2$—, *—C(=O)—C($R^9$)$_2$—, *—C($R^9$)$_2$—C(=O)—, —C($R^9$)=C($R^9$)—, *—C(=O)—N($R^9$)—, *—C(=O)—O—, *—C($R^9$)$_2$—O—, and *—C($R^9$)$_2$—N$R^9$—; wherein the * indicates point of attachment to the phenylene ring;
Y is selected from heterocyclyl, heterocyclylalkyl, heteroaryl or heteroarylalkyl;
Z is —C($R^1$)($R^2$)—;
$R^1$ and $R^2$ are each independently selected from hydrogen, halogen, alkyl, fluoroalkyl, —O$R^9$, —N$R^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and R² and R⁴ together form a direct bond to provide a triple bond;

R³ and R⁴ are each independently selected from hydrogen, halogen, $C_1$-$C_5$ alkyl, fluoroalkyl, —OR⁹ or —NR¹⁰R¹¹; or R³ and R⁴ together form an oxo;

R⁵ and R⁶ are each independently selected from hydrogen, alkyl, alkenyl, fluoroalkyl, aryl, heteroaryl, carbocyclyl or C-attached heterocyclyl; or R⁵ and R⁶ together with the carbon atom to which they are attached, form a carbocyclyl or heterocyclyl; or R⁵ and R⁶ together form an imino;

R⁷ and R⁸ are each independently selected from hydrogen, alkyl, carbocyclyl, —C(=O)R¹³, SO₂R¹³, CO₂R¹³ or SO₂NR¹⁰R¹¹; or R⁷ and R⁸, together with the nitrogen atom to which they are attached, form an N-heterocyclyl;

each R⁹ independently hydrogen or alkyl;

each R¹⁰ and R¹¹ is independently selected from hydrogen, alkyl, carbocyclyl, heterocyclyl, —C(=O)R¹³, SO₂R¹³, CO₂R¹³ or SO₂NR¹⁰R¹¹; or R¹⁰ and R¹¹ together with the nitrogen atom to which they are attached, form an N-heterocyclyl;

each R¹³ is independently selected from alkyl, heteroalkyl, alkenyl, aryl, aralkyl, carbocyclyl, heteroaryl or heterocyclyl; and each R¹³ is independently selected from halogen, OR⁹, alkyl, or fluoroalkyl, and n is 0, 1, 2, 3, or 4, with the provision that the compound is not

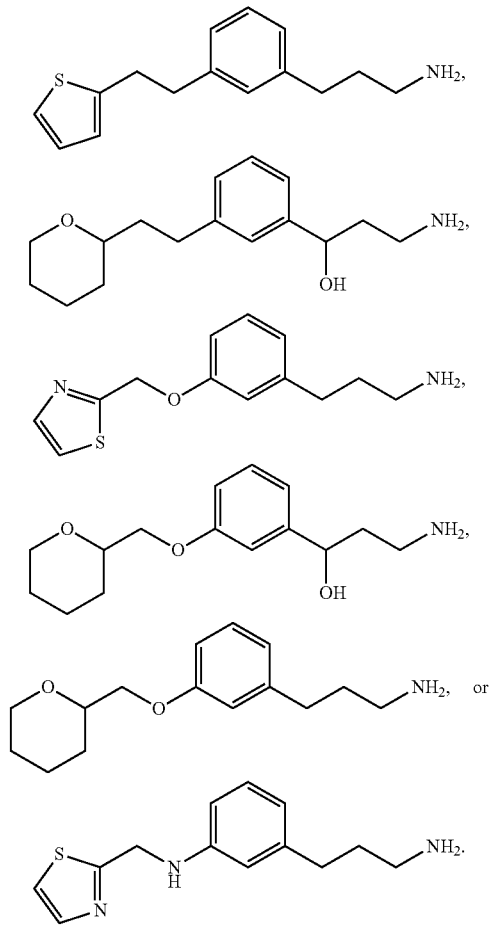

In one embodiment, R³ and R⁴ are both hydrogen. In another embodiment, R⁵ and R⁶ are both hydrogen. In another embodiment, R³, R⁴, R⁵ and R⁶ are hydrogen. In another embodiment, R¹ and R² are both hydrogen. In another embodiment, R¹ is hydrogen and R² is —OH. In another embodiment, R¹ and R² together form an oxo. In another embodiment, R⁷ and R⁸ are both hydrogen. In another embodiment, R⁷ is hydrogen and R⁸ is —C(=O)R¹³ or CO₂R¹³. In a further embodiment, R¹³ is an alkyl. In another further embodiment, wherein R⁸ is CO₂R¹³ and R¹³ is

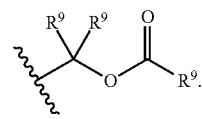

In another embodiment, R¹, R³, and R⁴ are all hydrogen, and R² is —OH. In another embodiment, R³, R⁴, R⁷ and R⁸ are all hydrogen. In another embodiment, R¹, R⁷, and R⁸ are all hydrogen, and R² is —OH. In another embodiment, R¹, R³, R⁴, R⁵, R⁶, R⁷, and R⁸ are all hydrogen, and R² is —OH.

In another embodiment, Y is selected from:

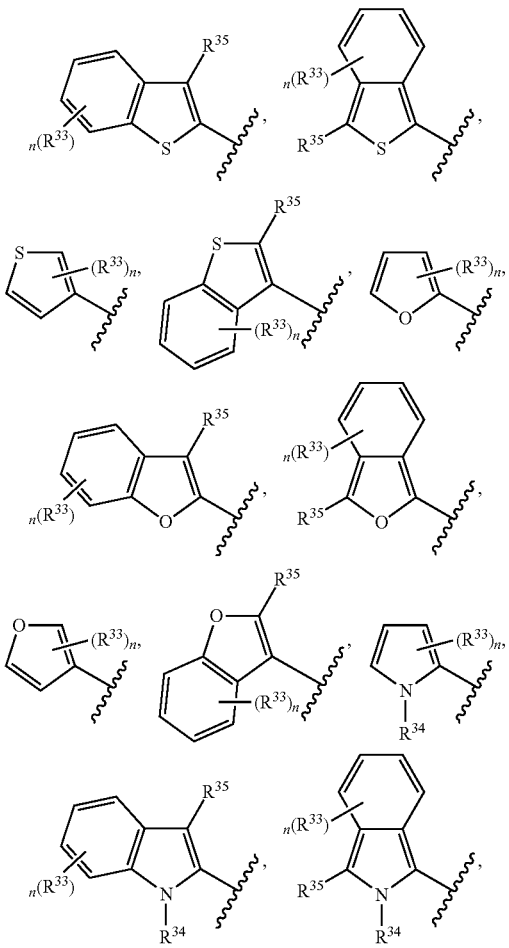

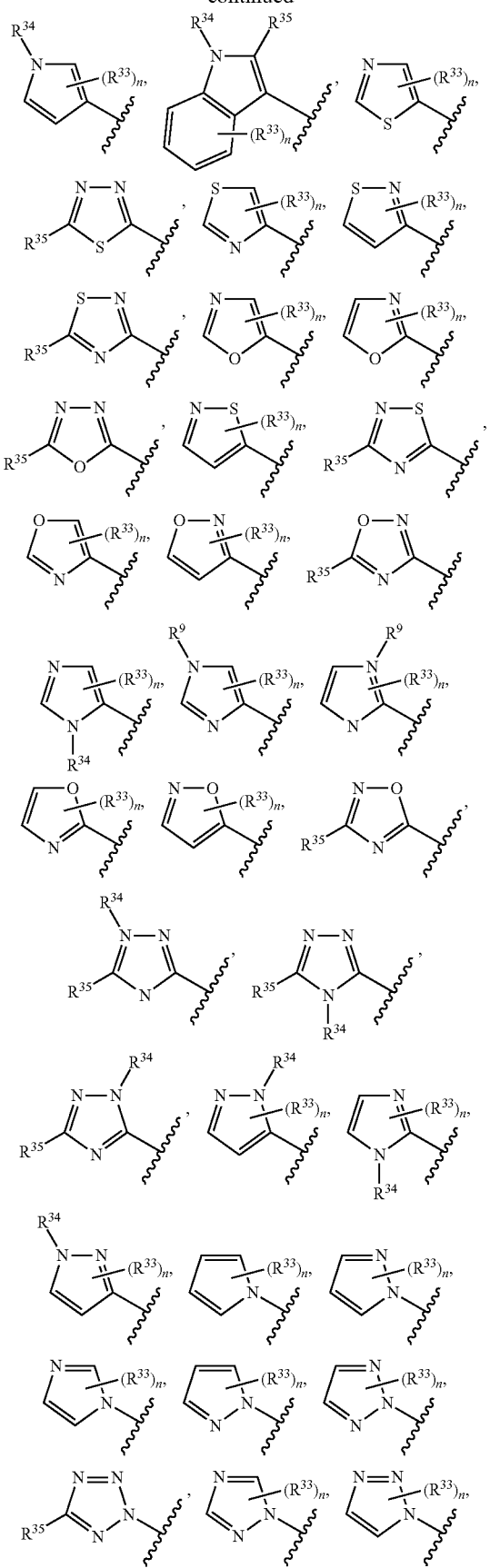

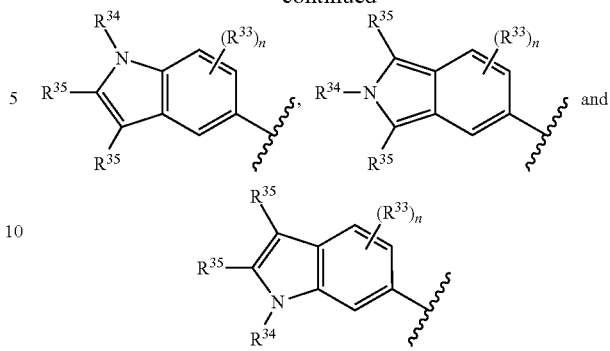

wherein $R^{34}$ is selected from hydrogen, alkyl, carbocyclyl, —C(=O)$R^{13}$, SO$_2$$R^{13}$, CO$_2$$R^{13}$ or SO$_2$NR$^{10}$$R^{11}$;

each $R^{35}$ is independently selected from hydrogen, halogen, OR$^9$, alkyl, or fluoroalkyl;

each $R^{10}$ and $R^{11}$ is independently selected from hydrogen, alkyl, carbocyclyl, heterocyclyl, —C(=O)$R^{13}$, SO$_2$$R^{13}$, CO$_2$$R^{13}$ or SO$_2$NR$^{10}$$R^{11}$; or $R^{10}$ and $R^{11}$ together with the nitrogen atom to which they are attached, form an N-heterocyclyl;

each $R^{13}$ is independently selected from alkyl, heteroalkyl, alkenyl, aryl, aralkyl, carbocyclyl, heteroaryl or heterocyclyl.

In another embodiment, Y is selected from:

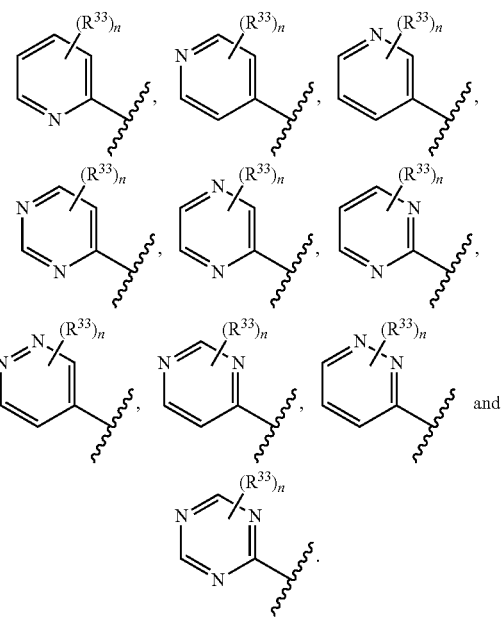

In another embodiment, Y is selected from:

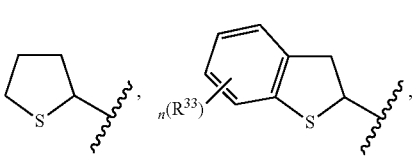

-continued

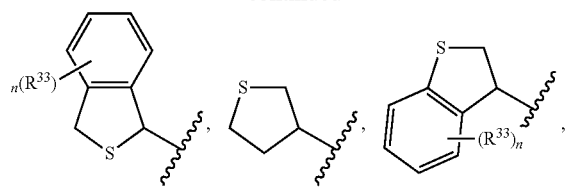

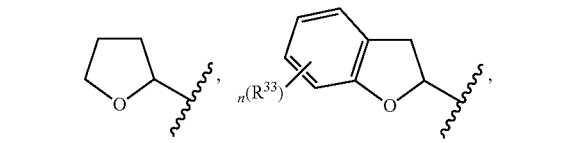

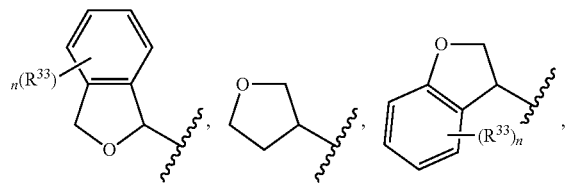

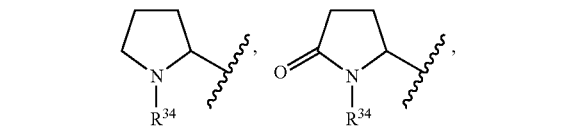

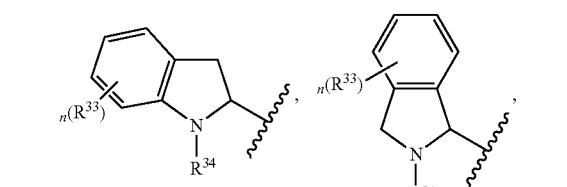

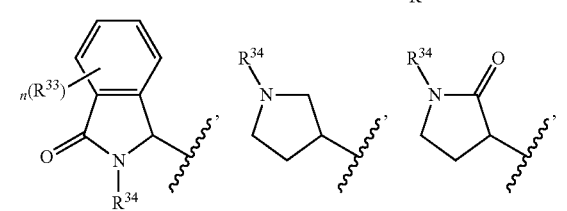

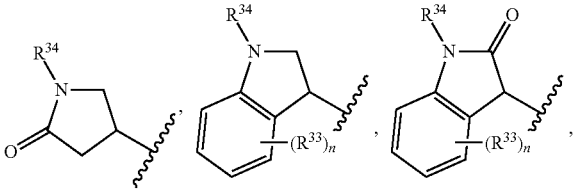

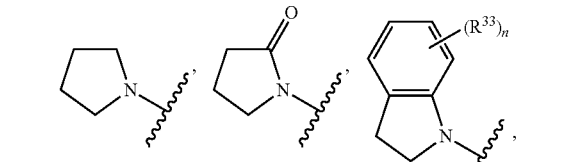

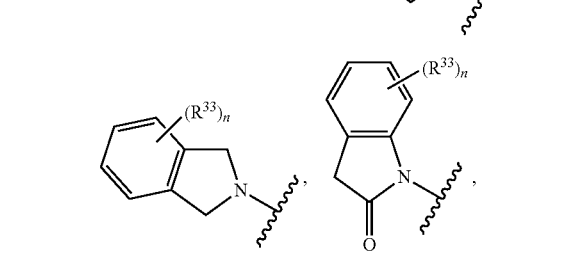

-continued

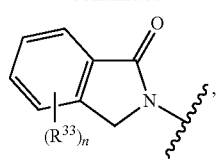

wherein $R^{34}$ is selected from hydrogen, alkyl, carbocyclyl, —C(=O)$R^{13}$, SO$_2$R$^{13}$, CO$_2$R$^{13}$ or SO$_2$NR$^{10}$R$^{11}$, each $R^{10}$ and $R^{11}$ is independently selected from hydrogen, alkyl, carbocyclyl, heterocyclyl, —C(=O)$R^{13}$, SO$_2$R$^{13}$, CO$_2$R$^{13}$ or SO$_2$NR$^{10}$R$^{11}$; or $R^{10}$ and $R^{11}$ together with the nitrogen atom to which they are attached, form an N-heterocyclyl;

each $R^{13}$ is independently selected from alkyl, heteroalkyl, alkenyl, aryl, aralkyl, carbocyclyl, heteroaryl or heterocyclyl.

In another embodiment, Y is selected from:

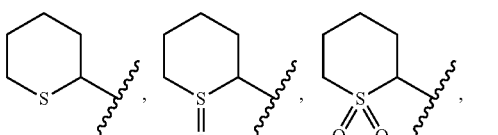

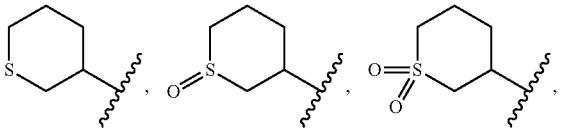

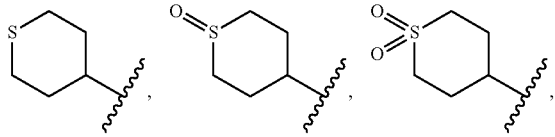

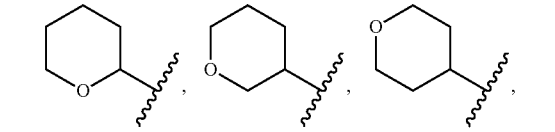

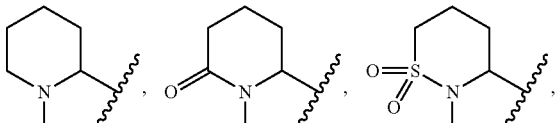

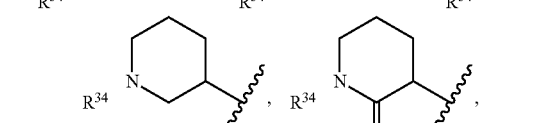

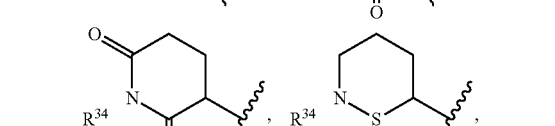

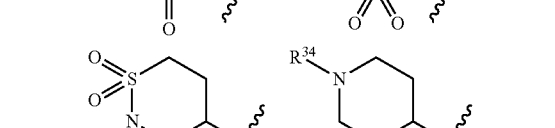

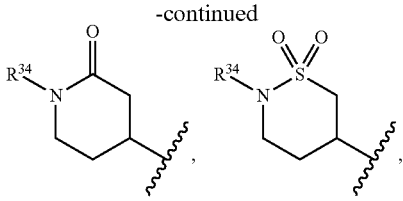

wherein $R^{34}$ is selected from hydrogen, alkyl, carbocyclyl, —C(=O)$R^{13}$, SO$_2$$R^{13}$, CO$_2$$R^{13}$ or SO$_2$NR$^{10}$R$^{11}$, each $R^{10}$ and $R^{11}$ is independently selected from hydrogen, alkyl, carbocyclyl, heterocyclyl, —C(=O)$R^{13}$, SO$_2$$R^{13}$, CO$_2$$R^{13}$ or SO$_2$NR$^{10}$R$^{11}$; or $R^{10}$ and $R^{11}$ together with the nitrogen atom to which they are attached, form an N-heterocyclyl;

each $R^{13}$ is independently selected from alkyl, heteroalkyl, alkenyl, aryl, aralkyl, carbocyclyl, heteroaryl or heterocyclyl.

In another embodiment, X is selected from *—O—C(R$^9$)$_2$—,*—S(O)$_2$—C(R$^9$)$_2$—, *—SO$_2$(NR$^9$)—, *—NR$^9$—C(R$^9$)$_2$—, *—NR$^9$—C(=O)—, and *—NR$^9$—S(O)$_2$—.

In another embodiment, X is selected from —C(R$^9$)$_2$—C(R$^9$)$_2$—, —C(R$^9$)=C(R$^9$)—, *—C(=O)—N(R$^9$)—, *—C(R$^9$)$_2$—O—, and *—C(R$^9$)$_2$—NR$^9$—.

In another embodiment, X is selected from *—O—C(R$^9$)$_2$—, or —C(R$^9$)$_2$—C(R$^9$)$_2$—.

In a further embodiment is a compound of Formula (A1), or a pharmaceutically acceptable salt thereof:

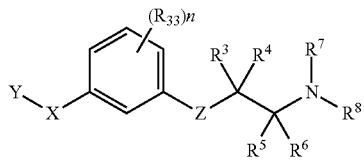

Formula (A1)

wherein,

X is selected from *—O—C(R$^9$)$_2$—, *—O—C(=O)—, *—S—C(R$^9$)$_2$—, *—S(O)—C(R$^9$)$_2$—, *—S(O)$_2$—C(R$^9$)$_2$—, *—SO$_2$(NR$^9$)—, *—NR$^9$—C(R$^9$)$_2$—, *—NR$^9$—C(=O)—, *—NR$^9$—S(O)$_2$—, —C(R$^9$)$_2$—C(R$^9$)$_2$—, *—C(=O)—C(R$^9$)$_2$—, *—C(R$^9$)$_2$—C(=O)—, —C(R$^9$)=C(R$^9$)—, *—C(=O)—N(R$^9$)—, *—C(=O)—O—, *—C(R$^9$)$_2$—O—, and *—C(R$^9$)$_2$—NR$^9$—; wherein the * indicates point of attachment to the phenylene ring;

Y is selected from heterocyclyl, heterocyclylalkyl, heteroaryl or heteroarylalkyl with the provision that Y is not

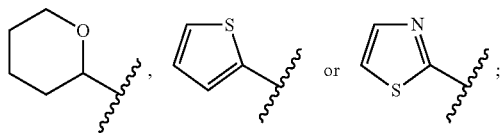 [SMILES: *C1CCCCO1 ; *c1cccs1 ; *c1nccs1]

Z is —C(R$^1$)(R$^2$)—;

$R^1$ and $R^2$ are each independently selected from hydrogen, halogen, alkyl, fluoroalkyl, —OR$^9$, —NR$^{10}$R$^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —OR$^9$ or —NR$^{10}$R$^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, SO$_2$$R^{13}$, CO$_2$$R^{13}$ or SO$_2$NR$^{10}$R$^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, SO$_2$$R^{13}$, CO$_2$$R^{13}$ or SO$_2$NR$^{10}$R$^{11}$; or $R^{10}$ and $R^{11}$ together with the nitrogen atom to which they are attached, form an N-heterocyclyl;

each $R^{13}$ is independently selected from alkyl, heteroalkyl, alkenyl, aryl, aralkyl, carbocyclyl, heteroaryl or heterocyclyl; and each $R^{33}$ is independently selected from halogen, OR$^9$, alkyl, or fluoroalkyl, and n is 0, 1, 2, 3, or 4.

In one embodiment, $R^3$ and $R^4$ are both hydrogen. In another embodiment, $R^5$ and $R^6$ are both hydrogen. In another embodiment, $R^3$, $R^4$, $R^5$ and $R^6$ are hydrogen. In another embodiment, $R^1$ and $R^2$ are both hydrogen. In another embodiment, $R^1$ is hydrogen and $R^2$ is —OH. In another embodiment, $R^1$ and $R^2$ together form an oxo. In another embodiment, $R^7$ and $R^8$ are both hydrogen. In another embodiment, $R^7$ is hydrogen and $R^8$ is —C(=O)$R^{13}$ or CO$_2$$R^{13}$. In a further embodiment, $R^{13}$ is an alkyl. In another further embodiment, wherein $R^8$ is CO$_2$$R^{13}$ and $R^{13}$ is

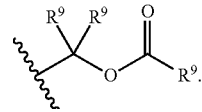

In another embodiment, $R^1$, $R^3$, and $R^4$ are all hydrogen, and $R^2$ is —OH. In another embodiment, $R^3$, $R^4$, $R^7$ and $R^8$ are all hydrogen. In another embodiment, $R^1$, $R^7$, and $R^8$ are all hydrogen, and $R^2$ is —OH. In another embodiment, $R^1$, $R^3$, $R^4$, $R^5$, $R^6$, $R^7$, and $R^8$ are all hydrogen, and $R^2$ is —OH.

In another embodiment, Y is selected from:

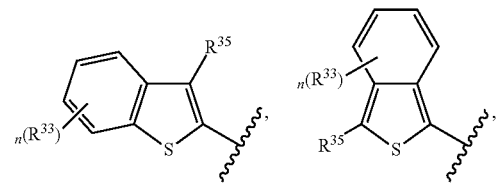

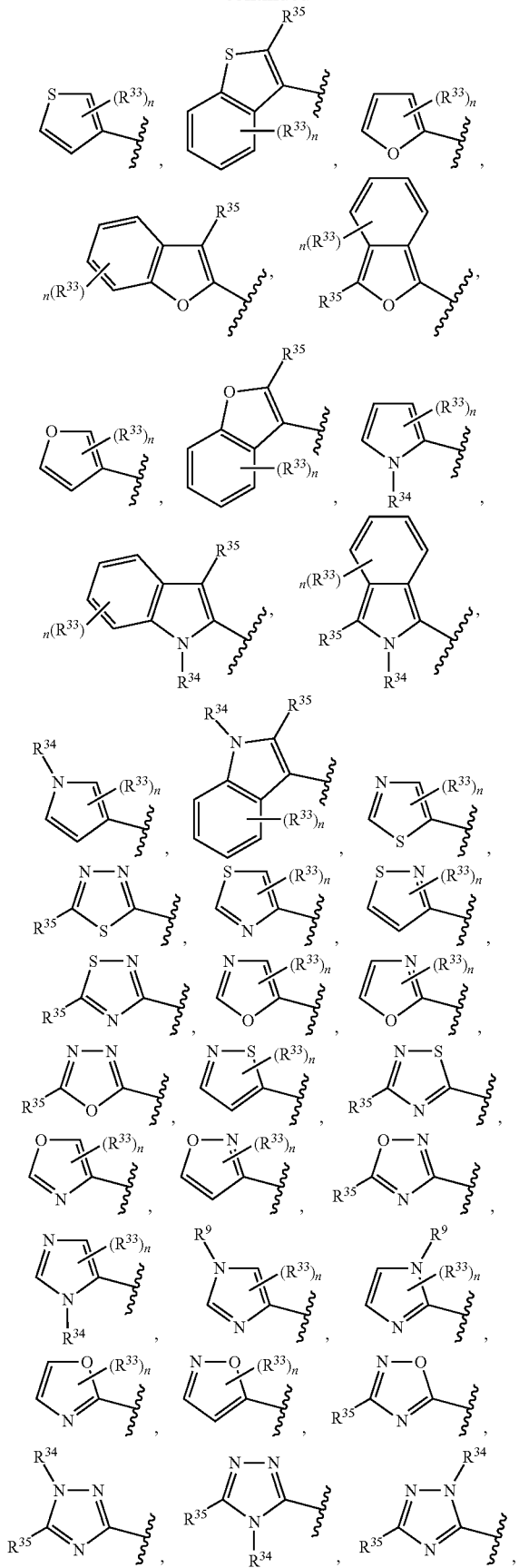
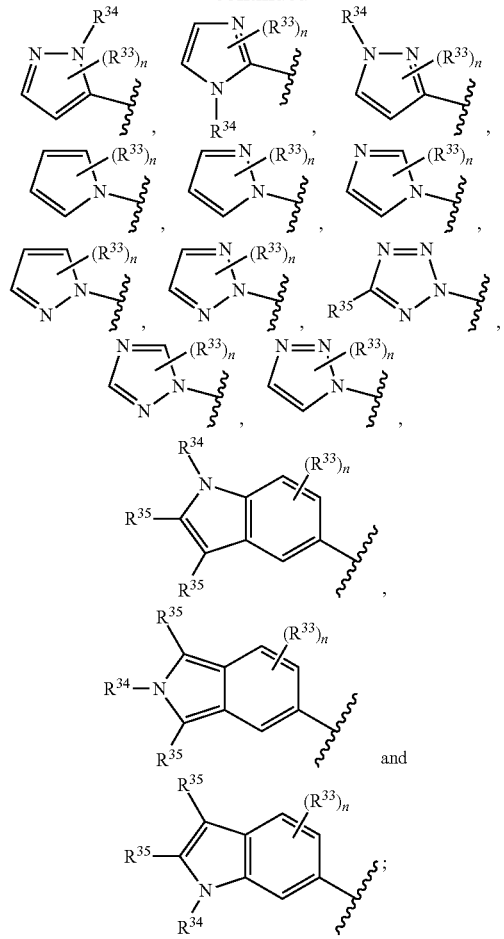

wherein $R^{34}$ is selected from hydrogen, alkyl, carbocyclyl, —C(=O)$R^{13}$, SO$_2$$R^{13}$, CO$_2$$R^{13}$ or SO$_2$NR$^{10}$R$^{11}$;

each $R^{35}$ is independently selected from hydrogen, halogen, OR$^9$, alkyl, or fluoroalkyl;

each $R^{10}$ and $R^{11}$ is independently selected from hydrogen, alkyl, carbocyclyl, heterocyclyl, —C(=O)$R^{13}$, SO$_2$$R^{13}$, CO$_2$$R^{13}$ or SO$_2$NR$^{10}$R$^{11}$; or $R^{10}$ and $R^{11}$ together with the nitrogen atom to which they are attached, form an N-heterocyclyl;

each $R^{13}$ is independently selected from alkyl, heteroalkyl, alkenyl, aryl, aralkyl, carbocyclyl, heteroaryl or heterocyclyl.

In another embodiment, Y is selected from:

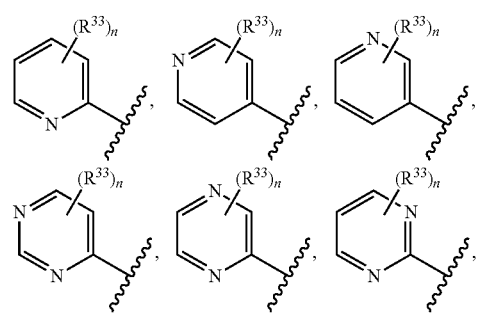

-continued

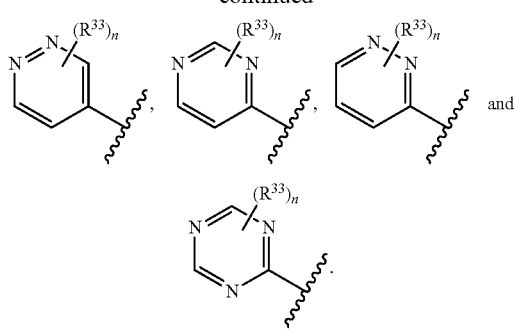

and

In another embodiment, Y is selected from:

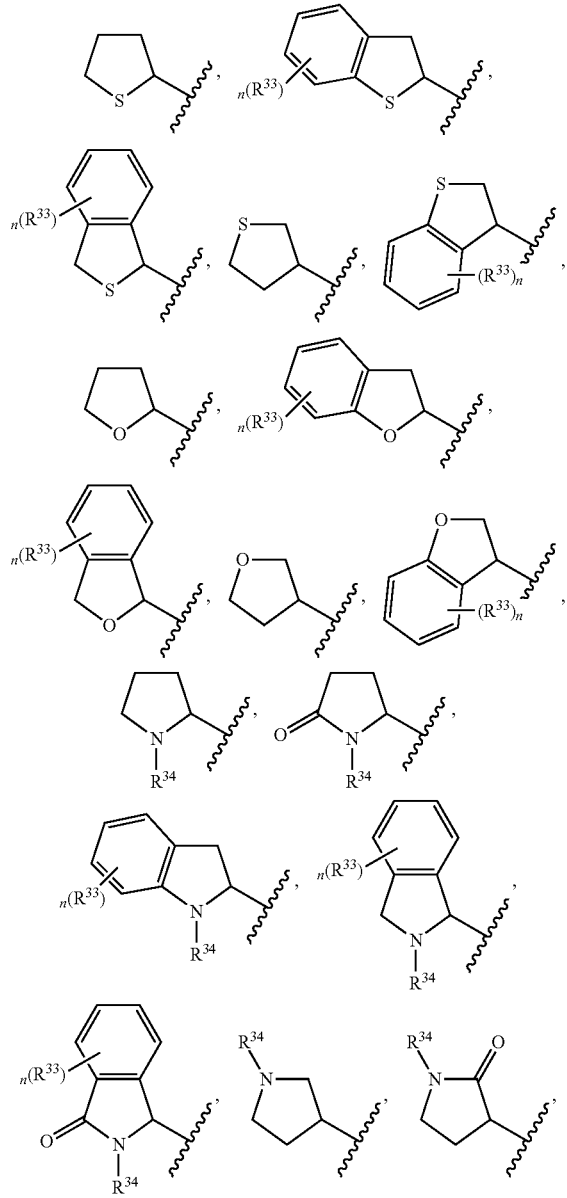

-continued

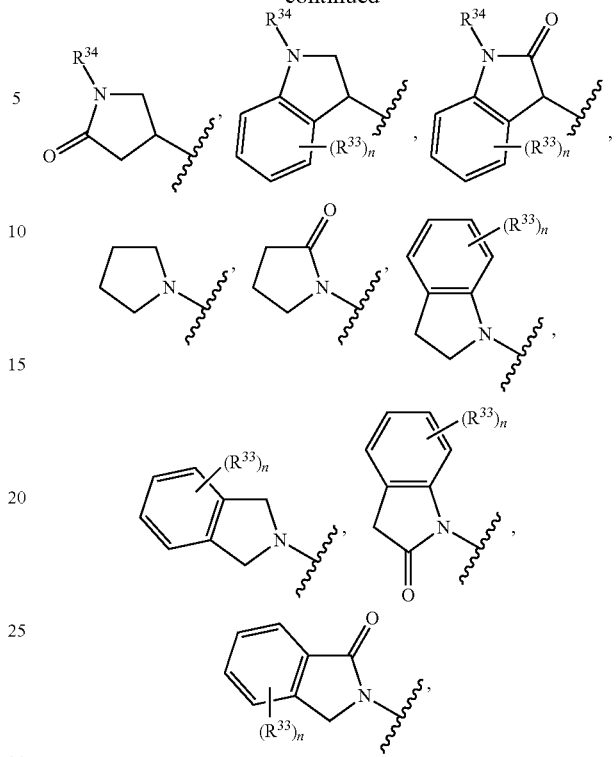

wherein $R^{34}$ is selected from hydrogen, alkyl, carbocyclyl, —C(=O)$R^{13}$, SO$_2$$R^{13}$, CO$_2$$R^{13}$ or SO$_2$NR$^{10}$R$^{11}$, each $R^{10}$ and $R^{11}$ is independently selected from hydrogen, alkyl, carbocyclyl, heterocyclyl, —C(=O)$R^{13}$, SO$_2$$R^{13}$, CO$_2$$R^{13}$ or SO$_2$NR$^{10}$R$^{11}$; or $R^{10}$ and $R^{11}$ together with the nitrogen atom to which they are attached, form an N-heterocyclyl;

each $R^{13}$ is independently selected from alkyl, heteroalkyl, alkenyl, aryl, aralkyl, carbocyclyl, heteroaryl or heterocyclyl.

In another embodiment, Y is selected from:

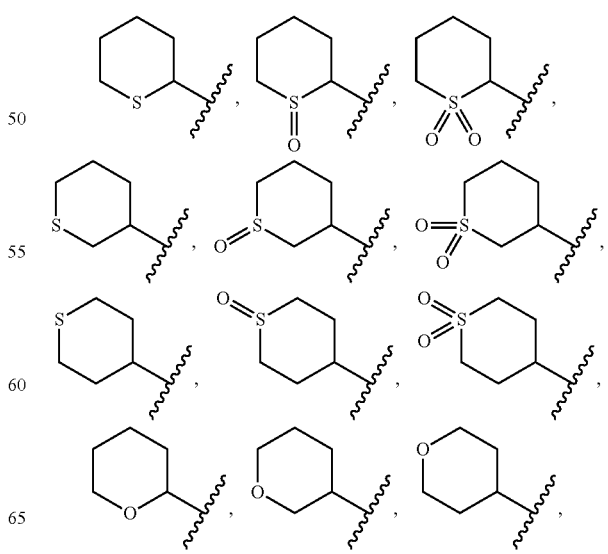

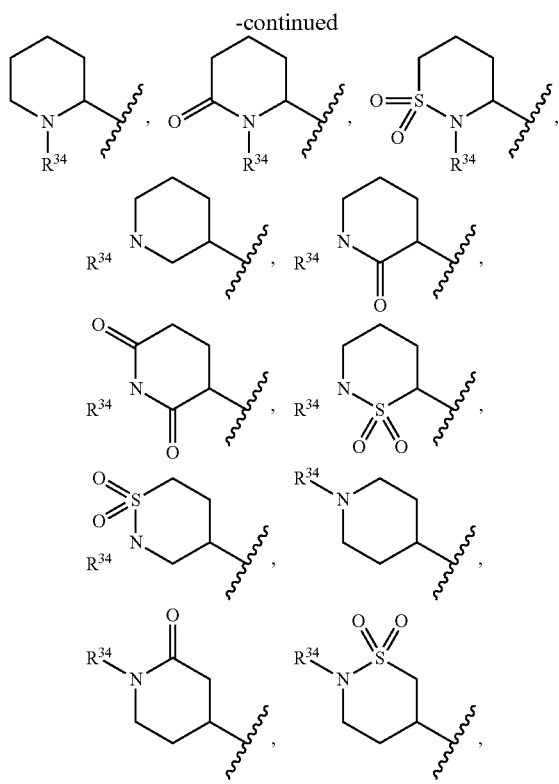

wherein R³⁴ is selected from hydrogen, alkyl, carbocyclyl, —C(=O)R¹³, SO₂R¹³, CO₂R¹³ or SO₂NR¹⁰R¹¹, each R¹⁰ and R¹¹ is independently selected from hydrogen, alkyl, carbocyclyl, heterocyclyl, —C(=O)R¹³, SO₂R¹³, CO₂R¹³ or SO₂NR¹⁰R¹¹; or R¹⁰ and R¹¹ together with the nitrogen atom to which they are attached, form an N-heterocyclyl;

each R¹³ is independently selected from alkyl, heteroalkyl, alkenyl, aryl, aralkyl, carbocyclyl, heteroaryl or heterocyclyl.

In another embodiment, X is selected from *—O—C(R⁹)₂—, *—S(O)₂—C(R⁹)₂—, *—SO₂(NR⁹)—, *—NR⁹—C(R⁹)₂—, *—NR⁹—C(=O)—, and *—NR⁹—S(O)₂—.

In another embodiment, X is selected from *—C(R⁹)₂—C(R⁹)₂—, —C(R⁹)=C(R⁹)—, *—C(=O)—N(R⁹)—, *—C(R⁹)₂—O—, and *—C(R⁹)₂—NR⁹—.

In another embodiment, X is selected from *—O—C(R⁹)₂—, or —C(R⁹)₂—C(R⁹)₂—.

In a further embodiment is a compound of Formula (A2), or a pharmaceutically acceptable salt thereof:

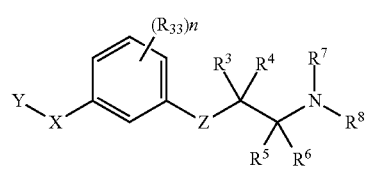

Formula (A2)

wherein,
X is selected from *—O—C(R⁹)₂—, *—O—C(=O)—, *—S—C(R⁹)₂—, *—S(O)—C(R⁹)₂—, *—S(O)₂—C(R⁹)₂—, *—SO₂(NR⁹)—, *—NR⁹—C(R⁹)₂—, *—NR⁹—C(=O)—, *—NR⁹—S(O)₂—, —C(R⁹)₂—C(R⁹)₂—, *—C(=O)—C(R⁹)₂—, *—C(R⁹)₂—C(=O)—, —C(R⁹)=C(R⁹)—, *—C(=O)—N(R⁹)—, *—C(=O)—O—, *—C(R⁹)₂—O—, and *—C(R⁹)₂—NR⁹—; wherein the * indicates point of attachment to the phenylene ring;

Y is selected from heterocyclyl, heterocyclylalkyl, heteroaryl or heteroarylalkyl;

Z is —O—;

R³ and R⁴ are each independently selected from hydrogen, halogen, C₁-C₅ alkyl, fluoroalkyl, —OR⁹ or —NR¹⁰R¹¹; or R³ and R⁴ together form an oxo;

R⁵ and R⁶ are each independently selected from hydrogen, alkyl, alkenyl, fluoroalkyl, aryl, heteroaryl, carbocyclyl or C-attached heterocyclyl; or R⁵ and R⁶ together with the carbon atom to which they are attached, form a carbocyclyl or heterocyclyl; or R⁵ and R⁶ together form an imino;

R⁷ and R⁸ are each independently selected from hydrogen, alkyl, carbocyclyl, —C(=O)R¹³, SO₂R¹³, CO₂R¹³ or SO₂NR¹⁰R¹¹; or R⁷ and R⁸, together with the nitrogen atom to which they are attached, form an N-heterocyclyl;

each R⁹ independently hydrogen or alkyl;

each R¹⁰ and R¹¹ is independently selected from hydrogen, alkyl, carbocyclyl, heterocyclyl, —C(=O)R¹³, SO₂R¹³, CO₂R¹³ or SO₂NR¹⁰R¹¹; or R¹⁰ and R¹¹ together with the nitrogen atom to which they are attached, form an N-heterocyclyl;

each R¹³ is independently selected from alkyl, heteroalkyl, alkenyl, aryl, aralkyl, carbocyclyl, heteroaryl or heterocyclyl; and each R³³ is independently selected from halogen, OR⁹, alkyl, or fluoroalkyl, and n is 0, 1, 2, 3, or 4, with the provision that the compound is not

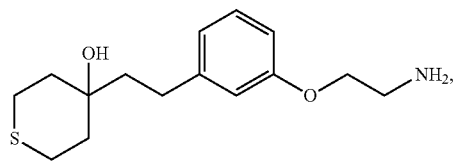

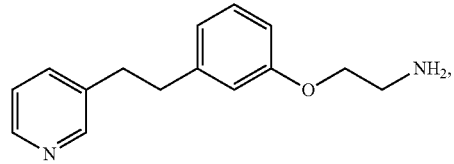

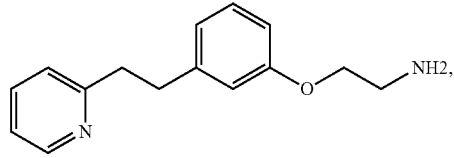

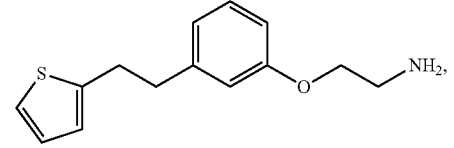

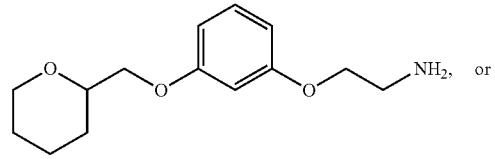

-continued

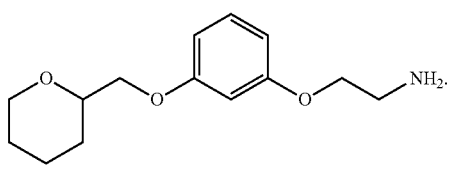

In one embodiment, $R^3$ and $R^4$ are both hydrogen. In another embodiment, $R^5$ and $R^6$ are both hydrogen. In another embodiment, $R^3$, $R^4$, $R^5$ and $R^6$ are hydrogen. In another embodiment, $R^7$ and $R^8$ are both hydrogen. In another embodiment $R^7$ is hydrogen and $R^8$ is —C(=O)$R^{13}$ or CO$_2$$R^{13}$. In a further embodiment, $R^{13}$ is an alkyl. In a further embodiment, $R^8$ is CO$_2$$R^{13}$ and $R^{13}$ is

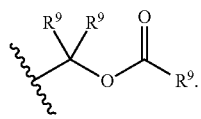

In another embodiment, $R^3$, $R^4$, $R^7$ and $R^8$ are all hydrogen. In another embodiment, $R^3$, $R^4$, $R^5$, $R^6$, $R^7$, and $R^8$ are all hydrogen.

In another embodiment, Y is selected from:

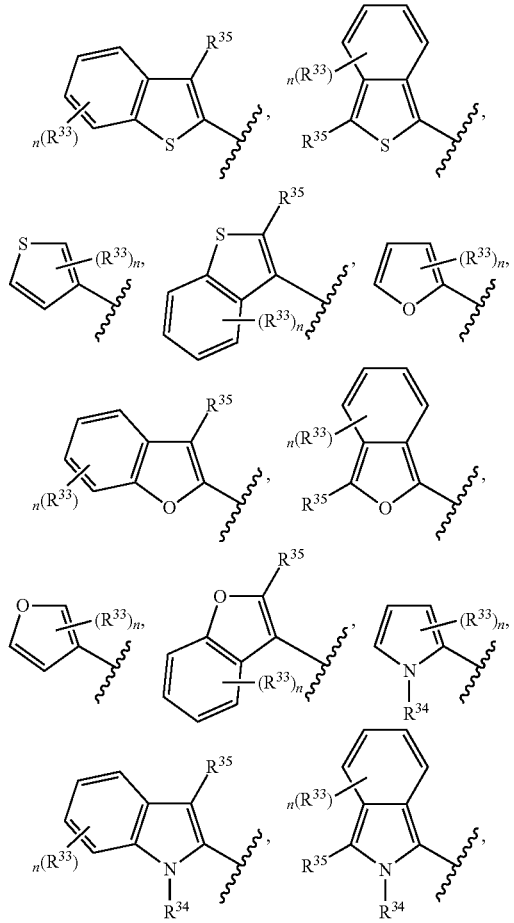

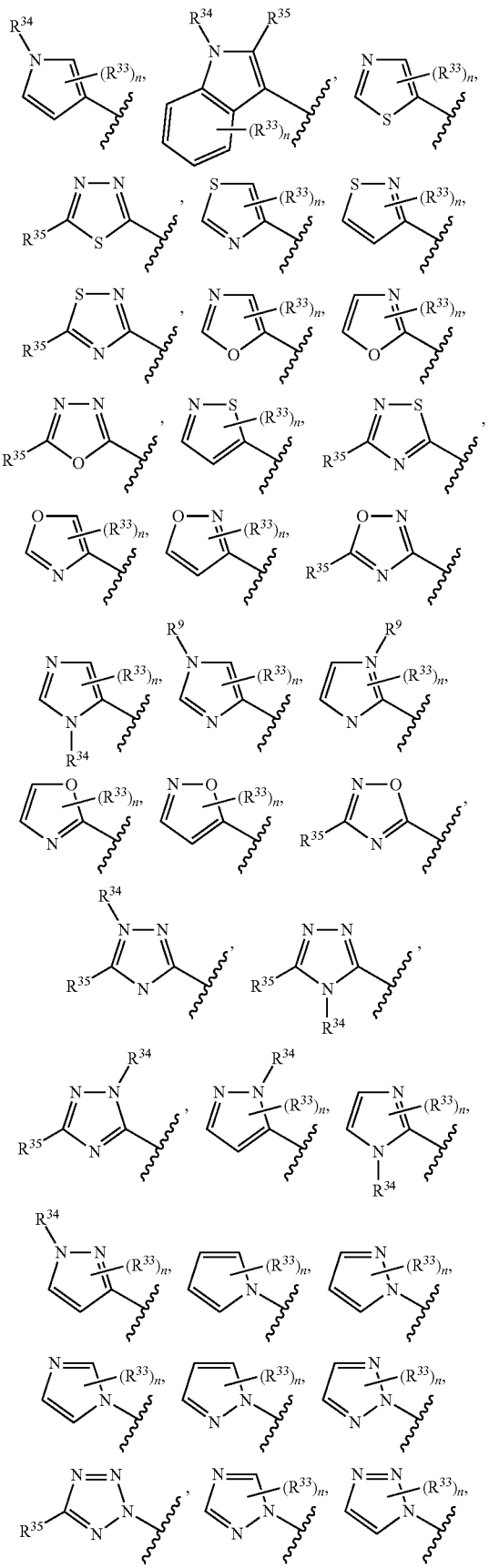

-continued

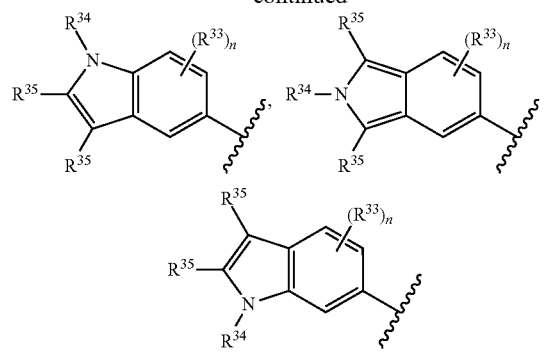

and

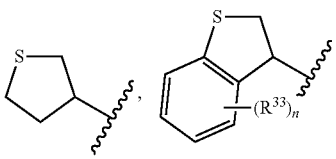

wherein R[34] is selected from hydrogen, alkyl, carbocyclyl, —C(=O)R[13], SO$_2$R[13], CO$_2$R[13] or SO$_2$NR[10]R[11];

each R[35] is independently selected from hydrogen, halogen, OR[9], alkyl, or fluoroalkyl;

each R[10] and R[11] is independently selected from hydrogen, alkyl, carbocyclyl, heterocyclyl, —C(=O)R[13], SO$_2$R[13], CO$_2$R[13] or SO$_2$NR[10]R[11]; or R[10] and R[11] together with the nitrogen atom to which they are attached, form an N-heterocyclyl;

each R[13] is independently selected from alkyl, heteroalkyl, alkenyl, aryl, aralkyl, carbocyclyl, heteroaryl or heterocyclyl.

In another embodiment, Y is selected from:

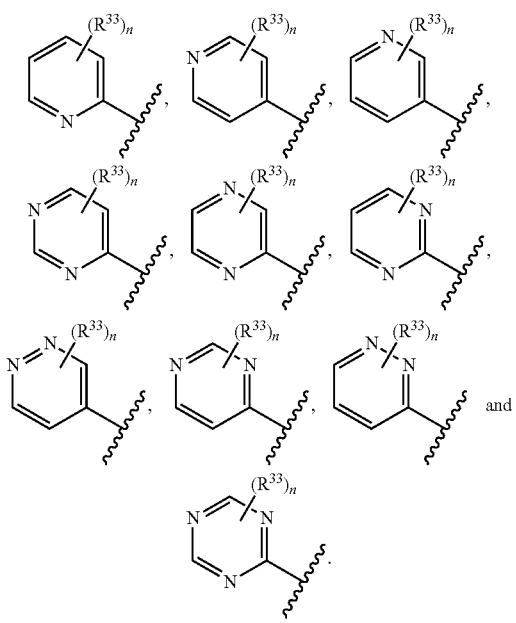

and

In another embodiment, Y is selected from:

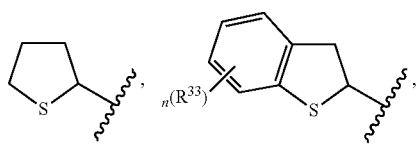

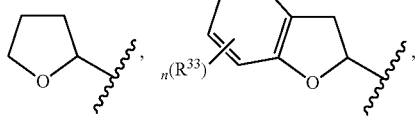

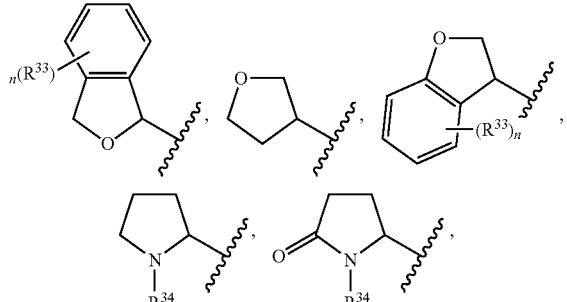

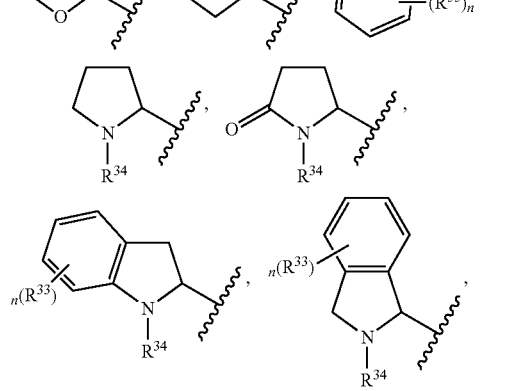

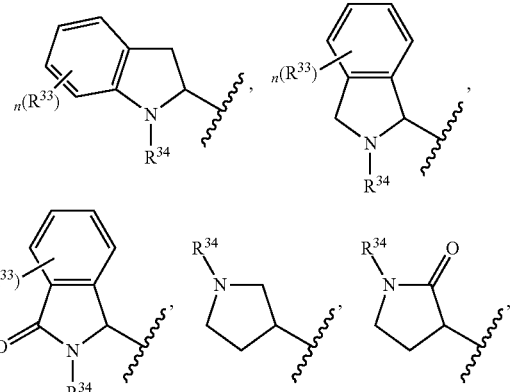

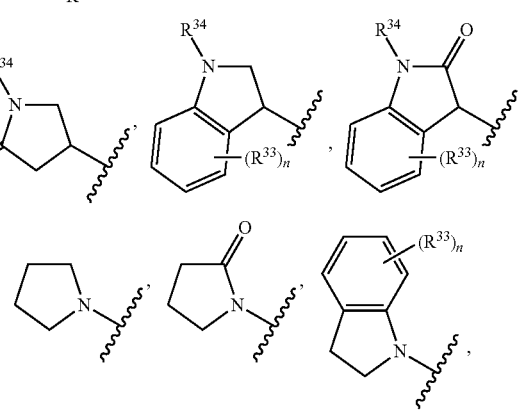

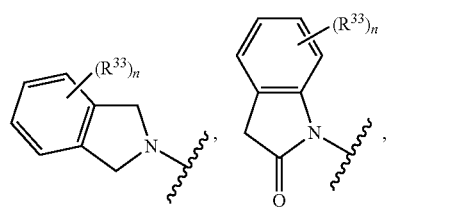

33
-continued

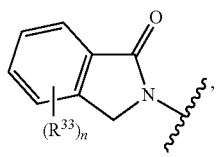

wherein R³⁴ is selected from hydrogen, alkyl, carbocyclyl, —C(=O)R¹³, SO₂R¹³, CO₂R¹³ or SO₂NR¹⁰R¹¹, each R¹⁰ and R¹¹ is independently selected from hydrogen, alkyl, carbocyclyl, heterocyclyl, —C(=O)R¹³, SO₂R¹³, CO₂R¹³ or SO₂NR¹⁰R¹¹; or R¹⁰ and R¹¹ together with the nitrogen atom to which they are attached, form an N-heterocyclyl;

each R¹³ is independently selected from alkyl, heteroalkyl, alkenyl, aryl, aralkyl, carbocyclyl, heteroaryl or heterocyclyl.

In another embodiment, Y is selected from:

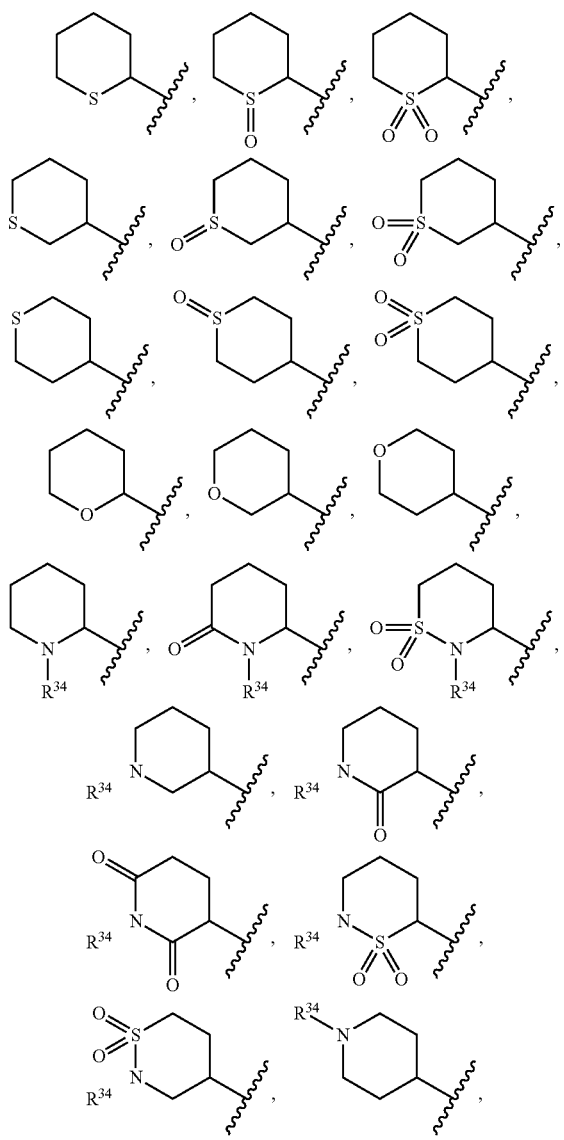

34
-continued

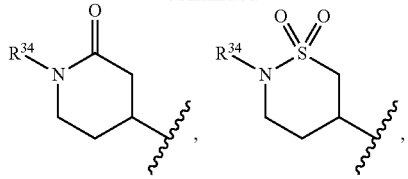

wherein R³⁴ is selected from hydrogen, alkyl, carbocyclyl, —C(=O)R¹³, SO₂R¹³, CO₂R¹³ or SO₂NR¹⁰R¹¹, each R¹⁰ and R¹¹ is independently selected from hydrogen, alkyl, carbocyclyl, heterocyclyl, —C(=O)R¹³, SO₂R¹³, CO₂R¹³ or SO₂NR¹⁰R¹¹; or R¹⁰ and R¹¹ together with the nitrogen atom to which they are attached, form an N-heterocyclyl;

each R¹³ is independently selected from alkyl, heteroalkyl, alkenyl, aryl, aralkyl, carbocyclyl, heteroaryl or heterocyclyl.

In another embodiment, X is selected from *—O—C(R⁹)₂—,*—S(O)₂—C(R⁹)₂—, *—SO₂(NR⁹)—, *—NR⁹—C(R⁹)₂—, *—NR⁹—C(=O)—, and *—NR⁹—S(O)₂—.

In another embodiment, X is selected from —C(R⁹)₂—C(R⁹)₂—, —C(R⁹)=C(R⁹)—, *—C(=O)—N(R⁹)—, *—C(R⁹)₂—O—, and *—C(R⁹)₂—NR⁹—.

In another embodiment, X is selected from *—O—C(R⁹)₂—, or —C(R⁹)₂—C(R⁹)₂—.

In a further embodiment is a compound Formula (A3), or a pharmaceutically acceptable salt thereof:

Formula (A3)

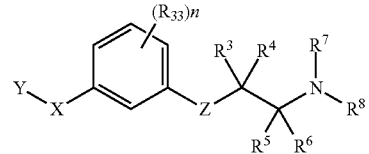

wherein,
X is selected from *—O—C(R⁹)₂—, *—O—C(=O)—, *—S—C(R⁹)₂—, *—S(O)—C(R⁹)₂—, *—S(O)₂—C(R⁹)₂—, *—SO₂(NR⁹)—, *—NR⁹—C(R⁹)₂—, *—NR⁹—C(=O)—, *—NR⁹—S(O)₂—, —C(R⁹)₂—C(R⁹)₂—, *—C(=O)—C(R⁹)₂—, *—C(R⁹)₂—C(=O)—, —C(R⁹)=C(R⁹)—, *—C(=O)—N(R⁹)—, *—C(=O)—O—, *—C(R⁹)₂—O—, and *—C(R⁹)₂—NR⁹—; wherein the * indicates point of attachment to the phenylene ring;

Y is

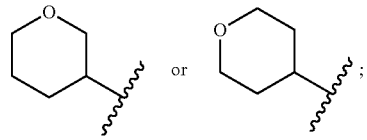 [SMILES: *C1CCCOC1 ; *C1CCOCC1]

Z is —C(R¹)(R²)— or —O—;
R¹ and R² are each independently selected from hydrogen, halogen, alkyl, fluoroalkyl, —OR⁹, —NR¹⁰R¹¹ or carbocyclyl; or R¹ and R² form an oxo; or optionally, R¹ and R³ together form a direct bond to provide a double bond; or optionally, R¹ and R³ together form a direct bond, and R² and R⁴ together form a direct bond to provide a triple bond;

$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, $SO_2R^{13}$, $CO_2R^{13}$ or $SO_2N^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, $SO_2R^{13}$, $CO_2R^{13}$ or $SO_2NR^{10}R^{11}$; or $R^{10}$ and $R^{11}$ together with the nitrogen atom to which they are attached, form an N-heterocyclyl;

each $R^{13}$ is independently selected from alkyl, heteroalkyl, alkenyl, aryl, aralkyl, carbocyclyl, heteroaryl or heterocyclyl; and each $R^{33}$ is independently selected from halogen, $OR^9$, alkyl, or fluoroalkyl, and n is 0, 1, 2, 3, or 4.

In one embodiment, $R^3$ and $R^4$ are both hydrogen. In another embodiment, $R^5$ and $R^6$ are both hydrogen. In another embodiment, $R^3$, $R^4$, $R^5$ and $R^6$ are hydrogen. In another embodiment, $R^7$ and $R^8$ are both hydrogen. In another embodiment, $R^7$ is hydrogen and $R^8$ is —C(=O)$R^{13}$ or $CO_2R^{13}$. In a further embodiment, $R^{13}$ is an alkyl. In a further embodiment, $R^8$ is $CO_2R^{13}$ and $R^{13}$ is

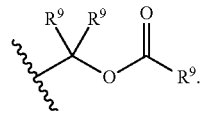

In another embodiment, $R^3$, $R^4$, $R^7$ and $R^8$ are all hydrogen.

In another embodiment, $R^3$, $R^4$, $R^5$, $R^6$, $R^7$, and $R^8$ are all hydrogen.

In another embodiment, X is selected from *—O—C($R^9$)$_2$—, *—S(O)$_2$—C($R^9$)$_2$—, *—SO$_2$(NR$^9$)—, *—NR$^9$—C($R^9$)$_2$—, *—NR$^9$—C(=O)—, and *—NR$^9$—S(O)$_2$—.

In another embodiment, X is selected from —C($R^9$)$_2$—C($R^9$)$_2$—, —C($R^9$)=C($R^9$)—, *—C(=O)—N($R^9$)—, *—C($R^9$)$_2$—O—, and *—C($R^9$)$_2$—NR$^9$—.

In another embodiment, X is selected from *—O—C($R^9$)$_2$—, or —C($R^9$)$_2$—C($R^9$)$_2$—.

In a further embodiment is a compound of Formula (A4), or a pharmaceutically acceptable salt thereof:

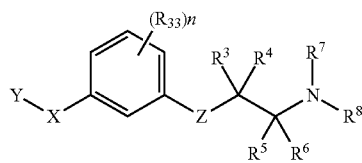

Formula (A4)

wherein,

X is selected from *—O—C($R^9$)$_2$—, *—O—C(=O)—, *—S—C($R^9$)$_2$—, *—S(O)—C($R^9$)$_2$—, *—S(O)$_2$—C($R^9$)$_2$—, *—SO$_2$(NR$^9$)—, *—NR$^9$—C($R^9$)$_2$—, *—NR$^9$—C(=O)—, *—NR$^9$—S(O)$_2$—, —C($R^9$)$_2$—C($R^9$)$_2$—, *—C(=O)—C($R^9$)$_2$—, *—C($R^9$)$_2$—C(=O)—, —C($R^9$)=C($R^9$)—, *—C(=O)—N($R^9$)—, *—C(=O)—O—, *—C($R^9$)$_2$—O—, and *—C($R^9$)$_2$—NR$^9$—; wherein the * indicates point of attachment to the phenylene ring;

Y is

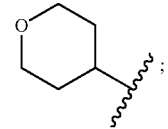

Z is —C($R^1$)($R^2$)— or —O—;

$R^1$ and $R^2$ are each independently selected from hydrogen, halogen, alkyl, fluoroalkyl, —$OR^9$, —$NR^{10}R^{11}$ or carbocyclyl; or $R^1$ and $R^2$ form an oxo; or optionally, $R^1$ and $R^3$ together form a direct bond to provide a double bond; or optionally, $R^1$ and $R^3$ together form a direct bond, and $R^2$ and $R^4$ together form a direct bond to provide a triple bond;

$R^3$ and $R^4$ are each independently selected from hydrogen, halogen, $C_1$-$C_5$ alkyl, fluoroalkyl, —$OR^9$ or —$NR^{10}R^{11}$; or $R^3$ and $R^4$ together form an oxo;

$R^5$ and $R^6$ are each independently selected from hydrogen, alkyl, alkenyl, fluoroalkyl, aryl, heteroaryl, carbocyclyl or C-attached heterocyclyl; or $R^5$ and $R^6$ together with the carbon atom to which they are attached, form a carbocyclyl or heterocyclyl; or $R^5$ and $R^6$ together form an imino;

$R^7$ and $R^8$ are each independently selected from hydrogen, alkyl, carbocyclyl, —C(=O)$R^{13}$, $SO_2R^{13}$, $CO_2R^{13}$ or $SO_2NR^{10}R^{11}$; or $R^7$ and $R^8$, together with the nitrogen atom to which they are attached, form an N-heterocyclyl;

each $R^9$ independently hydrogen or alkyl;

each $R^{10}$ and $R^{11}$ is independently selected from hydrogen, alkyl, carbocyclyl, heterocyclyl, —C(=O)$R^{13}$, $SO_2R^{13}$, $CO_2R^{13}$ or $SO_2NR^{10}R^{11}$; or $R^{10}$ and $R^{11}$ together with the nitrogen atom to which they are attached, form an N-heterocyclyl;

each $R^{13}$ is independently selected from alkyl, heteroalkyl, alkenyl, aryl, aralkyl, carbocyclyl, heteroaryl or heterocyclyl; and each $R^{33}$ is independently selected from halogen, $OR^9$, alkyl, or fluoroalkyl, and n is 0, 1, 2, 3, or 4.

In one embodiment, $R^3$ and $R^4$ are both hydrogen. In another embodiment, $R^5$ and $R^6$ are both hydrogen. In another embodiment, $R^3$, $R^4$, $R^5$ and $R^6$ are hydrogen. In another embodiment, $R^7$ and $R^8$ are both hydrogen. In another embodiment, $R^7$ is hydrogen and $R^8$ is —C(=O)$R^{13}$ or $CO_2R^{13}$. In a further embodiment, $R^{13}$ is an alkyl. In a further embodiment, $R^8$ is $CO_2R^{13}$ and $R^{13}$ is

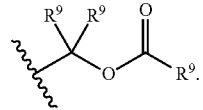

In another embodiment, $R^3$, $R^4$, $R^7$ and $R^8$ are all hydrogen.

In another embodiment, $R^3$, $R^4$, $R^5$, $R^6$, $R^7$, and $R^8$ are all hydrogen.

In another embodiment, X is selected from *—O—C(R$^9$)$_2$—, *—S(O)$_2$—C(R$^9$)$_2$—, *—SO$_2$(NR$^9$)—, *—NR$^9$—C(R$^9$)$_2$—, *—NR$^9$—C(=O)—, and *—NR$^9$—S(O)$_2$—.

In another embodiment, X is selected from —C(R$^9$)$_2$—C(R$^9$)$_2$—, —C(R$^9$)=C(R$^9$)—, *—C(=O)—N(R$^9$)—, *—C(R$^9$)$_2$—O—, and *—C(R$^9$)$_2$—NR$^9$—.

In another embodiment, X is selected from *—O—C(R$^9$)$_2$—, or —C(R$^9$)$_2$—C(R$^9$)$_2$—.

One embodiment provides a compound of Formula (B), or a pharmaceutically acceptable salt thereof:

Formula (B)

wherein,

X is selected from *—O—CH$_2$—, *—S—CH$_2$—, *—S(O)—CH$_2$—, *—S(O)$_2$—CH$_2$—, *—NH—CH$_2$—, *—NH—C(=O)—, —CH$_2$—CH$_2$—, or —CH=CH—; wherein the * indicates point of attachment to the phenylene ring;

Y is selected from heterocyclyl, heterocyclylalkyl, heteroaryl or heteroarylalkyl;

Z is —C(H)(H)—C(H)(H)—, *—C(H)(OH)—C(H)(H)—, *—C(=O)—C(H)(H)—, —CH=CH—, —C≡C—; wherein the * indicates point of attachment to the phenylene ring;

R$^1$ and R$^2$ are each independently selected from hydrogen, C$_1$-C$_4$ alkyl, —C(=O)R$^3$;

R$^3$ is selected from alkyl, alkoxy, or —OCH$_2$OC(O)R$^4$, wherein R$^4$ is an alkyl or alkoxy;

with the provision that the compound is not

Another embodiment provides the compound of Formula (B), wherein Z is —C(H)(OH)—C(H)(H)—. Another embodiment provides the compound of Formula (B), wherein R$^1$ and R$^2$ are both hydrogen. Another embodiment provides the compound of Formula (B), wherein R$^1$ is hydrogen and R$^2$ is C$_1$-C$_4$ alkyl. Another embodiment provides the compound of Formula (B), wherein R$^1$ is hydrogen and R$^2$ is —C(=O)R$^3$. Another embodiment provides the compound of Formula (B), wherein X is selected from *—O—CH$_2$—, —CH$_2$—CH$_2$—, or —CH=CH—. Another embodiment provides the compound of Formula (B), wherein X is selected from *—O—CH$_2$—, or —CH$_2$—CH$_2$—. Another embodiment provides the compound of Formula (B), wherein X is *—O—CH$_2$—.

Another embodiment provides the compound of Formula (B), wherein Y is selected from:

Another embodiment provides the compound of Formula (B), wherein Y is selected from:

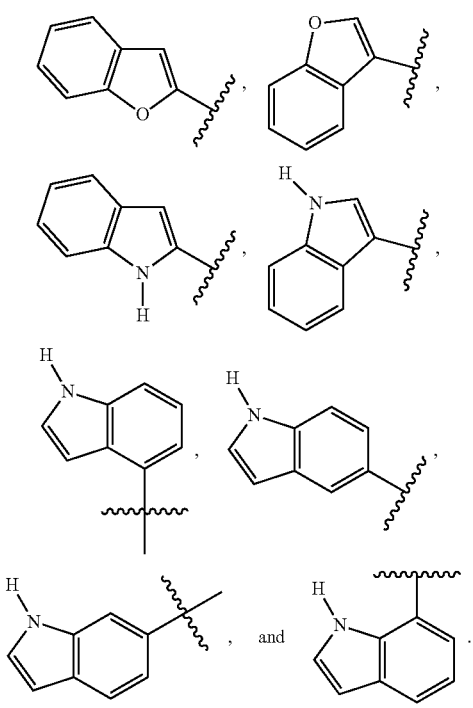
Another embodiment provides the compound of Formula (B), wherein Y is selected from:
Another embodiment provides the compound of Formula (B), wherein Y is selected from:
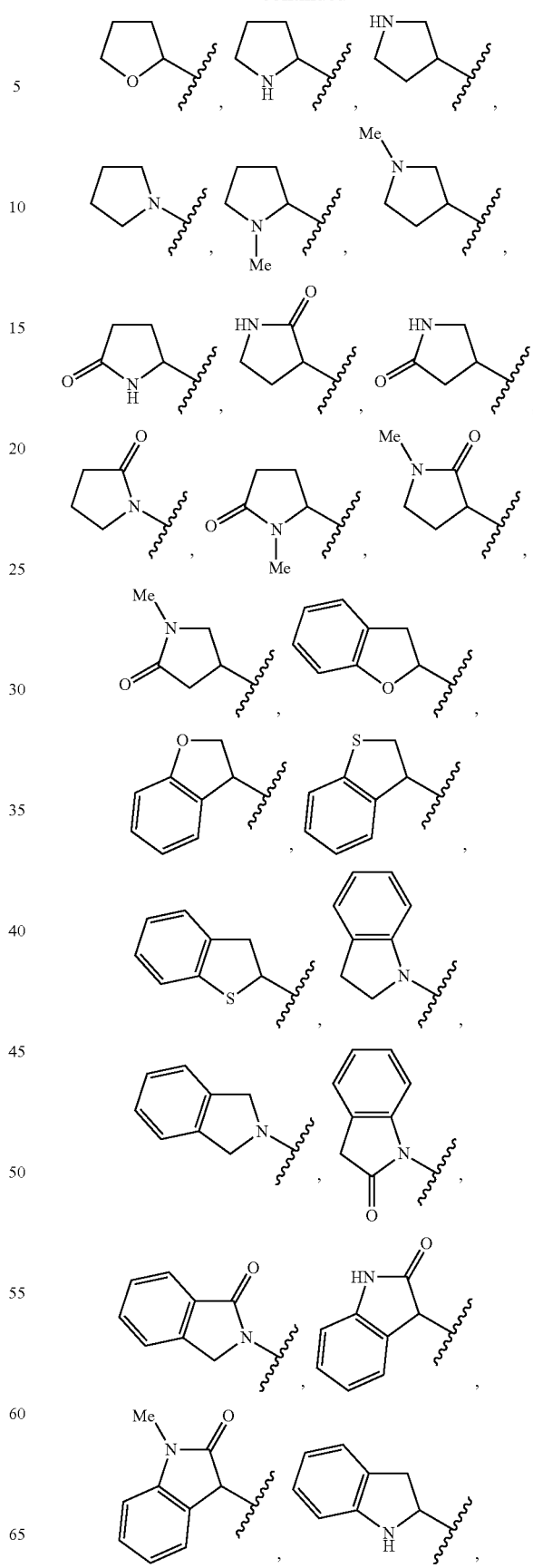

-continued

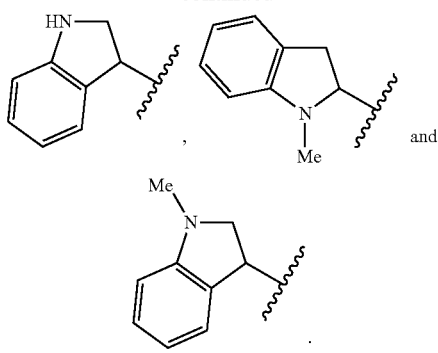

Another embodiment provides the compound of Formula (B), wherein Y is selected from:

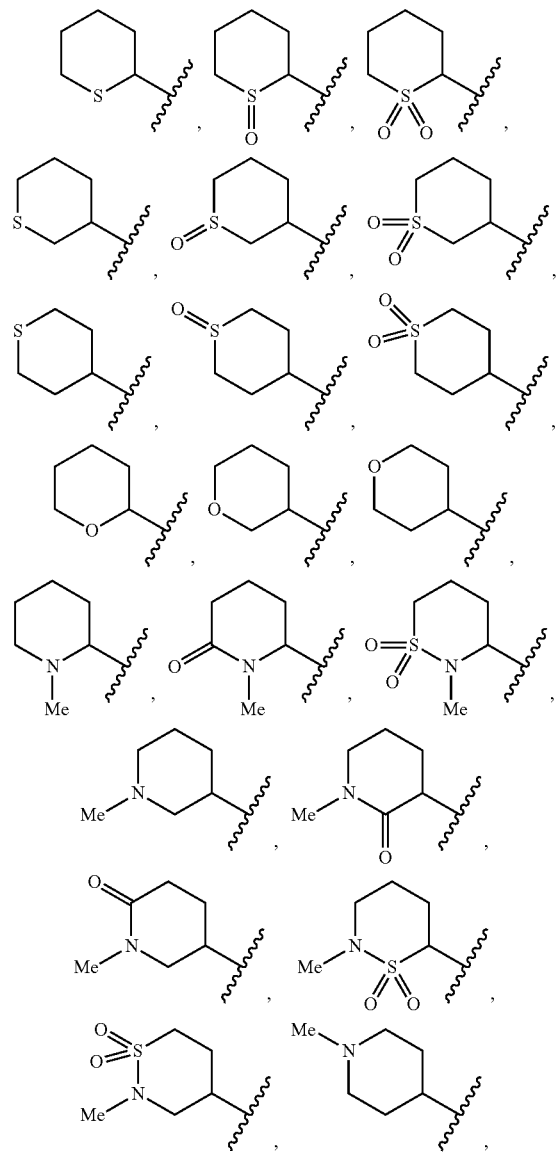

-continued

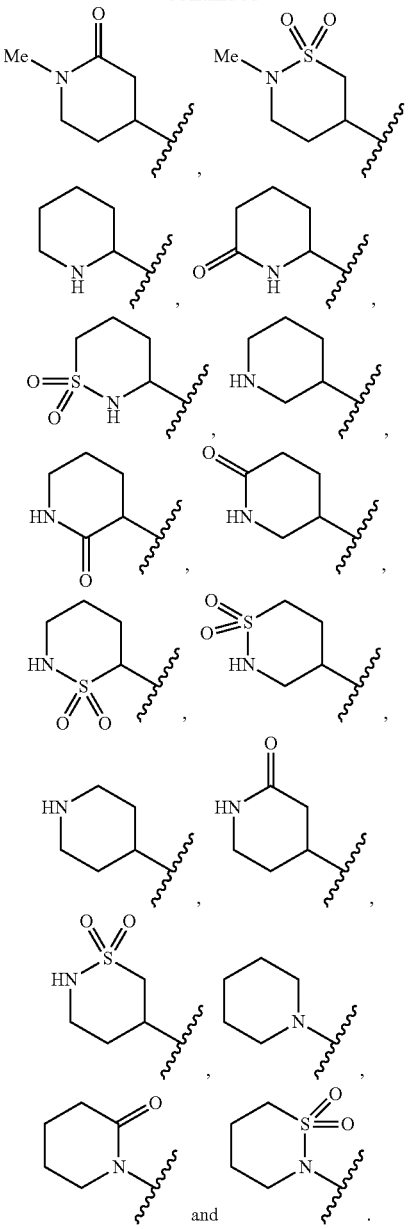

and

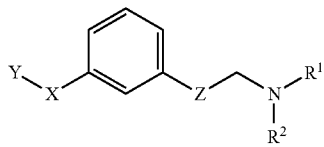

One embodiment provides a compound of Formula (B1), or a pharmaceutically acceptable salt thereof:

Formula (B1)

Y—X—[phenylene]—Z—CH₂—N(R¹)(R²)

wherein,
X is selected from *—O—CH$_2$—, *—S—CH$_2$—, *—S(O)—CH$_2$—, *—S(O)$_2$—CH$_2$—, *—NH—CH$_2$—, *—NH—C(=O)—, —CH$_2$—CH$_2$—, or —CH=CH—; wherein the * indicates point of attachment to the phenylene ring;

Y is selected from heterocyclyl, heterocyclylalkyl, heteroaryl or heteroarylalkyl;

Z is —C(H)(H)—C(H)(H)—, *—C(H)(OH)—C(H)(H)—, *—C(=O)—C(H)(H)—, —CH=CH—, —C≡C—; wherein the * indicates point of attachment to the phenylene ring;

R¹ and R² are each independently selected from hydrogen, C₁-C₄ alkyl, —C(=O)R³;

R³ is selected from alkyl, alkoxy, or —OCH₂OC(O)R⁴, wherein R⁴ is an alkyl or alkoxy;

with the provision that Y is not

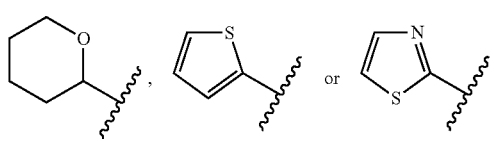

Another embodiment provides the compound of Formula (B1), wherein Z is —C(H)(OH)—C(H)(H)—. Another embodiment provides the compound of Formula (B1), wherein R¹ and R² are both hydrogen. Another embodiment provides the compound of Formula (B1), wherein R¹ is hydrogen and R² is C₁-C₄ alkyl. Another embodiment provides the compound of Formula (B1), wherein R¹ is hydrogen and R² is —C(=O)R³. Another embodiment provides the compound of Formula (B1), wherein X is selected from *—O—CH₂—, —CH₂—CH₂—, or —CH=CH—. Another embodiment provides the compound of Formula (B1), wherein X is selected from *—O—CH₂—, or —CH₂—CH₂—. Another embodiment provides the compound of Formula (B1), wherein X is *—O—CH₂—.

Another embodiment provides the compound of Formula (B1), wherein Y is selected from:

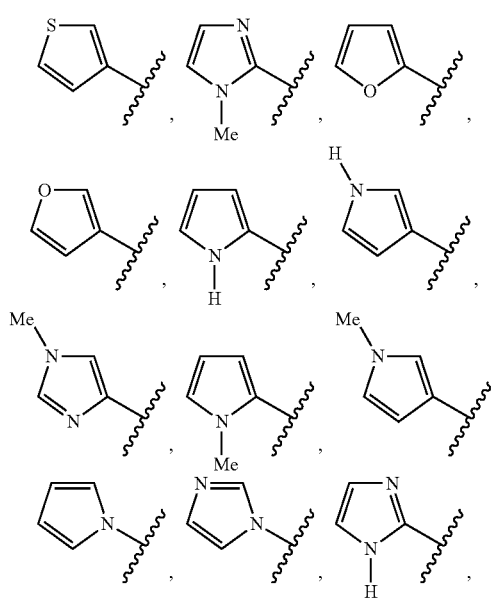

Another embodiment provides the compound of Formula (B1), wherein Y is selected from:

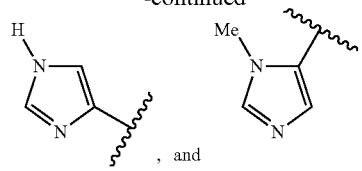

Another embodiment provides the compound of Formula (B1), wherein Y is selected from:

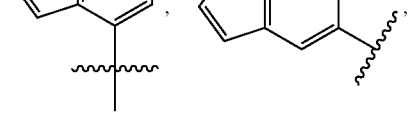
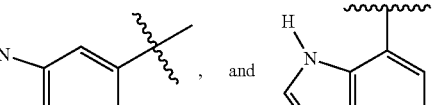
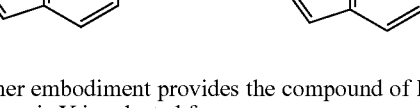
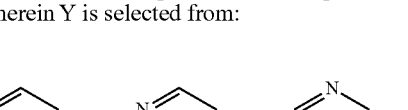
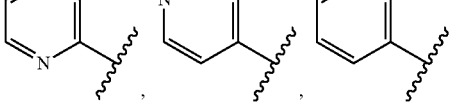
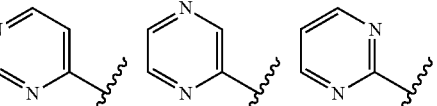
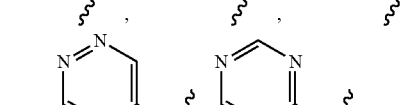
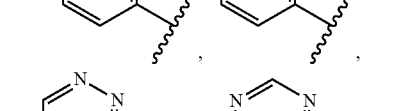

Another embodiment provides the compound of Formula (B1), wherein Y is selected from:

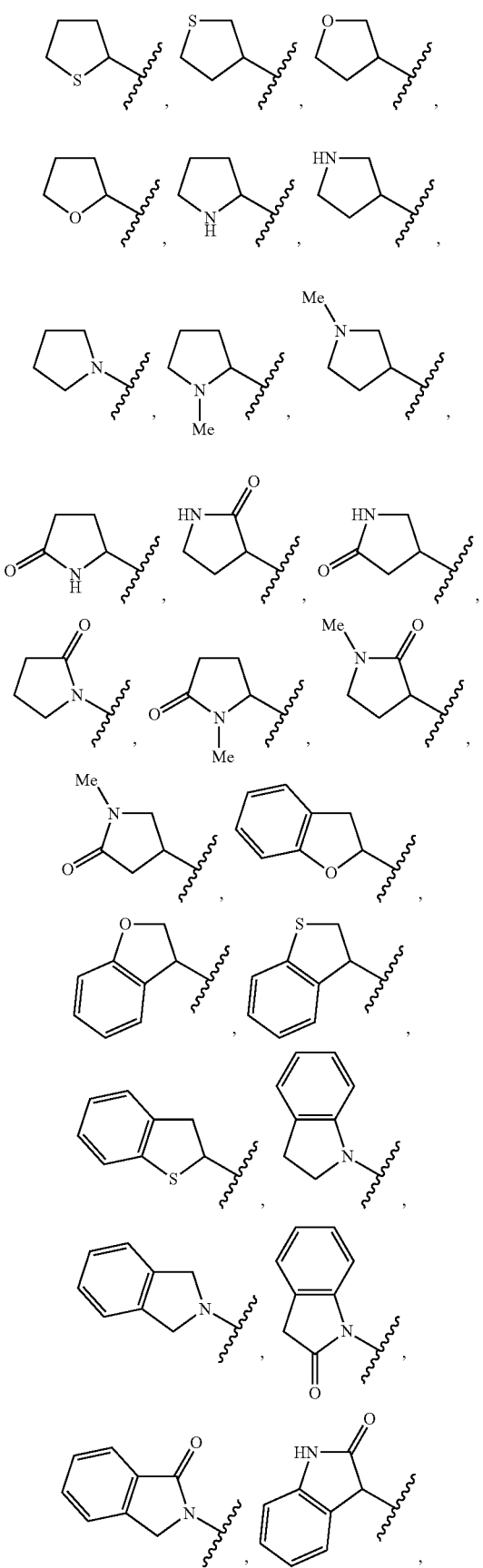
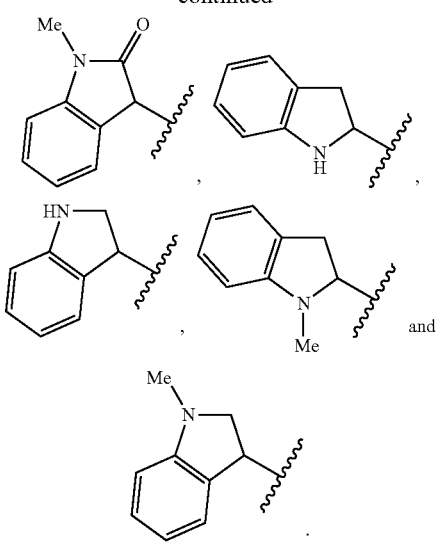
Another embodiment provides the compound of Formula (B1), wherein Y is selected from:
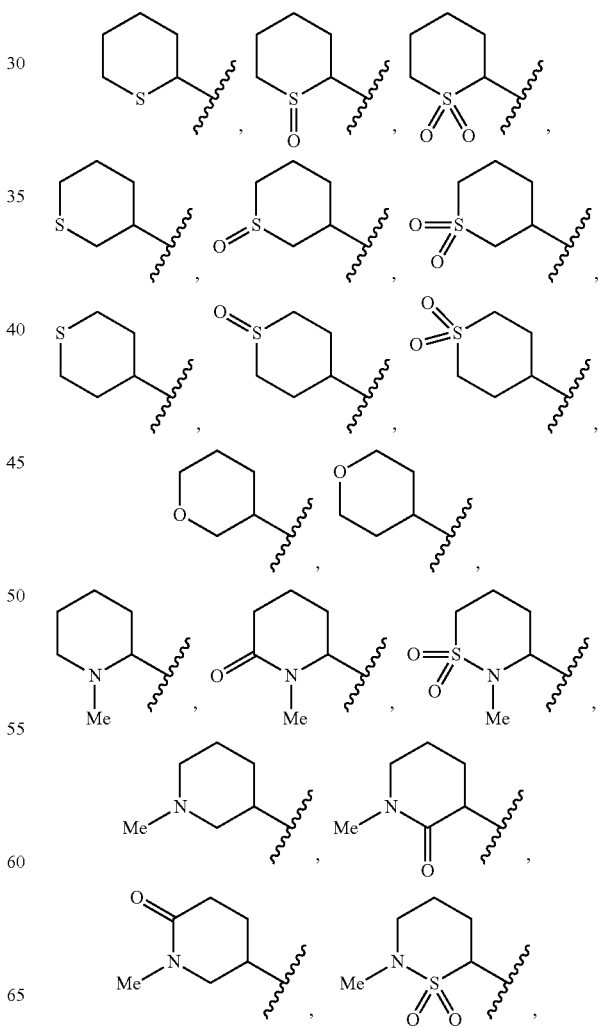

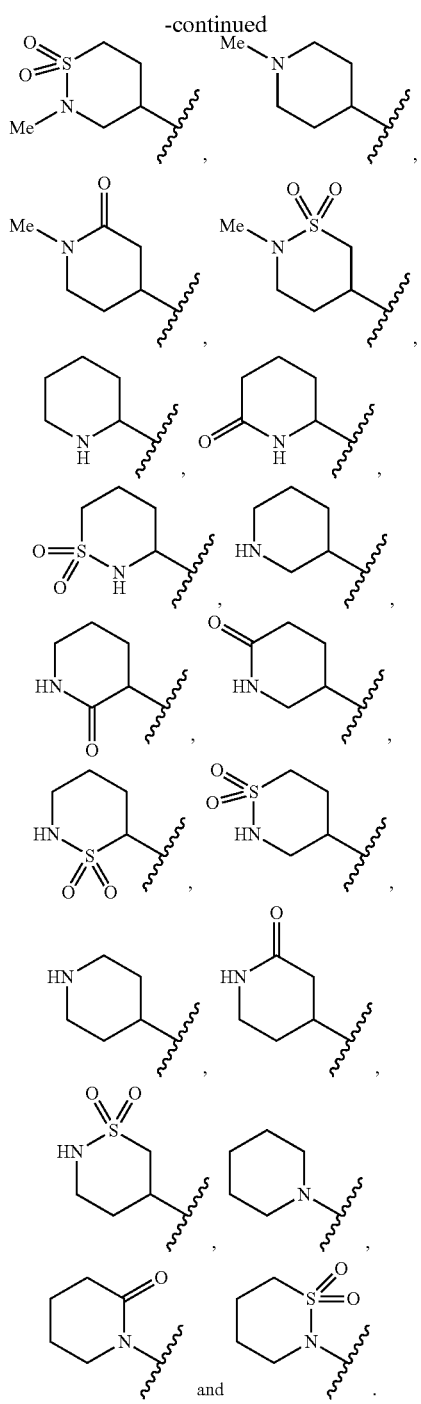

One embodiment provides a compound of Formula (B2), or a pharmaceutically acceptable salt thereof:

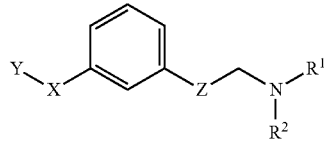

Formula (B2)

wherein,

X is selected from *—O—CH$_2$—, *—S—CH$_2$—, *—S(O)—CH$_2$—, *—S(O)$_2$—CH$_2$—, *—NH—CH$_2$—, *—NH—C(=O)—, —CH$_2$—CH$_2$—, or —CH=CH—; wherein the * indicates point of attachment to the phenylene ring;

Y is

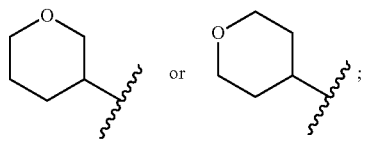 [SMILES: *C1CCCOC1 ; *C1CCOCC1]

Z is —C(H)(H)—C(H)(H)—, *—C(H)(OH)—C(H)(H)—, *—C(=O)—C(H)(H)—, —CH=CH—, —C≡C—; wherein the * indicates point of attachment to the phenylene ring;

R$^1$ and R$^2$ are each independently selected from hydrogen, C$_1$-C$_4$ alkyl, —C(=O)R$^3$; and R$^3$ is selected from alkyl, alkoxy, or —OCH$_2$OC(O)R$^4$, wherein R$^4$ is an alkyl or alkoxy.

Another embodiment provides the compound of Formula (B2), wherein Z is —C(H)(OH)—C(H)(H)—. Another embodiment provides the compound of Formula (B2), wherein R$^1$ and R$^2$ are both hydrogen. Another embodiment provides the compound of Formula (B2), wherein R$^1$ is hydrogen and R$^2$ is C$_1$-C$_4$ alkyl. Another embodiment provides the compound of Formula (B2), wherein R$^1$ is hydrogen and R$^2$ is —C(=O)R$^3$. Another embodiment provides the compound of Formula (B2), wherein X is selected from *—O—CH$_2$—, —CH$_2$—CH$_2$—, or —CH=CH—. Another embodiment provides the compound of Formula (B2), wherein X is selected from *—O—CH$_2$—, or —CH$_2$—CH$_2$—. Another embodiment provides the compound of Formula (B2), wherein X is *—O—CH$_2$—. Another embodiment provides the compound of Formula (B2), wherein Y is

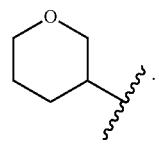 [SMILES: *C1CCCOC1]

Another embodiment provides the compound of Formula (B2), wherein Y is

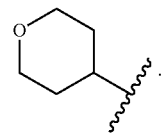

One embodiment provides a compound of Formula (B3), or a pharmaceutically acceptable salt thereof:

Formula (B3)

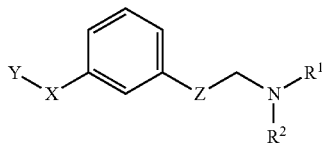

wherein,
X is selected from *—O—CH$_2$—, *—S—CH$_2$—, *—S(O)—CH$_2$—, *—S(O)$_2$—CH$_2$—, *—NH—CH$_2$—, *—NH—C(=O)—, —CH$_2$—CH$_2$—, or —CH=CH—; wherein the * indicates point of attachment to the phenylene ring;
Y is

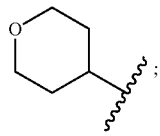 [SMILES: *C1CCOCC1];

Z is —C(H)(H)—C(H)(H)—, *—C(H)(OH)—C(H)(H)—, *—C(=O)—C(H)(H)—, —CH=CH—, —C≡C—; wherein the * indicates point of attachment to the phenylene ring;
$R^1$ and $R^2$ are each independently selected from hydrogen, $C_1$-$C_4$ alkyl, —C(=O)$R^3$; and
$R^3$ is selected from alkyl, alkoxy, or —OCH$_2$OC(O)$R^4$, wherein $R^4$ is an alkyl or alkoxy.

Another embodiment provides the compound of Formula (B3), wherein Z is *—C(H)(OH)—C(H)(H)—. Another embodiment provides the compound of Formula (B3), wherein $R^1$ and $R^2$ are both hydrogen. Another embodiment provides the compound of Formula (B3), wherein $R^1$ is hydrogen and $R^2$ is $C_1$-$C_4$ alkyl. Another embodiment provides the compound of Formula (B3), wherein $R^1$ is hydrogen and $R^2$ is —C(=O)$R^3$. Another embodiment provides the compound of Formula (B3), wherein X is selected from *—O—CH$_2$—, —CH$_2$—CH$_2$—, or —CH=CH—. Another embodiment provides the compound of Formula (B3), wherein X is selected from *—O—CH$_2$—, or —CH$_2$—CH$_2$—. Another embodiment provides the compound of Formula (B3), wherein X is *—O—CH$_2$—.

One embodiment provides a compound of Formula (C), or a pharmaceutically acceptable salt thereof:

Formula (C)

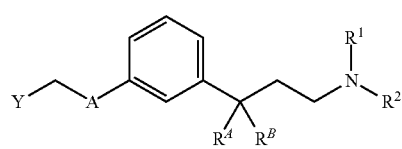

wherein,
A is selected from —O— or —CH$_2$—;
Y is

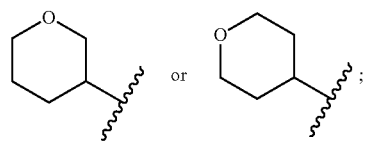 [SMILES: *C1CCCOC1 ; *C1CCOCC1];

$R^A$ is OH, $R^B$ is H; or optionally, $R^A$ and $R^B$ together form an oxo;

$R^1$ and $R^2$ are each independently selected from hydrogen, $C_1$-$C_4$ alkyl, —C(=O)$R^3$; and
$R^3$ is selected from alkyl, alkoxy, or —OCH$_2$OC(O)$R^4$, wherein $R^4$ is an alkyl or alkoxy.

Another embodiment provides the compound of Formula (C), wherein A is —O—. Another embodiment provides the compound of Formula (C), wherein A is —CH$_2$—. Another embodiment provides the compound of Formula (C), wherein $R^A$ is OH and $R^B$ is H. Another embodiment provides the compound of Formula (C), wherein $R^1$ and $R^2$ are both hydrogen. Another embodiment provides the compound of Formula (C), wherein $R^1$ is hydrogen and $R^2$ is $C_1$-$C_4$ alkyl. Another embodiment provides the compound of Formula (C), wherein $R^1$ is hydrogen and $R^2$ is —C(=O)$R^3$. Another embodiment provides the compound of Formula (C), wherein Y is

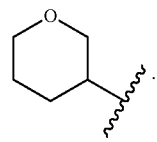.

Another embodiment provides the compound of Formula (C), wherein Y is

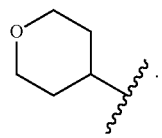.

Another embodiment provides the compound of Formula (C), wherein Y is

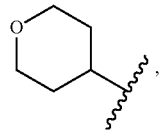, and $R^1$ and $R^2$ are both hydrogen. Another embodiment provides the compound of Formula (C), wherein Y is

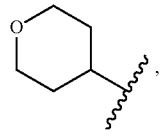,

A is —O—, and $R^1$ and $R^2$ are both hydrogen. Another embodiment provides the compound of Formula (C), wherein Y is

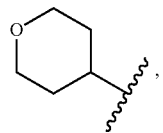,

A is —O—, $R^A$ is OH, $R^B$ is H, and $R^1$ and $R^2$ are both hydrogen.

Certain compounds disclosed herein have the structures shown in Table 1. The example number refers to a specific chemical synthesis Example herein that describes the preparation of the compound having the structure and name shown.

TABLE 1

| Example | Structure | Name |
|---------|-----------|------|
| 1 | 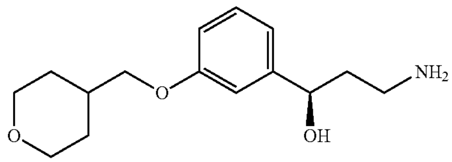 [SMILES: NCC[C@@H](O)c1cccc(OCC2CCOCC2)c1] | (R)-3-Amino-1-(3-((tetrahydro-2H-pyran-4-yl)methoxy)phenyl)propan-1-ol |
| 2 | 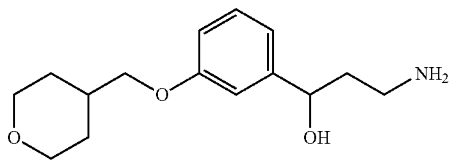 | 3-Amino-1-(3-((tetrahydro-2H-pyran-4-yl)methoxy)phenyl)propan-1-ol |
| 3 | 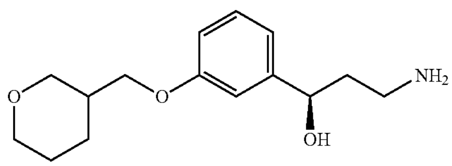 [SMILES: NCC[C@@H](O)c1cccc(OCC2CCCOC2)c1] | (1R)-3-Amino-1-(3-((tetrahydro-2H-pyran-3-yl)methoxy)phenyl)propan-1-ol |
| 4 | 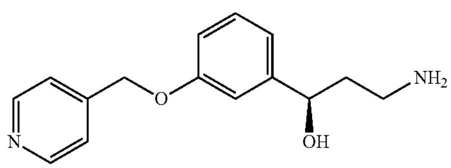 [SMILES: NCC[C@@H](O)c1cccc(OCc2ccncc2)c1] | (R)-3-Amino-1-(3-(pyridin-4-ylmethoxy)phenyl)propan-1-ol |
| 5 | 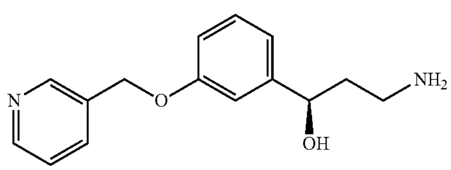 [SMILES: NCC[C@@H](O)c1cccc(OCc2cccnc2)c1] | (R)-3-Amino-1-(3-(pyridin-3-ylmethoxy)phenyl)propan-1-ol |
| 6 | 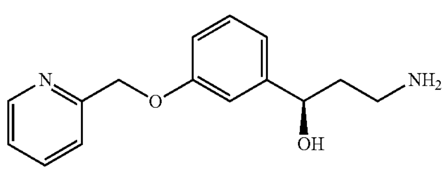 [SMILES: NCC[C@@H](O)c1cccc(OCc2ccccn2)c1] | (R)-3-Amino-1-(3-(pyridin-2-ylmethoxy)phenyl)propan-1-ol |
| 7 | 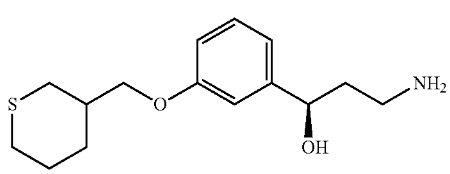 [SMILES: NCC[C@@H](O)c1cccc(OCC2CCCSC2)c1] | (1R)-3-amino-1-(3-((tetrahydro-2H-thiopyran-3-yl)methoxy)phenyl)propan-1-ol |
| 8 | 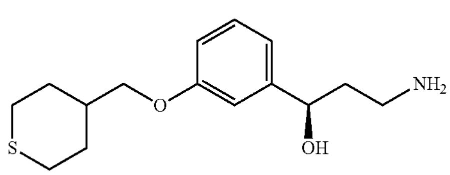 | (R)-3-Amino-1-(3-((tetrahydro-2H-thiopyran-4-yl)methoxy)phenyl)propan-1-ol |
| 9 | 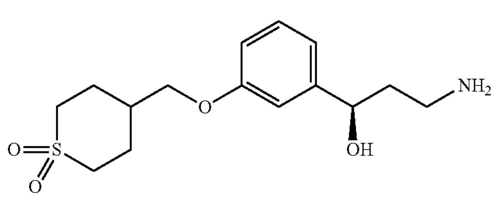 [SMILES: NCC[C@@H](O)c1cccc(OCC2CCS(=O)(=O)CC2)c1] | (R)-4-((3-(3-Amino-1-hydroxypropyl)-phenoxy)methyl)tetrahydro-2H-thiopyran 1,1-dioxide |

TABLE 1-continued

| Example | Structure | Name |
|---|---|---|
| 10 | 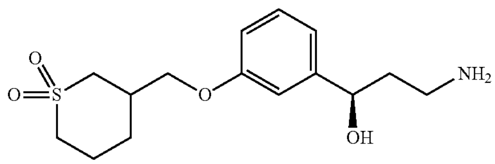 [SMILES: NCC[C@@H](O)c1cccc(OCC2CCCS(=O)(=O)C2)c1] | 3-((3((R)-3-Amino-1-hydroxypropyl)phenoxy)methyl)tetrahydro-2H-thiopyran 1,1-dioxide |
| 11 | 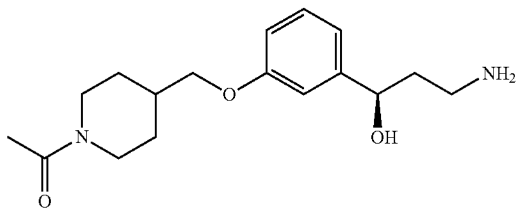 [SMILES: CC(=O)N1CCC(COc2cccc([C@H](O)CCN)c2)CC1] | (R)-1-(4-((3-(3-amino-1-hydroxypropyl)phenoxy)methyl)piperidin-1-yl)ethanone |
| 12 | 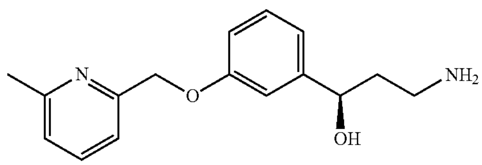 [SMILES: Cc1cccc(COc2cccc([C@H](O)CCN)c2)n1] | (R)-3-Amino-1-(3-((6-methylpyridin-2-yl)methoxy)phenyl)propan-1-ol |
| 13 | 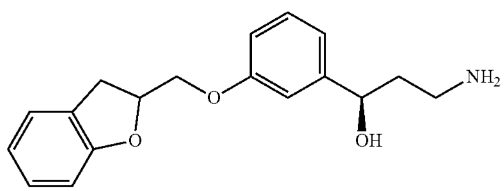 [SMILES: NCC[C@@H](O)c1cccc(OCC2Cc3ccccc3O2)c1] | (1R)-3-Amino-1-(3-((2,3-dihydro-benzofuran-2-yl)methoxy)phenyl)propan-1-ol |
| 14 | 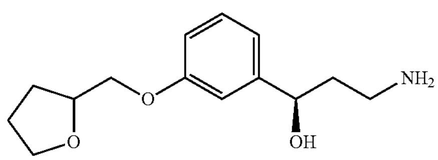 [SMILES: NCC[C@@H](O)c1cccc(OCC2CCCO2)c1] | (1R)-3-Amino-1-(3-((tetrahydrofuran-2-yl)methoxy)phenyl)propan-1-ol |
| 15 | 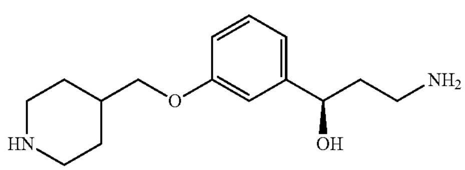 [SMILES: NCC[C@@H](O)c1cccc(OCC2CCNCC2)c1] | (R)-3-Amino-1-(3-(piperidin-4-ylmethoxy)phenyl)propan-1-ol |
| 16 | 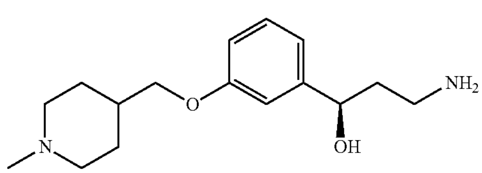 [SMILES: CN1CCC(COc2cccc([C@H](O)CCN)c2)CC1] | (R)-3-Amino-1-(3-((1-methylpiperidin-4-yl)methoxy)phenyl)propan-1-ol |
| 17 | 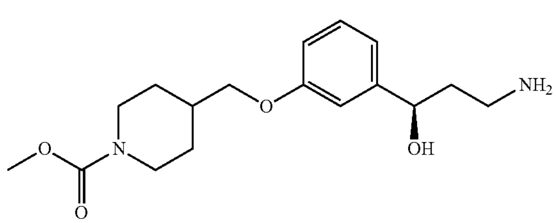 [SMILES: COC(=O)N1CCC(COc2cccc([C@H](O)CCN)c2)CC1] | (R)-Methyl 4-((3-(3-amino-1-hydroxypropyl)phenoxy)methyl)piperidine-1-carboxylate |

TABLE 1-continued

| Example | Structure | Name |
|---|---|---|
| 18 | 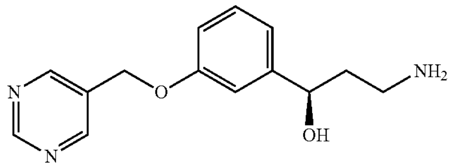 [SMILES: NCC[C@@H](O)c1cccc(OCc2cncnc2)c1] | (R)-3-Amino-1-(3-(pyrimidin-5-ylmethoxy)phenyl)propan-1-ol |
| 19 | 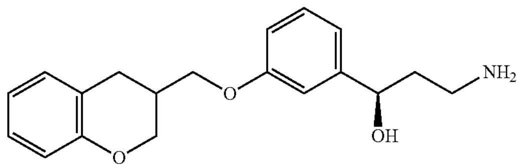 [SMILES: NCC[C@@H](O)c1cccc(OCC2COc3ccccc3C2)c1] | (1R)-3-Amino-1-(3-(chroman-3-ylmethoxy)phenyl)propan-1-ol |
| 20 | 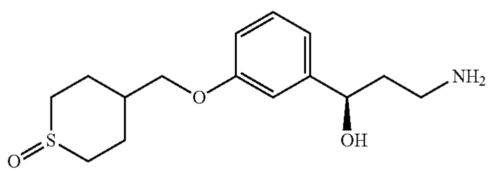 [SMILES: NCC[C@@H](O)c1cccc(OCC2CCS(=O)CC2)c1] | (R)-4-((3-(3-Amino-1-hydroxypropyl)phenoxy)methyl)tetrahydro-2H-thiopyran 1-oxide |
| 21 | 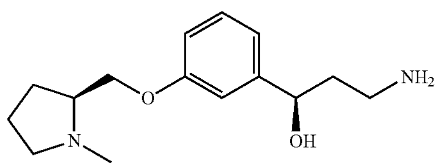 [SMILES: CN1CCC[C@H]1COc1cccc([C@H](O)CCN)c1] | (R)-3-Amino-1-(3-(((S)-1-methylpyrrolidin-2-yl)methoxy)phenyl)propan-1-ol |
| 22 | 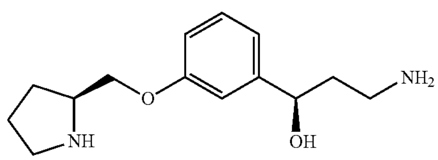 [SMILES: NCC[C@@H](O)c1cccc(OC[C@@H]2CCCN2)c1] | (R)-3-Amino-1-(3-((S)-pyrrolidin-2-ylmethoxy)phenyl)propan-1-ol |
| 23 | 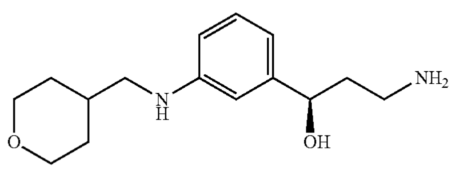 [SMILES: NCC[C@@H](O)c1cccc(NCC2CCOCC2)c1] | (R)-3-Amino-1-(3-(((tetrahydro-2H-pyran-4-yl)methyl)amino)phenyl)propan-1-ol |
| 24 | 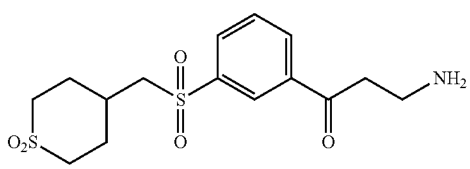 [SMILES: NCCC(=O)c1cccc(S(=O)(=O)CC2CCS(=O)(=O)CC2)c1] | 3-Amino-1-(3-(((1,1-dioxidotetrahydro-2H-thiopyran-4-yl)methyl)sulfonyl)phenyl)propan-1-one |
| 25 | 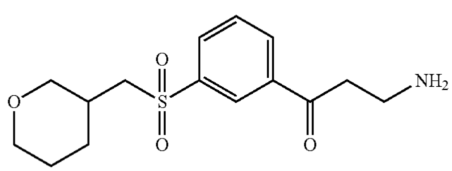 [SMILES: NCCC(=O)c1cccc(S(=O)(=O)CC2CCCOC2)c1] | 3-Amino-1-(3-(((tetrahydro-2H-pyran-3-yl)methyl)sulfonyl)phenyl)propan-1-one |
| 26 | 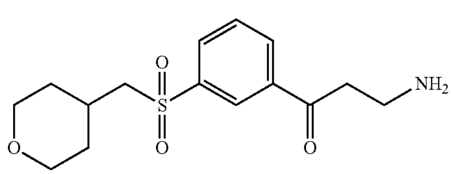 [SMILES: NCCC(=O)c1cccc(S(=O)(=O)CC2CCOCC2)c1] | 3-Amino-1-(3-(((tetrahydro-2H-pyran-4-yl)methyl)sulfonyl)phenyl)propan-1-one |

TABLE 1-continued

| Example | Structure | Name |
|---|---|---|
| 27 | 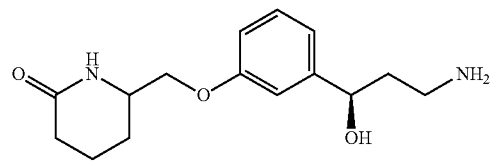 [SMILES: NCC[C@@H](O)c1cccc(OCC2CCCC(=O)N2)c1] | 3-((3-((R)-3-Amino-1-hydroxypropyl)phenoxy)methyl)piperidin-2-one |
| 28 | 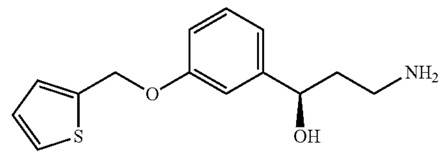 | (R)-3-Amino-1-(3-(thiophen-2-ylmethoxy)phenyl)propan-1-ol |
| 29 | 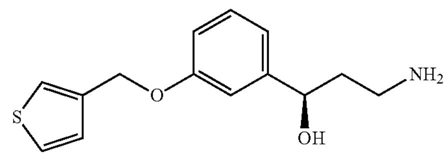 [SMILES: NCC[C@@H](O)c1cccc(OCc2ccsc2)c1] | (R)-3-Amino-1-(3-(thiophen-3-ylmethoxy)phenyl)propan-1-ol |
| 30 | 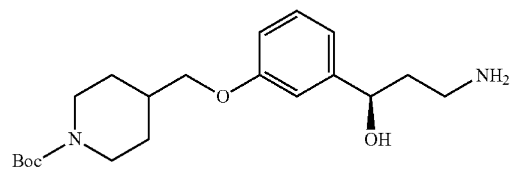 [SMILES: CC(C)(C)OC(=O)N1CCC(COc2cccc([C@H](O)CCN)c2)CC1] | (R)-tert-Butyl 4-((3-(3-amino-1-hydroxypropyl)phenoxy)methyl)piperidine-1-carboxylate |
| 31 | 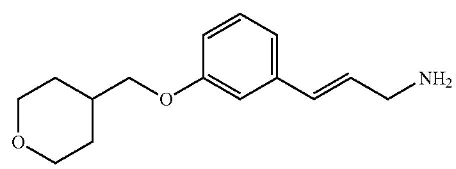 [SMILES: NC/C=C/c1cccc(OCC2CCOCC2)c1] | (E)-3-(3-((Tetrahydro-2H-pyran-4-yl)methoxy)phenyl)prop-2-en-1-amine |
| 32 | 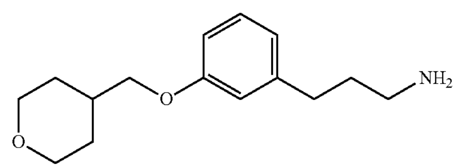 [SMILES: NCCCc1cccc(OCC2CCOCC2)c1] | 3-(3-((Tetrahydro-2H-pyran-4-yl)methoxy)phenyl)propan-1-amine |
| 33 | 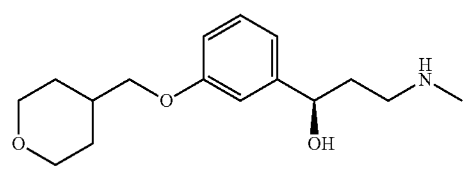 [SMILES: CNCC[C@@H](O)c1cccc(OCC2CCOCC2)c1] | (R)-3-(Methylamino)-1-(3-((tetrahydro-2H-pyran-4-yl)methoxy)phenyl)propan-1-ol |
| 34 | 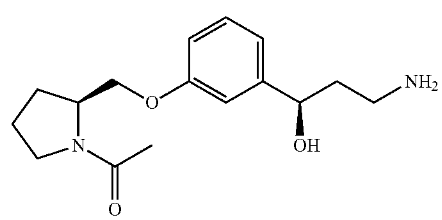 [SMILES: CC(=O)N1CCC[C@H]1COc1cccc([C@H](O)CCN)c1] | 1-((S)-2-((3-((R)-3-Amino-1-hydroxypropyl)phenoxy)methyl)pyrrolidin-1-yl)ethanone |
| 35 | 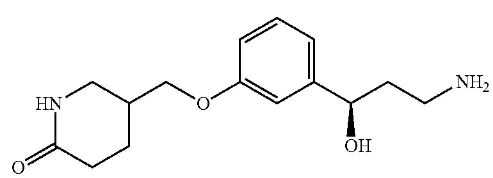 [SMILES: NCC[C@@H](O)c1cccc(OCC2CCC(=O)NC2)c1] | 5-((3-((R)-3-Amino-1-hydroxypropyl)phenoxy)methyl)piperidin-2-one |

TABLE 1-continued

| Example | Structure | Name |
|---|---|---|
| 36 | 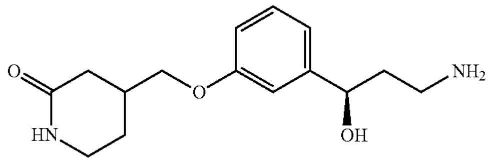 [SMILES: NCC[C@@H](O)c1cccc(OCC2CCNC(=O)C2)c1] | 4-((3-((R)-3-Amino-1-hydroxypropyl)phenoxy)methyl)piperidin-2-one |
| 37 | 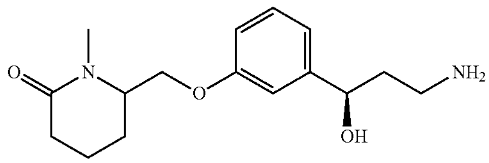 [SMILES: CN1C(=O)CCCC1COc1cccc([C@H](O)CCN)c1] | 6-((3-((R)-3-Amino-1-hydroxypropyl)phenoxy)methyl)-1-methylpiperidin-2-one |
| 38 | 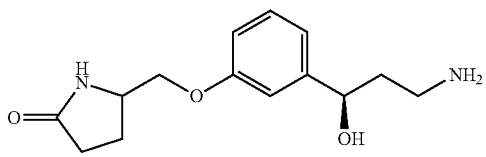 [SMILES: NCC[C@@H](O)c1cccc(OCC2CCC(=O)N2)c1] | 5-((3-((R)-3-Amino-1-hydroxypropyl)phenoxy)methyl)pyrrolidin-2-one |
| 39 | 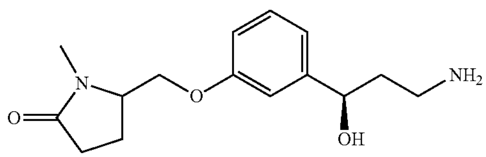 [SMILES: CN1C(=O)CCC1COc1cccc([C@H](O)CCN)c1] | 5-((3-((R)-3-Amino-1-hydroxypropyl)phenoxy)methyl)-1-methylpyrrolidin-2-one |
| 40 | 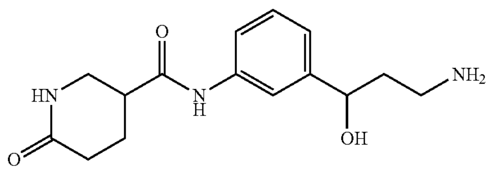 [SMILES: NCCC(O)c1cccc(NC(=O)C2CCC(=O)NC2)c1] | N-(3-(3-Amino-1-hydroxypropyl)phenyl)-6-oxopiperidine-3-carboxamide |
| 41 | 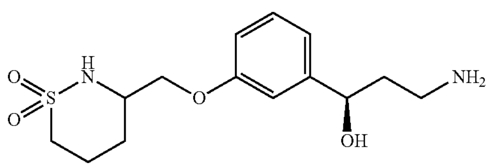 [SMILES: NCC[C@@H](O)c1cccc(OCC2CCCS(=O)(=O)N2)c1] | 3-((3-((R)-3-Amino-1-hydroxypropyl)phenoxy)methyl)-1,2-thiazinane 1,1-dioxide |
| 42 | 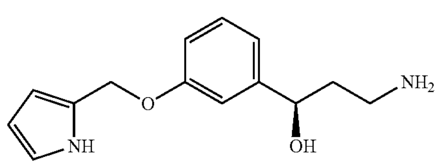 [SMILES: NCC[C@@H](O)c1cccc(OCc2ccc[nH]2)c1] | (R)-1-(3-((1H-Pyrrol-2-yl)methoxy)phenyl)-3-aminopropan-1-ol |
| 43 | 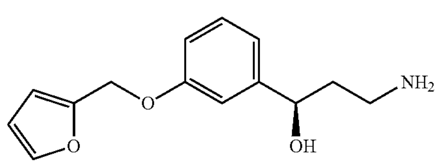 | (R)-3-Amino-1-(3-(furan-2-ylmethoxy)phenyl)propan-1-ol |
| 44 | 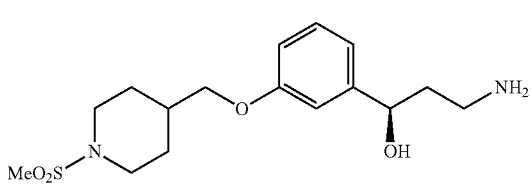 [SMILES: CS(=O)(=O)N1CCC(COc2cccc([C@H](O)CCN)c2)CC1] | (R)-3-Amino-1-(3-((1-(methylsulfonyl)piperidin-4-yl)methoxy)phenyl)propan-1-ol |

TABLE 1-continued

| Example | Structure | Name |
|---|---|---|
| 45 | 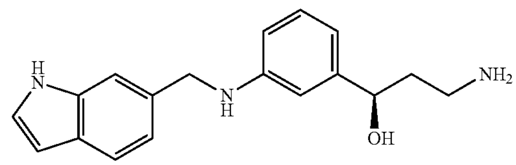 [SMILES: NCC[C@@H](O)c1cccc(NCc2ccc3cc[nH]c3c2)c1] | (R)-1-(3-(((1H-Indol-6-yl)methyl)amino)phenyl)-3-aminopropan-1-ol |
| 46 | 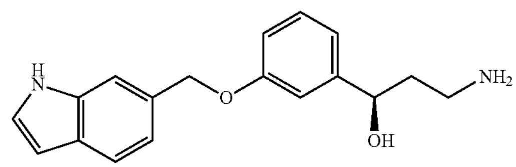 [SMILES: NCC[C@@H](O)c1cccc(OCc2ccc3cc[nH]c3c2)c1] | (R)-1-(3-((1H-Indol-6-yl)methoxy)phenyl)-3 aminopropan-1-ol |
| 47 | 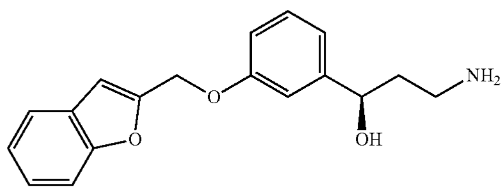 [SMILES: NCC[C@@H](O)c1cccc(OCc2cc3ccccc3o2)c1] | (R)-3-Amino-1-(3-(benzofuran-2-ylmethoxy)phenyl)propan-1-ol |
| 48 | 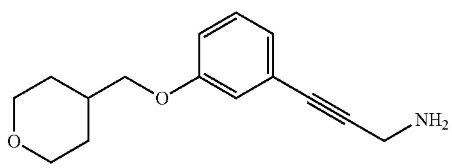 [SMILES: NCC#Cc1cccc(OCC2CCOCC2)c1] | 3-(3-((Tetrahydro-2H-pyran-4-yl)methoxy)phenyl)prop-2-yn-1-amine |
| 49 | 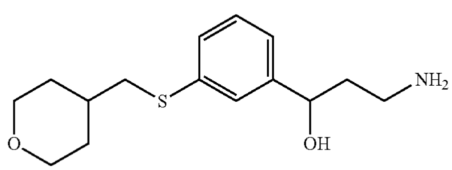 [SMILES: NCCC(O)c1cccc(SCC2CCOCC2)c1] | 3-Amino-1-(3-(((tetrahydro-2H-pyran-4-yl)methyl)thio)phenyl)propan-1-ol |
| 50 | 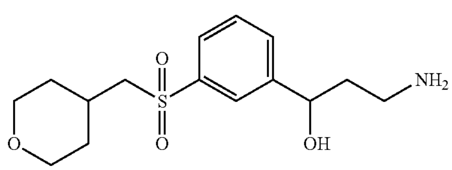 [SMILES: NCCC(O)c1cccc(S(=O)(=O)CC2CCOCC2)c1] | 3-Amino-1-(3-(((tetrahydro-2H-pyran-4-yl)methyl)sulfonyl)phenyl)propan-1-ol |
| 51 | 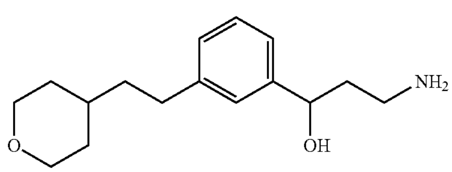 [SMILES: NCCC(O)c1cccc(CCC2CCOCC2)c1] | 3-Amino-1-(3-(2-(tetrahydro-2H-pyran-4-yl)ethyl)phenyl)propan-1-ol |
| 52 | 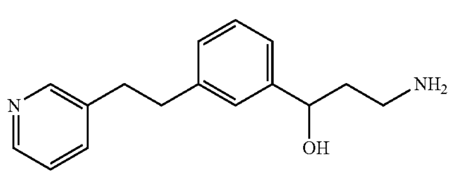 [SMILES: NCCC(O)c1cccc(CCc2cccnc2)c1] | 3-Amino-1-(3-(2-(pyridin-3-yl)ethyl)phenyl)propan-1-ol |
| 53 | 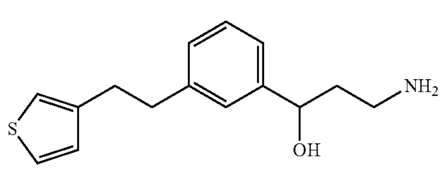 [SMILES: NCCC(O)c1cccc(CCc2ccsc2)c1] | 3-Amino-1-(3-(2-(thiophen-3-yl)ethyl)phenyl)propan-1-ol |

TABLE 1-continued

| Example | Structure | Name |
|---|---|---|
| 54 | 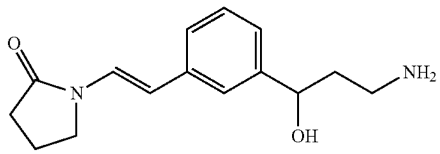 [SMILES: NCCC(O)c1cccc(/C=C/N2CCCC2=O)c1] | (E)-1-(3-(3-Amino-1-hydroxypropyl)styryl)pyrrolidin-2-one |
| 55 | 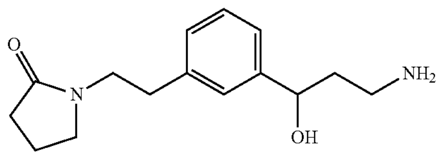 [SMILES: NCCC(O)c1cccc(CCN2CCCC2=O)c1] | 1-(3-(3-Amino-1-hydroxypropyl)phenethyl)pyrrolidin-2-one |
| 56 | 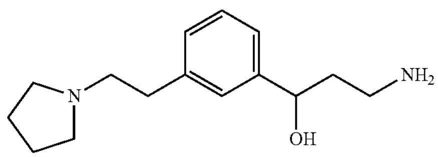 [SMILES: NCCC(O)c1cccc(CCN2CCCC2)c1] | 3-Amino-1-(3-(2-(pyrrolidin-1-yl)ethyl)phenyl)propan-1-ol |
| 57 | 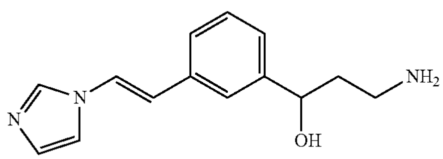 [SMILES: NCCC(O)c1cccc(/C=C/n2ccnc2)c1] | (E)-1-(3-(2-(1H-Imidazol-1-yl)vinyl)phenyl)-3-aminopropan-1-ol |
| 58 | 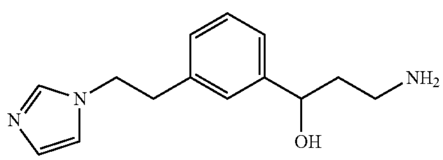 [SMILES: NCCC(O)c1cccc(CCn2ccnc2)c1] | 1-(3-(2-(1H-Imidazol-1-yl)ethyl)phenyl)-3-aminopropan-1-ol |
| 59 | 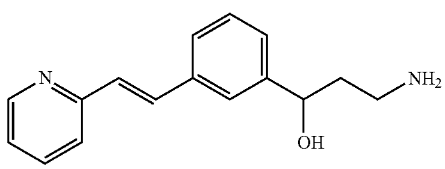 [SMILES: NCCC(O)c1cccc(/C=C/c2ccccn2)c1] | (E)-3-Amino-1-(3-(2-(pyridin-2-yl)vinyl)phenyl)propan-1-ol |
| 60 | 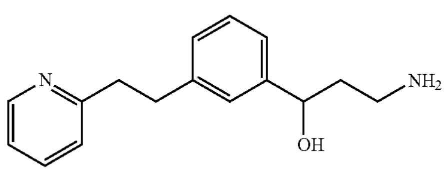 [SMILES: NCCC(O)c1cccc(CCc2ccccn2)c1] | 3-Amino-1-(3-(2-(pyridin-2-yl)ethyl)phenyl)propan-1-ol |
| 61 | 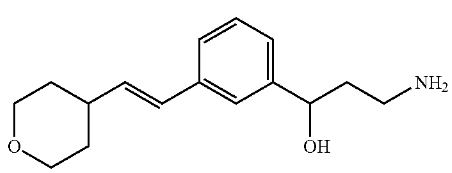 [SMILES: NCCC(O)c1cccc(/C=C/C2CCOCC2)c1] | (E)-3-Amino-1-(3-(2-(tetrahydro-2H-pyran-4-yl)vinyl)phenyl)propan-1-ol |
| 62 | 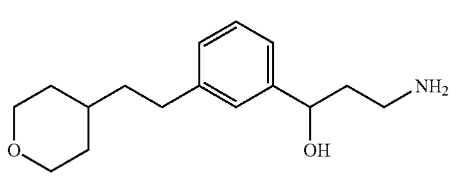 [SMILES: NCCC(O)c1cccc(CCC2CCOCC2)c1] | 3-Amino-1-(3-(2-(tetrahydro-2H-pyran-4-yl)ethyl)phenyl)propan-1-ol |

Preparation of the Substituted 3-Phenylpropylamine Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the 3-phenylpropylamine derivative compound as described herein is P. H. Stahl & C. G. Wermuth "Handbook of Pharmaceutical Salts", Verlag Helvetica Chimica Acta, Zurich, 2002.

Pharmaceutical Compositions

In certain embodiments, a 3-phenylpropylamine derivative compound as described herein are administered as a pure chemical. In other embodiments, the 3-phenylpropylamine derivative compound is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)), the disclosure of which is hereby incorporated herein by reference, in its entirety.

One embodiment provides a pharmaceutical composition comprising a pharmaceutically acceptable carrier and a compound of Formula (A), or a pharmaceutically acceptable salt thereof.

One embodiment provides a pharmaceutical composition comprising a pharmaceutically acceptable carrier and a compound of Formula (A1), or a pharmaceutically acceptable salt thereof.

One embodiment provides a pharmaceutical composition comprising a pharmaceutically acceptable carrier and a compound of Formula (A2), or a pharmaceutically acceptable salt thereof.

One embodiment provides a pharmaceutical composition comprising a pharmaceutically acceptable carrier and a compound of Formula (A3), or a pharmaceutically acceptable salt thereof.

One embodiment provides a pharmaceutical composition comprising a pharmaceutically acceptable carrier and a compound of Formula (A4), or a pharmaceutically acceptable salt thereof.

One embodiment provides a pharmaceutical composition comprising a pharmaceutically acceptable carrier and a compound of Formula (B), or a pharmaceutically acceptable salt thereof.

One embodiment provides a pharmaceutical composition comprising a pharmaceutically acceptable carrier and a compound of Formula (B1), or a pharmaceutically acceptable salt thereof.

One embodiment provides a pharmaceutical composition comprising a pharmaceutically acceptable carrier and a compound of Formula (B2), or a pharmaceutically acceptable salt thereof.

One embodiment provides a pharmaceutical composition comprising a pharmaceutically acceptable carrier and a compound of Formula (B3), or a pharmaceutically acceptable salt thereof.

One embodiment provides a pharmaceutical composition comprising a pharmaceutically acceptable carrier and a compound of Formula (C), or a pharmaceutically acceptable salt thereof.

One embodiment provides a pharmaceutical composition comprising a pharmaceutically acceptable carrier and a compound described in Table 1, or a pharmaceutically acceptable salt thereof.

Accordingly, provided herein is a pharmaceutical composition comprising one or more 3-phenylpropylamine derivative compounds as described herein, or a stereoisomer, prodrug, pharmaceutically acceptable salt, hydrate, solvate, acid salt hydrate, or N-oxide thereof, together with one or more pharmaceutically acceptable carriers and, optionally, other therapeutic and/or prophylactic ingredients. The carrier(s) (or excipient(s)) is acceptable or suitable if the carrier is compatible with the other ingredients of the composition and not deleterious to the recipient (i.e., the subject) of the composition. A pharmaceutically acceptable or suitable composition includes an ophthalmologically suitable or acceptable composition.

In an additional embodiment is a pharmaceutical composition comprising a pharmaceutically acceptable carrier and any of the compounds disclosed herein, or tautomer, stereoisomer, geometric isomer, or pharmaceutically acceptable solvate, hydrate, salt, or N-oxide thereof.

A pharmaceutical composition (e.g., for oral administration or delivery by injection, or combined devices, or for application as an eye drop) may be in the form of a liquid or solid. A liquid pharmaceutical composition optionally include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation is optionally enclosed in ampoules, disposable syringes or multiple dose vials made of glass or plastic. Physiological saline is commonly used as an excipient, and an injectable pharmaceutical composition or a composition that is delivered ocularly is preferably sterile.

The 3-phenylpropylamine derivative compounds are administered to human or other nonhuman vertebrates. In certain embodiments, the compound is substantially pure, in that it contains less than about 5% or less than about 1%, or less than about 0.1%, of other organic small molecules, such as contaminating intermediates or by-products that are created, for example, in one or more of the steps of a synthesis method. In other embodiments, a combination of one or more 3-phenylpropylamine derivative compounds is administered.

The 3-phenylpropylamine derivative compound is optionally delivered to a subject by any suitable means, including, for example, orally, parenterally, intraocularly, intravenously, intraperitoneally, intranasally (or other delivery methods to the mucous membranes, for example, of the nose, throat, and bronchial tubes), or by local administration to the eye, or by an intraocular or periocular device. Modes of local administration include, for example, eye drops, intraocular injection or periocular injection. Periocular injection typically involves injection of the synthetic isomerization inhibitor, i.e., 3-phenylpropylamine derivative compound as described herein under the conjunctiva or into the Tennon's space (beneath the fibrous tissue overlying the eye). Intraocular injection typically involves injection of the 3-phenylpropylamine derivative compound as described herein into the vitreous. In certain embodiments, the administration is non-invasive, such as by eye drops or oral dosage form, or as a combined device.

The 3-phenylpropylamine derivative compound described herein is optionally formulated for administration using pharmaceutically acceptable (suitable) carriers or vehicles as well as techniques routinely used in the art. A pharmaceutically acceptable or suitable carrier includes an ophthalmologically suitable or acceptable carrier. A carrier is selected according to the solubility of the 3-phenylpropylamine derivative compound as described herein. Suitable ophthalmological compositions include those that are administrable locally to the eye, such as by eye drops, injection or the like. In the case of eye drops, the formulation also optionally includes, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives are optionally employed, for example, at a level of from about 0.001 to about 1.0% weight/volume. The pH of the formulation is usually within the range acceptable to ophthalmologic formulations, such as within the range of about pH 4 to 8.

For injection, the 3-phenylpropylamine derivative compound as described herein is optionally provided in an injection grade saline solution, in the form of an injectable liposome solution, slow-release polymer system or the like. Intraocular and periocular injections are known to those skilled in the art and are described in numerous publications including, for example, Spaeth, Ed., *Ophthalmic Surgery: Principles of Practice*, W. B. Sanders Co., Philadelphia, Pa., 85-87, 1990.

For delivery of a composition comprising at least one of the 3-phenylpropylamine derivative compound described herein via a mucosal route, which includes delivery to the nasal passages, throat, and airways, the composition is optionally delivered in the form of an aerosol. The compound is optionally in a liquid or powder form for intramucosal delivery. For example, the composition may be delivered via a pressurized aerosol container with a suitable propellant, such as a hydrocarbon propellant (e.g., propane, butane, isobutene). The composition is optionally delivered via a non-pressurized delivery system such as a nebulizer or atomizer.

Suitable oral dosage forms include, for example, tablets, pills, sachets, or capsules of hard or soft gelatin, methylcellulose or of another suitable material easily dissolved in the digestive tract. Suitable nontoxic solid carriers include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The 3-phenylpropylamine derivative compound described herein are optionally formulated for sustained or slow-release. Such compositions may generally be prepared using well known technology and administered by, for example, oral, periocular, intraocular, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained-release formulation depends upon the site of implantation, the rate and expected duration of release, and the nature of the condition to be treated or prevented.

Systemic drug absorption of a drug or composition administered via an ocular route is known to those skilled in the art (see, e.g., Lee et al., *Int. J. Pharm.* 233:1-18 (2002)). In one embodiment, a 3-phenylpropylamine derivative compound is delivered by a topical ocular delivery method (see, e.g., *Curr. Drug Metab.* 4:213-22 (2003)). The composition is optionally in the form of an eye drop, salve, or ointment or the like, such as, aqueous eye drops, aqueous ophthalmic suspensions, non-aqueous eye drops, and non-aqueous ophthalmic suspensions, gels, ophthalmic ointments, etc. For preparing a gel, for example, carboxyvinyl polymer, methyl cellulose, sodium alginate, hydroxypropyl cellulose, ethylene maleic anhydride polymer and the like can be used.

The dose of the composition comprising at least one of the 3-phenylpropylamine derivative compounds described herein may differ, depending upon the patient's (e.g., human) condition, that is, stage of the disease, general health status, age, and other factors that a person skilled in the medical art will use to determine dose. When the composition is used as eye drops, for example, one to several drops per unit dose, preferably 1 or 2 drops (about 50 µl per 1 drop), are applied about 1 to about 6 times daily.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with neurodegeneration of retinal neuronal cells and/or degeneration of other mature retinal cells such as RPE cells. Optimal doses are generally determined using experimental models and/or clinical trials. The optimal dose depends upon the body mass, weight, or blood volume of the patient.

The doses of the 3-phenylpropylamine derivative compound described herein are suitably selected depending on the clinical status, condition and age of the subject, dosage form and the like. In the case of eye drops, a 3-phenylpropylamine derivative compound as described herein is administered, for example, from about 0.01 mg, about 0.1 mg, or about 1 mg, to about 25 mg, to about 50 mg, to about 90 mg per single dose. Eye drops are administered one or more times per day, as needed. In the case of injections, suitable doses are, for example, about 0.0001 mg, about 0.001 mg, about 0.01 mg, or about 0.1 mg to about 10 mg, to about 25 mg, to about 50 mg, or to about 90 mg of the 3-phenylpropylamine derivative compound as described herein, one to seven times per week. In other embodiments, about 1.0 to about 30 mg of the 3-phenylpropylamine derivative compound described herein is administered one to seven times per week.

Oral doses typically range from 1.0 to 1000 mg, one to four times, or more, per day. An exemplary dosing range for oral administration is from 10 to 250 mg one to three times per day. If the composition is a liquid formulation, the composition comprises at least 0.1% active compound at particular mass or weight (e.g., from 1.0 to 1000 mg) per unit volume of carrier, for example, from about 2% to about 60%.

In certain embodiments, at least one 3-phenylpropylamine derivative compound described herein is administered under conditions and at a time that inhibits or prevents dark adaptation of rod photoreceptor cells. In certain embodiments, the compound is administered to a subject at least 30 minutes (half hour), 60 minutes (one hour), 90 minutes (1.5 hour), or 120 minutes (2 hours) prior to sleeping. In certain embodiments, the compound is administered at night before the subject sleeps. In other embodiments, a light stimulus is blocked or removed during the day or under normal light conditions by placing the subject in an environment in which light is removed, such as placing the subject in a darkened room or by applying an eye mask over the eyes of the subject. When the light stimulus is removed in such a manner or by other means contemplated in the art, the agent may be administered prior to sleeping.

The doses of the 3-phenylpropylamine derivative compound described herein that are administered to prevent or inhibit dark adaptation of a rod photoreceptor cell are suitably selected depending on the clinical status, condition and age of the subject, dosage form and the like. In the case of eye drops, the compound (or the composition comprising the compound) is administered, for example, from about 0.01 mg, about 0.1 mg, or about 1 mg, to about 25 mg, to about 50 mg, to about 90 mg per single dose. In the case of injections, suitable doses are, for example, about 0.0001 mg, about 0.001 mg, about 0.01 mg, or about 0.1 mg to about 10 mg, to about 25 mg, to about 50 mg, or to about 90 mg of the compound, administered any number of days between one to seven days per week prior to sleeping or prior to removing the subject from all light sources. In certain other embodiments, for administration of the compound by eye drops or injection, the dose is between 1-10 mg (compound)/kg (body weight of subject) (i.e., for example, 80-800 mg total per dose for a subject weighing 80 kg). In other embodiments, about 1.0 to about 30 mg of compound is administered one to seven times per week. Oral doses typically range from about 1.0 to about 1000 mg, administered any number of days between one to seven days per week. An exemplary dosing range for oral administration is from about 10 to about 800 mg once per day prior to sleeping. In other embodiments, the composition is delivered by intravitreal administration.

Also provided are methods of manufacturing the compounds and pharmaceutical compositions described herein. A composition comprising a pharmaceutically acceptable excipient or carrier and at least one of the 3-phenylpropylamine derivative compound described herein are optionally prepared by synthesizing the compound according to any one of the methods described herein or practiced in the art and then formulating the compound with a pharmaceutically acceptable carrier. Formulation of the composition will be appropriate and dependent on several factors, including but not limited to, the delivery route, dose, and stability of the compound.

Treatment of Ophthalmic Diseases and Disorders

Age-related macular degeneration (AMD) affects between ten and fifteen million patients in the United States, and it is the leading cause of blindness in aging populations worldwide. AMD affects central vision and causes the loss of photoreceptor cells in the central part of retina called the macula.

Macular degeneration is classified into two types: dry-form and wet-form. The dry-form is more common than the wet; about 90% of age-related macular degeneration patients are diagnosed with the dry-form. The wet-form of the disease and geographic atrophy, which is the end-stage phenotype of dry-form AMD, causes the most serious vision loss. All patients who develop wet-form AMD are believed to previously have developed dry-form AMD for a prolonged period of time. The exact causes of AMD are still unknown. The dry-form of AMD may result from the senescence and thinning of macular tissues associated with the deposition of pigment in the macular retinal pigment epithelium. In wet-form AMD, new blood vessels grow beneath the retina, form scar tissue, bleed, and leak fluid. The overlying retina can be severely damaged, creating "blind" areas in the central vision.

For the vast majority of patients who have the dry-form of AMD, no effective treatment is yet available. Because the dry-form of AMD precedes development of the wet-form of AMD, therapeutic intervention to prevent or delay disease progression in the dry-form AMD would benefit patients with dry-form of AMD and might reduce the incidence of the wet-form of AMD.

Decline of vision noticed by the patient or characteristic features detected by an ophthalmologist during a routine eye exam may be the first indicator of AMD. The formation of "drusen," or membranous debris beneath the retinal pigment epithelium of the macula is often the first physical sign that AMD is developing. Late symptoms include the perceived distortion of straight lines and, in advanced cases, a dark, blurry area or area with absent vision appears in the center of vision; and/or there may be color perception changes.

Different forms of genetically-linked macular degenerations may also occur in younger patients. In other maculopathies, factors in the disease are heredity, nutritional, traumatic, infection, or other ecologic factors.

Neuronal cell death underlies the pathology of retinal diseases. Unfortunately, very few compositions and methods that enhance retinal neuronal cell survival, particularly photoreceptor cell survival, have been discovered. A need therefore exists to identify and develop compositions that can be used for treatment and prophylaxis of a number of retinal diseases and disorders that have neuronal cell death as a primary, or associated, element in their pathogenesis.

In vertebrate photoreceptor cells, the irradiance of a photon causes isomerization of 11-cis-retinylidene chromophore to all-trans-retinylidene and uncoupling from the visual opsin receptors. This photoisomerization triggers conformational changes of opsins, which, in turn, initiate the biochemical chain of reactions termed phototransduction (Filipek et al., *Annu. Rev. Physiol.* 65:851-79 (2003)). Regeneration of the visual pigments requires that the chromophore be converted back to the 11-cis-configuration in the processes collectively called the retinoid (visual) cycle (see, e.g., McBee et al., *Prog. Retin. Eye Res.* 20:469-52 (2001)). First, the chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-87 (2004)).

In Stargardt's disease (Allikmets et al., *Nat. Genet.* 15:236-46 (1997)), a disease associated with mutations in the ABCR transporter that acts as a flippase, the accumulation of all-trans-retinal may be responsible for the formation of a lipofuscin pigment, A2E, which is toxic towards retinal pigment epithelial cells and causes progressive retinal degeneration and, consequently, loss of vision (Mata et al., *Proc. Natl. Acad. Sci. USA* 97:7154-59 (2000); Weng et al., *Cell* 98:13-23 (1999)). Treating patients with an inhibitor of retinol dehydrogenases, 13-cis-RA (Isotretinoin, Accutane®, Roche), has been considered as a therapy that might prevent or slow the formation of A2E and might have protective properties to maintain normal vision (Radu et al., *Proc. Natl. Acad. Sci. USA* 100:4742-47 (2003)). 13-cis-RA has been used to slow the synthesis of 11-cis-retinal by inhibiting 11-cis-RDH (Law et al., *Biochem. Biophys. Res. Commun.* 161:825-9 (1989)), but its use can also be associated with significant night blindness. Others have proposed that 13-cis-RA works to prevent chromophore regeneration by binding RPE65, a protein essential for the isomerization process in the eye (Gollapalli et al., *Proc. Natl. Acad. Sci. USA* 101:10030-35 (2004)). Gollapalli et al. reported that 13-cis-RA blocked the formation of A2E and suggested that this treatment may inhibit lipofuscin accumulation and, thus, delay either the onset of visual loss in Stargardt's disease or age-related macular degeneration, which are both associated with retinal pigment-associated lipofuscin accumulation. However, blocking the retinoid cycle and forming unliganded opsin may result in more severe consequences and worsening of the patient's prognosis (see, e.g., Van Hooser et al., *J. Biol. Chem.* 277: 19173-82 (2002); Woodruff et al., *Nat. Genet.* 35:158-164 (2003)). Failure of the chromophore to form may lead to progressive retinal degeneration and may produce a phenotype similar to Leber Congenital Amaurosis (LCA), which is a very rare genetic condition affecting children shortly after birth.

In an additional embodiment is a method for treating an ophthalmic disease or disorder in a subject, comprising administering to the subject any of the compounds disclosed herein, or tautomer, stereoisomer, geometric isomer or a pharmaceutically acceptable solvate, hydrate, salt, or N-oxide thereof.

In a further embodiment is the method of treating an ophthalmic disease or disorder in a subject as described herein resulting in a reduction of lipofuscin pigment accumulated in an eye of the subject. In a further embodiment is the method of treating an ophthalmic disease or disorder in a subject as described herein resulting in a reduction of lipofuscin pigment accumulated in an eye of the subject, wherein the lipofuscin pigment is N-retinylidene-N-retinyl-ethanolamine (A2E). In an additional embodiment is a method of reducing lipofuscin pigment accumulated in a subject's retina wherein the lipofuscin is N-retinylidene-N-retinyl-ethanolamine (A2E). In an additional embodiment is a method of inhibiting or reducing lipofuscin pigment accumulated in a subject's retina comprising administering to the subject a pharmaceutical composition comprising a pharmaceutically acceptable carrier and a compound as described herein. In another embodiment is a method of reducing lipofuscin pigment accumulated in a subject's retina comprising administering to the subject a pharmaceutical composition comprising a pharmaceutically acceptable carrier and any of the compounds disclosed herein, or tautomer, stereoisomer, geometric isomer or a pharmaceutically acceptable solvate, hydrate, salt, or N-oxide thereof.

In a further embodiment is the method of treating an ophthalmic disease or disorder in a subject as described herein, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound of Formula (A), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound of Formula (A1), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound of Formula (A2), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound of Formula (A3), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound of Formula (A4), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound of Formula (B), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound of Formula (B1), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound of Formula (B2), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound of Formula (B3), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound of Formula (C), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder in a subject, comprising administering to the subject a compound described in Table 1, or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound of Formula (A), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound of Formula (A1), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound of Formula (A2), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound of Formula (A3), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound of Formula (A4), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound of Formula (B), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound of Formula (B1), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound of Formula (B2), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound of Formula (B3), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound of Formula (C), or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

One embodiment provides a method for treating an ophthalmic disease or disorder resulting at least in part from lipofuscin accumulation in a subject, comprising administering to the subject a compound described in Table 1, or a pharmaceutically acceptable salt thereof. A further embodiment is the method, wherein the ophthalmic disease or disorder is age-related macular degeneration or Stargardt's macular dystrophy. Another embodiment provides the method for treating an ophthalmic disease or disorder in a subject, wherein the ophthalmic disease or disorder is geographic atrophy (GA) associated with dry age-related macular degeneration.

3-Phenylpropylamine derivative compounds as described in detail herein are useful for treating ophthalmic diseases or disorders. The compounds described herein, may inhibit, block, or in some manner interfere with the isomerization step in the visual cycle, in particular the activity of trans-cis isomerase (also including a visual cycle trans-cis isomerohydrolase). In a particular embodiment, the compound inhibits isomerization of an all-trans-retinyl ester; in certain embodiments, the all-trans-retinyl ester is a fatty acid ester of all-trans-retinol, and the compound inhibits isomerization of all-trans-retinol to 11-cis-retinol. The compound may bind to, or in some manner interact with, and inhibit the isomerase activity of at least one visual cycle isomerase, which may also be referred to herein and in the art as a retinal isomerase or an isomerohydrolase. The compound may block or inhibit binding of an all-trans-retinyl ester substrate to an isomerase. Alternatively, or in addition, the compound may bind to the catalytic site or region of the isomerase, thereby inhibiting the capability of the enzyme to catalyze isomerization of an all-trans-retinyl ester substrate. On the basis of scientific data to date, at least one isomerase that catalyzes the isomerization of all-trans-retinyl esters is believed to be located in the cytoplasm of RPE cells. As discussed herein, each step, enzyme, substrate, intermediate, and product of the visual cycle is not yet elucidated (see, e.g., Moiseyev et al., *Proc. Natl. Acad. Sci. USA* 102:12413-18 (2004); Chen et al., *Invest. Ophthalmol. Vis. Sci.* 47:1177-84 (2006); Lamb et al. supra).

A method for determining the effect of a compound on isomerase activity is performed in vitro as described herein and in the art (Stecher et al., *J Biol Chem* 274:8577-85 (1999); see also Golczak et al., *Proc. Natl. Acad. Sci. USA* 102:8162-67 (2005). Retinal pigment epithelium (RPE) microsome membranes isolated from an animal (such as bovine, porcine, human, for example) may serve as the source of the isomerase. The capability of the 3-phenylpropylamine derivative compounds to inhibit isomerase may also be determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem* 85:944-956 (2003); Van Hooser et al., *J Biol Chem* 277: 19173-82, 2002). Electroretinographic (ERG) recording may be performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Ophthalmologica* 100:77-92 (2000)). See also Deigner et al., *Science*, 244: 968-971 (1989); Gollapalli et al., *Biochim Biophys Acta.* 1651: 93-101 (2003); Parish, et al., *Proc. Natl. Acad. Sci. USA* 95:14609-13 (1998); Radu, et al., *Proc Natl Acad Sci USA* 101: 5928-33 (2004)). In certain embodiments, compounds that are useful for treating a subject who has or who is at risk of developing any one of the ophthalmic and retinal diseases or disorders described herein have $IC_{50}$ levels (compound concentration at which 50% of isomerase activity is inhibited) as measured in the isomerase assays described herein or known in the art that is less than about 1 µM; in other embodiments, the determined $IC_{50}$ level is less than about 10 nM; in other embodiments, the determined $IC_{50}$ level is less than about 50 nM; in certain other embodiments, the determined $IC_{50}$ level is less than about 100 nM; in other certain embodiments, the determined $IC_{50}$ level is less than about 10 µM; in other embodiments, the determined $IC_{50}$ level is less than about 50 µM; in other certain embodiments, the determined $IC_{50}$ level is less than about 100 µM or about 500 µM; in other embodiments, the determined $IC_{50}$ level is between about 1 µM and 10 µM; in other embodiments, the determined $IC_{50}$ level is between about 1 nM and 10 nM. When administered into a subject, one or more compounds of the present invention exhibits an $ED_{50}$ value of about 5 mg/kg or less as ascertained by inhibition of an isomerase reaction that results in production of 11-cis retinol. In some embodiments, the compounds of the present invention have $ED_{50}$ values of about 1 mg/kg when administered into a subject. In other embodiments, the compounds of the present invention have $ED_{50}$ values of about 0.1 mg/kg when administered into a subject. The $ED_{50}$ values can be measured after about 2 hours, 4 hours, 6 hours, 8 hours or longer upon administering to a subject a 3-phenylpropylamine derivative compound or a pharmaceutical composition thereof.

The 3-phenylpropylamine derivative compounds described herein are useful for treating a subject who has an ophthalmic disease or disorder, particularly a retinal disease or disorder such as age-related macular degeneration or Stargardt's macular dystrophy. In one embodiment, the compounds described herein may inhibit (i.e., prevent, reduce, slow, abrogate, or minimize) accumulation of lipofuscin pigments and lipofuscin-related and/or associated molecules in the eye. In another embodiment, the compounds may inhibit (i.e., prevent, reduce, slow, abrogate, or minimize) N-retinylidene-N-retinylethanolamine (A2E) accumulation in the eye. The ophthalmic disease may result, at least in part, from lipofuscin pigments accumulation and/or from accumulation of A2E in the eye. Accordingly, in certain embodiments, methods are provided for inhibiting or preventing accumulation of lipofuscin pigments and/or A2E in the eye of a subject. These methods comprise administering to the subject a composition comprising a pharmaceutically acceptable or suitable excipient (i.e., pharmaceutically acceptable or suitable carrier) and a 3-phenylpropylamine derivative compound as described in detail herein, or a pharmaceutically acceptable salt thereof.

Accumulation of lipofuscin pigments in retinal pigment epithelium (RPE) cells has been linked to progression of retinal diseases that result in blindness, including age-related macular degeneration (De Laey et al., *Retina* 15:399-406 (1995)). Lipofuscin granules are autofluorescent lysosomal residual bodies (also called age pigments). The major fluorescent species of lipofuscin is A2E (an orange-emitting fluorophore), which is a positively charged Schiff-base condensation-product formed by all-trans retinaldehyde with phosphatidylethanolamine (2:1 ratio) (see, e.g., Eldred et al., *Nature* 361:724-6 (1993); see also, Sparrow, *Proc. Natl. Acad. Sci. USA* 100:4353-54 (2003)). Much of the indigestible lipofuscin pigment is believed to originate in photoreceptor cells; deposition in the RPE occurs because the RPE internalize membranous debris that is discarded daily by the photoreceptor cells. Formation of this compound is not believed to occur by catalysis by any enzyme, but rather A2E forms by a spontaneous cyclization reaction. In addition, A2E has a pyridinium bisretinoid structure that once formed may not be enzymatically degraded. Lipofuscin, and thus A2E, accumulate with aging of the human eye and also accumulate in a juvenile form of macular degeneration called Stargardt's disease, and in several other congenital retinal dystrophies.

A2E may induce damage to the retina via several different mechanisms. At low concentrations, A2E inhibits normal proteolysis in lysosomes (Holz et al., *Invest. Ophthalmol. Vis. Sci.* 40:737-43 (1999)). At higher, sufficient concentrations, A2E may act as a positively charged lysosomotropic detergent, dissolving cellular membranes, and may alter lysosomal function, release proapoptotic proteins from mitochondria, and ultimately kill the RPE cell (see, e.g., Eldred et al., supra; Sparrow et al., *Invest. Ophthalmol. Vis. Sci.* 40:2988-95 (1999); Holz et al., supra; Finneman et al., *Proc. Natl. Acad. Sci. USA* 99:3842-347 (2002); Suter et al., *J. Biol. Chem.* 275:39625-30 (2000)). A2E is phototoxic and initiates blue light-induced apoptosis in RPE cells (see, e.g., Sparrow et al., *Invest. Ophthalmol. Vis. Sci.* 43:1222-27 (2002)). Upon exposure to blue light, photooxidative products of A2E are formed (e.g., epoxides) that damage cellular macromolecules, including DNA (Sparrow et al., *J. Biol. Chem.* 278(20):18207-13 (2003)). A2E self-generates singlet oxygen that reacts with A2E to generate epoxides at carbon-carbon double bonds (Sparrow et al., supra). Generation of oxygen reactive species upon photoexcitation of A2E causes oxidative damage to the cell, often resulting in cell death. An indirect method of blocking formation of A2E by inhibiting biosynthesis of the direct precursor of A2E, all-trans-retinal, has been described (see U.S. Patent Application Publication No. 2003/0032078). However, the usefulness of the method described therein is limited because generation of all-trans retinal is an important component of the visual cycle. Other therapies described include neutralizing damage caused by oxidative radical species by using superoxide-dismutase mimetics (see, e.g., U.S. Patent Application Publication No. 2004/0116403) and inhibiting A2E-induced cytochrome C oxidase in retinal cells with negatively charged phospholipids (see, e.g., U.S. Patent Application Publication No. 2003/0050283).

The 3-phenylpropylamine derivative compounds described herein are useful for preventing, reducing, inhibiting, or decreasing accumulation (i.e., deposition) of A2E and A2E-related and/or derived molecules in the RPE. Because the RPE is critical for the maintenance of the integrity of photoreceptor cells, preventing, reducing, or inhibiting damage to the RPE may inhibit degeneration (i.e., enhance the survival or increase or prolong cell viability) of retinal neuronal cells, particularly, photoreceptor cells. Compounds that bind specifically to, or interact with, A2E, A2E-related and/or derived molecules, or that affect A2E formation or accumulation may also reduce, inhibit, prevent, or decrease one or more toxic effects of A2E or of A2E-related and/or derived molecules that result in retinal neuronal cell (including a photoreceptor cell) damage, loss, or neurodegeneration, or in some manner decrease retinal neuronal cell viability. Such toxic effects include induction of apoptosis, self-generation of singlet oxygen and generation of oxygen reactive species; self-generation of singlet oxygen to form A2E-epoxides that induce DNA lesions, thus damaging cellular DNA and inducing cellular damage; dissolving cellular membranes; altering lysosomal function; and effecting release of proapoptotic proteins from mitochondria.

Retinyl esters may be analyzed by gradient HPLC according to methods practiced in the art (see, for example, Mata et al., *Neuron* 36:69-80 (2002); Trevino et al. *J. Exp. Biol.* 208: 4151-57 (2005)). To measure 11-cis and all-trans retinals, retinoids may be extracted by a formaldehyde method (see, e.g., Suzuki et al., *Vis. Res.* 28:1061-70 (1988); Okajima and Pepperberg, *Exp. Eye Res.* 65:331-40 (1997)) or by a hydroxylamine method (see, e.g., Groenendijk et al., *Biochim. Biophys. Acta.* 617:430-38 (1980)) before being analyzed on isocratic HPLC (see, e.g., Trevino et al., supra). The retinoids may be monitored spectrophotometrically (see, e.g., Maeda et al., *J. Neurochem.* 85:944-956 (2003); Van Hooser et al., *J. Biol. Chem.* 277:19173-82 (2002)).

The ophthalmic disease may result, at least in part, from lipofuscin pigment(s) accumulation and/or from accumulation of N-retinylidene-N-retinylethanolamine (A2E) in the eye. Accordingly, in certain embodiments, methods are provided for inhibiting or preventing accumulation of lipofuscin pigment(s) and/or A2E in the eye of a subject. These methods comprise administering to the subject a composition comprising a pharmaceutically acceptable carrier and a 3-phenylpropylamine derivative compound as described in detail herein, or a pharmaceutically acceptable salt thereof.

The 3-phenylpropylamine derivative compound described herein can be administered to a subject who has an excess of a retinoid in an eye (e.g., an excess of 11-cis-retinol or 11-cis-retinal), an excess of retinoid waste products or intermediates in the recycling of all-trans-retinal, or the like. Methods described herein and practiced in the art may be used to determine whether the level of one or more endogenous retinoids in a subject are altered (increased or decreased in a statistically significant or biologically significant manner) during or after administration of any one of the compounds described herein. Rhodopsin, which is composed of the protein opsin and retinal (a vitamin A form), is located in the membrane of the photoreceptor cell in the retina of the eye and catalyzes the only light-sensitive step in vision. The 11-cis-retinal chromophore lies in a pocket of the protein and is isomerized to all-trans retinal when light is absorbed. The isomerization of retinal leads to a change of the shape of rhodopsin, which triggers a cascade of reactions that lead to a nerve impulse that is transmitted to the brain by the optic nerve.

Methods of determining endogenous retinoid levels in a vertebrate eye, and an excess or deficiency of such retinoids, are disclosed in, for example, U.S. Patent Application Publication No: 2005/0159662 (the disclosure of which is incorporated by reference herein in its entirety). Other methods of determining endogenous retinoid levels in a subject, which is useful for determining whether levels of such retinoids are above the normal range, and include for example, analysis by high pressure liquid chromatography (HPLC) of retinoids in a biological sample from a subject. For example, retinoid levels can be determined in a biological sample that is a blood sample (which includes serum or plasma) from a subject. A biological sample may also include vitreous fluid, aqueous humor, intraocular fluid, subretinal fluid, or tears.

For example, a blood sample can be obtained from a subject, and different retinoid compounds and levels of one or more of the retinoid compounds in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of a 3-phenylpropylamine derivative compound can reduce or eliminate the requirement for endogenous retinoid. In certain embodiments, the level of endogenous retinoid may be compared before and after one or more doses of a 3-phenylpropylamine derivative compound as described herein is administered to a subject to determine the effect of the compound on the level of endogenous retinoids in the subject.

A biological sample may be a blood sample (from which serum or plasma may be prepared), biopsy specimen, body fluids (e.g., vitreous fluid, aqueous humor, intraocular fluid, subretinal fluid, or tears), tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., a retinal cell culture), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like. Mature retinal cells, including retinal neuronal cells, RPE cells, and Müller glial cells, may be present in or isolated from a biological sample as described herein. For example, the mature retinal cell may be obtained from a primary or long-term cell culture or may be present in or isolated from a biological sample obtained from a subject (human or non-human animal).

In Vivo and In Vitro Methods for Determining Therapeutic Effectiveness of Compounds In one embodiment, methods are provided for using the compounds described herein for enhancing or prolonging retinal cell survival, including retinal neuronal cell survival and RPE cell survival. Also provided herein are methods for inhibiting or preventing degeneration of a retinal cell, including a retinal neuronal cell (e.g., a photoreceptor cell, an amacrine cell, a horizontal cell, a bipolar cell, and a ganglion cell) and other mature retinal cells such as retinal pigment epithelial cells and Müller glial cells using the compounds described herein. Such methods comprise, in certain embodiments, administration of a 3-phenylpropylamine derivative compound as described herein. Such a compound is useful for enhancing retinal cell survival, including photoreceptor cell survival and retinal pigment epithelia survival, inhibiting or slowing degeneration of a retinal cell, and thus increasing retinal cell viability, which results in slowing or halting the progression of an ophthalmic disease or disorder or retinal injury, which are described herein.

The effect of a 3-phenylpropylamine derivative compound on retinal cell survival (and/or retinal cell degeneration) may be determined by using cell culture models, animal models, and other methods that are described herein and practiced by persons skilled in the art. By way of example, and not limitation, such methods and assays include those described in Oglivie et al., *Exp. Neurol.* 161:675-856 (2000); U.S. Pat. No. 6,406,840; WO 01/81551; WO 98/12303; U.S. Patent Application No. 2002/0009713; WO 00/40699; U.S. Pat. No. 6,117,675; U.S. Pat. No. 5,736,516; WO 99/29279; WO 01/83714; WO 01/42784; U.S. Pat. No. 6,183,735; U.S. Pat. No. 6,090,624; WO 01/09327; U.S. Pat. No. 5,641,750; U.S. Patent Application Publication No. 2004/0147019; and U.S. Patent Application Publication No. 2005/0059148.

The compounds described herein that are useful for treating an ophthalmic disease or disorder (including a retinal disease or disorder) may inhibit, block, impair, or in some manner interfere with one or more steps in the visual cycle (also called the retinoid cycle herein and in the art). The 3-phenylpropylamine derivative compound as described herein inhibits or blocks an isomerization step in the visual cycle, for example, by inhibiting or blocking a functional activity of a visual cycle trans-cis isomerase. The compounds described herein inhibit, directly or indirectly, isomerization of all-trans-retinol to 11-cis-retinol. The compounds bind to, or in some manner interact with, and inhibit the isomerase activity of at least one isomerase in a retinal cell. Any one of the compounds described herein directly or indirectly inhibit or reduce the activity of an isomerase that is involved in the visual cycle. The compound blocks or inhibits the capability of the isomerase to bind to one or more substrates, including but not limited to, an all-trans-retinyl ester substrate or all-trans-retinol. Alternatively, or in addition, the compound binds to the catalytic site or region of the isomerase, thereby inhibiting the capability of the enzyme to catalyze isomerization of at least one substrate. On the basis of scientific data to date, an at least one isomerase that catalyzes the isomerization of a substrate during the visual cycle is believed to be located in the cytoplasm of RPE cells. As discussed herein, each step, enzyme, substrate, intermediate, and product of the visual cycle is not yet elucidated. While a polypeptide called RPE65, which has been found in the cytoplasm and membrane bound in RPE cells, is hypothesized to have isomerase activity (and has also been referred to in the art as having isomerohydrolase activity) (see, e.g., Moiseyev et al., *Proc. Natl. Acad. Sci. USA* 102:12413-18 (2004); Chen et al., *Invest. Ophthalmol. Vis. Sci.* 47:1177-84 (2006)), other persons skilled in the art believe that the RPE65 acts primarily as a chaperone for all-trans-retinyl esters (see, e.g., Lamb et al. supra).

Exemplary methods are described herein and practiced by persons skilled in the art for determining the level of enzymatic activity of a visual cycle isomerase in the presence of any one of the 3-phenylpropylamine derivative compounds described herein. A compound that decreases isomerase activity may be useful for treating an ophthalmic disease or disorder. Thus, methods are provided herein for detecting inhibition of isomerase activity comprising contacting (i.e., mixing, combining, or in some manner permitting the compound and isomerase to interact) a biological sample comprising the isomerase and a 3-phenylpropylamine derivative compound as described herein and then determining the level of enzymatic activity of the isomerase. A person having skill in the art will appreciate that as a control, the level of activity of the isomerase in the absence of a compound or in the presence of a compound known not to alter the enzymatic activity of the isomerase can be determined and compared to the level of activity in the presence of the compound. A decrease in the level of isomerase activity in the presence of the compound compared to the level of isomerase activity in the absence of the compound indicates that the compound may be useful for treating an ophthalmic disease or disorder, such as age-related macular degeneration or Stargardt's disease.

Animal models may be used to characterize and identify compounds that may be used to treat retinal diseases and disorders. A recently developed animal model may be useful for evaluating treatments for macular degeneration has been described by Ambati et al. (*Nat. Med.* 9:1390-97 (2003); Epub 2003 Oct. 19). This animal model is one of only a few exemplary animal models presently available for evaluating a compound or any molecule for use in treating (including preventing) progression or development of a retinal disease or disorder. Animal models in which the ABCR gene, which encodes an ATP-binding cassette transporter located in the rims of photoreceptor outer segment discs, may be used to evaluate the effect of a compound. Mutations in the ABCR gene are associated with Stargardt's disease, and heterozygous mutations in ABCR have been associated with AMD. Accordingly, animals have been generated with partial or total loss of ABCR function and may used to characterize the 3-phenylpropylamine derivative compounds described herein. (See, e.g., Mata et al., *Invest. Ophthalmol. Sci.* 42:1685-90 (2001); Weng et al., *Cell* 98:13-23 (1999); Mata et al., *Proc. Natl. Acad. Sci. USA* 97:7154-49 (2000); US 2003/0032078; U.S. Pat. No. 6,713,300). Other animal models include the use of mutant ELOVL4 transgenic mice to determine lipofuscin accumulation, electrophysiology, and photoreceptor degeneration, or prevention or inhibition thereof (see, e.g., Karan et al., *Proc. Natl. Acad. Sci. USA* 102:4164-69 (2005)).

A method for determining the effect of a compound on isomerase activity may be performed in vitro as described herein and in the art (Stecher et al., *J. Biol. Chem.* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the 3-phenylpropylamine derivative compounds to inhibit isomerase may also be determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem.* 85:944-956 (2003); Van Hooser et al., *J. Biol. Chem.* 277: 19173-82, 2002). Electroretinographic (ERG) recording may be performed as previously described (Haeseleer et al., *Nat. Neurosci.* 7:1079-87 (2004); Sugitomo et al., *J. Toxicol. Sci.*

22 Suppl 2:315-25 (1997); Keating et al., *Documenta Ophthalmologica* 100:77-92 (2000)). See also Deigner et al., *Science*, 244: 968-971 (1989); Gollapalli et al., *Biochim. Biophys. Acta* 1651: 93-101 (2003); Parish, et al., *Proc. Natl. Acad. Sci. USA* 95:14609-13 (1998); Radu et al., *Proc Natl Acad Sci USA* 101: 5928-33 (2004).

In the vertebrate eye, for example, a mammalian eye, the formation of A2E is a light-dependent process and its accumulation leads to a number of negative effects in the eye. These include destabilization of retinal pigment epithelium (RPE) membranes, sensitization of cells to blue-light damage, and impaired degradation of phospholipids. Products of the oxidation of A2E (and A2E related molecules) by molecular oxygen (oxiranes) were shown to induce DNA damage in cultured RPE cells. All these factors lead to a gradual decrease in visual acuity and eventually to vision loss. If reducing the formation of retinals during vision processes were possible, this reduction would lead to decreased amounts of A2E in the eye. Decreased accumulation of A2E may reduce or delay degenerative processes in the RPE and retina and thus may slow down or prevent vision loss in dry AMD and Stargardt's Disease.

In another embodiment, the subject is being treated for Stargardt's disease or Stargardt's macular degeneration. In Stargardt's disease, which is associated with mutations in the ABCA4 (also called ABCR) transporter, the accumulation of all-trans-retinal has been proposed to be responsible for the formation of a lipofuscin pigment, A2E, which is toxic towards retinal cells and causes retinal degeneration and consequently loss of vision.

In yet another embodiment, the subject is being treated for age-related macular degeneration (AMD). In some embodiments, AMD is dry-form. In other embodiments, the AMD condition is dry-form AMD associated with geographic atrophy. In AMD, vision loss primarily occurs when complications late in the disease either cause new blood vessels to grow under the macula or the macula atrophies. The accumulation of all-trans-retinal has been proposed to be responsible for the formation of a lipofuscin pigment, N-retinylidene-N-retinylethanolamine (A2E) and A2E related molecules, which are toxic towards RPE and retinal cells and cause retinal degeneration and consequently loss of vision.

A neurodegenerative retinal disease or disorder for which the compounds and methods described herein may be used for treating, curing, preventing, ameliorating the symptoms of, or slowing, inhibiting, or stopping the progression of, is a disease or disorder that leads to or is characterized by retinal neuronal cell loss, which is the cause of visual impairment. Such a disease or disorder includes but is not limited to age-related macular degeneration (including dry-form of macular degeneration) and Stargardt's macular dystrophy.

Age-related macular degeneration as described herein is a disorder that affects the macula (central region of the retina) and results in the decline and loss of central vision. Age-related macular degeneration occurs typically in individuals over the age of 55 years. The etiology of age-related macular degeneration may include both environmental influences and genetic components (see, e.g., Lyengar et al., *Am. J. Hum. Genet.* 74:20-39 (2004) (Epub 2003 Dec. 19); Kenealy et al., *Mol. Vis.* 10:57-61 (2004); Gorin et al., *Mol. Vis.* 5:29 (1999)). More rarely, macular degeneration occurs in younger individuals, including children and infants, and generally, these disorders results from a genetic mutation. Types of juvenile macular degeneration include Stargardt's disease (see, e.g., Glazer et al., *Ophthalmol. Clin. North Am.* 15:93-100, viii (2002); Weng et al., *Cell* 98:13-23 (1999)); Doyne's honeycomb retinal dystrophy (see, e.g., Kermani et al., *Hum. Genet.* 104:77-82 (1999)); Sorsby's fundus dystrophy, Malattia Levintinese, fundus flavimaculatus, and autosomal dominant hemorrhagic macular dystrophy (see also Seddon et al., *Ophthalmology* 108:2060-67 (2001); Yates et al., *J. Med. Genet.* 37:83-7 (2000); Jaakson et al., *Hum. Mutat.* 22:395-403 (2003)). Geographic atrophy of the RPE is an advanced form of non-neovascular dry-type age-related macular degeneration, and is associated with atrophy of the choriocapillaris, RPE, and retina.

Stargardt's macular degeneration, a recessive inherited disease, is an inherited blinding disease of children. The primary pathologic defect in Stargardt's disease is also an accumulation of toxic lipofuscin pigments such as A2E in cells of the retinal pigment epithelium (RPE). This accumulation appears to be responsible for the photoreceptor death and severe visual loss found in Stargardt's patients. The compounds described herein may slow the synthesis of 11-cis-retinaldehyde (11cRAL or retinal) and regeneration of rhodopsin by inhibiting isomerase in the visual cycle. Light activation of rhodopsin results in its release of all-trans-retinal, which constitutes the first reactant in A2E biosynthesis. Treatment with 3-phenylpropylamine derivative compounds may inhibit lipofuscin accumulation and thus delay the onset of visual loss in Stargardt's and AMD patients without toxic effects that would preclude treatment with a 3-phenylpropylamine derivative compound. The compounds described herein may be used for effective treatment of other forms of retinal or macular degeneration associated with lipofuscin accumulation.

Administration of a 3-phenylpropylamine derivative compound as described herein to a subject prevents formation of the lipofuscin pigment, A2E (and A2E related molecules), that is toxic towards retinal cells and causes retinal degeneration. In certain embodiments, administration of the 3-phenylpropylamine derivative compound lessens the production of waste products, e.g., lipofuscin pigment, A2E (and A2E related molecules), ameliorate the development of AMD (e.g., dry-form) and Stargardt's disease, and subsequently reduce or slow vision loss (e.g., choroidal neovascularization and/or chorioretinal atrophy). In previous studies, with 13-cis-retinoic acid (Accutane® or Isotretinoin), a drug commonly used for the treatment of acne and an inhibitor of 11-cis-retinol dehydrogenase, has been administered to patients to prevent A2E accumulation in the RPE. However, a major drawback in this proposed treatment is that 13-cis-retinoic acid can easily isomerize to all-trans-retinoic acid. All-trans-retinoic acid is a very potent teratogenic compound that adversely affects cell proliferation and development. Retinoic acid also accumulates in the liver and may be a contributing factor in liver diseases.

In yet other embodiments, the 3-phenylpropylamine derivative compound described herein is administered to a subject such as a human with a mutation in the ABCA4 transporter in the eye. The 3-phenylpropylamine derivative compound described herein is optionally administered to an aging subject. As used herein, an aging human subject is typically at least 45, or at least 50, or at least 60, or at least 65 years old. In Stargardt's disease, which is associated with mutations in the ABCA4 transporter, the accumulation of all-trans-retinal has been proposed to be responsible for the formation of a lipofuscin pigment, A2E (and A2E related molecules), that is toxic towards retinal cells and causes retinal degeneration and consequently loss of vision. The 3-phenylpropylamine derivative compound described herein is a strong inhibitor of an isomerase involved in the visual cycle. Treating patients with a 3-phenylpropylamine derivative compound as described herein may prevent or slow the formation of A2E (and A2E related molecules) and have protective properties for normal vision.

As used herein, a patient (or subject) may be any mammal, including a human, that may have or be afflicted with a neurodegenerative disease or condition, including an ophthalmic disease or disorder, or that may be free of detectable disease. Accordingly, the treatment may be administered to a subject who has an existing disease, or the treatment may be prophylactic, administered to a subject who is at risk for developing the disease or condition. Treating or treatment refers to any indicia of success in the treatment or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being.

The treatment or amelioration of symptoms is based on objective or subjective parameters; including the results of a physical examination. The term "therapeutic effect" refers to the reduction, elimination, or optionally, prevention of the disease, symptoms of the disease, or sequelae of the disease in the subject. Treatment also includes restoring or improving retinal neuronal cell functions (including photoreceptor function) in a vertebrate visual system, for example, such as visual acuity and visual field testing etc., as measured over time (e.g., as measured in weeks or months). Treatment also includes stabilizing disease progression (i.e., slowing, minimizing, or halting the progression of an ophthalmic disease and associated symptoms) and minimizing additional degeneration of a vertebrate visual system. Treatment also optionally includes prophylaxis and refers to the administration of a 3-phenylpropylamine derivative compound as described herein to a subject to prevent degeneration or further degeneration or deterioration or further deterioration of the vertebrate visual system of the subject and to prevent or inhibit development of the disease and/or related symptoms and sequelae.

Various methods and techniques practiced by a person skilled in the medical and ophthalmological arts to determine and evaluate a disease state and/or to monitor and assess a therapeutic regimen include, for example, fluorescein angiogram, fundus photography, indocyanine green dye tracking of the choroidal circulatory system, opthalmoscopy, optical coherence tomography (OCT), and visual acuity testing.

A fluorescein angiogram involves injecting a fluorescein dye intravenously and then observing any leakage of the dye as it circulates through the eye. Intravenous injection of indocyanine green dye may also be used to determine if vessels in the eye are compromised, particularly in the choroidal circulatory system that is just behind the retina. Fundus photography may be used for examining the optic nerve, macula, blood vessels, retina, and the vitreous. Microaneurysms are visible lesions in diabetic retinopathy that may be detected in digital fundus images early in the disease (see, e.g., U.S. Patent Application Publication No. 2007/0002275). An ophthalmoscope may be used to examine the retina and vitreous. Opthalmoscopy is usually performed with dilated pupils, to allow the best view inside the eye. Two types of ophthalmoscopes may be used: direct and indirect. The direct ophthalmoscope is generally used to view the optic nerve and the central retina. The periphery, or entire retina, may be viewed by using an indirect ophthalmoscope. Optical coherence tomography (OCT) produces high resolution, high speed, non-invasive, cross-sectional images of body tissue. OCT is noninvasive and provides detection of microscopic early signs of disruption in tissues.

A subject or patient refers to any vertebrate or mammalian patient or subject to whom the compositions described herein is administered. The term "vertebrate" or "mammal" includes humans and non-human primates. Subjects in need of treatment using the methods described herein are identified according to accepted screening methods in the medical art that are employed to determine risk factors or symptoms associated with an ophthalmic disease or condition described herein or to determine the status of an existing ophthalmic disease or condition in a subject. These and other routine methods allow the clinician to select patients in need of therapy using the methods and formulations described herein.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Flash column chromatography and thin layer chromatography (TLC) were performed on silica gel unless otherwise noted. Proton and carbon nuclear magnetic resonance spectra were obtained with a Varian VnmrJ 400 at 400 MHz for proton and 100 MHz for carbon. Spectra are given in ppm (δ) and coupling constants, J are reported in Hertz. For proton spectra the solvent peak was used as the reference peak. For carbon spectra the solvent peak was used as the reference. HPLC/LC-MS was performed using the following method: Agilent HP 1100 system with diode array detection at 220 nm on Phenomenex Gemini 4.6×150 mm 5 μcolumn, mobile phase 0.05% TFA CH$_3$CN/H$_2$O gradient with mass-spectral detection using electrospray ionization (ES+) mode.

Intermediate 1

Preparation of (R)-tert-Butyl (3-hydroxy-3-(3-hydroxyphenyl)propyl)-carbamate

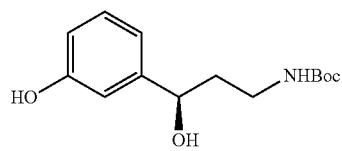 [SMILES: CC(C)(C)OC(=O)NCC[C@@H](O)c1cccc(O)c1]

(R)-tert-Butyl (3-hydroxy-3-(3-hydroxyphenyl)propyl) carbamate was prepared following the method shown in Scheme 1:

Scheme 1

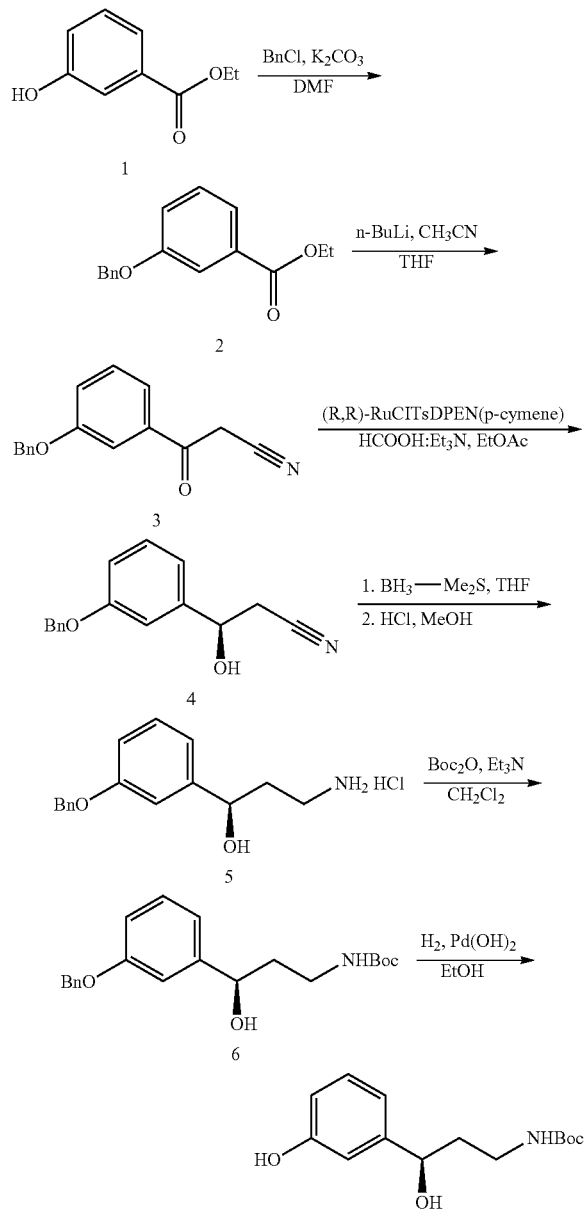

Step 1: K$_2$CO$_3$ (66.8 g, 0.48 mol) was added to a stirred solution of ethyl 3-hydroxybenzoate (1) (40.0 g, 0.24 mol) and (chloromethyl)benzene (33.5 g, 0.26 mol) in DMF (256 mL) and the reaction mixture was heated at 90° C. for 3 h. The reaction mixture was filtered through Celite, the filtrate was diluted with water (500 mL), extracted with EtOAc (500 mL). The organic layer was washed with brine (500 mL), dried over anhydrous Na$_2$SO$_4$ and concentrated under reduced pressure to give ethyl 3-(benzyloxy)benzoate (2) as colorless liquid. Yield (61.0 g, 98%); $^1$H NMR (400 MHz, DMSO-d$_6$) δ 7.56-7.53 (m, 2H), 7.47-7.44 (m, 3H), 7.39 (t, J=7.2 Hz, 2H), 7.35-7.29 (m, 2H), 5.17 (s, 2H), 4.30 (q, J=7.2 Hz, 2H), 1.31 (t, J=7.2 Hz, 3H).

Step 2: n-BuLi (1.6 M in hexanes, 146 mL, 234 mmol) was added dropwise at −78° C. to a solution of CH$_3$CN (10.39 mL, 199 mmol) in THF (600 mL) and the reaction mixture was stirred for 30 min. A solution of ester (2) (30.0 g, 117 mmol) in THF (50 mL) was added and the mixture was further stirred for 30 min at −78° C. The reaction mixture was quenched at −78° C. by addition of aqueous NH$_4$Cl (200 mL), diluted with EtOAc (500 mL), the organic layer was dried over anhydrous Na$_2$SO$_4$ and concentrated under reduced pressure to give 3-(3-(benzyloxy)phenyl)-3-oxopropanenitrile (3) as a pale yellow solid. Yield (25.0 g, 85%); $^1$H NMR (400 MHz, CDCl$_3$) δ 7.53 (s, 1H), 7.48-7.36 (m, 6H), 7.35-7.33 (m, 1H), 7.27-7.26 (m, 1H), 5.12 (s, 2H), 4.05 (s, 2H).

Step 3: HCOOH (30.75 mL, 795 mmol) was added dropwise to a cooled (0° C.) solution of Et$_3$N (41.0 mL, 318 mmol) in EtOAc (400 mL) while maintaining the temperature at 0° C. (R,R)—RuCl-TsDPEN (p-cymene) (100 mg, 0.2 mol %) was added to the reaction mixture followed by the addition of oxonitrile (3) (40.0 g, 159 mmol) and the reaction mixture was stirred at room temperature for 24 h. NaHCO$_3$ (10%, 500 mL) was added and the mixture was extracted with EtOAc (500 mL). Organic layer was dried over anhydrous Na$_2$SO$_4$ and concentrated under reduced pressure to give (R)-3-(3-(benzyloxy)phenyl)-3-hydroxypropanenitrile (4) as a pale yellow solid. Yield (38.0 g, 95%); $^1$H NMR (400 MHz, DMSO-d$_6$) δ 7.46-7.44 (m, 2H), 7.41-7.37 (m, 2H), 7.33 (t, J=7.2 Hz, 1H), 7.26 (t, J=8.0 Hz, 1H), 7.07 (s, 1H), 6.99 (d, J=7.6 Hz, 1H), 6.92 (d, J=8.0 Hz, 1H), 5.95 (d, J=4.4 Hz, 1H), 5.09 (s, 2H), 4.86 (d, J=5.2 Hz, 1H), 2.90 (dd, J=16.8, 4.8 Hz, 1H), 2.80 (dd, J=16.8, 6.8 Hz, 1H).

Step 4: BH$_3$-Me$_2$S complex (35.5 mL, 355.7 mmol) was added to the solution of (R)-hydroxynitrile (4) (30.0 g, 118.6 mmol) in THF (150 mL) and the reaction mixture was heated at 70° C. under reflux for 18 h. The reaction mixture was quenched with MeOH (50 mL), dioxane/HCl (30 mL) was added and the reaction mixture was further heated under reflux for 1 h. The reaction mixture was concentrated under reduced pressure to give (R)-3-amino-1-(3-(benzyloxy)phenyl)propan-1-ol hydrochloride (5) as a white solid. Yield (31.0 g, 89%); $^1$H NMR (400 MHz, DMSO-d$_6$) δ 7.87 (bs, 3H), 7.45 (d, J=7.2 Hz, 2H), 7.39 (t, J=7.2 Hz, 2H), 7.34-7.31 (m, 1H), 7.25 (t, J=8.0 Hz, 1H), 7.0 (s, 1H), 6.92-6.88 (m, 2H), 5.56 (d, J=4.4 Hz, 1H), 5.09 (s, 2H), 4.66 (q, J=4.0 Hz, 1H), 3.56 (s, 2H), 2.87-2.82 (m, 2H), 1.89-1.76 (m, 2H).

Step 5: Et$_3$N (24.27 mL, 174.84 mmol) was added at 0° C. to a mixture of amine (5) (30 g, 116.6 mmol) and CH$_2$Cl$_2$ (150 mL) and the resulting mixture was stirred for 1 h. Boc$_2$O (32.13 mL, 139.9 mmol) was added to the reaction mixture and the latter was further stirred for 18 h at rt. The reaction mixture was diluted with H$_2$O (100 mL), extracted with CH$_2$Cl$_2$ (500 mL), organic layer was dried over anhydrous Na$_2$SO$_4$ and concentrated under reduced pressure to give (R)-tert-butyl 3-(3-(benzyloxy)phenyl)-3-hydroxypropylcarbamate (6) as colorless oil. Yield (41.0 g, 98%); $^1$H NMR (400 MHz, DMSO-d$_6$) δ 7.45 (d, J=7.2 Hz, 2H), 7.39 (t, J=7.2 Hz, 2H), 7.34-7.30 (m, 1H), 7.21 (t, J=8.0 Hz, 1H), 6.98 (s, 1H), 6.90-6.84 (m, 2H), 6.76 (s, 1H), 5.20 (d, J=4.8 Hz, 1H), 5.11 (s, 2H), 4.53-4.49 (m, 1H), 2.99-2.94 (m, 2H), 1.67 (q, J=6.8 Hz, 2H), 1.37 (s, 9H).

Step 6: A solution of carbamate (6) (41.0 g, 115 mmol) in EtOH (500 mL) was degassed by applying vacuum once. Pd/C (10% wt, 20.0 g) was added and the mixture was degassed by alternating vacuum/H$_2$ three times. The reaction mixture was stirred under H$_2$ pressure of 50 psi for 4 h. The reaction mixture was filtered through Celite, the filtrate was concentrated in vacuum and the residue was purified by crystallization (10% EtOAc in hexane) to give (R)-tert-butyl 3-hydroxy-3-(3-hydroxyphenyl)propylcarbamate (Intermediate I) as a white solid. Yield (24.0 g, 78%); $^1$H NMR (400 MHz, DMSO-d$_6$) δ 9.25 (s, 1H), 7.07 (t, J=7.6 Hz, 1H), 6.75-6.69 (m, 3H), 6.59 (d, J=8.0 Hz, 1H), 5.11 (d, J=4.0 Hz, 1H), 4.46-4.42 (m, 1H), 2.96 (t, J=6.8 Hz, 2H), 1.66-1.61 (m, 2H), 1.36 (s, 9H); RP-HPLC: $t_R$=1.51 min, 98.13% (AUC); ESI MS m/z 266.28[M−H]⁺; Chiral HPLC 97.5% (R)-isomer.

Stereochemical Correlation of Intermediate 1

Preparation of (R)-3-amino-1-phenylpropan-1-ol from Intermediate I

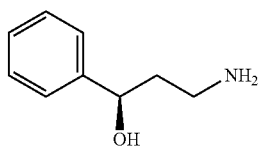 [SMILES: NCC[C@@H](O)c1ccccc1]

(R)-3-Amino-1-phenylpropan-1-ol was prepared following the method shown below:

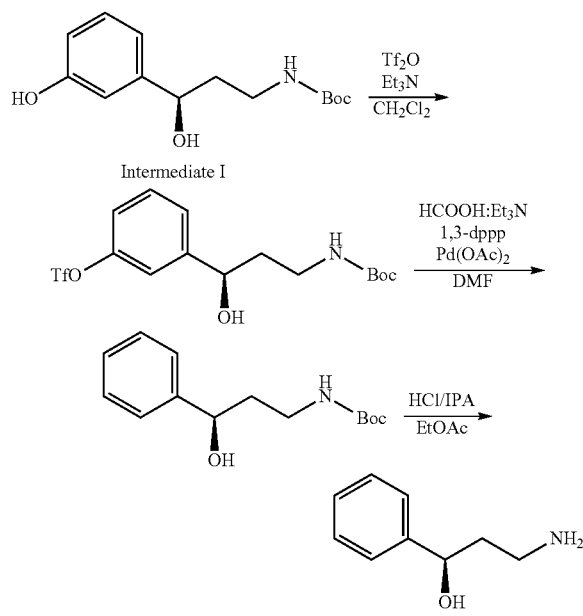

Step 1: Et₃N (1.5 mL, 10.76 mmol) was added to a suspension of Intermediate I (1.00 g, 3.74 mmol) in anhydrous CH₂Cl₂ (20 mL), and a clear solution resulted. The reaction mixture was cooled to 0° C. under N₂ and Tf₂O (0.7 mL, 4.14 mmol) was added slowly via syringe. The reaction mixture was stirred for 2 h, water was added and the mixture was extracted with CH₂Cl₂ twice. Combined organic layers were washed with brine and concentrated under reduced pressure. Purification by flash chromatography (10%-50% EtOAc-hexanes gradient) gave (R)-3-(3-((tert-butoxycarbonyl)amino)-1-hydroxypropyl)phenyl trifluoromethanesulfonate as a colorless oil. Yield (1.10 g, 74%); ¹H NMR (400 MHz, DMSO-d₆); δ 7.45-7.52 (m, 1H), 7.39-7.43 (m, 1H), 7.33-7.38 (m, 1H), 7.27-7.32 (m, 1H), 6.72 (br. t, 1H), 5.45 (d, J=4.7 Hz, 1H), 4.56-4.66 (m, 1H), 2.86-3.2 (m, 2H), 1.60-1.70 (m, 2H), 1.33 (s, 9H).

Step 2: Et₃N (2.0 mL, 14.35 mmol) and HCOOH (0.4 mL, 10.60 mmol) were added to a solution of (R)-3-(3-((tert-butoxycarbonyl)amino)-1-hydroxypropyl)phenyl trifluoromethanesulfonate (1.05 g, 2.63 mmol) and Ar was bubbled through the mixture for one minute. 1,3-Bis(diphenylphosphino)propane (1,3-dppp) (0.080 g, 0.194 mmol) and Pd(OAc)₂ (0.050 g, 0.223 mmol) were added to the reaction mixture and the later was degassed by applying vacuum/Ar cycle three times. The reaction mixture was heated at +60° C. for 5 h and concentrated under reduced pressure. Aqueous NH₄Cl (25%) was added to the residue and the mixture was extracted with MTBE twice. Combined organic layers were washed with brine and concentrated under reduced pressure. Purification by flash chromatography (10%-50% EtOAc-hexanes gradient) gave (R)-tert-butyl (3-hydroxy-3-phenylpropyl)carbamate as a colorless oil. Yield (0.64 g, 97%); ¹H NMR (400 MHz, DMSO-d₆) δ 7.22-7.30 (m, 4H), 7.14-7.21 (m, 1H), 6.72 (br. t, 1H), 5.14 (d, J=4.4 Hz, 1H), 4.51 (dd, J=6.5, 10.9 Hz, 1H), 2.87-2.98 (m, 2H), 1.60-1.70 (m, 2H), 1.33 (s, 9H).

Step 3: Deprotection of (R)-tert-butyl (3-hydroxy-3-phenylpropyl)carbamate following the method used in Example 1 (method 2, step 2) gave (R)-3-amino-1-phenylpropan-1-ol hydrochloride. The salt was dissolved in MeOH and treated with 7N NH₃/MeOH. The mixture was concentrated under reduced pressure. Purification by flash chromatography (4%-20% 4N NH₃/MeOH—CH₂Cl₂ gradient) gave (R)-3-amino-1-phenylpropan-1-ol. Yield (0.18 g, 47%); ¹H NMR (400 MHz, CD₃OD) δ 7.26-7.38 (m, 4H), 7.18-7.25 (m, 1H), 4.71 (dd, J=5.4, 8.3 Hz, 1H), 2.65-2.77 (m, 2H), 1.77-1.94 (m, 2H); $[\alpha]_D$=+ 43.3° (23° C., c=1.6 g/100 mL in EtOH, 1.0 dm path, 589 nM). Literature (Mitchell, D.; Koenig, T. M. Synthetic Communications, 1995, 25(8), 1231-1238): +40.5°. Conclusion: The optical rotation of (R)-3-amino-1-phenylpropan-1-ol matched the value reported in the literature, thus Intermediate I and Example 1 are of (R)-configuration.

Example 1

Preparation of (R)-3-amino-1-(3-((tetrahydro-2H-pyran-4-yl)methoxy)phenyl)-propan-1-ol by method 1

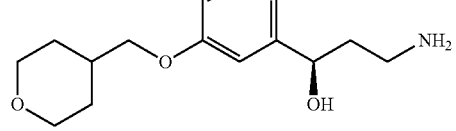

(R)-3-Amino-1-(3-((tetrahydro-2H-pyran-4-yl)methoxy)phenyl)propan-1-ol was prepared following the method shown in Scheme 2:

Scheme 2

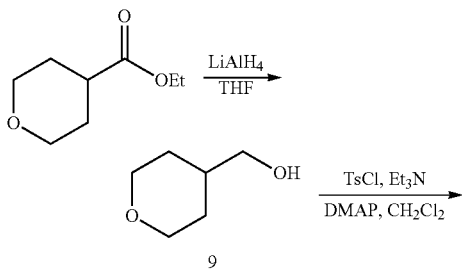

-continued

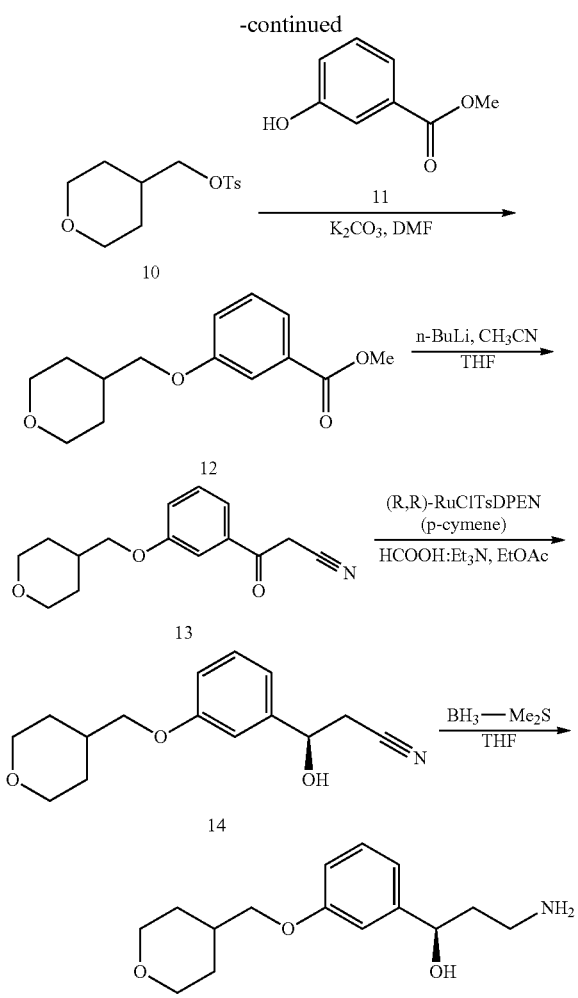

Step 1: Ethyl tetrahydro-2H-pyran-4-carboxylate (5.0 g, 34.7 mmol) was added to a stirred solution of LiAlH$_4$ (4.0 g, 104 mmol) in THF (100 mL) at 0° C. and the reaction mixture was stirred for 1 h. Ethyl acetate (20 mL) was added dropwise to the reaction mixture followed by addition of 10% aq.NaOH and the resulting mixture was stirred for additional 30 min. Reaction mass was filtered through Celite and the filtrate was concentrated under reduced pressure to give (tetrahydro-2H-pyran-4-yl)methanol (9) as a colorless oil. Yield (3.9 g, 96%); $^1$H NMR (400 MHz, DMSO-d$_6$) δ 4.46 (bs, 1H), 3.82 (dd, J=10.8, 8.0 Hz, 2H), 3.25-3.22 (m, 4H), 1.62-1.52 (m, 3H), 1.18-1.04 (m, 1H).

Step 2: TsCl (7.22 g, 37.9 mmol) was added portionwise to a solution of alcohol (9) (4.0 g, 34.44 mmol), Et$_3$N (7.0 g, 69 mmol) and DMAP (0.05 g, 0.35 mmol) in dry DCM (50 mL) at 0° C. The reaction mixture was allowed to warm to room temperature and further stirred for 1 h. The reaction mixture was diluted with water, extracted with EtOAc, dried over anhydrous Na$_2$SO$_4$ and concentrated under reduced pressure to give (tetrahydro-2H-pyran-4-yl)methyl 4-methylbenzenesulfonate (10) as white solid. Yield (8.5 g, 91%); $^1$H NMR (400 MHz, DMSO-d$_6$) δ 7.78 (d, J=8.0 Hz, 2H), 7.48 (d, J=8.0 Hz, 2H), 3.87 (d, J=6.4 Hz, 2H), 3.78 (dd, J=11.2, 4.2 Hz, 2H), 3.22 (dt, J=11.6, 1.6 Hz, 2H), 2.42 (s, 3H), 1.88-1.79 (m, 1H), 1.46 (dd, J=12.8, 1.6 Hz, 2H), 1.18-1.07 (m, 2H).

Step 3: K$_2$CO$_3$ (8.2 g, 59.2 mmol) was added to a stirred solution of methyl 3-hydroxybenzoate (11) (3.0 g, 19.72 mmol) sulfonate (10) (5.33 g, 19.72 mmol) in DMF (30 mL) and the reaction mixture was stirred at 90° C. for 16 h. The reaction mixture was concentrated under reduced pressure. Purification by column chromatography (100-200 silica mesh, 30% EtOAc in hexanes) gave methyl 3-((tetrahydro-2H-pyran-4-yl)methoxy)benzoate (12) as a light yellow solid. Yield (4.8 g, 97%); $^1$H NMR (400 MHz, DMSO-d$_6$) δ 7.53 (d, J=7.6 Hz, 1H), 7.44-7.40 (m, 2H), 7.22 (dd, J=8.4, 2.4 Hz, 1H), 3.88-3.82 (m, 7H), 3.32 (t, J=1.2 Hz, 2H), 2.02-1.96 (m, 1H), 1.69-1.66 (m, 2H), 1.38-1.28 (m, 2H).

Step 4: The solution of CH$_3$CN (0.37 g, 8.9 mmol) in THF (40 mL) was added to n-BuLi (1.6 M in hexanes, 0.58 g, 8.9 mmol) at −78° C. and the reaction mixture was stirred for 30 min. Solution of ester (12) (1.5 g, 5.9 mmol) in THF (10 mL) was added to the reaction mixture and the resulting solution was further stirred for 30 min. The reaction mixture was quenched by addition of aq.NH$_4$Cl (200 mL) and extracted with EtOAc (100 mL). Drying over anhydrous Na$_2$SO$_4$ and concentration under reduced pressure gave 3-oxo-3-(3-((tetrahydro-2H-pyran-4-yl)methoxy)phenyl)propanenitrile (13). Yield (1.5 g, 96%); $^1$H NMR (400 MHz, DMSO-d$_6$) δ 7.43-7.37 (m, 3H), 7.26-7.21 (m, 1H), 4.75 (bs, 2H), 3.89-3.83 (m, 4H), 3.32 (t, J=11.6 Hz, 2H), 2.03-1.98 (m, 1H), 1.69-1.66 (m, 2H), 1.38-1.28 (m, 2H).

Step 5: The solution of Et$_3$N (0.78 g, 7.6 mmol) in EtOAc (50 mL) was cooled to 0° C. for 15 min. HCOOH (0.88 g, 19 mmol) was added dropwise to the reaction mixture and the solution was stirred for 20 min at same temperature. The solution of 0.2 mol % (R,R)RuCl-TsDPEN(p-cymene) (10 mg) in EtOAc was added to the reaction mixture, followed by addition of ketonitrile (13) (1.0 g, 3.8 mmol) in EtOAc at 0° C. The reaction mixture was stirred for 18 h at rt. After completion of the reaction (as monitored by TLC) the reaction mixture was diluted with water, extracted with EtOAc, dried over anhydrous Na$_2$SO$_4$, and concentrated under reduced pressure. Purification by column chromatography (100-200 silica mesh, 20-25% EtOAc in hexanes) gave (R)-3-hydroxy-3-(3-((tetrahydro-2H-pyran-4-yl)methoxy)phenyl)propanenitrile (14) as a white solid. Yield (0.75 g, 75%); $^1$H NMR (400 MHz, DMSO-d$_6$) δ 7.24 (t, J=8.0 Hz, 1H), 6.98-6.95 (m, 2H), 6.83 (dd, J=8.0, 4.0 Hz, 1H), 5.92 (d, J=4.8 Hz, 1H), 4.85 (dd, J=11.2, 4.8 Hz, 1H), 3.89-3.81 (m, 4H), 3.35-3.30 (m, 2H), 2.84 (dq, J=16.8, 4.8 Hz, 2H), 2.04-1.96 (m, 1H), 1.69-1.66 (m, 2H), 1.37-1.27 (m, 2H).

Step 6: BH$_3$-DMS (0.56 g, 7.4 mmol) was added dropwise to a solution of hydroxynitrile (14) (0.65 g, 2.4 mmol) in dry THF (50 mL). The reaction mixture was refluxed 18 h at 65° C. After completion of the reaction (as monitored by TLC) the MeOH (15 mL) was added to the reaction mixture which was stirred at rt for an additional 1 h. The mixture was then concentrated under reduced pressure followed by purification by column chromatography (100-200 silica mesh, 4-6% MeOH in DCM) to give Example 1 as a white solid. Yield (0.75 g, 99%); $^1$H NMR (400 MHz, DMSO-d$_6$) δ 7.80 (bs, 3H), 7.24 (t, J=8.0 Hz, 1H), 6.89-6.87 (m, 2H), 6.82-6.80 (m, 1H), 5.54 (bs, 1H), 4.65 (bs, 1H), 3.87 (dd, J=11.4, 2.8 Hz, 2H), 3.81 (d, J=6.4 Hz, 2H), 3.37-3.30 (m, 2H), 2.87-2.79 (m, 2H), 2.02-1.96 (m, 1H), 1.88-1.80 (m, 2H), 1.69-1.65 (m, 2H), 1.34-1.27 (m, 2H); RP HPLC $t_R$=1.10 min, 94.5% (AUC); ESI MS m/z 266.27 [M+H]$^+$.

Example 1

Preparation of (R)-3-amino-1-(3-((tetrahydro-2H-pyran-4-yl)methoxy)phenyl)-propan-1-ol by method 2

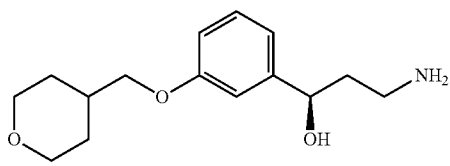 [SMILES: NCC[C@@H](O)c1cccc(OCC2CCOCC2)c1]

(R)-3-Amino-1-(3-((tetrahydro-2H-pyran-4-yl)methoxy)phenyl)propan-1-ol was prepared following the method shown below.

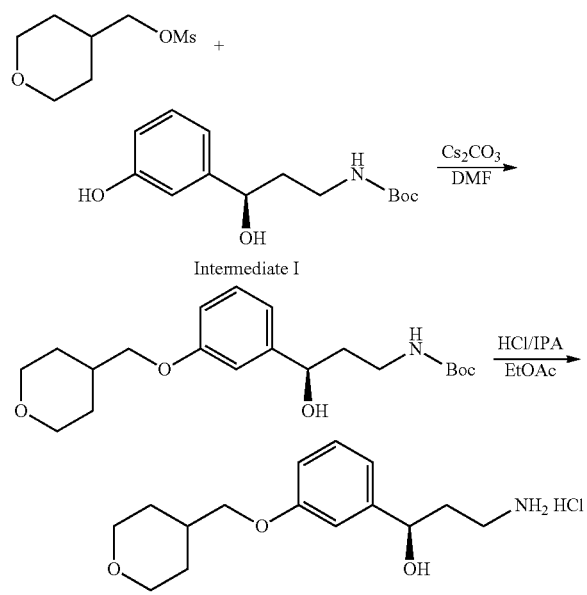

Step 1: Cs$_2$CO$_3$ (2.34 g, 7.18 mmol) was added to a solution of (tetrahydro-2H-pyran-4-yl)methyl methanesulfonate (1.05 g, 5.41 mmol) and Intermediate I (1.13 g, 4.23 mmol) in anhydrous DMF (11 mL) and the reaction mixture was heated at +70° C. under Ar for 22 hrs. Aqueous NH$_4$Cl (25%) was added and the reaction mixture was extracted with MTBE twice. Combined organic layers were washed with brine, concentrated under reduced pressure. Purification by flash chromatography (25%-100% EtOAc-hexanes gradient) gave (R)-tert-butyl (3-hydroxy-3-(3-((tetrahydro-2H-pyran-4-yl)methoxy)phenyl)propyl)carbamate as a colorless oil. Yield (0.47 g, 30%); $^1$H NMR (400 MHz, DMSO-d$_6$) δ 7.18 (t, J=8.0 Hz, 1H), 6.85-6.84 (m, 2H), 6.76-6.74 (m, 2H), 5.15 (d, J=4.4 Hz, 1H), 4.49 (q, J=4.4 Hz, 1H), 3.88-3.84 (m, 2H), 3.79 (d, J=6.4 Hz, 2H), 2.94 (q, J=6.4 Hz, 2H), 1.70-1.62 (m, 4H), 1.38-1.26 (m, 11H).

Step 2: HCl/i-PrOH (5.5 M, 3 mL) was added to a solution of (R)-tert-butyl (3-hydroxy-3-(3-((tetrahydro-2H-pyran-4-yl)methoxy)phenyl)propyl)carbamate (0.45 g, 1.23 mmol) in EtOAc (5 mL). The reaction mixture was stirred for 5.5 hrs at room temperature, concentrated under reduced pressure. The residue was dissolved in boiling 25% i-PrOH/EtOAc, cooled to room temperature and sonicated. White precipitate was collected by filtration, washed with EtOAc and hexanes, dried to give Example 1 hydrochloride as a white solid. Yield (0.244 g, 66%); $^1$H NMR (400 MHz, DMSO-d$_6$) δ 7.85 (s, 3H), 7.20 (t, J=7.8 Hz, 1H), 6.82-6.90 (m, 2H), 6.75-6.80 (m, 1H), 5.49 (d, J=4.4 Hz, 1H), 4.62 (m, 1H), 3.84 (dd, J=3.0, 11.3 Hz, 2H), 3.78 (d, J=6.3 Hz, 2H), 3.24-3.35 (m, 2H), 2.78 (br. s, 2H), 1.90-2.05 (m, 1H), 1.74-1.88 (m, 2H), 1.60-1.68 (m, 2H), 1.23-1.35 (m, 2H); [α]$_D$=+30.9° (23° C., c=1.5 g/100 mL in EtOH, 1.0 dm path, 589 nM).

Example 2

Preparation of 3-amino-1-(3-((tetrahydro-2H-pyran-4-yl)methoxy)phenyl)propan-1-ol

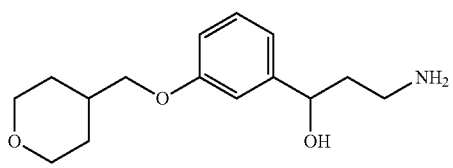 [SMILES: NCCC(O)c1cccc(OCC2CCOCC2)c1]

3-Amino-1-(3-((tetrahydro-2H-pyran-4-yl)methoxy)phenyl)propan-1-ol was prepared following method 1 used in Example 1:

Step 1: BH$_3$-Me$_2$S (0.43 g, 5.8 mmol) was added dropwise to a solution of ketonitrile (13) (0.5 g, 1.9 mmol) in THF (50 mL). The reaction mixture was heated at 65° C. under reflux for 18 h. After completion of the reaction (as monitored by TLC) the reaction mixture was quenched by MeOH (15 mL) and stirred at rt for an additional 1 h. The reaction mixture was concentrated and purification by column chromatography (100-200 silica mesh, 4-6% MeOH in DCM) gave Example 2 as a pale yellow semi-solid. Yield (0.48 g, 96%); $^1$H NMR (400 MHz, DMSO-d$_6$) δ 7.80 (bs, 3H), 7.24 (t, J=8.0 Hz, 1H), 6.89-6.87 (m, 2H), 6.82-6.80 (m, 1H), 5.54 (bs, 1H), 4.65 (bs, 1H), 3.87 (dd, J=11.4, 2.8 Hz, 2H), 3.81 (d, J=6.4 Hz, 2H), 3.37-3.30 (m, 2H), 2.87-2.79 (m, 2H), 2.02-1.96 (m, 1H), 1.88-1.80 (m, 2H), 1.69-1.65 (m, 2H), 1.34-1.27 (m, 2H); RP HPLC: t$_R$=3.89 min, 95% (AUC); ESI MS m/z 266.27 [M+H]$^+$.

Example 3

Preparation of (1R)-3-amino-1-(3-((tetrahydro-2H-pyran-3-yl)methoxy)phenyl)propan-1-ol

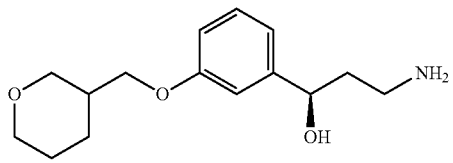 [SMILES: NCC[C@@H](O)c1cccc(OCC2CCCOC2)c1]

(1R)-3-Amino-1-(3-((tetrahydro-2H-pyran-3-yl)methoxy)phenyl)propan-1-ol was prepared following the method used in Example 1:

Step 1: Reaction between (tetrahydro-2H-pyran-3-yl)methyl 4-methylbenzenesulfonate and phenol (11) following the method used in Example 1 gave methyl 3-((tetrahydro-2H-pyran-3-yl)methoxy)benzoate as a white solid. Yield (88%); $^1$H NMR (400 MHz, DMSO-d$_6$) δ 7.53 (d, J=7.6 Hz, 1H), 7.44-7.38 (m, 2H), 7.22 (dd, J=8.4, 2.0 Hz, 1H), 3.91-3.86 (m, 3H), 3.84 (s, 3H), 3.75-3.71 (m, 1H), 3.38-3.35 (m, 1H), 3.29-3.24 (m, 1H), 2.00-1.99 (m, 1H), 1.85-1.82 (m, 1H), 1.60-1.58 (m, 1H), 1.52-1.49 (m, 1H), 1.41-1.38 (m, 1H).

Step 2: Reaction between methyl 3-((tetrahydro-2H-pyran-3-yl)methoxy)benzoate and CH$_3$CN following the method used in Example 1 gave 3-oxo-3-(3-((tetrahydro-2H-pyran-3-yl)methoxy)phenyl)propanenitrile as a white solid. Yield (84%); $^1$H NMR (400 MHz, DMSO-d$_6$) δ 7.52-7.45 (m, 2H), 7.43 (s, 1H), 7.29-7.26 (m, 1H), 4.75 (s, 2H), 3.93-3.87 (m, 3H), 3.75-3.71 (m, 1H), 3.39-3.36 (m, 1H), 3.28-3.25 (m, 1H), 2.01-1.98 (m, 1H), 1.86-1.83 (m, 1H), 1.60-1.58 (m, 1H), 1.53-1.49 (m, 1H), 1.42-1.39 (m, 1H).

Step 3: Reduction of 3-oxo-3-(3-((tetrahydro-2H-pyran-3-yl)methoxy)phenyl)propanenitrile following the method used in Example 1 gave Example 3 as a mixture of diastereomers as a white solid. Yield (81%); $^1$H NMR (400 MHz, DMSO-d$_6$) δ 7.73 (bs, 3H), 7.24 (t, J=7.6 Hz, 1H), 6.89-6.88 (m, 2H), 6.81 (dd, J=8.4, 2.0 Hz, 1H), 5.54 (bs, 1H), 4.85 (dd, J=8.0, 4.8 Hz, 1H), 3.89-3.81 (m, 3H), 3.75-3.72 (m, 1H), 3.38-3.35 (m, 1H), 3.28-3.23 (m, 1H), 2.85-2.80 (m, 2H), 1.98 (bs, 1H), 1.86-1.80 (m, 3H), 1.59-1.52 (m, 2H), 1.40-1.37 (m, 1H); RP HPLC: t$_R$=1.31 min, 98.8% (AUC); ESI MS m/z 266.31 [M+H]$^+$.

Example 4

Preparation of (R)-3-amino-1-(3-(pyridin-4-ylmethoxy)phenyl)propan-1-ol

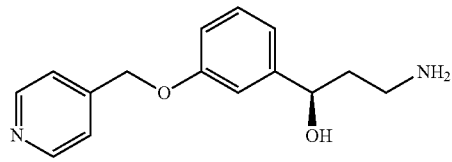 [SMILES: NCC[C@@H](O)c1cccc(OCc2ccncc2)c1]

(R)-3-amino-1-(3-(pyridin-4-ylmethoxy)phenyl)propan-1-ol was prepared following the method shown in Scheme 3:

Scheme 3

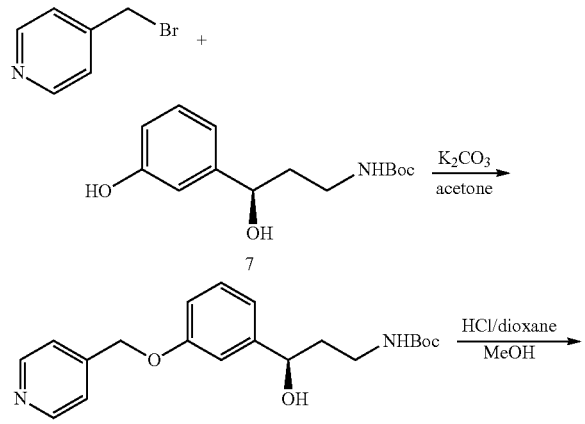

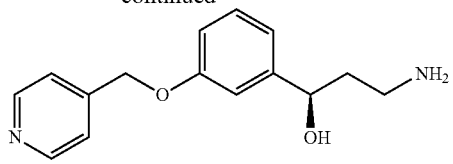

Step 1: 4-(Bromomethyl)pyridine (298 mg, 1.17 mmol) and K$_2$CO$_3$ (774 mg, 5.61 mmol) were added to a solution of phenol (7, Intermediate I) (300 mg, 1.12 mmol) in acetone (20 mL). The reaction mixture was stirred overnight at ambient temperature, diluted with EtOAc and water. The organic layer was washed with 5% aq. NaOH, dried over anhydrous Na$_2$SO$_4$ and concentrated under reduced pressure. Purification by flash chromatography (50% EtOAc:hexane) gave (R)-tert-butyl (3-hydroxy-3-(3-(pyridin-4-ylmethoxy)phenyl)propyl)carbamate (15) as dark brown solid. Yield (0.183 g, 46%); $^1$H NMR (400 MHz, DMSO-d$_6$): δ 8.61 (d, J=5.2 Hz, 2H), 7.36 (d, J=5.2 Hz, 2H), 7.28-7.24 (m, 1H), 7.03 (s, 1H), 6.96 (d, J=8.0 Hz, 1H), 6.85-6.83 (m, 1H), 5.10 (s, 2H), 4.86 (bs, 1H), 4.74-4.71 (m, 1H), 3.52-3.49 (m, 1H), 3.39 (bs, 1H), 3.19-3.12 (m, 1H), 1.86-1.77 (m, 2H), 1.45 (s, 9H); MS: m/z 359.19 [M+H]$^+$.

Step 2: HCl/dioxane (4M, 3 mL) was added at 0° C. to a solution of carbamate (15) (0.16 g, 0.44 mmol) in methanol (5 mL) and the reaction mixture was stirred at ambient temperature for 2 h. The reaction mixture was concentrated under reduced pressure to give after trituration in diethyl ether Example 4 hydrochloride as a white solid. Yield (0.130 g, 98%); $^1$H NMR (400 MHz, DMSO-d$_6$) δ 8.83 (d, J=6.0 Hz, 2H), 7.89-7.85 (m, 5H), 7.29 (t, J=8.0 Hz, 1H), 7.05 (s, 1H), 6.97-6.91 (m, 2H), 5.39 (s, 2H), 4.69-4.66 (m, 1H), 2.83 (bs, 2H), 1.92-1.79 (m, 2H); MS: m/z 259.22 [M+H]$^+$.

Example 5

Preparation of (R)-3-amino-1-(3-(pyridin-3-ylmethoxy)phenyl)propan-1-ol

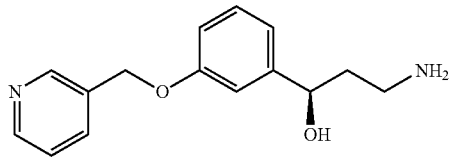 [SMILES: NCC[C@@H](O)c1cccc(OCc2cccnc2)c1]

(R)-3-Amino-1-(3-(pyridin-3-ylmethoxy)phenyl)propan-1-ol was prepared following the method used in Example 4:

Step 1: Reaction between 3-(bromomethyl)pyridine and phenol (7, Intermediate I) following the method used in Example 4 gave after purification by flash chromatography (50% EtOAc:hexane) (R)-tert-butyl (3-hydroxy-3-(3-(pyridin-3-ylmethoxy)phenyl)propyl)carbamate as a pale yellow solid. Yield (0.17 g, 41%); $^1$H NMR (400 MHz, CDCl$_3$): δ 8.68 (s, 1H), 8.58 (s, 1H), 7.78 (d, J=8.0 Hz, 1H), 7.34-7.31 (m, 1H), 7.29-7.26 (m, 1H), 7.04 (s, 1H), 6.96 (d, J=8.0 Hz, 1H), 6.88-6.85 (m, 1H), 5.09 (s, 2H), 4.86 (bs, 1H), 4.73-4.71 (m, 1H), 3.50-3.49 (m, 1H), 3.32 (bs, 1H), 3.20-3.12 (m, 1H), 1.87-1.82 (m, 2H), 1.45 (s, 9H); MS: m/z 359.26 [M+H]$^+$.

Step 2: Deprotection of (R)-tert-butyl (3-hydroxy-3-(3-(pyridin-3-ylmethoxy)phenyl)propyl)carbamate following the method used in Example 4 gave Example 5 hydrochloride as a yellow semi-solid. Yield (0.12 g, 98%); $^1$H NMR (400

MHz, DMSO-$d_6$) δ 8.80 (s, 1H), 8.68 (d, J=6.0 Hz, 1H), 8.14 (bs, 1H), 7.72 (br.s., 4H), 7.29 (t, J=1.6 Hz, 1H), 7.02 (s, 1H), 6.94 (d, J=8.0 Hz, 2H), 5.21 (s, 2H), 4.68-4.65 (m, 1H), 2.84 (br.s., 2H), 1.86-1.80 (m, 2H); MS: m/z 259.26 [M+H]$^+$.

Example 6

Preparation of (R)-3-amino-1-(3-(pyridin-2-ylmethoxy)phenyl)propan-1-ol

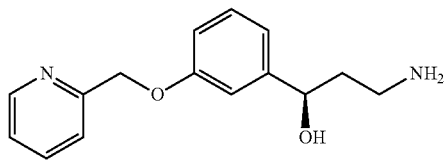 [SMILES: NCC[C@@H](O)c1cccc(OCc2ccccn2)c1]

(R)-3-amino-1-(3-(pyridin-2-ylmethoxy)phenyl)propan-1-ol was prepared following the method used in Example 4:

Step 1: Reaction between 2-(bromomethyl)pyridine and phenol (7, Intermediate I) following the method used in Example 4 gave after purification by flash chromatography (40% EtOAc:hexane) (R)-tert-butyl (3-hydroxy-3-(3-(pyridin-2-ylmethoxy)phenyl)propyl)carbamate as a pale yellow solid. Yield (0.26 g, 88%); $^1$H NMR (400 MHz, CDCl$_3$): δ 8.59 (d, J=4.8 Hz, 1H), 7.71 (t, J=7.6, 1.6 Hz, 1H), 7.52 (d, J=7.6 Hz, 1H), 7.27-7.20 (m, 2H), 7.03 (s, 1H), 6.96 (d, J=10.4 Hz, 1H), 6.87 (d, J=5.6 Hz, 1H), 5.21 (s, 2H), 4.87 (bs, 1H), 4.73-4.70 (m, 1H), 3.50-3.48 (m, 1H), 3.21-3.11 (m, 1H), 1.84-1.61 (m, 2H), 1.45 (s, 9H); MS: m/z 359.26 [M+H]$^+$.

Step 2: Deprotection of (R)-tert-butyl (3-hydroxy-3-(3-(pyridin-2-ylmethoxy)phenyl)propyl)carbamate following the method used in Example 4 gave after purification by flash chromatography (5% MeOH: CH$_2$Cl$_2$) followed by trituration in diethyl ether Example 5 hydrochloride as a white solid. Yield (0.25 g, 96%); $^1$H NMR (400 MHz, DMSO-$d_6$): δ 8.64 (d, J=4.8 Hz, 1H), 7.96 (t, J=8.4 Hz, 1H), 7.75 (s, 3H), 7.61 (d, J=8.0 Hz, 1H), 7.47-7.44 (m, 1H), 7.27 (t, J=8.0 Hz, 1H), 7.02 (s, 1H), 6.94-6.90 (m, 2H), 5.22 (s, 2H), 4.67-4.64 (m, 1H), 2.83 (bs, 2H), 1.87-1.80 (m, 2H); MS: m/z 259.26 [M+H]$^+$.

Example 7

Preparation of (1R)-3-amino-1-(3-((tetrahydro-2H-thiopyran-3-yl)methoxy)phenyl)propan-1-ol

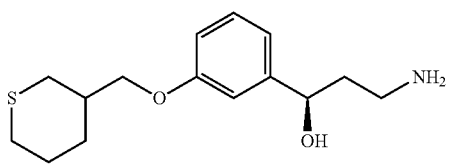

(1R)-3-Amino-1-(3-((tetrahydro-2H-thiopyran-3-yl)methoxy)phenyl)propan-1-ol was prepared following the method below.

Step 1: K$_2$CO$_3$ (0.72 g, 5.24 mmol) and phenol (7, Intermediate I) (0.3 g, 1.05 mmol) were added to a solution of (tetrahydro-2H-thiopyran-3-yl)methyl 4-methylbenzenesulfonate (0.29 g, 1.10 mmol) in DMF (10 mL). The reaction mixture was heated at 100° C. under reflux overnight and then cooled. The reaction mixture was extracted with EtOAc, organic layer was dried over anhydrous Na$_2$SO$_4$ and concentrated under reduced pressure. Purification by flash chromatography (EtOAc:hexane 10-40% gradient) gave tert-butyl ((3R)-3-hydroxy-3-(3-((tetrahydro-2H-thiopyran-3-yl)methoxy)phenyl)propyl)carbamate as a light green solid. Yield (0.21 g, 52%); $^1$H NMR (400 MHz, CDCl$_3$): δ 7.24 (t, J=8.0 Hz, 1H), 6.91 (d, J=8.0 Hz, 2H), 6.78 (d, 1H), 4.87 (bs, 1H), 4.71 (bs, 1H), 3.84-3.80 (m, 2H), 3.49 (bs, 1H), 3.21-3.13 (m, 2H), 2.82-2.77 (m, 1H), 2.62-2.47 (m, 3H), 2.18 (bs, 1H), 2.08-2.04 (m, 1H), 1.91-1.74 (m, 4H), 1.45 (s, 9H), 1.30-1.20 (m, 3H); MS: m/z 382.2 [M+H]$^+$.

Step 2: HCl/dioxane (4M, 2 mL) was added to a solution of tert-butyl ((3R)-3-hydroxy-3-(3-((tetrahydro-2H-thiopyran-3-yl)methoxy)phenyl)propyl)carbamate (0.20 g, 0.52 mmol) in CH$_2$Cl$_2$ (10 mL) at 0° C. and the reaction mixture was stirred at room temperature for 2 h. After completion of the reaction (as monitored by TLC) the solvent was removed under vacuo. The residue was triturated in diethyl ether to give Example 10 hydrochloride as a mixture of diastereomers as a white solid. Yield (0.15 g, 78%); $^1$H NMR (400 MHz, DMSO-$d_6$): δ 7.64 (bs, 2H), 7.26-7.23 (m, 1H), 6.88 (d, J=12.0 Hz, 2H), 6.82 (d, J=8.0 Hz, 1H), 5.55-5.54 (s, 1H), 4.63 (bs, 1H), 3.86-3.82 (m, 2H), 2.83 (m, 2H), 2.67 (m, 1H), 2.5 (m, 2H), 2.07-1.97 (m, 3H), 1.83-1.81 (m, 3H), 1.62-1.56 (m, 1H), 1.24-1.19 (m, 1H); MS: m/z 282.14 [M+H]$^+$.

Example 8

Preparation of (R)-3-amino-1-(3-((tetrahydro-2H-thiopyran-4-yl)methoxy)phenyl)propan-1-ol

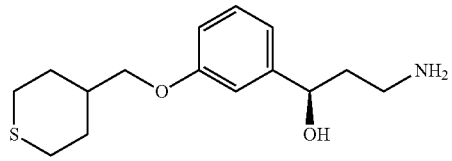 [SMILES: NCC[C@@H](O)c1cccc(OCC2CCSCC2)c1]

(R)-3-Amino-1-(3-((tetrahydro-2H-thiopyran-4-yl)methoxy)phenyl)propan-1-ol was prepared following the method used in Example 7:

Step 1: Pyridine (7.6 mL, 98.4 mmol) was added at 0° C. to a solution of (tetrahydro-2H-thiopyran-4-yl)methanol (1.3 g, 9.84 mmol) in CH$_2$Cl$_2$ (20 mL) followed by the addition of TsCl (2.0 g, 10.83 mmol). The reaction mixture was stirred at ambient temperature for 18 h, diluted with H$_2$O (200 mL) and extracted with CH$_2$Cl$_2$ (200 mL). Drying over anhydrous Na$_2$SO$_4$ followed by concentration in vacuo gave (tetrahydro-2H-thiopyran-4-yl)methyl 4-methylbenzenesulfonate as an off white solid. The crude was carried forward to the next step without additional purification. Yield (0.75 g, 30%).

Step 2: Reaction between (tetrahydro-2H-thiopyran-4-yl)methyl 4-methylbenzenesulfonate and phenol (7, Intermediate I) following the method used in Example 7 gave after purification by flash chromatography (40% ethyl acetate/hexanes) (R)-tert-butyl (3-hydroxy-3-(3-((tetrahydro-2H-thiopyran-4-yl)methoxy)phenyl)propyl)carbamate as a brown oil. Yield (58%); $^1$H NMR (400 MHz, DMSO-$d_6$): δ 7.20 (t, J=8.0 Hz, 1H), 6.86 (d, J=8.0 Hz, 2H), 6.78-6.76 (m, 1H), 5.20-5.17 (m, 1H), 4.50-4.49 (bs, 1H), 4.05-3.98 (m, 2H), 2.96-2.89 (m, 3H), 2.80-2.75 (m, 1H), 2.62-2.61 (m, 1H), 2.26-2.25 (m, 1H), 2.16-2.11 (m, 1H), 1.86-1.77 (m, 2H), 1.67-1.64 (m, 2H), 1.36 (s, 9H).

Step 3: Deprotection of (R)-tert-butyl (3-hydroxy-3-(3-((tetrahydro-2H-thiopyran-4-yl)methoxy)phenyl)propyl)carbamate following the method used in Example 7 gave Example 8 hydrochloride as a white solid. Yield (92%); $^1$H NMR (400 MHz, DMSO-d$_6$): δ 7.79 (bs, 2H), 7.26-7.21 (m, 1H), 6.89 (d, J=4.0 Hz, 2H), 6.83-6.79 (m, 1H), 5.5 (s, 1H), 4.65 (bs, 1H), 4.02-3.99 (m, 2H), 3.78 (d, J=6.4 Hz, 1H), 2.93-2.89 (m, 1H), 2.84-2.80 (m, 3H), 2.66-2.61 (m, 1H), 2.20-2.35 (m, 1H), 2.14-2.10 (m, 1H), 1.88-1.79 (m, 4H), 1.60-1.57 (m, 1H).

Example 9

Preparation of (R)-4-((3-(3-amino-1-hydroxypropyl)phenoxy)methyl)tetrahydro-2H-thiopyran 1,1-dioxide

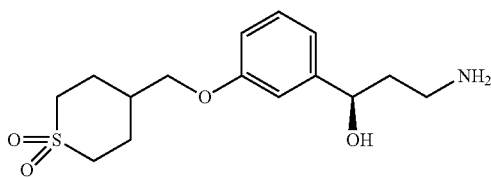 [SMILES: NCC[C@@H](O)c1cccc(OCC2CCS(=O)(=O)CC2)c1]

(R)-4-((3-(3-Amino-1-hydroxypropyl)phenoxy)methyl)tetrahydro-2H-thiopyran 1,1-dioxide was prepared following the method used in Example 7:

Step 1: Reaction between (1,1-dioxidotetrahydro-2H-thiopyran-4-yl)methyl 4-methylbenzenesulfonate and phenol (7, Intermediate I) following the method used in Example 7 gave (R)-tert-butyl (3-(3-((1,1-dioxidotetrahydro-2H-thiopyran-4-yl)methoxy)phenyl)-3-hydroxypropyl)carbamate as colorless oil. Yield (58%); $^1$H NMR (400 MHz, DMSO-d$_6$): δ 7.20 (t, J=8.0 Hz, 1H), 6.87 (d, J=8.0 Hz, 2H), 6.78 (d, J=4.0 Hz, 1H), 5.19 (d, J=4.4 Hz, 1H), 4.51-4.49 (bs, 1H), 3.87-3.85 (d, J=8.0 Hz, 1H), 3.22-3.15 (m, 2H), 3.08-3.05 (m, 2H), 2.96-2.94 (m, 2H), 2.15-2.11 (m, 3H), 1.79-1.74 (m, 2H), 1.67-1.65 (m, 2H), 1.36 (s, 9H).

Step 2: Deprotection of (R)-tert-butyl (3-(3-((1,1-dioxidotetrahydro-2H-thiopyran-4-yl)methoxy)phenyl)-3-hydroxypropyl)carbamate following the method used in Example 7 gave Example 9 hydrochloride as a white solid. Yield (86%); $^1$H NMR (400 MHz, DMSO-d$_6$): δ 7.66 (bs, 2H), 7.25 (t, J=8.0 Hz, 1H), 6.90-6.88 (m, 2H), 6.82 (d, J=8.0 Hz, 1H), 5.55 (d, J=4.0 Hz, 1H), 4.64 (bs, 1H), 3.85 (d, J=4.0 Hz, 2H), 3.19-3.16 (m, 2H), 3.09-3.06 (m, 2H), 2.85-2.80 (m, 2H), 2.14-2.11 (m, 3H), 1.85-1.74 (m, 4H).

Example 10

Preparation of 3-((3-((R)-3-amino-1-hydroxypropyl)phenoxy)methyl)tetrahydro-2H-thiopyran 1,1-dioxide

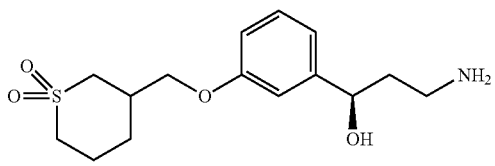 [SMILES: NCC[C@@H](O)c1cccc(OCC2CCCS(=O)(=O)C2)c1]

3-((3-((R)-3-Amino-1-hydroxypropyl)phenoxy)methyl)tetrahydro-2H-thiopyran 1,1-dioxide was prepared following the method used in Example 7:

Step 1: Reaction between methyl 3-(bromomethyl)tetrahydro-2H-thiopyran 1,1-dioxide and phenol (7, Intermediate I) following the method used in Example 7 gave tert-butyl ((3R)-3-(3-((1,1-dioxidotetrahydro-2H-thiopyran-3-yl)methoxy)phenyl)-3-hydroxypropyl)carbamate as a light pink semi-solid. Yield (0.43 g, 65%); $^1$H NMR (400 MHz, CDCl$_3$): δ 7.24 (t, J=8.0 Hz, 1H), 6.93 (d, J=8.0 Hz, 2H), 6.77-6.75 (m, 1H), 4.86 (bs, 1H), 4.72-4.70 (m, 1H), 3.95-3.92 (m, 1H), 3.90-3.88 (m, 1H), 3.38 (s, 1H), 3.26-3.22 (m, 1H), 3.18-3.13 (m, 1H), 3.06 (d, J=4.0 Hz 1H), 2.97-2.88 (m, 2H), 2.65 (bs, 1H), 2.20-2.04 (m, 2H), 1.99-1.95 (m, 1H), 1.84-1.81 (m, 2H), 1.45 (s, 9H). MS: m/z 414.43 [M+H]$^+$.

Step 2: Deprotection of tert-butyl ((3R)-3-(3-((1,1-dioxidotetrahydro-2H-thiopyran-3-yl)methoxy)phenyl)-3-hydroxypropyl)carbamate following the method used in Example 7 gave Example 10 hydrochloride as a mixture of diastereomers as a white solid. Yield (0.36 g, 99%); $^1$H NMR (400 MHz, DMSO-d$_6$): δ 7.79 (bs, 2H), 7.25 (t, J=8.0 Hz, 1H), 6.91-6.90 (m, 2H), 6.84-6.81 (m, 1H), 5.57 (bs, J=12.0 Hz, 1H), 4.65 (dd, J=8.0, 4.0 Hz, 1H), 3.96-3.84 (m, 2H), 3.18-3.15 (m, 1H), 3.11-3.02 (m, 3H), 2.84-2.81 (m, 2H), 2.38 (bs, 1H), 2.10-2.07 (dd, J=10.8, 3.6 Hz, 1H), 1.86-1.79 (m, 4H); MS: m/z 314 [M+H]$^+$.

Example 11

Preparation of (R)-1-(4-((3-(3-amino-1-hydroxypropyl)phenoxy)methyl)piperidin-1-yl)ethanone

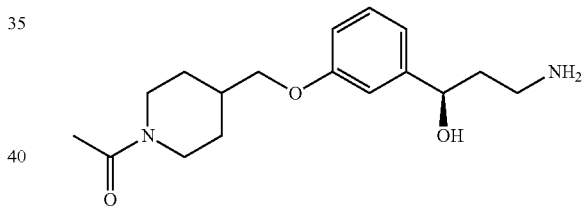

(R)-1-(4-((3-(3-Amino-1-hydroxypropyl)phenoxy)methyl)piperidin-1-yl)ethanone was prepared following the method below.

Step 1: Et$_3$N (0.16 g, 1.60 mmol) and DMAP (0.39 g, 0.32 mmol) were added to a solution of methyl 4-(hydroxymethyl)piperidine-1-carboxylate (1.0 g, 3.20 mmol) in DCM (20 mL). The reaction mixture was cooled to 0° C. and TsCl (0.73 g, 3.80 mmol) was added. The reaction mixture was stirred for 1 h at room temperature, diluted with EtOAc, washed with water, dried over anhydrous Na$_2$SO$_4$ and concentrated under reduced pressure. Purification by flash chromatography (50% EtOAc:hexane) gave (1-acetylpiperidin-4-yl)methyl 4-methylbenzenesulfonate as a pale yellow semi-solid. Yield (1.2 g, 63%); $^1$H NMR (400 MHz, CDCl$_3$); δ 7.77 (d, J=8.4 Hz, 2H), 7.63 (d, J=7.6 Hz, 2H), 4.64 (d, J=14.4 Hz, 2H), 3.92 (dd, J=6.0, 2.4 Hz, 2H), 3.84 (t, J=3.2 Hz, 4H), 3.02 (d, J=13.6 Hz, 2H), 2.54-2.49 (m, 2H), 2.45 (s, 3H), 1.72-1.62 (m, 1H), 1.16 (dt, J=12.4, 3.6 Hz, 1H); MS: m/z 312.05 [M+H]$^+$.

Step 2: Phenol (7, Intermediate I) (0.850 g, 3.20 mmol) and K$_2$CO$_3$ (1.32 g, 9.60 mmol) were added to a solution of (1-acetylpiperidin-4-yl)methyl 4-methylbenzenesulfonate (1.0 g, 3.20 mmol) in DMF (10 mL). The reaction mixture was heated at 90° C. overnight. The reaction mixture was diluted with EtOAc and washed with water and brine.

Organic layer was dried over anhydrous Na₂SO₄) and concentrated under reduced pressure to give after purification by column chromatography to give (R)-tert-butyl (3-(3-((1-acetylpiperidin-4-yl)methoxy)phenyl)-3-hydroxypropyl) carbamate as a colorless semi solid. Yield (600 mg, 46%); ¹H NMR (400 MHz, DMSO-d₆); δ 7.18 (d, J=4.0 Hz, 1H), 6.93 (s, 1H), 6.86 (d, J=7.6 Hz, 1H), 6.76 (d, J=6.0 Hz, 1H), 5.17 (d, J=4.4 Hz, 1H), 4.50 (d, J=4.8 Hz, 1H), 4.39 (d, J=11.6 Hz, 1H), 3.81 (d, J=6.4 Hz, 2H), 3.06-2.94 (m, 4H), 1.99 (s, 3H), 1.78 (t, J=14 Hz, 2H), 1.65 (t, J=7.2, 2H), 1.36 (s, 9H), 1.23 (s, 3H), 1.55-0.88 (m, 1H); MS: m/z 407.05 [M+H]⁺.

Step 3: HCl/dioxane (4M, 2 mL) was added to a solution of (R)-tert-butyl (3-(3-((1-acetylpiperidin-4-yl)methoxy)phenyl)-3-hydroxypropyl)carbamate (0.60 g, 1.40 mmol) in CH₂Cl₂ (10 mL) at 0° C. and the reaction mixture was stirred at room temperature for 2 h. The reaction mixture was concentrated under reduced pressure to give after purification by triturating in diethyl ether Example 11 hydrochloride as a white solid. Yield (0.40 g, 88%); ¹H NMR (400 MHz, DMSO-d₆); δ 7.18 (t, J=7.8 Hz, 1H), 6.84 (d, J=7.6 Hz, 2H), 6.75 (d, J=7.6 Hz, 1H), 4.60 (t, J=6.4 Hz, 1H), 4.38 (d, J=14.8 Hz, 1H), 4.11 (s, 2H), 3.79 (d, J=6 Hz, 3H), 3.02 (t, J=11.2, 1H), 2.64 (d, J=3.2 Hz, 2H), 2.54 (s, 1H), 1.97 (s, 4H), 1.76 (t, J=16.0 Hz, 2H), 1.66-1.61 (m, 2H), 1.26-1.04 (m, 2H); MS: m/z 307.01 [M+H]⁺.

Example 12

Preparation of (R)-3-Amino-1-(3-((6-methylpyridin-2-yl)methoxy)phenyl)propan-1-ol

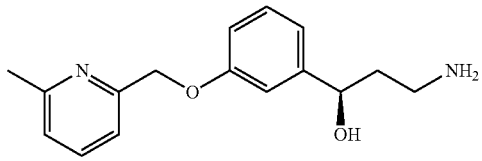 [SMILES: Cc1cccc(COc2cccc([C@H](O)CCN)c2)n1]

(R)-3-Amino-1-(3-((6-methylpyridin-2-yl)methoxy)phenyl)propan-1-ol was prepared following the method described below.

Step 1: Phenol (7, Intermediate I) (0.50 g, 1.87 mmol) and K₂CO₃ (1.29 g, 9.35 mmol) were added to a solution of (6-methylpyridin-2-yl)methyl methanesulfonate (412 mg, 2.05 mmol) in DMF (20 mL) and the reaction mixture was heated under reflux at 90° C. for 18 h. The reaction mixture was diluted with EtOAc and washed with water and brine. Drying over anhydrous Na₂SO₄ and concentration under reduced pressure gave (R)-tert-butyl (3-hydroxy-3-(3-((6-methylpyridin-2-yl)methoxy)phenyl)propyl)carbamate as pale yellow liquid. Yield (200 mg, 72%); ¹H NMR (400 MHz, CDCl₃); δ 7.59 (t, J=8.0 Hz, 1H), 7.32 (d, J=7.2 Hz, 1H), 7.23 (s, 1H), 7.07 (d, J=8.0 Hz, 1H), 7.03 (s, 1H), 6.95 (d, J=7.6 Hz, 1H), 6.87 (dd, J=8.0, 2.4 Hz, 1H), 5.17 (s, 2H), 4.86 (bs, 1H), 4.71 (bs, 1H), 3.49-3.48 (m, 1H), 3.19-3.11 (m, 2H), 2.57 (s, 3H), 1.88-1.82 (m, 2H), 1.45 (s, 9H); MS: m/z 373.20 [M+H]⁺.

Step 2: HCl/dioxane (4M, 2 mL) was added at 0° C. to a solution of (R)-tert-butyl (3-hydroxy-3-(3-((6-methylpyridin-2-yl)methoxy)phenyl)propyl)carbamate (200 mg, 0.54 mmol) in MeOH (3 mL) and the reaction mixture was stirred at room temperature for 2 h. The reaction mixture was concentrated under reduced pressure to give after purification by triturating in diethyl ether Example 12 hydrochloride as a white solid. Yield (0.15 g, 52%); ¹H NMR (400 MHz, DMSO-d₆) δ 7.92 (bs, 1H), 7.74 (bs, 3H), 7.47 (bs, 1H), 7.40 (bs, 1H), 7.28 (t, J=8.0 Hz, 1H), 7.02 (s, 1H), 6.95-6.90 (m, 2H), 5.20 (s, 2H), 4.68-4.65 (m, 1H), 2.84 (bs, 2H), 2.56 (s, 3H), 1.88-1.83 (m, 2H); MS: m/z 273.20 [M+H]⁺.

Example 13

Preparation of (1R)-3-amino-1-(3-((2,3-dihydrobenzofuran-2-yl)methoxy)phenyl)propan-1-ol

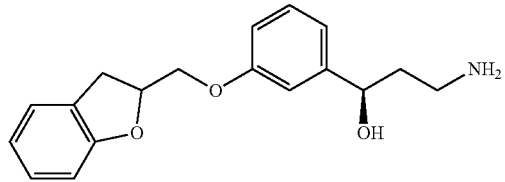

(1R)-3-Amino-1-(3-((2,3-dihydrobenzofuran-2-yl)methoxy)phenyl)propan-1-ol was prepared following the method used in Example 12.

Step 1: Reaction between ((2,3-dihydrobenzofuran-2-yl)methyl 4-methylbenzenesulfonate and phenol (7, Intermediate I) following the method used in Example 12 gave tert-butyl ((3R)-3-(3-((2,3-dihydrobenzofuran-2-yl)methoxy)phenyl)-3-hydroxypropyl)carbamate as a white solid. Yield (65%); ¹H NMR (400 MHz, CDCl₃): δ 7.24-7.18 (m, 2H), 7.12 (t, J=8 Hz, 1H), 6.94 (t, J=8.4 Hz, 2H), 6.88-6.81 (m, 3H), 5.16-5.13 (m, 1H), 4.87 (s, 1H), 4.71 (s, 1H), 4.20 (dd, J=10.0, 6.8 Hz m, 1H), 4.10 (dd, J=6.0, 4.8 Hz, 1H), 3.41 (s, 1H), 3.39-3.35 (m, 1H), 3.25 (s, 1H), 3.17-3.11 (m, 2H), 1.85-1.80 (m, 2H), 1.45 (s, 9H); MS: m/z 400 [M+H]⁺.

Step 2: Deprotection of tert-butyl ((3R)-3-(3-((2,3-dihydrobenzofuran-2-yl)methoxy)phenyl)-3-hydroxypropyl)carbamate following the method used in Example 12 gave Example 13 hydrochloride as a mixture of diastereomers as a white solid. Yield (91%); ¹H NMR (400 MHz, DMSO-d₆): δ 7.81 (s, 3H), 7.27-7.24 (m, 2H), 7.09 (t, J=7.6 Hz, 1H), 6.91 (d, J=7.2 Hz, 2H), 6.82-6.81 (m, 2H), 6.77 (d, J=8 Hz, 1H), 5.54 (d, J=12 Hz, 1H), 5.31 (t, J=3.6 Hz m, 1H), 4.65 (t, J=3.6 Hz, 1H), 4.20-4.10 (m, 2H), 3.07 (dd, J=16.0, 7.6 Hz, 1H), 2.81 (s, 2H), 1.88-1.81 (m, 2H); MS: m/z 300 [M+H]⁺.

Example 14

Preparation of (1R)-3-amino-1-(3-((tetrahydrofuran-2-yl)methoxy)phenyl)propan-1-ol

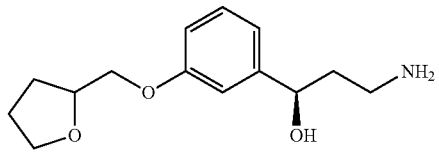 [SMILES: NCC[C@@H](O)c1cccc(OCC2CCCO2)c1]

(1R)-3-Amino-1-(3-((tetrahydrofuran-2-yl)methoxy)phenyl)propan-1-ol was prepared following the method used in Example 12.

Step 1: tert-Butyl ((3R)-3-hydroxy-3-(3-((tetrahydrofuran-2-yl)methoxy)phenyl)propyl)-carbamate was prepared by the reaction between rac-(tetrahydrofuran-2-yl)methyl 4-methylbenzenesulfonate and phenol (7, Intermediate I) at +100° C. following the method used in Example 12 with the following exception. After the reaction was complete (as judged by TLC), the reaction mixture was diluted with EtOAc, dried over anhydrous $Na_2SO_4$ and concentrated under reduced pressure. Purification by flash chromatography (EtOAc:hexane 10-40% gradient) gave the product as an off-white semi-solid. Yield (0.36 g, 66%); $^1$H NMR (400 MHz, CDCl$_3$): δ 7.23 (t, J=8.0 Hz, 1H), 6.95 (s, 1H), 6.91 (d, J=8.0 Hz, 1H), 6.82 (d, 1H), 4.88 (bs, 1H), 4.71 (bs, 1H), 4.28-4.25 (m, 1H), 3.96-3.90 (m, 3H), 3.85-3.82 (m, 1H), 3.49 (bs, 1H), 3.19-3.13 (m, 2H), 1.97-1.92 (m, 2H), 1.83-1.74 (m, 3H), 1.60 (s, 1H), 1.45 (s, 9H); MS: m/z 352.8 [M+H]$^+$.

Step 2: HCl/dioxane (4M, 2.5 mL) was added at 0° C. to a solution of tert-butyl ((3R)-3-hydroxy-3-(3-((tetrahydrofuran-2-yl)methoxy)phenyl)propyl)carbamate (0.25 g, 0.71 mmol) in DCM (10 mL) and the reaction mixture was stirred at room temperature for 2 h. After completion of the reaction the solvent was removed under reduced pressure. Purification by column chromatography (MeOH:DCM with 1% aq. NH$_4$OH, 1-10% gradient) gave Example 14 as a mixture of diastereomers as an off white semi-solid. Yield (0.22 g, 95%); $^1$H NMR (400 MHz, DMSO-d$_6$): δ 7.20 (t, J=8.0 Hz, 1H), 6.87 (d, J=8.0 Hz, 2H), 6.78-6.76 (m, 1H), 4.64-4.61 (m, 1H), 4.15-4.11 (dd, 1H), 3.93-3.87 (m, 2H), 3.78-3.75 (m, 1H), 3.70-3.64 (m, 1H), 2.69-2.66 (m, 2H), 2.01-1.95 (m, 1H), 1.88-1.79 (m, 2H), 1.70-1.65 (dd, J=6.8 Hz, 3H); MS: m/z 252.14 [M+H]$^+$.

Example 15

Preparation of (R)-3-amino-1-(3-(piperidin-4-ylmethoxy)phenyl)propan-1-ol

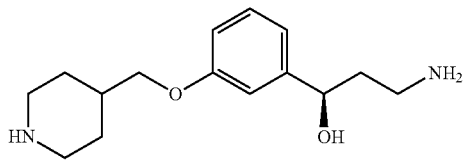 [SMILES: NCC[C@@H](O)c1cccc(OCC2CCNCC2)c1]

(R)-3-Amino-1-(3-(piperidin-4-ylmethoxy)phenyl)propan-1-ol was prepared following the method used in Example 11.

Step 1: Reaction between phenol (7, Intermediate I) and tert-butyl 4-((tosyloxy)methyl)piperidine-1-carboxylate following the method used in Example 11 gave (R)-tert-butyl 4-((3-(3-((tert-butoxycarbonyl)amino)-1-hydroxypropyl)phenoxy)methyl)piperidine-1-carboxylate as a colorless oil. Yield (53%); $^1$H NMR (400 MHz, CDCl$_3$): δ 3.49 (d, J=2.0 Hz, 2H), 2.69 (t, J=11.6 Hz, 2H), 1.72 (s, 2H), 1.70 (d, J=14.0 Hz, 1H), 1.51-1.49 (m, 2H), 1.44 (s, 9H), 1.13 (dq, J=4.40, 8.0 Hz, 2H); MS: m/z 317.18 [M+H]$^+$.

Step 2: Deprotection of (R)-tert-butyl 4-((3-(3-((tert-butoxycarbonyl)amino)-1-hydroxypropyl)phenoxy)methyl)piperidine-1-carboxylate following the method used in Example 11 gave Example 15 dihydrochloride as a white solid. Yield (98%); $^1$H NMR (400 MHz, DMSO-d$_6$); δ 8.74 (d, J=20.8 Hz, 1H), 8.58 (d, J=35 Hz, 2H), 7.79 (s, 2H), 7.25 (t, J=8 Hz, 1H), 6.89 (d, J=7.2 Hz, 1H), 6.82 (d, J=7.2 Hz, 1H), 5.53 (d, J=4.4 Hz, 1H), 4.65 (t, J=4.4 Hz, 1H), 3.84 (d, J=6.4 Hz, 1H), 3.25 (s, 3H), 3.16-2.83 (m, 4H), 2.65 (s, 1H), 1.98-1.75 (m, 3H), 1.52-1.44 (m, 1H), 1.36-1.14 (s, 1H); MS: m/z 265.05 [M+H]$^+$.

Example 16

Preparation of (R)-3-amino-1-(3-((1-methylpiperidin-4-yl)methoxy)phenyl)propan-1-ol

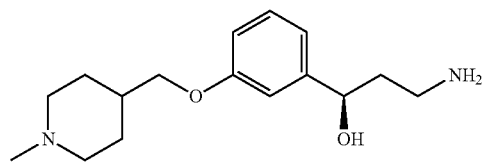 [SMILES: CN1CCC(COc2cccc([C@H](O)CCN)c2)CC1]

(R)-3-Amino-1-(3-((1-methylpiperidin-4-yl)methoxy)phenyl)propan-1-ol was prepared following the method used in Example 11.

Step 1: Tosylation of tert-butyl 4-(hydroxymethyl)piperidine-1-carboxylate following the method used in Example 11 gave tert-butyl 4-((tosyloxy)methyl)piperidine-1-carboxylates a colorless oil. Yield (1.5 g, 88%).

Step 2: Alkylation of phenol (7, Intermediate I) with tert-butyl 4-((tosyloxy)methyl)piperidine-1-carboxylate following the method used in Example 11 gave (R)-tert-butyl 4-((3-(3-((tert-butoxycarbonyl)amino)-1-hydroxypropyl)phenoxy)methyl)piperidine-1-carboxylate as a colorless oil. Yield (0.70 g, 80%).

Step 3: (R)-tert-Butyl 4-((3-(3-((tert-butoxycarbonyl)amino)-1-hydroxypropyl)phenoxy)methyl)piperidine-1-carboxylate (0.70 g, 1.50 mmol) was added at 0° C. to a suspension of LiAlH$_4$ (0.171 g, 4.5 mmol) in anhydrous THF (10 mL) and the reaction mixture was stirred at room temperature for 1 h. After completion of the reaction as judged by TLC, the reaction mixture was quenched with EtOAc (10 mL) and 10% aqueous NaOH, filtered through Celite, dried over anhydrous Na$_2$SO$_4$ and concentrated under reduced pressure. Purification by column chromatography (CH$_2$Cl$_2$-10% MeOH: CH$_2$Cl$_2$, 0-5% gradient) gave (R)-tert-butyl (3-hydroxy-3-(3-((1-methylpiperidin-4-yl)methoxy)phenyl)propyl) carbamate as a pale yellow semi-solid. Yield (0.50 g, 87%); $^1$H NMR (400 MHz, CDCl$_3$): δ 7.22 (t, J=4.40 Hz, 1H), 6.92 (s, 2H), 6.76 (d, J=8.0 Hz, 1H), 4.31 (s, 1H), 3.85 (d, J=5.6 Hz, 2H), 3.69 (s, 1H), 3.27 (d, J=6.8 Hz, 2H), 2.58 (s, 2H), 2.46 (s, 2H), 2.04-1.91 (m, 4H), 1.84 (t, J=5.20 Hz, 4H), 1.70-1.67 (m, 1H), 1.45 (s, 9H); MS: m/z 379.28 [M+H]$^+$.

Step 4: Deprotection of (R)-tert-butyl (3-hydroxy-3-(3-((1-methylpiperidin-4-yl)methoxy)phenyl)propyl)carbamate following the method used in Example 11 gave Example 16 hydrochloride as a white solid. Yield (0.40 g, 97%); $^1$H NMR (400 MHz, DMSO-d$_6$): δ 7.99 (bs, 2H), 7.24 (t, J=7.6 Hz, 1H), 6.89 (d, J=7.6 Hz, 2H), 6.81 (d, J=7.60 Hz, 1H), 4.65 (dd, J=7.2, 4.4 Hz, 1H), 3.82 (d, J=6 Hz, 2H), 3.38 (t, J=7.2 Hz, 2H), 3.09 (s, 2H), 2.81 (s, 2H), 2.45 (s, 3H), 1.84 (d, J=10 Hz, 5H), 1.86 (d, J=10.8 Hz, 2H), 1.08 (t, J=7.2 Hz, 1H).

Example 17

Preparation of (R)-methyl 4-((3-(3-amino-1-hydroxypropyl)phenoxy)methyl)piperidine-1-carboxylate

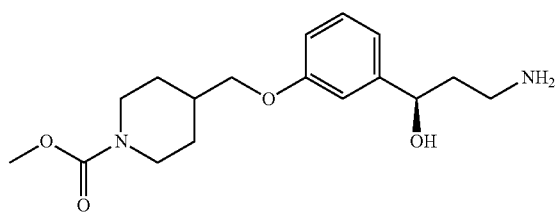 [SMILES: COC(=O)N1CCC(COc2cccc([C@H](O)CCN)c2)CC1]

(R)-Methyl 4-((3-(3-amino-1-hydroxypropyl)phenoxy)methyl)piperidine-1-carboxylate was prepared following the method used in Examples 16 and 11.

Step 4: Deprotection of (R)-methyl 4-((3-(3-((tert-butoxycarbonyl)amino)-1-hydroxypropyl)phenoxy)methyl)piperidine-1-carboxylate following the method used in Example 11 gave Example 17 hydrochloride as a white solid. Yield (89%); $^1$H NMR (400 MHz, DMSO-d$_6$): δ 7.18 (t, J=8.0 Hz, 1H), 6.86 (d, J=7.6 Hz, 2H), 6.75 (d, J=7.2 Hz, 1H), 4.62 (t, J=6.0 Hz, 1H), 4.00 (s, 2H), 3.80 (d, J=6.4 Hz, 2H), 3.58 (s, 3H), 2.80 (s, 2H), 2.66-2.60 (m, 2H), 1.92 (s, 1H), 1.76 (d, J=13.2 Hz, 2H), 1.62 (dd, J=12.4, 6.4 Hz, 2H), 1.16 (dd, J=20.4, 8.8 Hz, 2H); MS: m/z 323.13 [M+H]$^+$.

Example 18

Preparation of (R)-3-amino-1-(3-(pyrimidin-5-ylmethoxy)phenyl)propan-1-ol

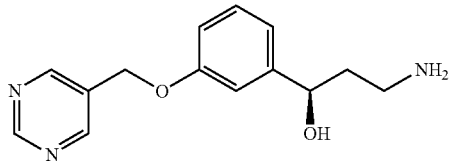 [SMILES: NCC[C@@H](O)c1cccc(OCc2cncnc2)c1]

(R)-3-Amino-1-(3-(pyrimidin-5-ylmethoxy)phenyl)propan-1-ol was prepared following the method below and described in Example 6.

Step 1: A solution of pyrimidin-5-ylmethanol (1.0 g, 9.08 mmol) in DCM (20 mL) was cooled to 0° C. PPh$_3$ (2.61 g, 9.99 mmol) and CBr$_4$ (3.3 g, 9.99 mmol) were added to the reaction mixture and the latter was stirred for 1 h at room temperature. The reaction mixture was extracted with EtOAc, dried over anhydrous Na$_2$SO$_4$ and concentrated under reduced pressure. Purification by flash chromatography (80% EtOAc in hexane) gave 5-(bromomethyl)pyrimidine as a pale yellow liquid. Yield (1.2 g, 60%); $^1$H NMR (400 MHz, DMSO-d$_6$); δ 9.13 (s, 1H), 8.92 (s, 2H), 4.74 (s, 2H).

Step 2: Alkylation of phenol (7, Intermediate I) with 5-(bromomethyl)pyrimidine following the method used in Example 6 gave after purification by flash chromatography (50-60% EtOAc in hexane gradient) (R)-tert-butyl (3-hydroxy-3-(3-(pyrimidin-5-ylmethoxy)phenyl)propyl)carbamate as a yellow semi-solid. Yield (1.4 g, 63%); $^1$H NMR (400 MHz, CDCl$_3$) δ 9.21 (s, 1H), 8.83 (s, 2H), 7.28 (m, 1H), 7.05 (s, 1H), 6.98 (d, J=7.6 Hz, 1H), 6.87 (d, J=8.0 Hz, 1H), 5.09 (s, 2H), 4.88 (bs, 1H), 4.74 (d, J=6.0 Hz, 1H), 3.52 (bs, 2H), 3.19-3.14 (m, 1H), 1.86-1.81 (m, 2H), 1.45 (s, 9H).

Step 3: Deprotection of (R)-tert-butyl (3-hydroxy-3-(3-(pyrimidin-5-ylmethoxy)phenyl)propyl)carbamate following the method used in Example 6 gave after trituration in diethyl ether Example 18 hydrochloride as a white solid. Yield (0.36 g, 100%); $^1$H NMR (400 MHz, DMSO-d$_6$) δ 9.18 (s, 1H), 8.92 (s, 2H), 7.73 (bs, 3H), 7.29 (t, J=8.0 Hz, 1H), 7.02 (s, 1H), 6.94 (d, J=8.0 Hz, 2H), 5.18 (s, 2H), 4.67 (s, 1H), 2.84 (bs, 2H), 1.86-1.81 (m, 2H).

Example 19

Preparation of (1R)-3-amino-1-(3-(chroman-3-ylmethoxy)phenyl)propan-1-ol

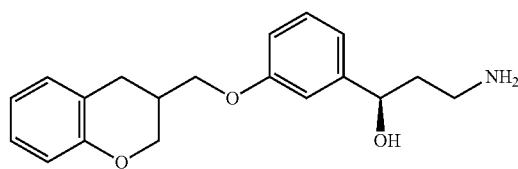 [SMILES: NCC[C@@H](O)c1cccc(OCC2COc3ccccc3C2)c1]

(1R)-3-Amino-1-(3-(chroman-3-ylmethoxy)phenyl)propan-1-ol was prepared following the method used in Example 12.

Step 1: Alkylation of phenol (7, Intermediate I) with chroman-3-ylmethyl 4-methylbenzenesulfonate following the method used in Example 12 gave tert-butyl ((3R)-3-(3-(chroman-3-ylmethoxy)phenyl)-3-hydroxypropyl)carbamate as a colorless oil. Yield (71%); $^1$H NMR (400 MHz, DMSO-d$_6$) δ 7.21 (t, J=7.6 Hz, 1H), 7.10-7.05 (m, 2H), 6.91 (s, 1H), 6.88 (d, J=7.6 Hz, 1H), 6.85-6.83 (m, 1H), 6.81-6.79 (m, 1H), 6.75 (d, J=8.4 Hz, 1H), 5.19 (d, J=4.8 Hz, 1H), 4.53-4.48 (m, 1H), 4.31-4.28 (m, 1H), 3.99-3.91 (m, 2H), 2.98-2.93 (m, 2H), 2.92-2.90 (m, 1H), 2.71-2.69 (m, 2H), 1.66 (q, J=6.8 Hz, 2H), 1.36 (s, 9H).

Step 2: Deprotection of tert-butyl ((3R)-3-(3-(chroman-3-ylmethoxy)phenyl)-3-hydroxypropyl)carbamate following the method used in Example 12 Example 19 hydrochloride as a mixture of diastereomers as a white solid. Yield (99%); $^1$H NMR (400 MHz, DMSO-d$_6$) δ 7.66 (bs, 3H), 7.25 (t, J=8.0 Hz, 1H), 7.09 (t, J=7.2 Hz, 1H), 7.05 (s, 1H), 6.93-6.89 (m, 2H), 6.86-6.82 (m, 2H), 6.76 (d, J=8.4 Hz, 1H), 5.53 (d, J=4.4 Hz, 1H), 4.66-4.64 (m, 1H), 4.29 (d, J=10.4 Hz, 1H), 4.05-3.92 (m, 3H), 2.96-2.95 (m, 1H), 2.92-2.81 (m, 2H), 2.73-2.65 (m, 2H), 1.87-1.80 (m, 2H).

Example 20

Preparation of (R)-4-((3-(3-amino-1-hydroxypropyl)phenoxy)methyl)tetrahydro-2H-thiopyran 1-oxide

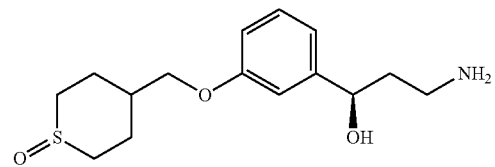 [SMILES: NCC[C@@H](O)c1cccc(OCC2CCS(=O)CC2)c1]

(R)-4-((3-(3-Amino-1-hydroxypropyl)phenoxy)methyl) tetrahydro-2H-thiopyran-1-oxide was prepared following the method used in Example 8.

Step 1: FeCl₃ (3.0 mg, 0.023 mmol) was added at room temperature to a stirred solution of (R)-tert-butyl (3-hydroxy-3-(3-((tetrahydro-2H-thiopyran-4-yl)methoxy)phenyl)propyl)carbamate (0.22 g, 0.576 mmol) in CH₃CN (3 mL) followed by HIO₄ (0.132 g, 0.691 mmol). The reaction mixture was stirred for 2 min, quenched by the addition of an aqueous solution of sodium thiosulfate (20%, 5 mL), extracted with EtOAc (50 mL) and dried over Na₂SO₄. Concentration in vacuo gave (R)-tert-butyl (3-hydroxy-3-(3-((1-oxidotetrahydro-2H-thiopyran-4-yl)methoxy)phenyl)propyl)carbamate as a pale yellow semi-solid. Yield (0.13 g, 57%). The crude was carried forward to the next step without additional purification.

Step 2: HCl/dioxane (4M, 1 mL) was added at 0° C. to a solution of (R)-tert-butyl (3-hydroxy-3-(3-((1-oxidotetrahydro-2H-thiopyran-4-yl)methoxy)phenyl)propyl)carbamate (0.12 g, 0.30 mmol) in CH₂Cl₂ (2 mL) and the reaction mixture was stirred at room temperature for 30 min. After completion of the reaction (as judged by TLC) the solvent was removed in vacuo. The compound was purified by preparative HPLC to give Example 20 as a colorless semi-solid. Yield (70.7 mg, 77%); MS: m/z 298.14 [M+H]⁺.

Example 21

Preparation of (R)-3-amino-1-(3-(((S)-1-methylpyrrolidin-2-yl)methoxy)phenyl)propan-1-ol

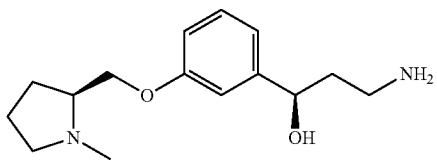 [SMILES: CN1CCC[C@H]1COc1cccc([C@H](O)CCN)c1]

(R)-3-Amino-1-(3-(((S)-1-methylpyrrolidin-2-yl)methoxy)phenyl)propan-1-ol was prepared following the method described below.

Step 1: A mixture of (S)-tert-butyl 2-((tosyloxy)methyl) pyrrolidine-1-carboxylate (1.6 g, 5.4 mmol), phenol (7, Intermediate I) (0.8 g, 2.9 mmol), t-BuO⁻K⁺ (0.5 g, 4.5 mmol) in anhydrous DMF (5 mL) was heated at +45° C. for 16 hrs. The reaction mixture was concentrated under reduced pressure, partitioned between EtOAc and 5% NaOH, organic layer was dried over anhydrous Na₂SO₄, concentrated under reduced pressure. Purification by column chromatography gave (S)-tert-butyl 2-((3-((R)-3-((tert-butoxycarbonyl)amino)-1-hydroxypropyl)phenoxy)methyl)pyrrolidine-1-carboxylate as a light yellow oil. Yield (0.8 g, 59%).

Step 2: Anhydrous THF (5 mL) was cooled to 0° C. and LiAlH₄ (0.016 g, 0.44 mmol) was added. (S)-tert-butyl 2-((3-((R)-3-((tert-butoxycarbonyl)amino)-1-hydroxypropyl)phenoxy)methyl)pyrrolidine-1-carboxylate (0.1 g, 0.22 mmol) was slowly added to reaction mixture and then kept at room temperature for 4 hrs. After completion of reaction as judged by TLC (10% MeOH/CH₂Cl₂) the reaction mixture was quenched by addition followed by saturated Na₂SO₄, extracted with EtOAc and organic layer was concentrated under reduced pressure to give tert-butyl ((R)-3-hydroxy-3-(3-(((S)-1-methylpyrrolidin-2-yl)methoxy)phenyl)propyl) carbamate as a light yellow oil which was used in the next step without additional purification. Yield (0.060 g, 75%).

Step 3: To a solution of tert-butyl ((R)-3-hydroxy-3-(3-(((S)-1-methylpyrrolidin-2-yl)methoxy)phenyl)propyl)carbamate (0.32 g, 0.87 mmol) in DCM (10 mL) was added HCl/dioxane (4 mL) at 0° C. and the reaction mixture was stirred at rt for 2 h. After completion of the reaction the solvent was removed in vacuo. The compound was purified by prep HPLC to obtain (R)-3-Amino-1-(3-(((S)-1-methylpyrrolidin-2-yl)methoxy)phenyl)propan-1-ol (Example 21) as a yellow semi solid. Yield (0.18 g, 68%); ¹H NMR (400 MHz, CD₃OD) δ 7.29 (t, J=8.0 Hz, 1H), 7.01-6.97 (m, 2H), 6.89-6.87 (m, 1H), 4.82-4.80 (m, 1H), 4.10-4.04 (m, 2H), 3.10-3.02 (m, 3H), 2.68 (s, 3H), 2.65-2.58 (m, 1H), 2.18-2.15 (m, 1H), 2.03-2.01 (m, 2H), 1.99-1.94 (m, 3H), 1.84-1.77 (m, 1H). MS: m/z 265.22 [M+H]⁺.

Example 22

Preparation of (R)-3-amino-1-(3-((S)-pyrrolidin-2-ylmethoxy)phenyl)propan-1-ol hydrochloride

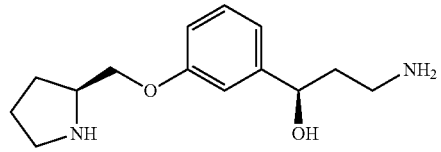 [SMILES: NCC[C@@H](O)c1cccc(OC[C@@H]2CCCN2)c1]

(R)-3-Amino-1-(3-((S)-pyrrolidin-2-ylmethoxy)phenyl)propan-1-ol was prepared following the method used in Example 21 and below.

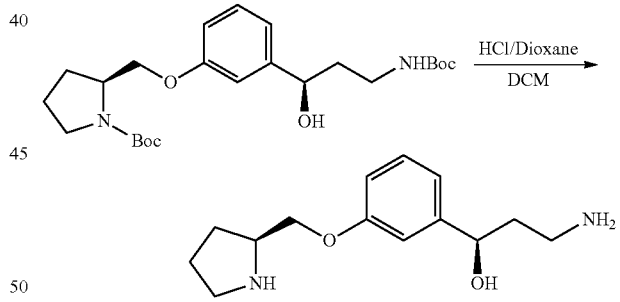

Step 1: To a solution of (S)-tert-butyl 2-((3-((R)-3-((tert-butoxycarbonyl)amino)-1-hydroxypropyl)phenoxy)methyl)pyrrolidine-1-carboxylate (0.3 g, 0.66 mmol) in DCM (10 mL) was added HCl/dioxane (3 mL) at 0° C. and the reaction mixture was stirred at rt for 2 h. After completion of the reaction the solvent was removed in vacuo. The residue was purified by prep HPLC to give (R)-3-Amino-1-(3-((S)-pyrrolidin-2-ylmethoxy)phenyl)propan-1-ol (Example 22) as a white solid. Yield (0.18 g, 89%); ¹H NMR (400 MHz, CD₃OD) δ 7.31 (t, J=8.0 Hz, 1H), 7.07 (s, 1H), 7.03 (d, J=7.6 Hz, 1H), 6.93 (d, J=8.0 Hz, 1H), 4.83-4.82 (m, 1H), 4.35 (dd, J=10.4, 3.2 Hz, 1H), 4.17-4.12 (m, 1H), 4.05-4.03 (m, 1H), 3.39-3.36 (m, 2H), 3.14-3.01 (m, 2H), 2.32-2.18 (m, 1H), 2.16-2.08 (m, 2H), 2.06-1.87 (m, 3H). MS: m/z 251.28 [M+H]⁺.

Example 23

Preparation of (R)-3-amino-1-(3-(((tetrahydro-2H-pyran-4-yl)methyl)amino)phenyl)propan-1-ol

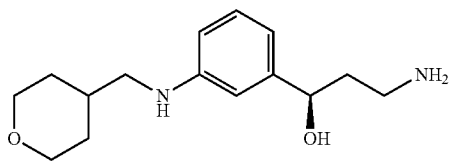 [SMILES: NCC[C@@H](O)c1cccc(NCC2CCOCC2)c1]

(R)-3-Amino-1-(3-(((tetrahydro-2H-pyran-4-yl)methyl)amino)phenyl)propan-1-ol was prepared following the method below.

Step 1: CH$_3$COOH (1 mL) was added to a solution of tetrahydro-2H-pyran-4-carbaldehyde (0.7 g, 6.12 mmol) and (R)-3-(3-aminophenyl)-3-hydroxypropanenitrile (1.0 g, 6.12 mmol) in CH$_2$Cl$_2$ (20 mL) at 0° C. followed by the addition of Na(OAc)$_3$BH (3.89 g, 18.34 mmol). The reaction mixture was stirred at room temperature overnight. The reaction mixture was diluted with NaHCO$_3$ (50 mL), extracted with EtOAc (200 mL), organic layer was dried over anhydrous Na$_2$SO$_4$ and concentrated under reduced pressure. Purification by flash chromatography (50% EtOAc: hexanes) gave (R)-3-hydroxy-3-(3-(((tetrahydro-2H-pyran-4-yl)methyl)amino)phenyl)propanenitrile as a pale yellow liquid. Yield (1.0 g, 63%); $^1$H NMR (400 MHz, DMSO-d$_6$) δ 7.02 (t, J=8.0 Hz, 1H), 6.62 (s, 1H), 6.51 (d, J=7.2 Hz, 1H), 6.47 (d, J=7.6 Hz, 1H), 5.77 (d, J=4.4 Hz, 1H), 5.68 (t, J=5.2 Hz, 1H), 4.73 (dd, J=10.8, 4.8 Hz, 1H), 3.85 (dd, J=10.8, 2.8 Hz, 2H), 3.26 (t, J=11.2 Hz, 2H), 2.89 (t, J=6.0 Hz, 2H), 2.82 (dd, J=16.8, 4.8 Hz, 1H), 2.73 (dd, J=16.8, 6.8 Hz, 1H), 1.81-1.75 (m, 1H), 1.66 (d, J=12.8 Hz, 2H), 1.23-1.19 (m, 2H).

Step 2: BH$_3$-Me$_2$S complex (0.4 mL) was added to a solution of (R)-3-hydroxy-3-(3-(((tetrahydro-2H-pyran-4-yl)methyl)amino)phenyl)propanenitrile (0.5 g, 1.92 mmol) in THF (20 mL). The reaction mixture was heated at 80° C. under reflux for 18 h. The reaction mixture was quenched with MeOH (10 mL) followed by HCl/dioxane (4N, 0.5 mL). The mixture was heated at 60° C. for 1 h and concentrated under reduced pressure to give Example 23 hydrochloride as a pale yellow oil. Yield (0.4 g, 80%); $^1$H NMR (400 MHz, CD$_3$OD) δ 7.59-7.51 (m, 3H), 7.42 (d, J=8.0 Hz, 1H), 4.93-4.91 (m, 2H), 3.97 (dd, J=11.2, 3.6 Hz, 2H), 3.42 (t, J=10.4 Hz, 2H), 3.33-3.29 (m, 2H), 3.12 (q, J=6.8 Hz, 2H), 2.11-2.03 (m, 2H), 2.01-1.93 (m, 1H), 1.75 (d, J=13.2 Hz, 1H), 1.43 (dq, J=12.0, 4.4 Hz, 2H).

Intermediate II

Preparation of S-(3-(3-((tert-butoxycarbonyl)amino)propanoyl)phenyl)benzothioate

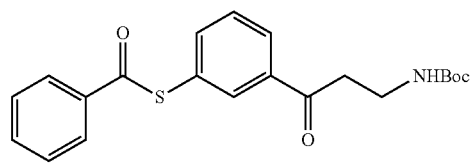 [SMILES: CC(C)(C)OC(=O)NCCC(=O)c1cccc(SC(=O)c2ccccc2)c1]

S-(3-(3-((tert-butoxycarbonyl)amino)propanoyl)phenyl)benzothioate was prepared following the method shown in Scheme 4:

Scheme 4

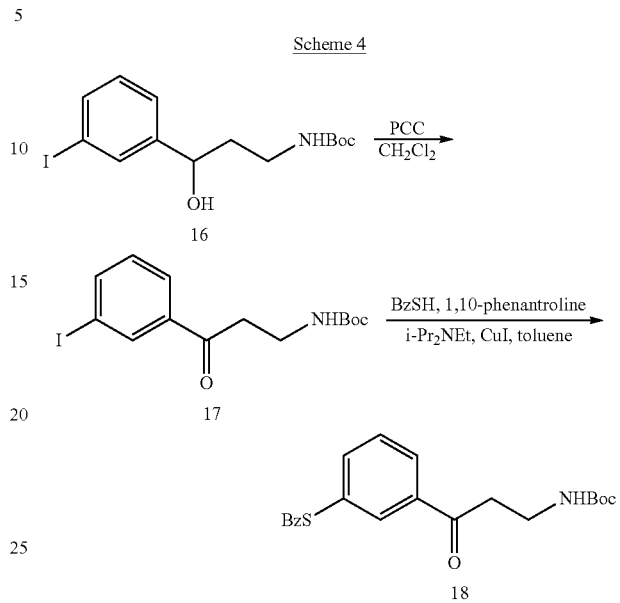

Step 1: Molecular sieves (20.0 g) and PCC (28.0 g, 127 mmol) were added portionwise to a stirred solution of tert-butyl (3-hydroxy-3-(3-iodophenyl)propyl)carbamate (16) (40.0 g, 106 mmol) in anhydrous CH$_2$Cl$_2$ (500 mL) under argon atmosphere at 0° C. The reaction mixture was allowed to warm to room temperature and stirred for 20 min. The reaction mixture was concentrated under reduced pressure, the residue was dissolved in water (300 mL), extracted with EtOAc (2×300 mL), washed with brine (300 mL), dried over anhydrous Na$_2$SO$_4$ and concentrated under reduced pressure. Purification by flash chromatography (100-200 silica mesh, 15-20% EtOAc-hexane) gave tert-butyl (3-(3-iodophenyl)-3-oxopropyl)carbamate (17) as a pale yellow oil. Yield (21.0 g, 54%); $^1$H NMR (400 MHz, CDCl$_3$) δ 8.27 (s, 1H), 7.95-7.91 (m, 2H), 7.21 (t, J=8.0 Hz, 1H), 3.57-3.51 (m, 2H), 3.18-3.12 (m, 2H), 1.83-1.76 (m, 1H), 1.45 (s, 9H); MS: m/z 378.12 [M+H]$^+$.

Step 2: BzSH (8.84 g, 63.9 mmol), 1,10-phenanthroline (1.92 g, 10.7 mmol) and i-Pr$_2$NEt (13.8 g, 106 mmol) were added to a stirred solution of aryl iodide (17) (20.0 g, 53.3 mmol) in toluene (200 mL) and the reaction mixture was degassed by bubbling argon for 10 min. CuI (1.0 g, 5.3 mmol) was added to the resulting reaction mixture and the mixture was heated at 110° C. for 18 h. After the completion of the reaction (monitored by TLC), the reaction mixture was concentrated under reduced pressure. Purification by column chromatography (100-200 silica mesh, 10-20% EtOAc-hexanes) gave S-(3-(3-((tert-butoxycarbonyl)-amino)propanoyl)phenyl)benzothioate (18, Intermediate II) as an off white solid. Yield (18.0 g, 87%); $^1$H NMR (400 MHz, DMSO-d$_6$): δ 8.07-8.05 (m, 2H), 8.01-7.99 (m, 2H), 7.81-7.74 (m, 2H), 7.69-7.60 (m, 3H), 6.82 (bs, 1H), 3.31-3.27 (m, 2H), 3.20-3.17 (m, 2H), 1.35 (s, 9H); MS: m/z 385.66 [M+H]$^+$.

Example 24

Preparation of 3-amino-1-(3-(((1,1-dioxidotetrahydro-2H-thiopyran-4-yl)methyl)sulfonyl)phenyl)propan-1-one

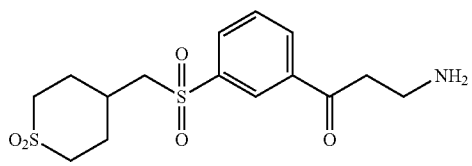 [SMILES: NCCC(=O)c1cccc(S(=O)(=O)CC2CCS(=O)(=O)CC2)c1]

3-Amino-1-(3-(((1,1-dioxidotetrahydro-2H-thiopyran-4-yl)methyl)sulfonyl)phenyl)propan-1-one was prepared following the method used in Example 8, Intermediate II and below.

Step 1: $K_2CO_3$ (1.61 g, 11.67 mmol) was added at 0° C. to a solution of thioester (18, Intermediate II) (1.5 g, 3.89 mmol) in MeOH (20 mL) followed by $NaBH_4$ (222 mg, 5.84 mmol). The reaction mixture was allowed to warm to room temperature and stirred for 30 min. The solvent was removed under reduced pressure. The residue was dissolved in DMF (10 mL), $K_2CO_3$ (1.16 g, 11.67 mmol), $NaBH_4$ (222 mg, 5.84 mmol) and (tetrahydro-2H-thiopyran-4-yl)methyl 4-methylbenzenesulfonate (1.15 g, 4.27 mmol) were added and the resulting mixture was heated at 90° C. under reflux overnight. The reaction mixture was diluted with EtOAc and washed with water and brine solution, dried over anhydrous $Na_2SO_4$ and concentrated under reduced pressure. Purification by column chromatography (40% EtOAc-hexanes) gave tert-butyl (3-hydroxy-3-(3-(((tetrahydro-2H-thiopyran-4-yl)methyl)thio)phenyl)propyl)carbamate as a dark brown liquid. Yield (0.67 g, 45%); $^1$H NMR (400 MHz, $CDCl_3$) δ 7.37-7.32 (m, 1H), 7.23-7.22 (m, 1H), 7.20 (s, 1H), 7.17-7.14 (m, 1H), 4.71 (s, 1H), 4.65 (s, 1H), 3.48-3.46 (m, 1H), 3.38 (s, 1H), 3.18-3.15 (m, 1H), 2.84-2.81 (m, 2H), 2.22-2.19 (m, 2H), 2.09-2.04 (m, 2H), 1.85-1.80 (m, 2H), 1.57 (s, 1H), 1.45 (s, 9H), 1.41-1.37 (m, 2H), 1.37-1.27 (m, 2H); MS: m/z 398.16 $[M+H]^+$.

Step 2: Ammonium molybdate (0.99 g, 0.50 mmol) was added to a solution of tert-butyl (3-hydroxy-3-(3-(((tetrahydro-2H-thiopyran-4-yl)methyl)thio)phenyl)propyl)carbamate (670 mg, 1.68 mmol) in EtOH (10 mL) followed by hydrogen peroxide (0.2 mL) at 0° C. and the reaction mixture was stirred at rt for 2 h. The reaction mixture was concentrated under reduced pressure to give after purification by column chromatography (50-60% EtOAc-hexanes) tert-butyl (3-(3-(((1,1-dioxidotetrahydro-2H-thiopyran-4-yl)methyl)sulfonyl)phenyl)-3-hydroxypropyl)carbamate as a pale yellow liquid. Yield (0.65 g, 97%); $^1$H NMR (400 MHz, $CDCl_3$) δ 7.93 (s, 1H), 7.79 (d, J=7.2 Hz, 1H), 7.71 (s, 1H), 7.58-7.53 (s, 1H), 4.86-4.82 (m, 2H), 4.29 (s, 1H), 3.65-3.52 (m, 1H), 3.29-3.20 (m, 2H), 2.91-2.79 (m, 1H), 2.36 (m, 4H), 2.04 (s, 3H), 1.84 (bs, 1H), 1.75-1.72 (m, 1H), 1.46 (s, 9H), 1.42 (s, 1H), 1.31-1.25 (m, 1H); MS: m/z 462.03 $[M+H]^+$.

Step 3: Pyridinium chlorochromate (218 mg, 1.01 mmol) and molecular sieves were added to a solution of tert-butyl (3-(3-(((1,1-dioxidotetrahydro-2H-thiopyran-4-yl)methyl)sulfonyl)phenyl)-3-hydroxypropyl)carbamate (650 mg, 1.40 mmol) in $CH_2Cl_2$ (20 mL) and the reaction mixture was stirred at room temperature for 2 h. The reaction mixture was filtered through a Celite, the filtrate was diluted with EtOAc, dried over anhydrous $Na_2SO_4$ and concentrated under reduced pressure. Purification by flash chromatography (60% EtOAc-hexanes gradient) gave tert-butyl (3-(3-(((1,1-dioxidotetrahydro-2H-thiopyran-4-yl)methyl)sulfonyl)phenyl)-3-oxopropyl)carbamate as a colorless liquid. Yield (0.438 g, 67%); $^1$H NMR (400 MHz, DMSO-$d_6$): δ 8.36 (s, 1H), 8.28 (d, J=7.6 Hz, 1H), 8.16 (d, J=7.6 Hz, 1H), 7.83 (t, J=8.0 Hz, 1H), 6.87 (s, 1H), 3.51 (d, J=6.4 Hz, 2H), 3.32-3.28 (m, 4H), 3.28-3.23 (m, 2H), 3.20-3.13 (m, 1H), 3.04-3.01 (m, 1H), 2.32 (bs, 1H), 2.17-2.14 (m, 2H), 1.85-1.76 (m, 2H), 1.35 (s, 9H); MS: m/z 460.23 $[M+H]^+$.

Step 4: HCl/dioxane (4N, 5 mL) was added at 0° C. to a solution of tert-butyl (3-(3-(((1,1-dioxidotetrahydro-2H-thiopyran-4-yl)methyl)sulfonyl)phenyl)-3-oxopropyl)carbamate (0.40 g, 0.87 mmol) in $CH_2Cl_2$ (10 mL) and the reaction mixture was stirred at room temperature for 2 h. The reaction mixture was concentrated under reduced pressure to give after purification by preparative HPLC Example 24 as a white solid. Yield (200 mg, 50%); $^1$H NMR (400 MHz, DMSO-$d_6$) δ 8.39 (s, 1H), 8.31 (d, J=7.6 Hz, 1H), 8.20 (d, J=7.6 Hz, 1H), 7.88 (m, 4H), 3.56-3.52 (m, 2H), 3.50-3.47 (m, 2H), 3.20-3.17 (m, 4H), 3.05-3.02 (m, 2H), 2.31 (bs, 1H), 2.17-2.14 (m, 2H), 1.85-1.77 (m, 2H); MS: m/z 360.18 $[M+H]^+$.

Example 25

Preparation of 3-amino-1-(3-(((tetrahydro-2H-pyran-3-yl)methyl)sulfonyl)phenyl)propan-1-one

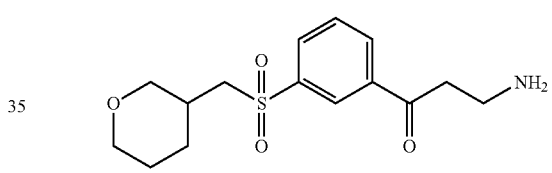

3-Amino-1-(3-(((tetrahydro-2H-pyran-3-yl)methyl)sulfonyl)phenyl)propan-1-one was prepared following the method used in Example 24 and below.

Step 1: Reaction between (tetrahydro-2H-pyran-3-yl)methyl 4-methylbenzenesulfonate and thioester (18, Intermediate II) following the method used in Example 24 gave after purification by flash chromatography using 50%-60% EtOAc-hexanes tert-butyl (3-hydroxy-3-(3-(((tetrahydro-2H-pyran-3-yl)methyl)thio)phenyl)propyl)carbamate as a pale yellow liquid. Yield (512 mg, 35%); $^1$H NMR (400 MHz, $CDCl_3$) δ 8.01 (s, 1H), 7.34 (s, 1H), 7.23 (s, 1H), 7.21 (s, 1H), 7.19-7.14 (m, 1H), 4.90 (s, 1H), 4.75 (s, 1H), 3.95 (s, 1H), 3.83-3.80 (m, 1H), 3.41-3.38 (m, 3H), 3.24-3.11 (m, 2H), 2.82 (d, J=8.0 Hz, 2H), 2.02 (m, 1H), 1.84-1.80 (m, 1H), 1.64-1.55 (m, 2H), 1.45 (s, 9H), 1.36-1.34 (m, 2H); MS: m/z 382.18 $[M+H]^+$.

Step 2: Oxidation of tert-butyl (3-hydroxy-3-(3-(((tetrahydro-2H-pyran-3-yl)methyl)thio)phenyl)propyl)carbamate following the method used in Example 24 gave after purification by flash chromatography using 60%-70% EtOAc-hexanes tert-butyl (3-hydroxy-3-(3-(((tetrahydro-2H-pyran-3-yl)methyl)sulfonyl)phenyl)propyl)carbamate as a pale yellow solid. Yield (0.42 g, 83%); $^1$H NMR (400 MHz, $CDCl_3$) δ 7.91 (s, 1H), 7.80 (d, J=8.0 Hz, 1H), 7.71 (d, J=4.0 Hz, 1H), 7.56-7.54 (m, 1H), 2.26 (bs, 1H), 1.98-1.96 (m, 2H), 1.86-1.82 (m, 1H), 1.76-1.72 (m, 2H), 1.60-1.58 (m, 2H), 1.58-1.57 (m, 2H), 1.45 (s, 9H), 1.39 (m, 2H), 1.33 (m, 1H), 1.30 (s, 1H), 1.28-1.25 (m, 2H); MS: m/z 414.10 $[M+H]^+$.

Step 3: Oxidation of tert-butyl (3-hydroxy-3-(3-(((tetrahydro-2H-pyran-3-yl)methyl)sulfonyl)phenyl)propyl)carbamate following the method used in Example 24 gave after purification by flash chromatography using 60% EtOAc-hexanes tert-butyl (3-oxo-3-(3-(((tetrahydro-2H-pyran-3-yl)methyl)sulfonyl)phenyl)propyl)carbamate as a colorless oil. Yield (0.18 g, 42%); $^1$H NMR (400 MHz, DMSO-d$_6$) δ 8.36 (s, 1H), 8.28 (d, J=8.4 Hz, 1H), 8.16 (d, J=7.6 Hz, 1H), 7.83 (t, J=4.0 Hz, 1H), 6.86 (s, 1H), 3.79-3.75 (m, 1H), 3.67-3.64 (m, 1H), 3.27-3.23 (m, 5H), 3.18-3.13 (m, 1H), 2.08 (s, 1H), 1.82 (bs, 1H), 1.61 (s, 1H), 1.55-1.51 (m, 1H), 1.44-1.42 (m, 1H), 1.35 (s, 9H), 1.27-1.24 (m, 2H); MS: m/z 412.01 [M+H]$^+$.

Step 4: Deprotection of tert-butyl (3-oxo-3-(3-(((tetrahydro-2H-pyran-3-yl)methyl)sulfonyl)phenyl)propyl)carbamate following the method used in Example 24 gave Example 25 as a pale yellow solid. Yield (0.150 g, 83%); $^1$H NMR (400 MHz, DMSO-d$_6$) δ 8.38 (s, 1H), 8.31 (d, J=8.0 Hz, 1H), 8.21 (d, J=7.6 Hz, 1H), 7.88 (t, J=7.6 Hz, 2H), 7.82 (bs, 2H), 3.77 (m, 2H), 3.67-3.63 (m, 1H), 3.49-3.46 (m, 2H), 3.37-3.31 (m, 3H), 3.18-3.16 (m, 3H), 1.98-1.93 (m, 1H), 1.84-1.81 (m, 1H), 1.53-1.51 (m, 1H), 1.45-1.35 (m, 1H); MS: m/z 312.28 [M+H]$^+$.

Example 26

Preparation of 3-amino-1-(3-(((tetrahydro-2H-pyran-4-yl)methyl)sulfonyl)phenyl)propan-1-one

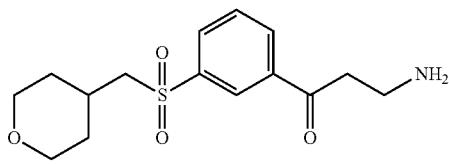 [SMILES: NCCC(=O)c1cccc(S(=O)(=O)CC2CCOCC2)c1]

3-Amino-1-(3-(((tetrahydro-2H-pyran-4-yl)methyl)sulfonyl)phenyl)propan-1-one was prepared following the method used in Example 24 and below.

Step 1: A mixture of (tetrahydro-2H-pyran-4-yl)methyl methanesulfonate (0.33 g, 1.7 mmol), thioester (18, Intermediate II) (0.65 g, 1.65 mmol) and Cs$_2$CO$_3$ (1.40 g, 4.2 mmol) in DMF (10 ml) and MeOH (5 ml) was degassed and saturated with argon. The resulting mixture was stirred at 65° C. under argon for 18 hr. Reaction mixture was concentrated under vacuum, partitioned between H$_2$O and EtOAc. Organic layer was dried over anhydrous Na$_2$SO$_4$ and concentrated under reduced pressure to give tert-butyl (3-oxo-3-(3-(((tetrahydro-2H-pyran-4-yl)methyl)thio)phenyl)propyl)carbamate which directly used in next step without further purification.

Step 2: Oxidation of tert-butyl (3-oxo-3-(3-(((tetrahydro-2H-pyran-4-yl)methyl)thio)phenyl)propyl)carbamate using ammonium molybdate and H$_2$O$_2$ following the method used in Example 24 except that the reaction was carried overnight gave tert-butyl (3-oxo-3-(3-(((tetrahydro-2H-pyran-4-yl)methyl)sulfonyl)phenyl)propyl)carbamate in quantitative yield. The product was used in the next step without further purification.

Step 3: Deprotection of tert-butyl (3-oxo-3-(3-(((tetrahydro-2H-pyran-4-yl)methyl)sulfonyl)phenyl)propyl)carbamate following method described in Example 24 gave Example 26 as a white solid. Yield (0.48 g, 84%); $^1$H NMR (400 MHz, CD$_3$OD) δ 8.51 (s, 1H), 8.36 (d, J=7.6 Hz, 1H), 8.22 (d, J=8.0 Hz, 1H), 7.84 (t, J=7.6 Hz, 1H), 3.91-3.84 (m, 2H), 3.53 (t, J=6.0 Hz, 2H), 3.44-3.34 (m, 4H), 3.26 (t, J=6.4 Hz, 2H), 2.24-2.14 (m, 1H), 1.82-1.74 (m, 2H), 1.51-1.39 (m, 2H); MS: m/z 312.1 [M+H]$^+$.

Example 27

Preparation of 3-((3-((R)-3-amino-1-hydroxypropyl)phenoxy)methyl)piperidin-2-one

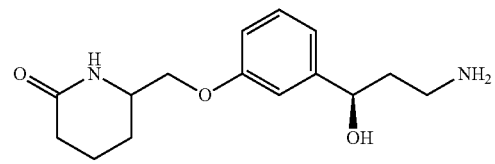

3-((3-((R)-3-Amino-1-hydroxypropyl)phenoxy)methyl)piperidin-2-one was prepared following the method below.

Step 1: 6-(Hydroxymethyl)piperidin-2-one (1.0 g, 7.8 mmol) and Et$_3$N (1.1 ml, 7.8 mmol) in DCM (5 ml) was added into mesyl chloride (0.88 g, 7.8 mmol) in DCM (20 ml) at 0° C. The reaction mixture was stirred at room temperature for 15 mins. The reaction mixture was washed with 1 N HCl (20 ml) and brine (40 ml), dried over anhydrous Na$_2$SO$_4$ and concentrated under reduced pressure to give (6-oxopiperidin-2-yl)methyl methanesulfonate which was used in the next step without additional purification. Yield (quant.).

Step 2: To a mixture of (6-oxopiperidin-2-yl)methyl methanesulfonate (0.44 g, 2.2 mmol) in DMF (15 ml) was added Cs$_2$CO$_3$ (3.5 g, 11 mmol) and phenol (Intermediate I) (0.88 g, 3.3 mmol). The reaction mixture was stirred at room temperature for 40 hours and partitioned between water and ethyl acetate. Organic layer was washed with brine, dried over anhydrous Na$_2$SO$_4$ and concentrated under reduced pressure. Purification by flash chromatography (20% MeOH-EtOAc) gave tert-butyl ((3R)-3-hydroxy-3-(3-((6-oxopiperidin-2-yl)methoxy)phenyl)propyl)carbamate as a yellow oil. Yield (0.17 g, 20%); $^1$H NMR (400 MHz, CD$_3$OD) δ 7.24 (t, J=8.0 Hz, 1H), 6.97-6.93 (m, 2H), 6.84 (d, J=8.0 Hz, 1H), 4.64 (t, J=7.2 Hz, 1H), 4.06-4.02 (m, 1H), 3.94-3.90 (m, 1H), 3.86-3.76 (m, 1H), 3.15-3.06 (m, 2H), 2.37-2.30 (m, 2H), 2.05-1.92 (m, 3H), 1.86-1.75 (m, 3H), 1.43 (s, 9H).

Step 3: To a solution of tert-butyl ((3R)-3-hydroxy-3-(3-((6-oxopiperidin-2-yl)methoxy)phenyl)propyl)carbamate (0.08 g, 0.21 mmol) in EtOAc (2 ml) was added HCl/i-PrOH (5.5 M, 27.5 mmol). The reaction mixture was stirred at room temperature for 2 hours and concentrated under reduced pressure. Hexane was added to the residue and the resulting mixture was sonicated and deasted. The residue was dried under reduced pressure to give Example 27 as a colorless oil. Yield (0.04 g, 60%); $^1$H NMR (400 MHz, CD$_3$OD) δ 7.28 (t, J=7.6 Hz, 1H), 7.01-6.97 (m, 2H), 6.88 (d, J=8.0 Hz, 1H), 4.85-4.80 (m, 1H), 4.09-4.05 (m, 1H), 3.95 (t, J=6.8 Hz, 1H), 3.90-3.82 (m, 1H), 3.12-3.0 (m, 2H), 2.44-2.36 (m, 2H), 2.06-1.94 (m, 4H), 1.86-1.66 (m, 2H); MS: m/z 279.2 [M+H]$^+$.

Example 28

Preparation of (R)-3-amino-1-(3-(thiophen-2-yl-methoxy)phenyl)propan-1-ol

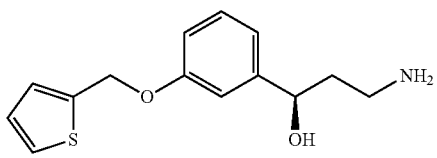

(R)-3-Amino-1-(3-(thiophen-2-ylmethoxy)phenyl)propan-1-ol was prepared following the method below.

Step 1: Alkylation of phenol (1) with 2-(bromomethyl) thiophene following the method used in Example 4 gave after flash column chromatography ethyl 3-(thiophen-2-ylmethoxy)benzoate as a colorless oil. Yield (2.80 g, 97%); $^1$H NMR (400 MHz, CDCl$_3$): δ 7.66 (d, J=1.2 Hz, 2H), 7.35-7.33 (m, 2H), 7.18-7.02 (m, 2H), 7.01 (d, J=4.0 Hz, 1H), 5.26 (s, 2H), 4.37 (q, J=7.2 Hz, 2H), 1.39 (t, J=7.2 Hz, 3H); MS: m/z 247 [M+H]$^+$.

Step 2: Condensation between ethyl 3-(thiophen-2-ylmethoxy)benzoate and acetonitrile following the method used in the preparation of phenol (Intermediate I) gave after flash column chromatography 3-oxo-3-(3-(thiophen-2-ylmethoxy)phenyl)propanenitrile as a colorless oil.

Yield (2.80 g, 95%); $^1$H NMR (400 MHz, CDCl$_3$) δ 7.53 (d, J=2.0 Hz, 1H), 7.49-7.41 (m, 2H), 7.35 (d, J=4.8 Hz, 1H), 7.28 (d, J=1.6 Hz, 1H), 7.14 (d, J=3.2 Hz, 1H), 7.02 (dd, J=4.8, 1.2 Hz, 1H), 5.28 (s, 1H), 4.05 (s, 1H); MS: m/z 258.06 [M+H]$^+$.

Step 3: Chiral reduction of 3-oxo-3-(3-(thiophen-2-ylmethoxy)phenyl)propanenitrile following the method used in the preparation of phenol (7, Intermediate I) gave after flash column chromatography (R)-3-hydroxy-3-(3-(thiophen-2-ylmethoxy)phenyl)propanenitrile as a white solid. Yield (2.6 g, 82%); $^1$H NMR (400 MHz, DMSO-d$_6$): δ 7.55 (d, J=4.8 Hz, 1H), 7.25 (t, J=8.0 Hz, 1H), 7.21 (d, J=3.2 Hz, 1H), 7.06-6.99 (m, 3H), 6.94 (dd, J=8.0, 2.0 Hz, 1H), 5.95 (d, J=4.4 Hz, 1H), 5.27 (s, 2H), 4.85 (dd, J=11.2, 4.8 Hz, 1H), 2.92-2.77 (m, 2H). Yield (2.6 g, 92%); MS: m/z 260.06 [M+H]$^+$.

Step 4: Borane-dimethylsulfide (1.0 mL, 10.5 mmol) was added to a stirred solution of (R)-3-hydroxy-3-(3-(thiophen-2-ylmethoxy)phenyl)propanenitrile (1.00 g, 3.856 mmol) in anhydrous THF (10 mL) and the reaction mixture was stirred under reflux at +80° C. for 1 hour, then at room temperature for 16 hrs, then again at +80° C. for 2 h. MeOH was added to the reaction mixture followed by HCl/MeOH (1.25 M, 5 mL). The mixture was stirred under reflux at +80° C. for 1 h then concentrated under reduced pressure. The residue was partitioned between EtOAc and 1N NaOH, organic layer was washed with brine, dried over anhydrous dried over anhydrous MgSO$_4$ and concentrated under reduced pressure. Purification by flash chromatography (5%-20% of 20% 7N NH$_3$/MeOH/CH$_2$Cl$_2$—CH$_2$Cl$_2$ gradient) gave Example 44 as a colorless oil. Yield (0.76 g, 75%); $^1$H NMR (400 MHz, CD$_3$OD) δ 7.38 (d, J=5.10 Hz, 1H), 7.23 (t, J=8.02 Hz, 1H), 7.12 (m, 1H), 6.97-7.02 (m, 2H), 6.94 (d, J=8.0 Hz, 1H), 6.85-6.90 (m, 1H), 5.25 (s, 2H), 4.69 (t, J=7.2 Hz, 1H), 2.65-2.78 (m, 2H), 1.76-1.90 (m, 2H); MS: m/z 264.1 [M+H]$^+$.

Example 29

Preparation of (R)-3-amino-1-(3-(thiophen-3-yl-methoxy)phenyl)propan-1-ol

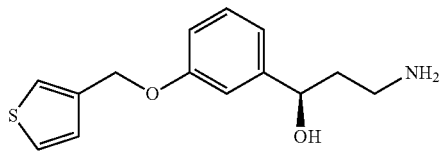 [SMILES: NCC[C@@H](O)c1cccc(OCc2ccsc2)c1]

(R)-3-Amino-1-(3-(thiophen-3-ylmethoxy)phenyl)propan-1-ol was prepared following the method used in Example 28.

Step 1: Alkylation of phenol (1) with 3-(bromomethyl) thiophene gave after flash column chromatography ethyl 3-(thiophen-3-ylmethoxy)benzoate as a pale yellow waxy solid. Yield (3.0 g, 96%); $^1$H NMR (400 MHz, CDCl$_3$): δ 7.66-7.64 (m, 2H), 7.36-7.26 (m, 3H), 7.17-7.14 (m, 2H), 5.11 (s, 2H), 4.37 (q, J=7.2 Hz, 2H), 1.41-1.36 (m, 3H); MS: m/z 247.09.

Step 2: Condensation between ethyl 3-(thiophen-2-ylmethoxy)benzoate and acetonitrile gave after flash column chromatography 3-oxo-3-(3-(thiophen-2-ylmethoxy)phenyl)propanenitrile as a pale yellow solid. Yield (2.60 g, 83%); $^1$H NMR (400 MHz, CDCl$_3$): δ 7.52 (s, 1H), 7.48-7.41 (m, 2H), 3.73 (d, J=3.2 Hz, 2H), 7.27 (s, 1H), 7.15 (d, J=4.8 Hz, 1H), 5.13 (s, 2H), 4.05 (s, 2H); MS: m/z 258.0.

Step 3: Chiral reduction of 3-oxo-3-(3-(thiophen-2-ylmethoxy)phenyl)propanenitrile gave after flash column chromatography (R)-3-hydroxy-3-(3-(thiophen-2-ylmethoxy) phenyl)propanenitrile as a white solid. Yield (1.7 g, 80%); $^1$H NMR (400 MHz, DMSO-d$_6$): δ 7.58 (s, 2H), 7.26 (t, J=7.6 Hz, 1H), 7.18 (s, 1H), 6.98 (d, J=17.6 Hz, 1H), 6.92 (d, J=7.6 Hz, 2H), 5.94 (s, 1H), 5.07 (s, 2H), 4.86 (s, 1H), 2.90-2.77 (m, 2H); MS: m/z 260.25.

Step 4: Reduction of (R)-3-hydroxy-3-(3-(thiophen-3-ylmethoxy)phenyl)propanenitrile following the method used in Example 28 gave Example 29 as a colorless oil. Yield (0.45 g, 74%); $^1$H NMR (400 MHz, CD$_3$OD) δ 7.37-7.42 (m, 2H), 7.23 (t, J=7.83 Hz, 1H), 7.11-7.16 (m, 1H), 7.01 (s, 1H), 6.93 (d, J=7.63 Hz, 1H), 6.84-6.89 (m, 1H), 5.09 (s, 2H), 4.69 (t, J=7.24 Hz, 1H), 2.64-2.76 (m, 2H), 1.76-1.92 (m, 2H); MS: m/z 264.1 [M+H]$^+$.

Example 30

Preparation of (R)-tert-butyl 4-((3-(3-amino-1-hydroxypropyl)phenoxy)methyl)piperidine-1-carboxylate

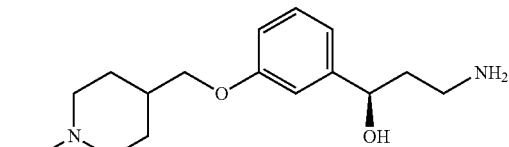

(R)-tert-Butyl 4-((3-(3-amino-1-hydroxypropyl)phenoxy) methyl)piperidine-1-carboxylate was prepared following the method below.

Step 1: A mixture of tert-butyl 4-(((methylsulfonyl)oxy)methyl)piperidine-1-carboxylate (1.91 g, 6.51 mmol), phenol (11) (1.25 g, 8.22 mmol), K$_2$CO$_3$ (1.11 g, 8.03 mmol) in anhydrous DMF (10 mL) was stirred under inert atmosphere at +80° C. for 18 hrs. The reaction mixture was partitioned between aqueous 25% NH$_4$Cl and EtOAc. Aqueous layer was extracted with EtOAc and combined organic layers were washed with brine, dried over anhydrous MgSO$_4$, and concentrated under reduced pressure to give tert-butyl 4-((3-(methoxycarbonyl)phenoxy)methyl)piperidine-1-carboxylate as a light yellow oil which was used in the next step without further purification. Yield (2.02 g, 89%).

Step 2: CH$_3$CN (0.25 mL, 4.79 mmol) was added to a cold (−78° C.) solution of t-BuO$^-$K$^+$ in THF (1M, 5.0 mL, 5.0 mmol) under Ar and the reaction mixture was stirred for 5 mins. Solution of tert-butyl 4-((3-(methoxycarbonyl)phenoxy)methyl)piperidine-1-carboxylate (1.01 g, 2.86 mmol) in anhydrous THF (7 mL) was added to the reaction mixture and the resulting mixture was stirred at −78° C. for 10 min, then warmed to room temperature over 30 mins. The reaction mixture was quenched with 5% aqueous NaHSO$_4$ and extracted twice with tert-butyl methyl ether. Combined organic layers were washed with brine and concentrated under reduced pressure. Purification by flash chromatography (20%-80% EtOAc-hexanes gradient) gave tert-butyl 4-((3-(2-cyanoacetyl)phenoxy)methyl)piperidine-1-carboxylate as a white solid. Yield (0.55 g, 54%); $^1$H NMR (400 MHz, DMSO-d$_6$) δ 7.39-7.51 (m, 3H), 7.23-7.28 (m, 1H), 4.73 (s, 2H), 3.84-4.00 (m, 2H), 3.90 (d, J=6.26 Hz, 2H), 2.60-2.80 (m, 2H), 1.86-1.97 (m, 1H), 1.70-1.78 (m, 2H), 1.38 (s, 9H), 1.08-1.23 (m, 2H).

Step 3: Chiral hydrogenation of tert-butyl 4-((3-(2-cyanoacetyl)phenoxy)methyl)piperidine-1-carboxylate in EtOH (10 mL) following the method used in Example 1 using HCOOH Et$_3$N mixture in EtOH (4.1M) gave after flash chromatography purification (25%-100% EtOAc-hexanes gradient) (R)-tert-butyl 4-((3-(2-cyano-1-hydroxyethyl)phenoxy)methyl)piperidine-1-carboxylate as a light brown oil. Yield (0.47 g, 94%); $^1$H NMR (400 MHz, DMSO-d$_6$) δ 7.23 (t, J=7.83 Hz, 1H), 6.92-6.98 (m, 2H), 6.79-6.84 (m, 1H), 5.89 (m, 1H), 4.83 (m, 1H), 3.66-4.00 (m, 2H), 3.81 (d, J=6.26 Hz, 2H), 2.60-2.90 (m, 4H), 1.84-1.96 (m, 1H), 1.68-1.78 (m, 2H), 1.38 (s, 9H), 1.08-1.18 (m, 2H).

Step 4: Reduction of (R)-tert-butyl 4-((3-(2-cyano-1-hydroxyethyl)phenoxy)methyl)piperidine-1-carboxylate was done following the method used in Example 28. After the reaction was complete, it was quenched with addition of 10% NaHCO$_3$. The mixture was stirred over 3 days and extracted with MTBE. Organic layer was washed with brine, concentrated under reduced pressure. Flash chromatography purification (10%-50% of 20% 7N NH$_3$/MeOH/CH$_2$Cl$_2$—CH$_2$Cl$_2$ gradient) gave Example 30 as a free base. HCl/i-PrOH (5.5 N) was added to solution of Example 30 in EtOAc (5 mL), the mixture was concentrated under reduced pressure, re-evaporated with EtOAc and some EtOAc was added. The mixture was sonicated until white precipitate formed; the latter was collected by filtration, washed with EtOAc, hexanes and dried on filter to give Example 30 hydrochloride as a white solid. Yield (0.187 g, 39%); $^1$H NMR (400 MHz, DMSO-d$_6$) δ 7.22 (t, J=7.43 Hz, 1H), 6.84-6.90 (m, 2H), 6.76-6.81 (m, 1H), 4.63 (dd, J=4.50, 7.63 Hz, 1H), 3.90-4.00 (m, 2H), 3.80 (d, J=6.26 Hz, 2H), 2.60-2.85 (m, 4H), 1.77-1.95 (m, 3H), 1.68-1.77 (m, 2H), 1.38 (s, 9H), 1.07-1.20 (m, 2H); MS: m/z 365.3 [M+H]$^+$.

Example 31

Preparation of (E)-3-(3-((tetrahydro-2H-pyran-4-yl)methoxy)phenyl)prop-2-en-1-amine

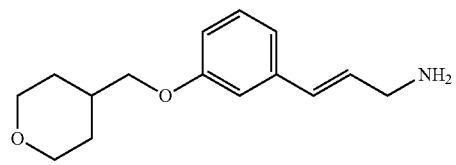 [SMILES: NC/C=C/c1cccc(OCC2CCOCC2)c1]

(E)-3-(3-((Tetrahydro-2H-pyran-4-yl)methoxy)phenyl)prop-2-en-1-amine was prepared following the method below.

Step 1: Alkylation of 3-bromophenol with (tetrahydro-2H-pyran-4-yl)methyl methanesulfonate following the method used in preparation of phenol (7, Intermediate I) gave 4-((3-bromophenoxy)methyl)tetrahydro-2H-pyran as a white solid which was used in the next step without additional purification. Yield (quant.).

Step 2: A mixture of 4-((3-bromophenoxy)methyl)tetrahydro-2H-pyran (1.86 g, 6.86 mmol), N-allyl-2,2,2-trifluoroacetamide (1.14 g, 7.45 mmol), P(o-Tol)$_3$ (0.31 g, 1.02 mmol), Pd(OAc)$_2$ (0.12 g, 0.534 mmol), Et$_3$N (2.0 mL, 14.35 mmol) and anhydrous DMF (10 mL) was degassed by bubbling Ar for at least 5 mins, then applying vacuum/Ar once. The reaction mixture was heated under Ar at +90° C. for 20 hrs then concentrated under reduced pressure. Aqueous NH$_4$Cl was added to the residue and extracted twice with EtOAc. Combined organic layers were washed with brine, treated with activated charcoal and dried over anhydrous MgSO$_4$ and concentrated under reduced pressure. Purification by flash chromatography (20%-50% EtOAc-hexanes gradient) gave (E)-2,2,2-trifluoro-N-(3-(3-((tetrahydro-2H-pyran-4-yl)methoxy)phenyl)allyl)acetamide as a light yellow oil. Yield (2.01 g, 85%); $^1$H NMR (400 MHz, DMSO-d$_6$) δ 9.70 (m, 1H), 7.21 (t, J=7.63 Hz, 1H), 6.94-7.00 (m, 2H), 6.78-6.83 (m, 1H), 6.48 (d, J=15.85 Hz, 1H), 6.25 (dt, J=15.85, 5.87 Hz, 1H), 3.90-4.00 (m, 2H), 3.75-3.90 (m, 4H), 3.31 (t, J=11.74 Hz, 2H), 1.90-2.04 (m, 1H), 1.60-1.70 (m, 2H), 1.24-1.37 (m, 2H).

Step 3: A mixture of (E)-2,2,2-trifluoro-N-(3-(3-((tetrahydro-2H-pyran-4-yl)methoxy)phenyl)allyl)acetamide (1.05 g, 3.06 mmol), K$_2$CO$_3$ (1.51 g, 10.93 mmol), MeOH (25 mL) and H$_2$O (10 mL) was stirred at room temperature over 3 days then concentrated under reduced pressure. Water was added and the mixture was extracted twice with MTBE. Combined organic layers were washed with brine, dried over anhydrous MgSO$_4$, concentrated under reduced pressure. The residue was dissolved in EtOAc and HCl/i-PrOH (5.5 M, 0.7 mL) was added. The precipitate was collected by filtration, washed with EtOAc and dried to give Example 31 hydrochloride as a white solid. Yield (0.604 g, 70%); $^1$H NMR (400 MHz, DMSO-d$_6$) δ 8.17 (br. s, 3H), 7.26 (t, J=7.83 Hz, 1H), 6.93-7.00 (m, 2H), 6.83-6.88 (m, 1H), 6.68 (d, J=16.04 Hz, 1H), 6.28 (dt, J=16.04, 6.06 Hz, 1H), 3.80-3.90 (m, 4H), 3.54-3.60 (m, 2H), 3.27-3.36 (m, 2H), 1.97 (m, 1H), 1.62-1.70 (m, 2H), 1.25-1.38 (m, 2H); MS: m/z 231.2 [M-NH$_3$]$^+$.

Example 32

Preparation of 3-(3-((tetrahydro-2H-pyran-4-yl)methoxy)phenyl)propan-1-amine

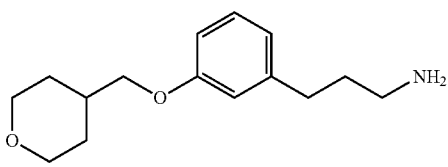 [SMILES: NCCCc1cccc(OCC2CCOCC2)c1]

3-(3-((Tetrahydro-2H-pyran-4-yl)methoxy)phenyl)propan-1-amine was prepared following the method below.

Step 1: Hydrogenation of Example 31 ((E)-3-(3-((tetrahydro-2H-pyran-4-yl)methoxy)phenyl)prop-2-en-1-amine hydrochloride) at 1 atm $H_2$ pressure using Pd/C (10% wt, 0.020 g) catalyst in EtOH (absolute, degassed, 20 mL) for 1.5 hrs gave after filtration through Celite and concentration of the filtrate under reduced pressure Example 32 hydrochloride as a white solid. Yield (0.150 g, 73%); $^1$H NMR (400 MHz, DMSO-$d_6$) δ 7.98 (br. s, 3H), 7.18 (t, J=7.83 Hz, 1H), 6.72-6.80 (m, 3H), 3.750-3.90 (m, 4H), 3.26-3.36 (m, 2H), 2.72 (t, J=7.24 Hz, 2H), 2.59 (t, J=7.43 Hz, 1H), 1.96 (m, 1H), 1.78-1.88 (m, 2H), 1.61-1.69 (m, 2H), 1.24-1.36 (m, 2H); MS: m/z 250.2 $[M+H]^+$.

Example 33

Preparation of (R)-3-(methylamino)-1-(3-((tetrahydro-2H-pyran-4-yl)methoxy)phenyl)propan-1-ol

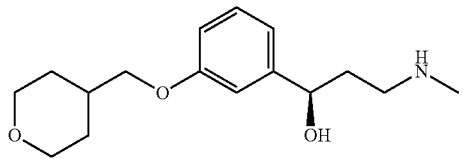 [SMILES: CNCC[C@@H](O)c1cccc(OCC2CCOCC2)c1]

(R)-3-(Methylamino)-1-(3-((tetrahydro-2H-pyran-4-yl)methoxy)phenyl)propan-1-ol was prepared following the method below.

Step 1: (Boc)$_2$O (0.22 g, 3.80 mmol) was added to a solution of (R)-3-amino-1-(3-((tetrahydro-2H-pyran-4-yl)methoxy)phenyl)propan-1-ol (Example 1) (1.0 g, 3.80 mmol) in DCM (20 mL) at room temperature. The reaction mixture was stirred at room temperature for 18 hrs and concentrated under reduced pressure. Purification by flash chromatography (60% EtOAc-hexane) gave tert-butyl (3-hydroxy-3-(3-((tetrahydro-2H-pyran-4-yl)methoxy)phenyl)propyl)carbamate as a colorless oil. Yield (1.1 g, 80%); $^1$H NMR (400 MHz, DMSO-$d_6$); δ 7.18 (t, J=8.0 Hz, 1H), 6.85-6.84 (m, 2H), 6.76-6.74 (m, 2H), 5.15 (d, J=4.4 Hz, 1H), 4.49 (q, J=4.4 Hz, 1H), 3.88-3.84 (m, 2H), 3.79 (d, J=6.4 Hz, 2H), 2.94 (q, J=6.4 Hz, 2H), 1.70-1.62 (m, 4H), 1.38-1.26 (m, 11H).

Step 2: LiAlH$_4$ (1 M in THF, 7.50 mmol) was added to a solution of tert-butyl (3-hydroxy-3-(3-((tetrahydro-2H-pyran-4-yl)methoxy)phenyl)propyl)carbamate (1.1 g, 3.00 mmol) in anhydrous THF (20 mL) at room temperature. The reaction mixture was stirred at 65° C. for 18 hours and cooled to room temperature. The reaction mixture was quenched by slow addition of saturated Na$_2$SO$_4$. MTBE was added and the mixture stirred for 30 min. Layers were separated and organic portion was dried over anhydrous Na$_2$SO$_4$ and concentrated under reduced pressure. The residue was dissolved in methanol (10 ml) and HCl/MeOH was added (1.25 M, 3.75 mmol), the mixture was concentrated under reduced pressure. EtOAc was added to the residue and the mixture was sonicated to give white solid which was collected by filtration and dried in vacuum to give Example 33 as a white solid. Yield (0.65 g, 6%); $^1$H NMR (400 MHz, DMSO-$d_6$); δ 7.26 (t, J=8.0 Hz, 1H), 6.95-6.93 (m, 2H), 6.83 (d, J=8.0 Hz, 1H), 4.82-4.79 (m, 1H), 4.0-3.86 (m, 2H), 3.84 (d, J=6.4 Hz, 2H), 3.49-3.46 (m, 2H), 3.20-3.04 (m, 2H), 2.70 (s, 3H), 2.12-1.96 (m, 3H), 1.77-1.74 (m, 2H), 1.50-1.38 (m, 2H); MS: m/z 280.2 $[M+H]^+$.

Example 34

Preparation of 1-((S)-2-((3-((R)-3-amino-1-hydroxypropyl)phenoxy)methyl)pyrrolidin-1-yl)ethanone

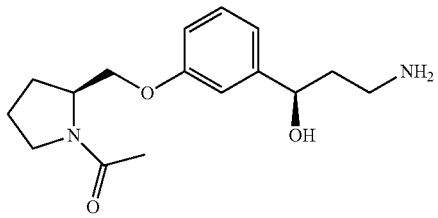 [SMILES: CC(=O)N1CCC[C@H]1COc1cccc([C@H](O)CCN)c1]

1-((S)-2-((3-((R)-3-Amino-1-hydroxypropyl)phenoxy)methyl)pyrrolidin-1-yl)ethanone is prepared following the method used in Example 11.

Step 1: Sulphonation of (S)-1-(2-(hydroxymethyl)pyrrolidin-1-yl)ethanone with TsCl gives (S)-(1-acetylpyrrolidin-2-yl)methyl 4-methylbenzenesulfonate.

Step 2: Alkylation of phenol (7, Intermediate I) with (S)-(1-acetylpyrrolidin-2-yl)methyl 4-methylbenzenesulfonate gives tert-butyl ((R)-3-(3-(((S)-1-acetylpyrrolidin-2-yl)methoxy)phenyl)-3-hydroxypropyl)carbamate.

Step 3: Deprotection of ((R)-3-(3-(((S)-1-acetylpyrrolidin-2-yl)methoxy)phenyl)-3-hydroxypropyl)carbamate gives Example 34.

Example 35

Preparation of 5-((3-((R)-3-amino-1-hydroxypropyl)phenoxy)methyl)piperidin-2-one

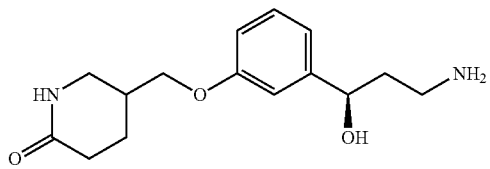 [SMILES: NCC[C@@H](O)c1cccc(OCC2CCC(=O)NC2)c1]

5-((3-((R)-3-Amino-1-hydroxypropyl)phenoxy)methyl)piperidin-2-one is prepared following the method used in Example 27.

Step 1: Sulphonation of 5-(hydroxymethyl)piperidin-2-one with MsCl gives (6-oxopiperidin-3-yl)methyl methanesulfonate.

Step 2: Alkylation of phenol (7, Intermediate I) with (6-oxopiperidin-3-yl)methyl methanesulfonate gives tert-butyl ((3R)-3-hydroxy-3-(3-((6-oxopiperidin-3-yl)methoxy)phenyl)propyl)carbamate.

Step 3: Deprotection of tert-butyl ((3R)-3-hydroxy-3-(3-((6-oxopiperidin-3-yl)methoxy)phenyl)propyl)carbamate gives Example 35.

Example 36

Preparation of 4-((3-((R)-3-amino-1-hydroxypropyl) phenoxy)methyl)piperidin-2-one

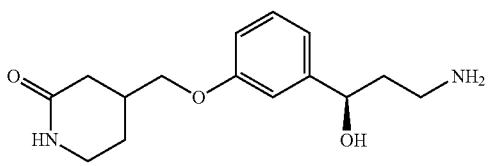 [SMILES: NCC[C@@H](O)c1cccc(OCC2CCNC(=O)C2)c1]

4-((3-((R)-3-Amino-1-hydroxypropyl)phenoxy)methyl) piperidin-2-one is prepared following the method used in Example 27.

Step 1: Sulphonation of 4-(hydroxymethyl)piperidin-2-one with MsCl gives (2-oxopiperidin-4-yl)methyl methanesulfonate.

Step 2: Alkylation of phenol (7, Intermediate I) with (2-oxopiperidin-4-yl)methyl methanesulfonate gives tert-butyl ((3R)-3-hydroxy-3-(3-((2-oxopiperidin-4-yl)methoxy)phenyl)propyl)carbamate.

Step 3: Deprotection of tert-butyl ((3R)-3-hydroxy-3-(3-((2-oxopiperidin-4-yl)methoxy)phenyl)propyl)carbamate gives Example 36.

Example 37

Preparation of 6-((3-((R)-3-amino-1-hydroxypropyl) phenoxy)methyl)-1-methylpiperidin-2-one

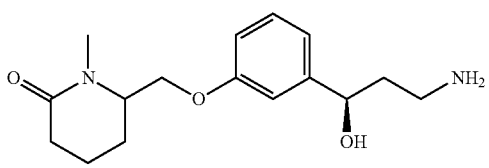 [SMILES: CN1C(=O)CCCC1COc1cccc([C@H](O)CCN)c1]

6-((3-((R)-3-Amino-1-hydroxypropyl)phenoxy)methyl)-1-methylpiperidin-2-one is prepared following the method used in Example 27.

Step 1: Sulphonation of 6-(hydroxymethyl)-1-methylpiperidin-2-one with MsCl gives (1-methyl-6-oxopiperidin-2-yl)methyl methanesulfonate.

Step 2: Alkylation of phenol (7, Intermediate I) with (1-methyl-6-oxopiperidin-2-yl)methyl methanesulfonate gives tert-butyl ((3R)-3-hydroxy-3-(3-((1-methyl-6-oxopiperidin-2-yl)methoxy)phenyl)propyl)carbamate.

Step 3: Deprotection of tert-butyl ((3R)-3-hydroxy-3-(3-((1-methyl-6-oxopiperidin-2-yl)methoxy)phenyl)propyl) carbamate gives Example 37.

Example 38

Preparation of 5-((3-((R)-3-amino-1-hydroxypropyl) phenoxy)methyl)pyrrolidin-2-one

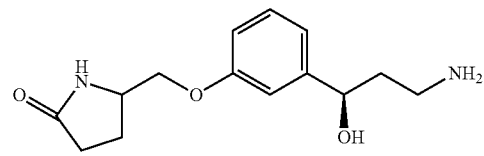 [SMILES: NCC[C@@H](O)c1cccc(OCC2CCC(=O)N2)c1]

5-((3-((R)-3-Amino-1-hydroxypropyl)phenoxy)methyl) pyrrolidin-2-one is prepared following the method used in Example 27.

Step 1: Alkylation of phenol (7, Intermediate I) with (5-oxopyrrolidin-2-yl)methyl methanesulfonate gives tert-butyl ((3R)-3-hydroxy-3-(3-((5-oxopyrrolidin-2-yl)methoxy)phenyl)propyl)carbamate.

Step 2: Deprotection of tert-butyl ((3R)-3-hydroxy-3-(3-((5-oxopyrrolidin-2-yl)methoxy)phenyl)propyl)carbamate gives Example 38.

Example 39

Preparation of 5-((3-((R)-3-Amino-1-hydroxypropyl) phenoxy)methyl)-1-methylpyrrolidin-2-one

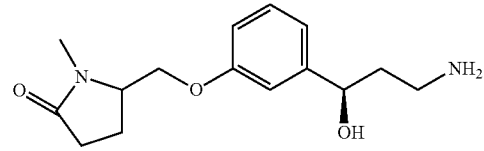 [SMILES: CN1C(=O)CCC1COc1cccc([C@H](O)CCN)c1]

5-((3-((R)-3-Amino-1-hydroxypropyl)phenoxy)methyl)-1-methylpyrrolidin-2-one is prepared following the method used in Example 38.

Step 1: Alkylation of phenol (7, Intermediate I) with (1-methyl-5-oxopyrrolidin-2-yl)methyl methanesulfonate gives tert-butyl ((3R)-3-hydroxy-3-(3-((1-methyl-5-oxopyrrolidin-2-yl)methoxy)phenyl)propyl)carbamate.

Step 2: Deprotection of tert-butyl ((3R)-3-hydroxy-3-(3-((1-methyl-5-oxopyrrolidin-2-yl)methoxy)phenyl)propyl) carbamate gives Example 39.

Example 40

Preparation of N-(3-(3-amino-1-hydroxypropyl)phenyl)-6-oxopiperidine-3-carboxamide

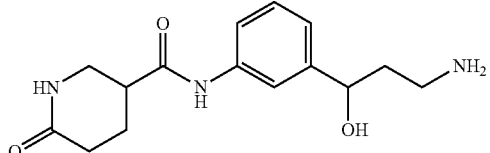

N-(3-(3-Amino-1-hydroxypropyl)phenyl)-6-oxopiperidine-3-carboxamide is prepared following the method below.

Step 1: Condensation between 6-oxopiperidine-3-carboxylic acid and tert-butyl (3-(3-aminophenyl)-3-hydroxypropyl)carbamate gives tert-butyl (3-hydroxy-3-(3-(6-oxopiperidine-3-carboxamido)phenyl)propyl)carbamate.

Step 2: Deprotection of tert-butyl (3-hydroxy-3-(3-(6-oxopiperidine-3-carboxamido)phenyl)propyl)carbamate gives Example 40.

Example 41

Preparation of 3-((3-((R)-3-amino-1-hydroxypropyl)phenoxy)methyl)-1,2-thiazinane 1,1-dioxide

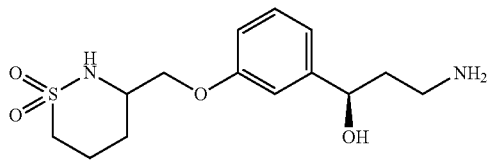 [SMILES: NCC[C@@H](O)c1cccc(OCC2CCCS(=O)(=O)N2)c1]

3-((3-((R)-3-Amino-1-hydroxypropyl)phenoxy)methyl)-1,2-thiazinane 1,1-dioxide was prepared following the method used in Example 27.

Step 1: Sulphonation of 3-(hydroxymethyl)-1,2-thiazinane 1,1-dioxide with MsCl gives (1,1-dioxido-1,2-thiazinan-3-yl)methyl methanesulfonate.

Step 2: Alkylation of phenol (7, Intermediate I) with (1,1-dioxido-1,2-thiazinan-3-yl)methyl methanesulfonate gives tert-butyl ((3R)-3-(3-((1,1-dioxido-1,2-thiazinan-3-yl)methoxy)phenyl)-3-hydroxypropyl)carbamate.

Step 3: Deprotection of tert-butyl ((3R)-3-(3-((1,1-dioxido-1,2-thiazinan-3-yl)methoxy)phenyl)-3-hydroxypropyl)carbamate gives Example 41.

Example 42

Preparation of (R)-1-(3-((1H-pyrrol-2-yl)methoxy)phenyl)-3-aminopropan-1-ol

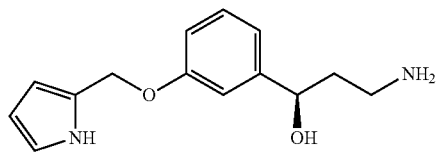

(R)-1-(3-((1H-Pyrrol-2-yl)methoxy)phenyl)-3-aminopropan-1-ol is prepared following the method used in Example 15.

Step 1: Alkylation of phenol (7, Intermediate I) with tert-butyl 2-(((methylsulfonyl)oxy)methyl)-1H-pyrrole-1-carboxylate gives (R)-tert-butyl 2-((3-(3-((tert-butoxycarbonyl)amino)-1-hydroxypropyl)phenoxy)methyl)-1H-pyrrole-1-carboxylate.

Step 2: Deprotection of (R)-tert-butyl 2-((3-(3-((tert-butoxycarbonyl)amino)-1-hydroxypropyl)phenoxy)methyl)-1H-pyrrole-1-carboxylate gives Example 42.

Example 43

Preparation of (R)-3-amino-1-(3-(furan-2-ylmethoxy)phenyl)propan-1-ol

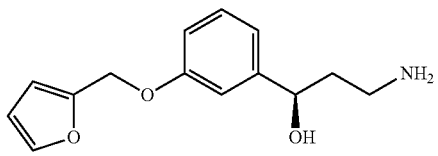 [SMILES: NCC[C@@H](O)c1cccc(OCc2ccco2)c1]

(R)-3-Amino-1-(3-(furan-2-ylmethoxy)phenyl)propan-1-ol is prepared following the method used in Example 27.

Step 1: Alkylation of phenol (7, Intermediate I) with furan-2-ylmethyl methanesulfonate gives (R)-tert-butyl (3-(3-(furan-2-ylmethoxy)phenyl)-3-hydroxypropyl)carbamate.

Step 2: Deprotection of (R)-tert-butyl (3-(3-(furan-2-ylmethoxy)phenyl)-3-hydroxypropyl)carbamate gives Example 43.

Example 44

Preparation of (R)-3-amino-1-(3-((1-(methylsulfonyl)piperidin-4-yl)methoxy)phenyl)propan-1-ol

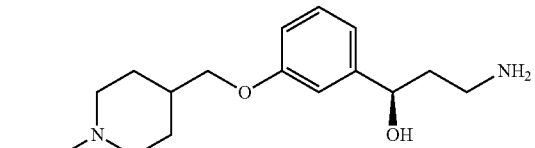

(R)-3-Amino-1-(3-((1-(methylsulfonyl)piperidin-4-yl)methoxy)phenyl)propan-1-ol is prepared following the method used in Example 4.

Step 1: Reaction between (1-(methylsulfonyl)piperidin-4-yl)methyl methanesulfonate and phenol (7, Intermediate I) gives (R)-tert-butyl (3-hydroxy-3-(3-((1-(methylsulfonyl)piperidin-4-yl)methoxy)phenyl)propyl)carbamate.

Step 2: Deprotection of (R)-tert-butyl (3-hydroxy-3-(3-((1-(methylsulfonyl)piperidin-4-yl)methoxy)phenyl)propyl)carbamate gives Example 44.

Example 45

Preparation of (R)-1-(3-(((1H-indol-6-yl)methyl)amino)phenyl)-3-aminopropan-1-ol

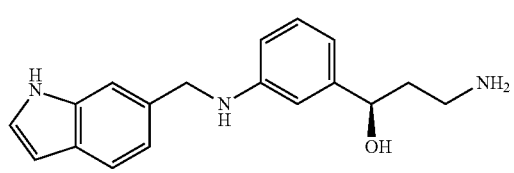 [SMILES: NCC[C@@H](O)c1cccc(NCc2ccc3cc[nH]c3c2)c1]

(R)-1-(3-(((1H-Indol-6-yl)methyl)amino)phenyl)-3-aminopropan-1-ol is prepared following the method used in Example 23.

Step 1: Reaction between 1H-indole-6-carbaldehyde and (R)-3-(3-aminophenyl)-3-hydroxypropanenitrile gives (R)-3-(3-(((1H-indol-6-yl)methyl)amino)phenyl)-3-hydroxypropanenitrile.

Step 2: Reduction of (R)-3-(3-(((1H-indol-6-yl)methyl)amino)phenyl)-3-hydroxypropanenitrile gives Example 45.

Example 46

Preparation of (R)-1-(3-((1H-indol-6-yl)methoxy)phenyl)-3-aminopropan-1-ol

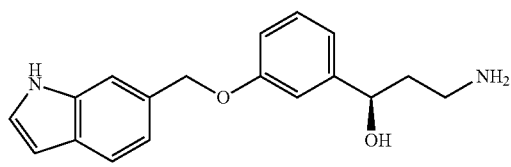 [SMILES: NCC[C@@H](O)c1cccc(OCc2ccc3cc[nH]c3c2)c1]

(R)-1-(3-((1H-Indol-6-yl)methoxy)phenyl)-3-aminopropan-1-ol is prepared following the method used in Example 42.

Step 1: Sulphonation of tert-butyl 6-(hydroxymethyl)-1H-indole-1-carboxylate with mesyl chloride gives tert-butyl 6-(((methylsulfonyl)oxy)methyl)-1H-indole-1-carboxylate.

Step 2: Alkylation of phenol (7, Intermediate I) with tert-butyl 6-(((methylsulfonyl)oxy)methyl)-1H-indole-1-carboxylate gives (R)-tert-butyl 6-((3-(3-((tert-butoxycarbonyl)amino)-1-hydroxypropyl)phenoxy)methyl)-1H-indole-1-carboxylate.

Step 3: Deprotection of (R)-tert-butyl 6-((3-(3-((tert-butoxycarbonyl)amino)-1-hydroxypropyl)-phenoxy)methyl)-1H-indole-1-carboxylate gives Example 46.

Example 47

Preparation of (R)-3-amino-1-(3-(benzofuran-2-ylmethoxy)phenyl)propan-1-ol

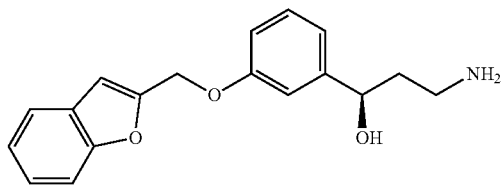 [SMILES: NCC[C@@H](O)c1cccc(OCc2cc3ccccc3o2)c1]

(R)-3-Amino-1-(3-(benzofuran-2-ylmethoxy)phenyl)propan-1-ol is prepared following the method used in Example 13.

Step 1: Sulphonation of benzofuran-2-ylmethanol with mesyl chloride gives benzofuran-2-ylmethyl methanesulfonate.

Step 2: Alkylation of phenol (7, Intermediate I) with benzofuran-2-ylmethyl methanesulfonate gives (R)-tert-butyl (3-(3-(benzofuran-2-ylmethoxy)phenyl)-3-hydroxypropyl)carbamate.

Step 3: Deprotection of (R)-tert-butyl (3-(3-(benzofuran-2-ylmethoxy)phenyl)-3-hydroxypropyl)carbamate gives Example 47.

Example 48

Preparation of 3-(3-((tetrahydro-2H-pyran-4-yl)methoxy)phenyl)prop-2-yn-1-amine

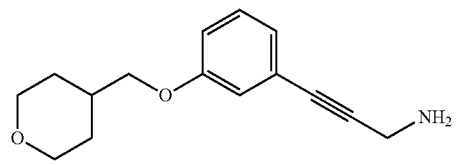 [SMILES: NCC#Cc1cccc(OCC2CCOCC2)c1]

3-(3-((Tetrahydro-2H-pyran-4-yl)methoxy)phenyl)prop-2-yn-1-amine is prepared following the method below.

Step 1: Sonogashira coupling between 4-((3-bromophenoxy)methyl)tetrahydro-2H-pyran and tert-butyl prop-2-yn-1-ylcarbamate gives tert-butyl (3-(3-((tetrahydro-2H-pyran-4-yl)methoxy)phenyl)prop-2-yn-1-yl)carbamate.

Step 2: Deprotection of tert-butyl (3-(3-((tetrahydro-2H-pyran-4-yl)methoxy)phenyl)prop-2-yn-1-yl)carbamate gives Example 48.

Example 49

Preparation of 3-amino-1-(3-(((tetrahydro-2H-pyran-4-yl)methyl)thio)phenyl)propan-1-ol

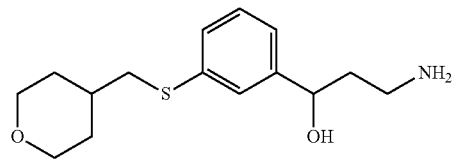

3-Amino-1-(3-(((tetrahydro-2H-pyran-4-yl)methyl)thio)phenyl)propan-1-ol is prepared following the method used in Example 26 and below.

Step 1: Reduction of tert-butyl (3-oxo-3-(3-(((tetrahydro-2H-pyran-4-yl)methyl)thio)phenyl)-propyl)carbamate with NaBH$_4$ gives tert-butyl (3-hydroxy-3-(3-(((tetrahydro-2H-pyran-4-yl)methyl)thio)phenyl)propyl)carbamate.

Step 2: Deprotection of tert-butyl (3-hydroxy-3-(3-(((tetrahydro-2H-pyran-4-yl)methyl)thio)-phenyl)propyl)carbamate gives Example 49.

Example 50

Preparation of 3-amino-1-(3-(((tetrahydro-2H-pyran-4-yl)methyl)sulfonyl)phenyl)propan-1-ol

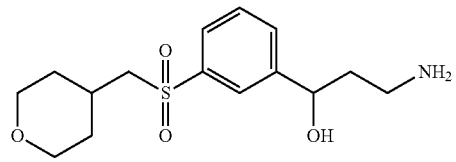 [SMILES: NCCC(O)c1cccc(S(=O)(=O)CC2CCOCC2)c1]

3-Amino-1-(3-(((tetrahydro-2H-pyran-4-yl)methyl)sulfonyl)phenyl)propan-1-ol is prepared following the method used in Examples 24, 26 and below.

Step 1: Oxidation of tert-butyl (3-hydroxy-3-(3-(((tetrahydro-2H-pyran-4-yl)methyl)thio)-phenyl)propyl)carbamate following the method used in Example 40 gives tert-butyl (3-hydroxy-3-(3-(((tetrahydro-2H-pyran-4-yl)methyl)sulfonyl)phenyl)propyl)carbamate.

Step 2: Deprotection of tert-butyl (3-hydroxy-3-(3-(((tetrahydro-2H-pyran-4-yl)methyl)-sulfonyl)phenyl)propyl)carbamate gives Example 50.

Example 51

Preparation of 3-amino-1-(3-(2-(tetrahydro-2H-pyran-4-yl)ethyl)phenyl)propan-1-ol

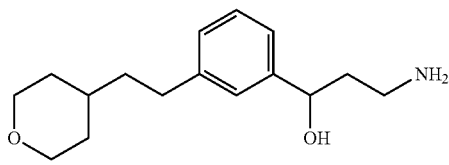 [SMILES: NCCC(O)c1cccc(CCC2CCOCC2)c1]

3-Amino-1-(3-(2-(tetrahydro-2H-pyran-4-yl)ethyl)phenyl)propan-1-ol is prepared following the method below.

Step 1: Sonogashira coupling between 4-ethynyltetrahydro-2H-pyran and tert-butyl (3-(3-bromophenyl)-3-hydroxypropyl)carbamate gives tert-butyl (3-hydroxy-3-(3-((tetrahydro-2H-pyran-4-yl)ethynyl)phenyl)propyl)carbamate.

Step 2: Deprotection of tert-butyl (3-hydroxy-3-(3-((tetrahydro-2H-pyran-4-yl)ethynyl)phenyl)-propyl)carbamate gives 3-Amino-1-(3-((tetrahydro-2H-pyran-4-yl)ethynyl)phenyl)propan-1-ol.

Step 3: Hydrogenation of gives 3-Amino-1-(3-((tetrahydro-2H-pyran-4-yl)ethynyl)phenyl)propan-1-ol gives Example 51.

Example 52

Preparation of 3-amino-1-(3-(2-(pyridin-3-yl)ethyl)phenyl)propan-1-ol

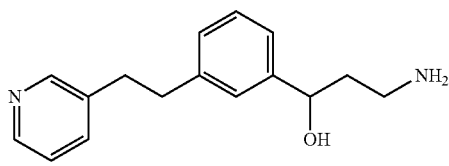 [SMILES: NCCC(O)c1cccc(CCc2cccnc2)c1]

3-Amino-1-(3-(2-(pyridin-3-yl)ethyl)phenyl)propan-1-ol is prepared following the method below.

Step 1: Sonogashira coupling between 3-ethynylpyridine and tert-butyl (3-(3-bromophenyl)-3-hydroxypropyl)carbamate gives tert-butyl (3-hydroxy-3-(3-(pyridin-3-ylethynyl)phenyl)-propyl)carbamate.

Step 2: Deprotection of tert-butyl (3-hydroxy-3-(3-(pyridin-3-ylethynyl)phenyl)propyl)-carbamate gives 3-Amino-1-(3-(pyridin-3-ylethynyl)phenyl)propan-1-ol.

Step 3: Hydrogenation of 3-Amino-1-(3-(pyridin-3-ylethynyl)phenyl)propan-1-ol gives Example 71.

Example 53

Preparation of 3-amino-1-(3-(2-(thiophen-3-yl)ethyl)phenyl)propan-1-ol

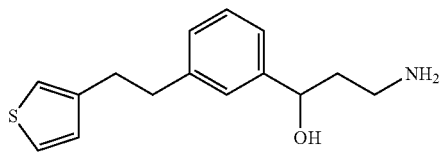 [SMILES: NCCC(O)c1cccc(CCc2ccsc2)c1]

3-Amino-1-(3-(2-(thiophen-3-yl)ethyl)phenyl)propan-1-ol is prepared following the method below.

Step 1: Sonogashira coupling between 3-ethynylthiophene and tert-butyl (3-(3-bromophenyl)-3-hydroxypropyl)carbamate gives tert-butyl (3-hydroxy-3-(3-(thiophen-3-ylethynyl)phenyl)propyl)carbamate.

Step 2: Deprotection of tert-butyl (3-hydroxy-3-(3-(thiophen-3-ylethynyl)phenyl)propyl)-carbamate gives 3-Amino-1-(3-(thiophen-3-ylethynyl)phenyl)propan-1-ol.

Step 3: Hydrogenation of 3-Amino-1-(3-(thiophen-3-ylethynyl)phenyl)propan-1-ol gives Example 53.

Example 54

Preparation of (E)-1-(3-(3-amino-1-hydroxypropyl)styryl)pyrrolidin-2-one

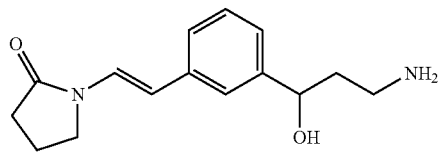 [SMILES: NCCC(O)c1cccc(/C=C/N2CCCC2=O)c1]

(E)-1-(3-(3-Amino-1-hydroxypropyl)styryl)pyrrolidin-2-one is prepared following the method used in Example 31 and below.

Step 1: Heck coupling between 1-vinylpyrrolidin-2-one and tert-butyl (3-(3-bromophenyl)-3-hydroxypropyl)carbamate gives (E)-tert-butyl (3-hydroxy-3-(3-(2-(2-oxopyrrolidin-1-yl)vinyl)phenyl)propyl)carbamate.

Step 2: Deprotection of (E)-tert-butyl (3-hydroxy-3-(3-(2-(2-oxopyrrolidin-1-yl)vinyl)phenyl)propyl)carbamate give Example 54.

Example 55

Preparation of 1-(3-(3-amino-1-hydroxypropyl)phenethyl)pyrrolidin-2-one

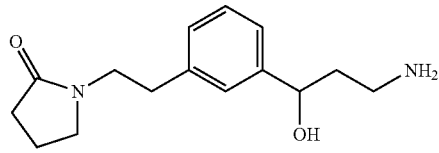 [SMILES: NCCC(O)c1cccc(CCN2CCCC2=O)c1]

1-(3-(3-Amino-1-hydroxypropyl)phenethyl)pyrrolidin-2-one is prepared following the method below.

Step 1: Heck coupling between 1-vinylpyrrolidin-2-one and tert-butyl (3-(3-bromophenyl)-3-hydroxypropyl)carbamate gives (E)-tert-butyl (3-hydroxy-3-(3-(2-(2-oxopyrrolidin-1-yl)vinyl)phenyl)propyl)carbamate.

Step 2: Deprotection of (E)-tert-butyl (3-hydroxy-3-(3-(2-(2-oxopyrrolidin-1-yl)vinyl)phenyl)propyl)carbamate give (E)-1-(3-(3-Amino-1-hydroxypropyl)styryl)pyrrolidin-2-one.

Step 3: Hydrogenation of (E)-1-(3-(3-Amino-1-hydroxypropyl)styryl)pyrrolidin-2-one gives Example 55.

Example 56

Preparation of 3-amino-1-(3-(2-(pyrrolidin-1-yl)ethyl)phenyl)propan-1-ol

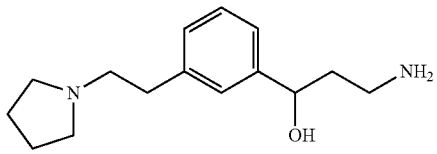 [SMILES: NCCC(O)c1cccc(CCN2CCCC2)c1]

3-Amino-1-(3-(2-(pyrrolidin-1-yl)ethyl)phenyl)propan-1-ol is prepared following the method used in Example 55 and below.

Step 1: Reduction of Example 55 with an appropriate reducing agent gives Example 56.

Example 57

Preparation of (E)-1-(3-(2-(1H-imidazol-1-yl)vinyl)phenyl)-3-aminopropan-1-ol

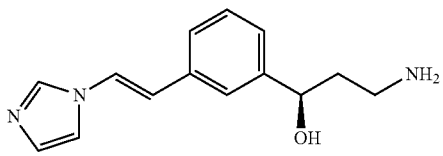 [SMILES: NCC[C@@H](O)c1cccc(/C=C/n2ccnc2)c1]

(E)-1-(3-(2-(1H-Imidazol-1-yl)vinyl)phenyl)-3-aminopropan-1-ol is prepared following the method below.

Step 1: Coupling between 1-vinyl-1H-imidazole and tert-butyl (3-(3-bromophenyl)-3-hydroxy-propyl)carbamate gives (E)-tert-butyl (3-(3-(2-(1H-imidazol-1-yl)vinyl)phenyl)-3-hydroxypropyl)carbamate.

Step 2: Deprotection of (E)-tert-butyl (3-(3-(2-(1H-imidazol-1-yl)vinyl)phenyl)-3-hydroxy-propyl)carbamate gives Example 57.

Example 58

Preparation of 1-(3-(2-(1H-imidazol-1-yl)ethyl)phenyl)-3-aminopropan-1-ol

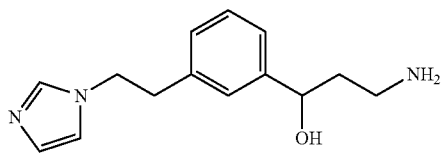

1-(3-(2-(1H-Imidazol-1-yl)ethyl)phenyl)-3-aminopropan-1-ol is prepared following the method below.

Step 1: Hydrogenation of Example 57 gives Example 58.

Example 59

Preparation of (E)-3-amino-1-(3-(2-(pyridin-2-yl)vinyl)phenyl)propan-1-ol

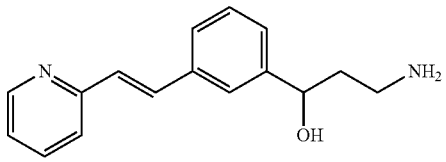 [SMILES: NCCC(O)c1cccc(/C=C/c2ccccn2)c1]

(E)-3-Amino-1-(3-(2-(pyridin-2-yl)vinyl)phenyl)propan-1-ol is prepared following the method below.

Step 1: Coupling between 2-vinylpyridine and tert-butyl (3-(3-bromophenyl)-3-hydroxypropyl)carbamate gives (E)-tert-butyl (3-hydroxy-3-(3-(2-(pyridin-2-yl)vinyl)phenyl)propyl)carbamate.

Step 2: Deprotection of (E)-tert-butyl (3-hydroxy-3-(3-(2-(pyridin-2-yl)vinyl)phenyl)propyl)carbamate gives Example 59.

Example 60

Preparation of 3-amino-1-(3-(2-(pyridin-2-yl)ethyl)phenyl)propan-1-ol

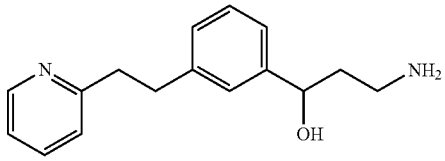 [SMILES: NCCC(O)c1cccc(CCc2ccccn2)c1]

3-Amino-1-(3-(2-(pyridin-2-yl)ethyl)phenyl)propan-1-ol is prepared following the method below.

Step 1: Hydrogenation of Example 59 gives Example 60.

Example 61

Preparation of (E)-3-amino-1-(3-(2-(tetrahydro-2H-pyran-4-yl)vinyl)phenyl)propan-1-ol

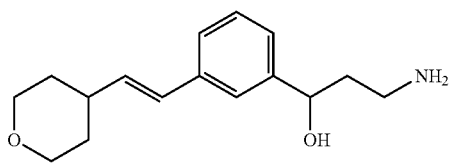 [SMILES: NCCC(O)c1cccc(/C=C/C2CCOCC2)c1]

(E)-3-Amino-1-(3-(2-(tetrahydro-2H-pyran-4-yl)vinyl)phenyl)propan-1-ol is prepared following the method below.

Step 1: Coupling between 4-vinyltetrahydro-2H-pyran and tert-butyl (3-(3-bromophenyl)-3-hydroxypropyl)carbamate gives (E)-tert-butyl (3-hydroxy-3-(3-(2-(tetrahydro-2H-pyran-4-yl)vinyl)phenyl)propyl)carbamate.

Step 2: Deprotection of (E)-tert-butyl (3-hydroxy-3-(3-(2-(tetrahydro-2H-pyran-4-yl)vinyl)phenyl)propyl)carbamate gives Example 61.

Example 62

Preparation of 3-amino-1-(3-(2-(tetrahydro-2H-pyran-4-yl)ethyl)phenyl)propan-1-ol

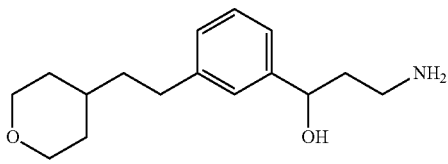 [SMILES: NCCC(O)c1cccc(CCC2CCOCC2)c1]

3-Amino-1-(3-(2-(tetrahydro-2H-pyran-4-yl)ethyl)phenyl)propan-1-ol is prepared following the method below.

Step 1: Hydrogenation of Example 61 gives Example 62.

II. Biological Evaluation

Example 1

In Vitro Isomerase Inhibition

The capability of compounds disclosed herein to inhibit the activity of a visual cycle isomerase was determined. In particular, the human in vitro isomerase assay was performed essentially as in Golczak et al. Proc. Natl. Acad. Sci. (2005) 102, 8162-8167, and in Imanishi, et al. J. Cell Biol. (2004), 164, 373-383.

Isolation of Human Apo Cellular Retinaldehyde-Binding Protein (CRALBP)

Recombinant human apo cellular retinaldehyde-binding protein (CRALBP) was cloned and expressed according to standard molecular biology methods (see Crabb et al., Protein Science 7:746-57 (1998); Crabb et al., J. Biol. Chem. 263: 18688-92 (1988)). Briefly, total RNA was prepared from confluent ARPE19 cells (American Type Culture Collection, Manassas, Va.), cDNA was synthesized using an oligo(dT)$_{12-18}$ primer, and then DNA encoding CRALBP was amplified by two sequential polymerase chain reactions (see Crabb et al., J. Biol. Chem. 263:18688-92 (1988); Intres, et al., J. Biol. Chem. 269:25411-18 (1994); GenBank Accession No. L34219.1). The PCR product was sub-cloned into pTrcHis2-TOPO TA vector according to the manufacturer's protocol (Invitrogen Inc., Carlsbad, Calif.; catalog no. K4400-01), and then the sequence was confirmed according to standard nucleotide sequencing techniques. Recombinant 6×His-tagged human CRALBP was expressed in One Shot TOP 10 chemically competent E. coli cells (Invitrogen), and the recombinant polypeptide was isolated from E. coli cell lysates by nickel affinity chromatography using nickel (Ni) Sepharose XK16-20 columns for HPLC (Amersham Bioscience, Pittsburgh, Pa.; catalog no. 17-5268-02). The purified 6×His-tagged human CRALBP was dialyzed against 10 mM bis-tris-Propane (BTP) and analyzed by SDS-PAGE. The molecular weight of the recombinant human CRALBP was approximately 39 kDal.

Isomerase Assay

Compounds disclosed herein and control compounds were reconstituted in ethanol to 0.1 M. Ten-fold serial dilutions ($10^{-2}$, $10^{-3}$, $10^{-4}$, $10^{-5}$, $10^{-6}$ M) in ethanol of each compound were prepared for analysis in the isomerase assay.

A homogenate of HEK293 cell clone co-expressing recombinant human RPE65 and LRAT were the source of the visual enzymes, and exogenous all-trans-retinol (about 20 µM) was used as the substrate. Recombinant human CRALBP (about 80 ug/mL) was added to enhance the formation of 11-cis-retinal. The 200 µL Bis-Tris Phosphate buffer (10 mM, pH 7.2) based reaction mixture also contains 0.5% BSA, and 1 mM NaPPi. In this assay, the reaction was carried out at 37° C. in duplicates for one hour and was terminated by addition of 300 µL methanol. The amount of reaction product, 11-cis-retinol, was measured by HPLC analysis following Heptane extraction of the reaction mixture. The Peak Area Units (PAUs) corresponding to 11-cis-retinol in the HPLC chromatograms were recorded and concentration dependent curves analyzed by GraphPad Prism for $IC_{50}$ values. The ability of the compounds disclosed herein to inhibit isomerization reaction was quantified and the respective $IC_{50}$ value was determined. Table 2 below provides the $IC_{50}$ values of various compounds disclosed herein determined by the above methods. In the human in vitro isomerase inhibition assay described herein, compound (R)-3-amino-1-(3-(cyclohexylmethoxy)phenyl)propan-1-ol (described in US Patent Application Publication US 2009/0326074) had an $IC_{50}$ of 4.4 nM, compound 3-amino-1-(3-((tetrahydro-2H-pyran-2-yl)methoxy)phenyl)propan-1-ol (described in US Patent Application Publication US 2009/0326074) had an $IC_{50}$ of 24 nM, and compound (R)-3-amino-1-(3-(cyclohexylmethylamino)phenyl)propan-1-ol (described in US Patent Application Publication US 2010/0113539) had an $IC_{50}$ of 6.3 nM.

TABLE 2

Human in vitro Inhibition data

| $IC_{50}$ (µM) | Compound/Example Number |
|---|---|
| ≤0.1 µM | 1, 2, 3, 4, 5, 6, 7, 8, 9, 10, 11, 12, 13, 14, 17, 19, 23, 25, 26, 27, 28, 29, 30, 31, 32 |
| >0.1 µM-≤1 µM | 16, 18, 20, 21, 22, 24, 33 |
| >1 µM-≤10 µM | 15 |
| >10 µM No detectable activity | |

Example 2

In Vivo Murine Isomerase Assay

The capability of compounds described herein to inhibit isomerase was determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo. Delayed recovery, as represented by lower 11-cis-retinal oxime levels, indicates inhibition of isomerization reaction. Procedures were performed essentially as described by Golczak et al., *Proc. Natl. Acad. Sci. USA* 102:8162-67 (2005). See also Deigner et al., *Science*, 244: 968-71 (1989); Gollapalli et al., *Biochim Biophys Acta.* 1651: 93-101 (2003); Parish, et al., *Proc. Natl. Acad. Sci. USA,* 14609-13 (1998); Radu, et al., *Proc Natl Acad Sci USA* 101: 5928-33 (2004).

Six-week old dark-adapted CD-1 (albino) male mice were orally gavaged with compound (0.03-3 mg/kg) dissolved in 100 µl corn oil containing 10% ethanol (five animals per group). Mice were gavaged with the test compound. After 2-24 hours in the dark, the mice were exposed to photobleaching of 5,000 lux of white light for 10 minutes. The mice were allowed to recover 2 hours in the dark. The animals were then sacrificed by carbon dioxide inhalation. Retinoids were extracted from the eye and the regeneration of 11-cis-retinal was assessed at various time intervals.

Eye Retinoid Extraction

All steps were performed in darkness with minimal redlight illumination (low light darkroom lights and redfiltered flashlights for spot illumination as needed) (see, e.g., Maeda et al., *J. Neurochem* 85:944-956, 2003; Van Hooser et al., *J Biol Chem* 277:19173-82, 2002). After the mice were sacrificed, the eyes were immediately removed and placed in liquid nitrogen for storage.

The eyes were placed in 500 µL of bis-tris propane buffer (10 mM, pH~7.3) and 20 µL of 0.8M hydroxile amine (pH~7.3). The eyes were cut up into small pieces with small iris scissors and then thoroughly homogenized at 30000 rpm with a mechanical homogenizer (Polytron PT 1300 D) in the tube until no visible tissue remained. 500 µL of methanol and 500 µL of heptane were added to each tube. The tubes were attached to a vortexer so that the contents were mixed thoroughly for 15 minutes in room temperature. The organic phase was separated from the aqueous phase by centrifugation for 10 min at 13K rpm, 4° C. 240 µL of the solution from the top layer (organic phase) was removed and transferred to clean 300 µl glass inserts in HPLC vials using glass pipette and the vials were crimped shut tightly.

The samples were analyzed on an Agilent 1100 HPLC system with normal phase column: SILICA (Beckman Coutlier, dp 5 µm, 4.6 mM×250 mM). The running method has a flow rate of 1.5 ml/min; solvent components were 15% solvent 1 (1% isopropanol in ethyl acetate), and 85% solvent 2 (100% hexanes). Loading volume for each sample was 100 µA detection wavelength was 360 nm. The area under the curve for 11-cis retinal oxime was calculated by Agilent Chemstation software and was recorded manually. Data processing was performed using Prizm software. Results from the in vivo murine isomerase assay are provided in Table 3.

Positive control mice (no compound administered) were sacrificed fully dark-adapted and the eye retinoids analyzed. Light (bleached) control mice (no compound administered) were sacrificed and retinoids isolated and analyzed immediately after light treatment.

A time course study was performed to determine the isomerase inhibitory activity of the test compound. Male Balb/c mice (4/group) received test compound orally by gavage. The animals were then "photo-bleached" (5000 Lux white light for 10 minutes) at 2, 4, 8, 16 and 24 hours after dosing, and returned to darkness to allow recovery of the 11-cis-retinal content of the eyes. Mice were sacrificed 2 hours after bleaching, eyes were enucleated, and retinoid content is analyzed by HPLC. FIG. 1 provides one example of the outcome of a time course experiment. In FIG. 1, compound A is (R)-3-amino-1-(3-((tetrahydro-2H-pyran-4-yl)methoxy)phenyl)propan-1-ol (Example 1 as described herein), compound B is (R)-3-amino-1-(3-(cyclohexylmethoxy)phenyl)propan-1-ol (described in US Patent Application Publication US 2009/0326074), and compound C is 3-amino-1-(3-((4,4-difluorocyclohexyl)methoxy)phenyl)propan-1-ol (described in US Patent Application Publication US 2009/0326074). Further examples of time course experiments are provided in Table 3.

Recovery control mice (vehicle-only treated) were light-treated and left to recover for 2 hours in the dark before sacrifice and analysis. Light control mice (vehicle only treated) were sacrificed for analysis immediately after photobleaching.

An in vivo dose response isomerase inhibition study was performed with test compound. Male Balb/c mice (8/group) were dosed orally with 0.03, 0.1, 0.3, 1 and 3 mg/kg of test compound in sterile water as solution, and photobleached 2 hours after dosing. Recovery and retinoid analysis were performed as described above. Dark control mice were vehicle-only treated, sacrificed fully dark adapted without light treatment, and analyzed. Recovery control mice and light control mice were included in the study as per the initial phase. Examples of dose response experiments are provided in Table 3.

In another experiment, male Balb/c mice are dosed with test compound as above but the dosing is repeated twice daily for 7 consecutive days. The animals are photobleached 4 hours after the last dose. Recovery and retinoid analysis is as per the initial phase and the $ED_{50}$ is estimated.

In the in vivo isomerase inhibition assay described herein, compound (R)-3-amino-1-(3-(cyclohexylmethoxy)phenyl)propan-1-ol (described in US Patent Application Publication US 2009/0326074) had 98-100% inhibition at 1 mg/kg concentration and 4 h time point, compound 3-amino-1-(3-((tetrahydro-2H-pyran-2-yl)methoxy)phenyl)propan-1-ol (described in US Patent Application Publication US 2009/0326074) had 57% inhibition at 1 mg/kg concentration and 4 h time point, and compound (R)-3-amino-1-(3-(cyclohexylmethylamino)phenyl)propan-1-ol (described in US Patent Application Publication US 2010/0113539) had 96% inhibition at 1 mg/kg concentration and 4 h time point.

Table 3 provides in vivo inhibition data for the indicted compounds disclosed herein.

TABLE 3 in vivo isomerase inhibition

| Example | Dose (mg/kg) | Time (h) | % Inhibition | St. Dev. |
|---|---|---|---|---|
| 1 | 0.03 | 2 | −2.7 | 7.2 |
|   | 0.1  | 2 | 3.4  | 6.6 |
|   | 0.3  | 2 | 58.4 | 10.0 |
|   | 0.3  | 2 | 40.2 | 16.1 |
|   | 0.3  | 4 | 15.7 | 9.6 |
|   | 0.3  | 8 | 10.4 | 7.2 |
|   | 0.3  | 16 | −2.7 | 8.6 |

TABLE 3-continued in vivo isomerase inhibition

| Example | Dose (mg/kg) | Time (h) | % Inhibition | St. Dev. |
|---|---|---|---|---|
|  | 0.3 | 24 | -4.4 | 6.0 |
|  | 0.5 | 2 | 89.9 | 2.2 |
|  | 0.81 | 2 | 98.2 | 0.7 |
|  | 0.81 | 4 | 87.9 | 6.2 |
|  | 0.81 | 6 | 75.8 | 5.9 |
|  | 0.81 | 8 | 51.8 | 4.2 |
|  | 0.81 | 16 | 5.5 | 8.9 |
|  | 0.81 | 24 | -4.8 | 6.4 |
|  | 1 | 2 | 96.9 | 0.7 |
|  | 1 | 2 | 96.7 | 0.8 |
|  | 1 | 4 | 91.1 | 2.3 |
|  | 1 | 4 | 92.8 | 1.8 |
|  | 1 | 8 | 62.0 | 18.2 |
|  | 1 | 16 | -1.2 | 11.4 |
|  | 1 | 24 | 3.8 | 9.8 |
|  | 3 | 2 | 100.9 | 1.8 |
| 2 | 1 | 4 | 89.9 | 4.7 |
| 3 | 0.01 | 2 | 1.2 | 9.3 |
|  | 0.03 | 2 | 2.7 | 9.8 |
|  | 0.1 | 2 | 4.2 | 10.0 |
|  | 0.3 | 2 | 75.2 | 7.1 |
|  | 0.3 | 2 | 75.1 | 6.3 |
|  | 0.3 | 4 | 59.7 | 4.6 |
|  | 0.3 | 8 | 14.8 | 12.0 |
|  | 0.3 | 16 | 1.6 | 8.6 |
|  | 0.3 | 24 | 4.1 | 8.3 |
|  | 1 | 2 | 98.7 | 1.1 |
|  | 1 | 4 | 94.2 | 3.6 |
|  | 3 | 2 | 101.9 | 0.6 |
| 4 | 1 | 4 | -8.7 | 8.6 |
| 5 | 1 | 4 | 3.1 | 17.4 |
| 7 | 1 | 2 | 60.5 | 12.1 |
|  | 1 | 4 | 68.0 | 6.0 |
|  | 1 | 8 | 40.3 | 6.0 |
| 8 | 1 | 4 | 33.2 | 9.3 |
| 9 | 1 | 4 | -8.2 | 9.2 |
| 10 | 1 | 4 | -7.6 | 8.4 |
| 11 | 1 | 2 | -4.7 | 9.4 |
|  | 1 | 4 | 2.6 | 11.3 |
|  | 1 | 8 | -3.8 | 9.5 |
| 12 | 1 | 4 | 11.2 | 8.1 |
| 13 | 1 | 2 | 62.1 | 5.6 |
| 14 | 1 | 2 | 79.2 | 4.3 |
|  | 1 | 4 | 59.8 | 14.0 |
|  | 1 | 8 | 0.8 | 14.5 |
| 17 | 0.01 | 2 | 0 | 6.8 |
|  | 0.03 | 2 | -2 | 8.0 |
|  | 0.1 | 2 | 9 | 4.2 |
|  | 0.3 | 2 | 8 | 12.1 |
|  | 1 | 2 | 93 | 2.3 |
|  | 1 | 2 | 93 | 2.6 |
|  | 1 | 4 | 88 | 2.9 |
|  | 1 | 4 | 85 | 3.7 |
|  | 1 | 8 | 25 | 5.9 |
|  | 1 | 16 | -1 | 9.0 |
|  | 1 | 24 | -8 | 7.7 |
|  | 3 | 2 | 100 | 1.2 |
| 19 | 0.3 | 2 | 49.4 | 9.2 |
|  | 0.3 | 4 | 40.0 | 11.6 |
|  | 0.3 | 8 | 15.5 | 9.8 |
|  | 1 | 4 | 91.4 | 1.2 |
| 23 | 1 | 2 | 4.4 | 5.3 |
|  | 1 | 4 | -1.4 | 8.7 |
|  | 1 | 8 | 1.5 | 5.3 |
| 27 | 1 | 4 | 9.0 | 3.7 |
| 28 | 1 | 4 | 50.6 | 3.2 |
| 29 | 1 | 4 | 27.4 | 12.7 |
| 31 | 1 | 2 | 11.3 | 10.6 |
| 32 | 1 | 2 | 14.2 | 3.6 |
| 33 | 1 | 2 | 65.2 | 11.3 |
|  | 1 | 4 | 54.5 | 12.9 |
|  | 1 | 8 | 10.9 | 8.4 |
|  | 1 | 16 | -0.8 | 5.3 |
|  | 1 | 24 | 1.8 | 10.4 |

Comparative In Vivo Murine Isomerase Assay—Dose Response Comparison of 3-amino-1-(3-((tetrahydro-2H-pyran-4-yl)methoxy)phenyl)propan-1-ol and 3-amino-1-(3-((tetrahydro-2H-pyran-2-yl)methoxy)phenyl)propan-1-ol Introduction Light is essential for vision but can also generate photochemical damage to the retina (Boulton et al., 2001). Protective effects against photo damage were observed when rhodopsin regeneration was reduced due to mutations in RPE65, a protein necessary for the regeneration of the retinoid chromophore 11-cis-retinal in the visual cycle (Grimm et al., 2000). Likewise, it is expected that drugs that inhibit regeneration of 11-cis retinal will have a protective effect against light mediated retinal damage and degenerative disorders. 11-cis-retinal is generated by oxidation of 11-cis retinol in the retina pigment epithelium (RPE). The isomerization reaction that forms 11-cis-retinol from all-trans retinylesters is rate limiting in the visual cycle and it can be expected that compounds that inhibit this reaction will limit the generation of 11-cis-retinal and thus have a therapeutic potential in the treatment of light-mediated retinal degenerative disorders. The rate of regeneration of 11-cis-retinal will affect the rate of functional photoreceptor recovery from bleaching light. The regeneration of 11-cis-retinal after bleach is used to screen for active cycle modulators.

Purpose

This study is intended to assess the effects of multiple dose levels of 3-amino-1-(3-((tetrahydro-2H-pyran-4-yl)methoxy)phenyl)propan-1-ol and 3-amino-1-(3-((tetrahydro-2H-pyran-2-yl)methoxy)phenyl)propan-1-ol on retinal isomerase activity in BALB/c mice 2 hours after oral doses of 0.03, 0.1, 0.3, 9.5, 1 and 3 mg/kg.

Materials and Methods

The test compounds were 3-amino-1-(3-((tetrahydro-2H-pyran-4-yl)methoxy)phenyl)propan-1-ol (compound A and Example 1 described herein) and 3-amino-1-(3-((tetrahydro-2H-pyran-2-yl)methoxy)phenyl)propan-1-ol (compound D and described in US Patent Application Publication US 2009/0326074). All test compounds were stored at room temperature, dessicated.

On the day prior to dose administration compound A and compound D were weighed into new empty glass vials. The compounds were dissolved in di-water at the concentration of 0.833 mg/mL compound A and 0.892 mg/mL compound D, serially diluted into various concentrations, and stored overnight at 4° C.

56 Male BALB/c mice (Charles River Laboratories) were used for this study. The mice were approximately 8 weeks at the initiation of dosing with an average body weight of 24 grams.

Assay

The day prior to dose administration 56 BALB/c mice were placed into a dark room and dark adapted for a minimum of 12 hours prior to dose administration. The mice were maintained in the dark for the duration of the study.

Each animal was removed from its cage and dosed accordingly to the study design in Table 4 (see below). Each animal was administered 0.1 mL of the appropriate compound or vehicle via oral gavage using a 1 mL syringe fitted with a 23 gauge oral gavage needle. Two hours following dose administration, animals were removed from the dark and exposed to 5000 Lux white light for 10 minutes to photobleach their eyes. Following the completion of the photobleach the animals were returned to the dark for 2 hours to allow for the regeneration of 11-cis-retinal in the eyes. Two hours after photobleaching each animal was euthanized with carbon dioxide followed by cervical dislocation, in the dark under red light. The light control group was euthanized immediately following photobleaching. Immediately following the cervical dislocation both eyes of each animal were removed and transferred into separate tubes, flash frozen in liquid nitrogen and stored in the dark at −80° C. until processing and analysis.

TABLE 4

Study Design

| Group | Treatment | Dose Level (mg/kg) | Conc. (mg/mL) | Dose Vol. (mL/animal) | Bleach Time (Hours) | Number of Animals | Total Number of Animals |
|---|---|---|---|---|---|---|---|
| 1 | cmpd A | 3 | 0.83 | 0.1 | 2 | 4 | 56 |
| 2 | cmpd A | 1 | 0.28 | 0.1 | 2 | 4 | |
| 3 | cmpd A | 0.5 | 0.14 | 0.1 | 2 | 4 | |
| 4 | cmpd A | 0.3 | 0.08 | 0.1 | 2 | 4 | |
| 5 | cmpd A | 0.1 | 0.03 | 0.1 | 2 | 4 | |
| 6 | cmpd A | 0.03 | 0.008 | 0.1 | 2 | 4 | |
| 7 | cmpd D | 3 | 0.89 | 0.1 | 2 | 4 | |
| 8 | cmpd D | 1 | 0.30 | 0.1 | 2 | 4 | |
| 9 | cmpd D | 0.5 | 0.15 | 0.1 | 2 | 4 | |
| 10 | cmpd D | 0.3 | 0.09 | 0.1 | 2 | 4 | |
| 11 | cmpd D | 0.1 | 0.03 | 0.1 | 2 | 4 | |
| 12 | cmpd D | 0.03 | 0.009 | 0.1 | 2 | 4 | |
| RC[1] | Vehicle[3] | 0 | 0 | 0.1 | 2 | 4 | |
| LC[2] | Vehicle | 0 | 0 | 0.1 | 2 | 4 | |

[1] RC = Recovery control
[2] LC = Light control
[3] Vehicle = di-water

Eye Sample Analysis

The right eye of each animal was processed according to the method listed in Table 5 (see below). All sample processing procedures were performed in the dark under red light.

TABLE 5

Eye Sample Processing

| Reagent/Step | Volume/Time |
|---|---|
| 10 mM Bis-Tris-Propane | 500 μL |
| 0.8M Hydroxylamine | 20 μL |
| Homogenized | 2x20 seconds @ 6000 RPM |
| Methanol | 500 μL |
| Heptane | 500 μL |
| Vortex | 15 minutes |
| Centrifuge | 10 minutes @ 13,200 RP< |
| Transfer to HPLC vial | 250 μL |

Extracted samples were analyzed using an Agilent 1100 HPLC system according to the procedure outlined in Table 6 (see below)

TABLE 6

HPLC Conditions
HPLC Conditions

Column: Normal Phase Silica column Beckman Coulter, 5 μM, 4.6 × 250 mm
Mobile Phase A (85%)   100% Hexanes
Mobile Phase B (15%)   Ethyl Acetate with 1% Isopropyl Alcohol
Flow Rate              1.5 mL/min Data Analysis HPLC analysis of the eyes measures the peak area units of the 110cis-Ral-Oxime_syn. Signal.

Data analysis % inhibition (drug vs. recovery control). % control (drug vs. light control), and One-way ANOVA (followed by Tukey's Multiple Comparison) were performed using peak area units and performed by Prism software. Data are represented as mean and standard deviation.

Results 3-amino-1-(3-((tetrahydro-2H-pyran-4-yl)methoxy)phenyl)propan-1-ol (compound A) percent inhibition of 11-cis-retinal at 2 hours following oral administration of 0.03, 0.1, 0.3, 0.5, 1 and 3 mg/kg dose are listed in Table 7 (see below). There was a statistically significant difference, P<0.001 for 0.3, 0.5, 1 and 3 mg/kg dose levels from the recovery control group (see Table 9).

3-amino-1-(3-((tetrahydro-2H-pyran-2-yl)methoxy)phenyl)propan-1-ol (compound D) percent inhibition of 11-cis-retinal at 2 hours following oral administration of 0.03, 0.1, 0.3, 0.5, 1 and 3 mg/kg dose are also listed in Table 7 (see below). There was a statistically significant difference, P<0.001 for 1 and 3 mg/kg dose levels from the recovery control group.

Conclusions

Figure 2:
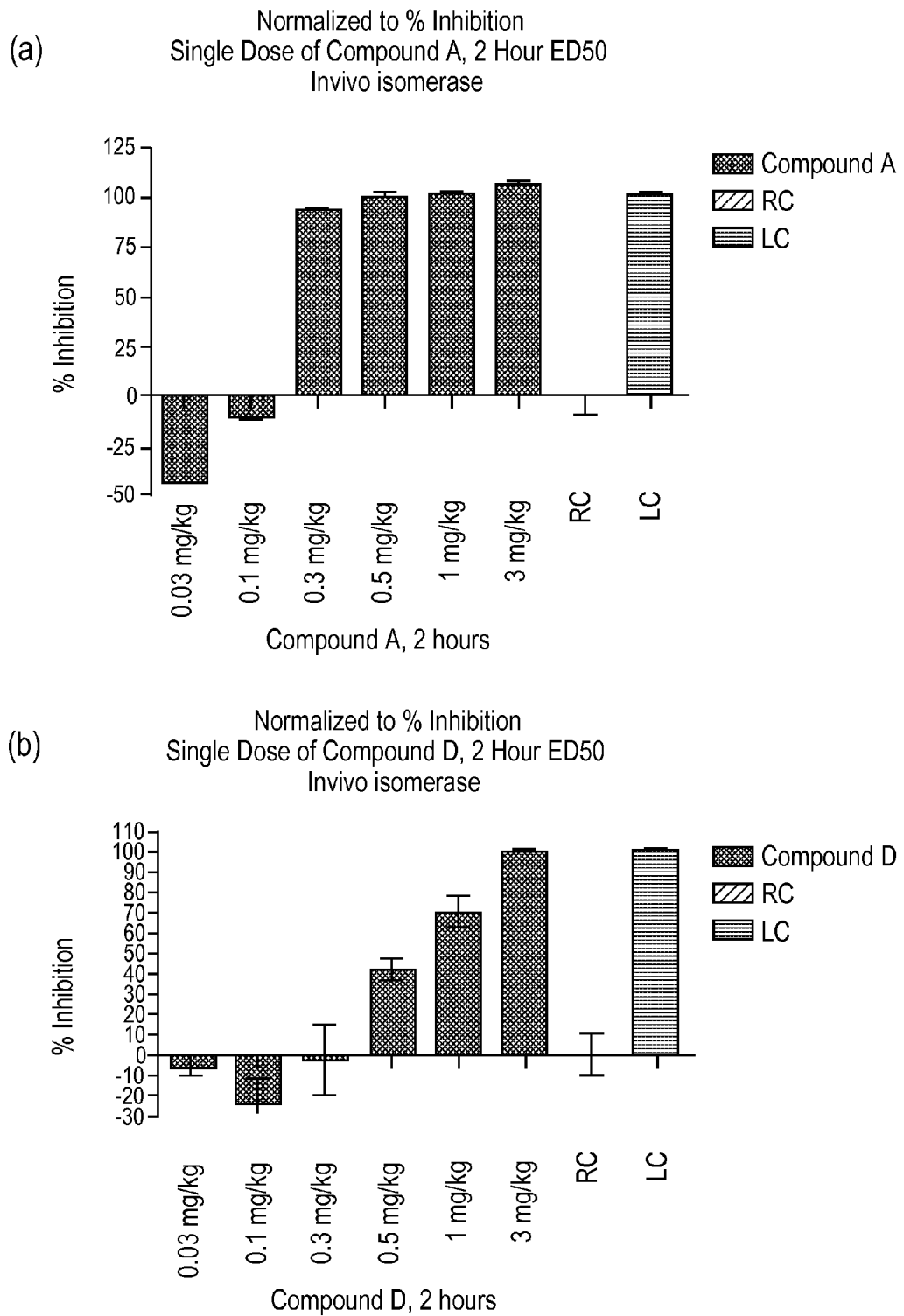
FIGS. 2(a) and (b) provides a summary of an illustrative dose response experiment comparing between 3-amino-1-(3-((tetrahydro-2H-pyran-4-yl)methoxy)phenyl)propan-1-ol (compound A) and 3-amino-1-(3-((tetrahydro-2H-pyran-2-yl)methoxy)phenyl)propan-1-ol (compound D)

3-Amino-1-(3-((tetrahydro-2H-pyran-4-yl)methoxy)phenyl)propan-1-ol (compound A) had a significant inhibitory effect at 0.3 mg/kg, 0.5 mg/kg, 1 mg/kg and 3 mg/kg dose levels on the recovery of 11-cis-retinal following a single oral dose, see FIG. 2(a).

3-Amino-1-(3-((tetrahydro-2H-pyran-2-yl)methoxy)phenyl)propan-1-ol (compound D) had a significant inhibitory effect at 1 mg/kg and 3 mg/kg dose levels on the recovery of 11-cis-retinal following a single oral dose, see FIG. 2(b).

Figure 3:
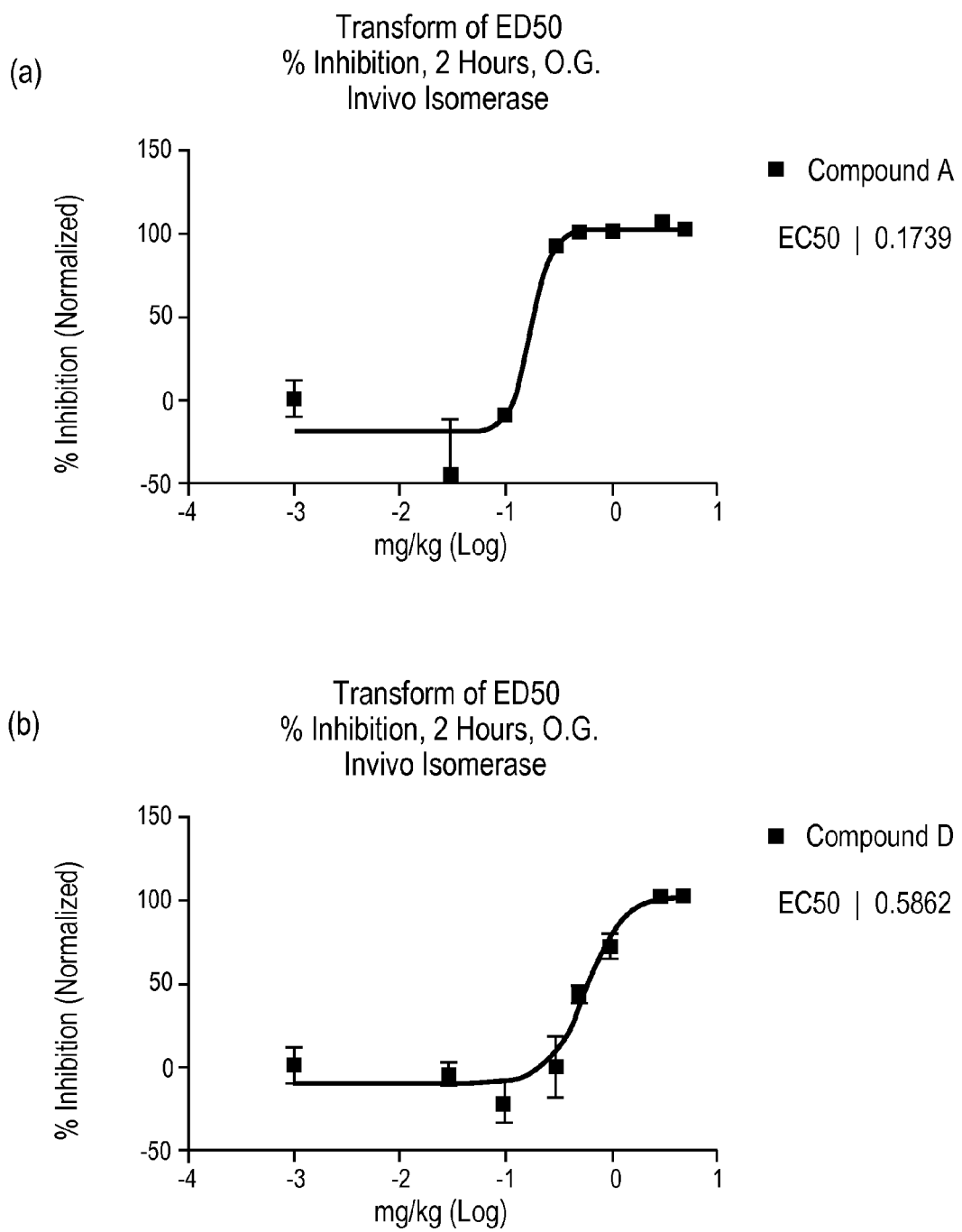
FIGS. 3(a) and (b) provides a summary of an illustrative dose response experiment comparing between 3-amino-1-(3-((tetrahydro-2H-pyran-4-yl)methoxy)phenyl)propan-1-ol (compound A) and 3-amino-1-(3-((tetrahydro-2H-pyran-2-yl)methoxy)phenyl)propan-1-ol (compound D)

The dose at which 11-cis-retinal recovery was inhibited by 50% was 0.17 mg/kg for 3-amino-1-(3-((tetrahydro-2H-pyran-4-yl)methoxy)phenyl)propan-1-ol (compound A) and 0.59 mg/kg for 3-amino-1-(3-((tetrahydro-2H-pyran-2-yl)methoxy)phenyl)propan-1-ol (compound D) (see FIGS. 3 (a) and (b)).

In this dose response experiment, 3-amino-1-(3-((tetrahydro-2H-pyran-4-yl)methoxy)phenyl)propan-1-ol (compound A) had an $IC_{50}$ of 0.17 mg/kg, and 3-amino-1-(3-((tetrahydro-2H-pyran-2-yl)methoxy)phenyl)propan-1-ol (compound D) had an $IC_{50}$ of 0.59 mg/kg. Thus, within this parameter, 3-amino-1-(3-((tetrahydro-2H-pyran-4-yl)methoxy)phenyl)propan-1-ol (compound A) is approximately 3-4× more active than 3-amino-1-(3-((tetrahydro-2H-pyran-2-yl)methoxy)phenyl)propan-1-ol (compound D).

In this same dose response experiment, 3-amino-1-(3-((tetrahydro-2H-pyran-4-yl)methoxy)phenyl)propan-1-ol (compound A) showed nearly 100% inhibition at a dose of 0.5 mg/kg, whereas 3-amino-1-(3-((tetrahydro-2H-pyran-2-yl)methoxy)phenyl)propan-1-ol (compound D) required a dose of 3.0 mg/kg to show the same level of inhibition. Thus, within this parameter, 3-amino-1-(3-((tetrahydro-2H-pyran-4-yl)methoxy)phenyl)propan-1-ol (compound A) is approximately 6× more active than 3-amino-1-(3-((tetrahydro-2H-pyran-2-yl)methoxy)phenyl)propan-1-ol (compound D).

In this same dose response experiment, 3-amino-1-(3-((tetrahydro-2H-pyran-4-yl)methoxy)phenyl)propan-1-ol (compound A) showed greater than 90% inhibition at a dose of 0.3 mg/kg, whereas 3-amino-1-(3-((tetrahydro-2H-pyran-2-yl)methoxy)phenyl)propan-1-ol (compound D) showed no inhibition at this same dose. Thus, within this parameter, 3-amino-1-(3-((tetrahydro-2H-pyran-4-yl)methoxy)phenyl)propan-1-ol (compound A) was greater than 10× more active than 3-amino-1-(3-((tetrahydro-2H-pyran-2-yl)methoxy)phenyl)propan-1-ol (compound D).

TABLE 7

Percent Inhibition at 2 Hours

| Compound ID | Dose Level (mg/kg) | Avg. % Inhibition | Standard Deviation | Number of Animals |
|---|---|---|---|---|
| cmpd A | 0.03 | −44.1 | −53.6 | 3 |
| cmpd A | 0.1 | −9.8 | −3.5 | 4 |
| cmpd A | 0.3 | 92.4 | −1.5 | 4 |
| cmpd A | 0.5 | 99.3 | −3.9 | 3 |
| cmpd A | 1 | 100.4 | −1.8 | 4 |
| cmpd A | 3 | 105.2 | −1.9 | 4 |
| cmpd D | 0.03 | −5.3 | −8.8 | 3 |
| cmpd D | 0.1 | −23.9 | −22.1 | 4 |
| cmpd D | 0.3 | −2.1 | −24.8 | 2 |
| cmpd D | 0.5 | 41.4 | −10.4 | 4 |
| cmpd D | 1 | 70.2 | −14.9 | 4 |
| cmpd D | 3 | 100 | −2.8 | 4 |

TABLE 8

Percent control at 2 Hours

| Compound ID | Dose Level (mg/kg) | Avg. % Inhibition | Standard Deviation | Number of Animals |
|---|---|---|---|---|
| cmpd A | 0.03 | 144.1 | 53.6 | 3 |
| cmpd A | 0.1 | 109.8 | 3.5 | 4 |
| cmpd A | 0.3 | 7.6 | 1.5 | 4 |
| cmpd A | 0.5 | 0.7 | 3.9 | 3 |
| cmpd A | 1 | −0.4 | 1.8 | 4 |
| cmpd A | 3 | −5.2 | 2.0 | 4 |
| cmpd D | 0.03 | 105.3 | 8.8 | 3 |
| cmpd D | 0.1 | 123.9 | 22.1 | 4 |
| cmpd D | 0.3 | 102.1 | 24.8 | 2 |
| cmpd D | 0.5 | 58.6 | 10.4 | 4 |
| cmpd D | 1 | 29.8 | 14.8 | 4 |
| cmpd D | 3 | 0 | 2.8 | 4 |

TABLE 9

One-way ANOVA

| Tukey's Multiple Comparison Test | Mean Diff. | q | P Value |
|---|---|---|---|
| Vehicle vs. 0.03 mg/kg cmpd A | −7.4 | 4.2 | P < 0.05 |
| Vehicle vs. 0.1 mg/kg cmpd A | −1.7 | 1.0 | P < 0.05 |
| Vehicle vs. 0.3 mg/kg cmpd A | 15.6 | 9.6 | P < 0.001 |
| Vehicle vs. 0.5 mg/kg cmpd A | 16.7 | 9.5 | P < 0.001 |
| Vehicle vs. 1 mg/kg cmpd A | 16.9 | 10.4 | P < 0.001 |
| Vehicle vs. 3 mg/kg cmpd A | 17.7 | 10.9 | P < 0.001 |
| Vehicle vs. 0.03 mg/kg cmpd D | −0.9 | 0.6 | P < 0.05 |
| Vehicle vs. 0.1 mg/kg cmpd D | −4.0 | 3.0 | P < 0.05 |
| Vehicle vs. 0.3 mg/kg cmpd D | −0.4 | 0.2 | P < 0.05 |
| Vehicle vs. 0.5 mg/kg cmpd D | 7.0 | 5.2 | P < 0.05 |
| Vehicle vs. 1 mg/kg cmpd D | 11.8 | 8.9 | P < 0.001 |
| Vehicle vs. 3 mg/kg cmpd D | 16.9 | 12.6 | P < 0.001 |

Single Dose Time Course of 3-amino-1-(3-((tetrahydro-2H-pyran-4-yl)methoxy)phenyl)propan-1-ol (example 1, compound A) and 3-amino-1-(3-((tetrahydro-2H-pyran-2-yl)methoxy)phenyl)propan-1-ol (compound D) in the in Vivo Isomerase Assay at 0.3 mg/kg in BALB/c Mice Introduction Light is essential for vision but can also generate photochemical damage to the retina (Boulton et al., 2001). Protective effects against photo damage were observed when rhodopsin regeneration was reduced due to mutations in RPE65, a protein necessary for the regeneration of the retinoid chromophore 11-cis-retinal in the visual cycle (Grimm et al., 2000). Likewise, it is expected that drugs that inhibit regeneration of 11-cis retinal will have a protective effect against light mediated retinal damage and degenerative disorders. 11-cis-retinal is generated by oxidation of 11-cis retinol in the retina pigment epithelium (RPE). The isomerization reaction that forms 11-cis-retinol from all-trans retinylesters is rate limiting in the visual cycle and it can be expected that compounds that inhibit this reaction will limit the generation of 11-cis-retinal and thus have a therapeutic potential in the treatment of light-mediated retinal degenerative disorders. The rate of regeneration of 11-cis-retinal will affect the rate of functional photoreceptor recovery from bleaching light. The regeneration of 11-cis-retinal after bleach is used to screen for active cycle modulators.

Purpose

The purpose of this study was to assess the effect over time of 3-amino-1-(3-((tetrahydro-2H-pyran-4-yl)methoxy)phenyl)propan-1-ol (compound A) and 3-amino-1-(3-((tetrahydro-2H-pyran-2-yl)methoxy)phenyl)propan-1-ol (compound D), on the regeneration of 11-cis-retinal following a single oral dose at 0.3 mg/kg to BALB/c mice.

Materials and Methods

The test compounds 3-amino-1-(3-((tetrahydro-2H-pyran-4-yl)methoxy)phenyl)propan-1-ol (compound A, example 1) and 3-amino-1-(3-((tetrahydro-2H-pyran-2-yl)methoxy)phenyl)propan-1-ol (compound D and described in US Patent Application Publication US 2009/0326074). All test compounds were stored at room temperature, dessicated.

On the day prior to dose administration 3-amino-1-(3-((tetrahydro-2H-pyran-4-yl)methoxy)phenyl)propan-1-ol (compound A) and 3-amino-1-(3-((tetrahydro-2H-pyran-2-yl)methoxy)phenyl)propan-1-ol (compound D) were weighed into new empty glass vials. The compounds were dissolved in di-water at the concentration of 0.068 mg/mL and stored overnight at 4° C.

52 Male BALB/c mice (Charles River Laboratories) were used for this study. The mice were approximately 8 weeks at the initiation of dosing with an average body weight of 23 grams.

Assay

The day prior to dose administration 52 BALB/c mice were placed into a dark room and dark adapted for a minimum of 12 hours prior to dose administration. The mice were maintained in the dark for the duration of the study.

Each animal was removed from its cage and dosed accordingly to the study design in Table 10 (see below). Each animal was administered 0.1 mL of the appropriate test article or vehicle orally using a 1 mL syringe fitted with a 23 gauge oral gavage needle. At 2, 4, 6, 8, 16 or 24 hours following dose administration, animals were removed from the dark and exposed to 5000 Lux white light for 10 minutes to photobleach their eyes. Following the completion of the photobleach the animals were returned to the dark for 2 hours to allow for the regeneration of 11-cis-retinal in the eyes. Two hours after photobleaching each animal was euthanized with carbon dioxide followed by cervical dislocation, in the dark under red light. The light control group was euthanized immediately following photobleaching. Immediately following the cervical dislocation both eyes of each animal were removed and transferred into separate tubes, flash frozen in liquid nitrogen and stored in the dark at −80° C. until processing and analysis.

TABLE 10

Study Design

| Group | Treatment | Dose Level (mg/kg) | Conc. (mg/mL) | Dose Vol. (mL/animal) | Bleach Time (Hours) | Number of Animals |
|---|---|---|---|---|---|---|
| 1 | cmpd A | 0.3 | 0.068 | 0.1 | 2 | 4 |
| 2 | cmpd A | 0.3 | 0.068 | 0.1 | 4 | 4 |
| 3 | cmpd A | 0.3 | 0.068 | 0.1 | 6 | 4 |
| 4 | cmpd A | 0.3 | 0.068 | 0.1 | 8 | 4 |
| 5 | cmpd A | 0.3 | 0.068 | 0.1 | 16 | 4 |
| 6 | cmpd A | 0.3 | 0.068 | 0.1 | 24 | 4 |
| 7 | cmpd D | 0.3 | 0.068 | 0.1 | 2 | 4 |
| 8 | cmpd D | 0.3 | 0.068 | 0.1 | 4 | 4 |
| 9 | cmpd D | 0.3 | 0.068 | 0.1 | 6 | 4 |
| 10 | cmpd D | 0.3 | 0.068 | 0.1 | 8 | 4 |
| 11 | cmpd D | 0.3 | 0.068 | 0.1 | 16 | 4 |
| 12 | cmpd D | 0.3 | 0.068 | 0.1 | 24 | 4 |
| RC[1] | Vehicle[3] | 0 | 0 | 0.1 | 4 | 2 |
| LC[2] | Vehicle | 0 | 0 | 0.1 | 4 | 2 |

[1]RC = Recovery Control
[2]LC = Light Control
[3]Vehicle = di-water

Eye Sample Analysis

The right eye of each animal was processed according to the method listed in Table 11 (see below). All sample processing procedures were performed in the dark under red light.

TABLE 11

Eye Sample Processing

| Reagent/Step | Volume/Time |
|---|---|
| 10 mM Bis-Tris-Propane | 500 μL |
| 0.8M Hydroxylamine | 20 μL |
| Homogenized | 2x 20 seconds @ 6000 RPM |
| Methanol | 500 μL |
| Heptane | 500 μL |
| Vortex | 15 minutes |
| Centrifuge | 10 minutes @ 13,200 RPM |
| Transfer to HPLC vial | 250 μL |

Extracted samples were analyzed using an Agilent 1100 HPLC system according to the procedure outlined in Table 12 (see below)

TABLE 12

HPLC Conditions

HPLC Conditions

Column: Normal Phase Silica column Beckman Coulter, 5 μM, 4.6 × 250 mm
Mobile Phase A (85%)   100% Hexanes
Mobile Phase B (15%)   Ethyle Acetate with 1% Isopropyl alcohol
Flow Rate              1.5 mL/min Data Analysis HPLC analysis of the eyes measures the peak area units of the 11Ocis-Ral-Oxime_syn. Signal.

Data analysis % inhibition (drug vs. recovery control). % control (drug vs. light control), and One-way ANOVA (followed by Tukey's Multiple Comparison) were performed using peak area units and performed by Prism software. Data are represented as mean and standard deviation.

Results

3-Amino-1-(3-((tetrahydro-2H-pyran-4-yl)methoxy)phenyl)propan-1-ol (compound A) percent inhibition of 11-cis-retinal at 2, 4, 6, 8, 16 and 24 hours following oral administration of a 0.3 mg/kg dose are listed in Table 13 (see below). There was a statistically significant difference, $P<0.001$, from the recovery control group for the 2, 4 and 6 hour time points (see Table 15). There was not a statistically significant difference, $P>0.05$ for the 8, 16 and 24 time points from the recovery control group.

3-Amino-1-(3-((tetrahydro-2H-pyran-2-yl)methoxy)phenyl)propan-1-ol (compound D) percent inhibition of 11-cis-retinal at 2, 4, 6, 8, 16 and 24 hours following oral administration of a 0.3 mg/kg dose are listed in Table 16 (see below). There was not a statistically significant difference, $P>0.05$ for any time points from the recovery control group. (see table 18)

Conclusions

3-Amino-1-(3-((tetrahydro-2H-pyran-4-yl)methoxy)phenyl)propan-1-ol (compound A) had a significant inhibitory effect at 2, 4 and 6 hours on the recovery of 11-cis-retinal following single dose administration at a dose level of 0.3 mg/kg. There was no significant effect on the recovery of 11-cis-retinal at the 8, 16 and 24 hour time points, see FIG. 4(a).

Figure 4:
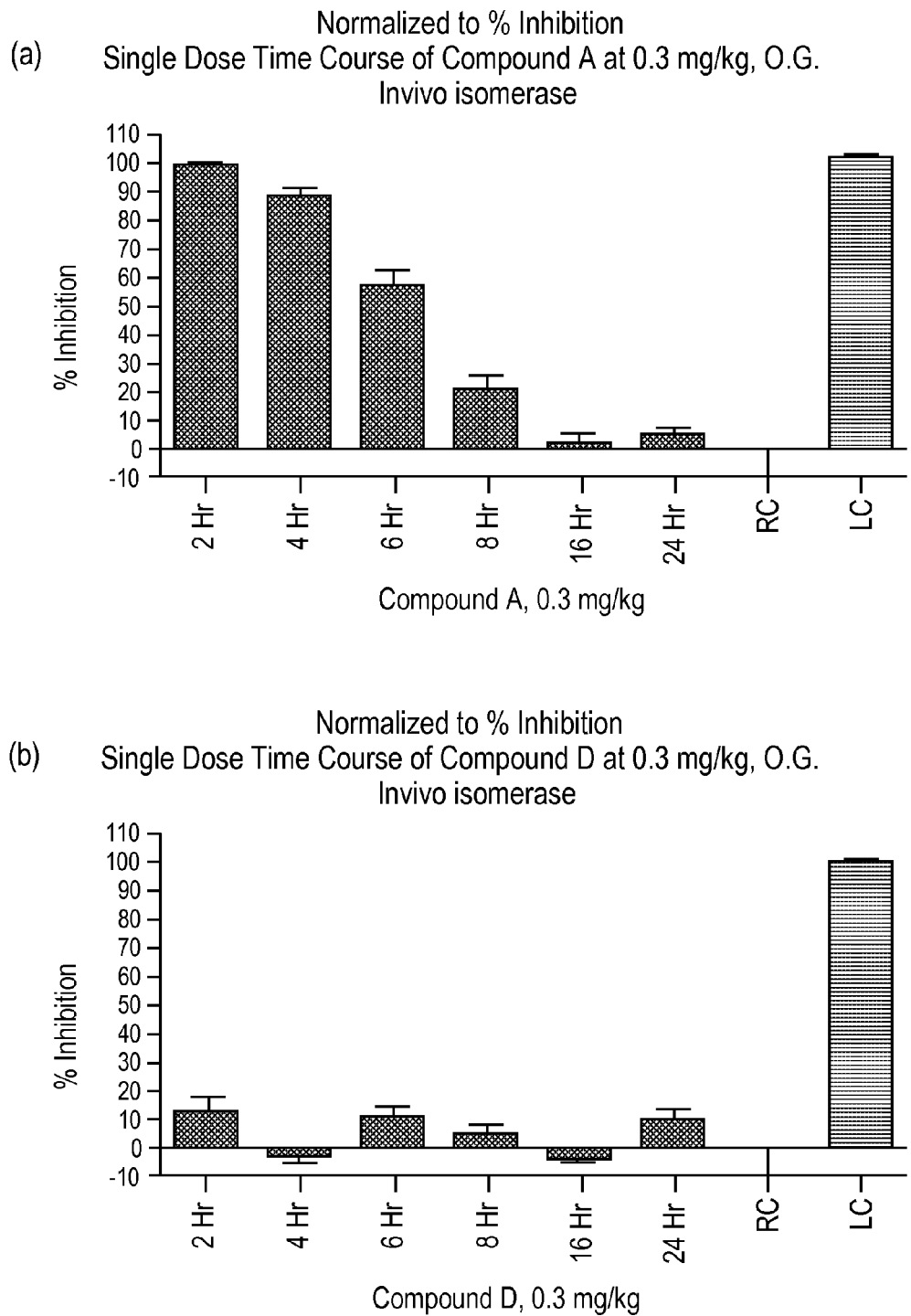
FIGS. 4(a) and (b) provides a summary of an illustrative time course experiment comparing between 3-amino-1-(3-((tetrahydro-2H-pyran-4-yl)methoxy)phenyl)propan-1-ol (compound A) and 3-amino-1-(3-((tetrahydro-2H-pyran-2-yl)methoxy)phenyl)propan-1-ol (compound D).

3-Amino-1-(3-((tetrahydro-2H-pyran-2-yl)methoxy)phenyl)propan-1-ol (compound D) had no significant inhibitory effect at any time points on the recovery of 11-cis-retinal following single dose administration at a dose level of 0.3 mg/kg, see FIG. 4(b).

The recovery control and the light control data were consistent with the historical data for both experiments.

In this time course experiment, determinations were made at 2, 4, 6, 8, 16 and 24 hours after dosing level of 0.3 mg/kg. The activity of 3-amino-1-(3-((tetrahydro-2H-pyran-4-yl)methoxy)phenyl)propan-1-ol (compound A) was statistically significant from the control group at the 2, 4, and 6 hour time points, whereas 3-amino-1-(3-((tetrahydro-2H-pyran-2-yl)methoxy)phenyl)propan-1-ol (compound D) did not exhibit a significant difference from the control group at any time point. Thus within these parameters, 3-amino-1-(3-((tetrahydro-2H-pyran-4-yl)methoxy)phenyl)propan-1-ol (compound A) was greater than 10× more active than 3-amino-1-(3-((tetrahydro-2H-pyran-2-yl)methoxy)phenyl)propan-1-ol (compound D).

TABLE 13

Percent Inhibition, 0.3 mg/kg, 3-amino-1-(3-((tetrahydro-2H-pyran-4-yl)methoxy)phenyl)propan-1-ol (compound A)

| Compound ID | Time Point (Hours) | Avg. % Inhibition | Standard Deviation | Number of Animals |
|---|---|---|---|---|
| cmpd A | 2 | 98.0 | 1.9 | 4 |
| cmpd A | 4 | 88.5 | 3.5 | 4 |
| cmpd A | 6 | 56.3 | 9.7 | 4 |
| cmpd A | 8 | 20.2 | 8.8 | 4 |
| cmpd A | 16 | 1.5 | 4.9 | 4 |
| cmpd A | 24 | 4.2 | 4.6 | 4 |

TABLE 14

Percent Control, 0.3 mg/kg, 3-amino-1-(3-((tetrahydro-2H-pyran-4-yl)methoxy)phenyl)propan-1-ol (compound A)

| Compound ID | Time Point (Hours) | Avg. % Inhibition | Standard Deviation | Number of Animals |
|---|---|---|---|---|
| cmpd A | 2 | 2.0 | 1.9 | 4 |
| cmpd A | 4 | 11.5 | 3.5 | 4 |
| cmpd A | 6 | 43.7 | 9.7 | 4 |
| cmpd A | 8 | 79.8 | 8.8 | 4 |
| cmpd A | 16 | 98.5 | 4.8 | 4 |
| cmpd A | 24 | 95.8 | 4.6 | 4 |

TABLE 15

One-way ANOVA, 0.3 mg/kg, 3-amino-1-(3-((tetrahydro-2H-pyran-4-yl)methoxy)phenyl)propan-1-ol (compound A)

| Tukey's Multiple Comparison Test | Mean Diff. | q | P value |
|---|---|---|---|
| Vehicle vs. 2 Hr | 46.9 | 21.4 | P < 0.001 |
| Vehicle vs. 4 Hr | 42.3 | 19.4 | P < 0.001 |
| Vehicle vs. 6 Hr | 26.9 | 12.3 | P < 0.001 |
| Vehicle vs. 8 Hr | 9.7 | 4.4 | P > 0.05 |
| Vehicle vs. 16 Hr | 0.73 | 0.33 | P > 0.05 |
| Vehicle vs. 24 Hr | 2.0 | 0.91 | P > 0.05 |

TABLE 16

Percent Inhibition, 0.3 mg/kg, 3-amino-1-(3-((tetrahydro-2H-pyran-2-yl)methoxy)phenyl)propan-1-ol (compound D)

| Compound ID | Time Point (Hours) | Avg. % Inhibition | Standard Deviation | Number of Animals |
|---|---|---|---|---|
| cmpd D | 2 | 13.2 | 10.0 | 4 |
| cmpd D | 4 | −1.8 | 6.4 | 4 |
| cmpd D | 6 | 12.1 | 4.6 | 4 |
| cmpd D | 8 | 5.4 | 6.0 | 4 |

TABLE 16-continued

Percent Inhibition, 0.3 mg/kg, 3-amino-1-(3-((tetrahydro-2H-pyran-2-yl)methoxy)phenyl)propan-1-ol (compound D)

| Compound ID | Time Point (Hours) | Avg. % Inhibition | Standard Deviation | Number of Animals |
|---|---|---|---|---|
| cmpd D | 16 | −4.1 | 4.5 | 4 |
| cmpd D | 24 | 10.5 | 4.8 | 4 |

TABLE 17

Percent Control, 0.3 mg/kg, 3-amino-1-(3-((tetrahydro-2H-pyran-2-yl)methoxy)phenyl)propan-1-ol (compound D)

| Compound ID | Time Point (Hours) | Avg. % Inhibition | Standard Deviation | Number of Animals |
|---|---|---|---|---|
| cmpd D | 2 | 86.8 | 10.0 | 4 |
| cmpd D | 4 | 101.8 | 6.5 | 4 |
| cmpd D | 6 | 87.9 | 4.6 | 4 |
| cmpd D | 8 | 94.6 | 6.0 | 4 |
| cmpd D | 16 | 104.1 | 4.5 | 4 |
| cmpd D | 24 | 89.5 | 4.8 | 4 |

TABLE 18

One-way ANOVA, 0.3 mg/kg, 3-amino-1-(3-((tetrahydro-2H-pyran-2-yl)methoxy)phenyl)propan-1-ol (compound D)

| Tukey's Multiple Comparison Test | Mean Diff. | q | P value |
|---|---|---|---|
| Vehicle vs. 2 Hr | 6.3 | 2.9 | P > 0.05 |
| Vehicle vs. 4 Hr | −0.88 | 0.40 | P > 0.05 |
| Vehicle vs. 6 Hr | 5.8 | 2.6 | P > 0.05 |
| Vehicle vs. 8 Hr | 2.6 | 1.2 | P > 0.05 |
| Vehicle vs. 16 Hr | −2.0 | 0.88 | P > 0.05 |
| Vehicle vs. 24 Hr | 5.0 | 2.3 | P > 0.05 |

Example 3

A2E Accumulation Model

The purpose of this study was to assess the ability of test compounds to inhibit the accumulation of A2E in the eyes of abca4$^{-/-}$, RPE65 Leu450Leu mice (ABCR) following 91 days of continuous dosing.

The test compound (R)-3-amino-1-(3-((tetrahydro-2H-pyran-4-yl)methoxy)phenyl)-propan-1-ol (Example 1) was stored in a freezer set to maintain at approximately −20° C. On the day prior to dosing and once weekly for 13 weeks the test articles were weighed into new empty glass scintillation vials. The compound was dissolved in ethanol (10% of final volume) and then diluted with deionized water (90% of total final volume) resulting in a concentrations of 0.2 mg/mL. This dosing solution was administered to the high dose groups (1 mg/kg). For the low dose groups (0.1 mg/kg) a 0.2 mg/mL dosing solution was prepared by diluting with vehicle (10% ethanol 90% water) to the appropriate concentration. The dosing solutions were stored in a refrigerator set to maintain between 2 to 8° C. and used for dose administration once per day for one week. The vehicle used for dosing control groups was 10% ethanol 90% deionized water.

Male and female abca4$^{-/-}$, and RPE65 Leu450Leu, mice (Charles River Laboratories) were used for this study. The mice were approximately 8-12 week old at the initiation of dosing with a starting average body weight of 19 grams for females and 27 grams for males.

Group 1 animals (Time zero for A2E accumulation) were euthanized with carbon dioxide followed by cervical dislocation on the first day of dosing. Immediately following the cervical dislocation both eyes of the animal was removed and transferred into separate tubes, flash frozen in liquid nitrogen and stored in the dark at −80° C. until processing and analysis.

The remaining groups (2-4) were dosed once each day for 13 weeks. When dosed each animal was administered a 5 mL/kg dose of the appropriate test compound or vehicle via oral gavage using a 1 mL syringe fitted with a 20 gauge oral gavage needle. Upon the completion of the study, animals were euthanized with carbon dioxide followed by cervical dislocation. Immediately following the cervical dislocation both eyes of the animal was removed and transferred into separate tubes, flash frozen in liquid nitrogen and stored in the dark at −80° C. until processing and analysis for A2E concentration.

TABLE 19

Study Design

| Group | Test Article Treatment | Dose Level (mg/kg) | Conc. (mg/mL) | Dose Vol. (mL/kg) | Number of Animals |
|---|---|---|---|---|---|
| 1 | No Dose | 0 | N/A | N/A | 8 |
| 2 | Vehicle[1] | 0 | 0 | 5 | 8 |
| 3 | Test cmpd | 0.1 | 0.02 | 5 | 8 |
| 4 | Test cmpd | 1 | 0.2 | 5 | 8 |

[1]Vehicle = 10% Ethanol, 90% Deionized Water

The left eye of each animal was analyzed for A2E concentration and was processed according to the method listed in Table 20 (See Below). All sample processing procedures were performed in the dark under red light.

TABLE 20

Eye Sample Extraction

| Reagent/Step | Volume/Time |
|---|---|
| Phosphate Buffered Saline | 500 µL |
| Homogenized | 30 seconds @ 30,000 RPM |
| Methanol | 600 µL |
| Chloroform | 750 µL |
| Vortex | 5 minutes |
| Equilibrate | 15 minutes |
| Vortex | 5 minutes |
| Centrifuge | 10 minutes @ 13,200 RPM |
| Speed Vac. | 1 hour |
| Reconstitution | |
| Methanol | 25 µL |
| 72% Acetonitrile/28% Water, 0.05% Trifluoroacetic acid (TFA) | 20 µL |
| Transfer to HPLC vial | 45 µL |

Extracted samples were analyzed using an Agilent 1100 HPLC system according to the procedure outlined in Table 21 (See Below)

TABLE 21

HPLC Conditions
HPLC Conditions

| Column: Luna 2.5 µm C18, 100A 250 mm × 2.0 mm (Phenomenex) | |
| Flow Rate | 0.4 mL/min |
| Injection Volume | 30 µL |

TABLE 21-continued

HPLC Conditions
HPLC Conditions

| Mobile Phase A | Acetonitrile with (0.05% TFA) |
| Mobile Phase B | Water with 0.05% TFA |

Gradient Profile

| Time (minutes) | Mobile Phase A | Mobile Phase B |
|---|---|---|
| 0 | 72 | 28 |
| 10 | 77 | 23 |
| 30 | 80 | 20 |
| 40 | 90 | 10 |

HPLC analysis of the eyes looks at the peak area units of the A2E present in the eyes following extraction as described above.

Data analysis % inhibition (drug vs. recovery control), % control (drug vs. light control), and One-way ANOVA (followed by Tukey's Multiple Comparison) were performed using peak area units and performed by Prism software. Data are represented as mean and standard deviation. A summary of the data collected is provided in Table 22.

TABLE 22

Day 91 A2E Concentrations

| | Concentration Pico Moles/eye Animal # | | | | | | | |
|---|---|---|---|---|---|---|---|---|
| Compound ID | 1 | 2 | 3 | 4 | 5 | 6 | 7 | 8 |
| T0 (no Dose) | 4.67 | 6.27 | 5.38 | 5.52 | 4.93 | 5 | 4.67 | 4.52 |
| Vehicle | 13.24 | 14.1 | 14.7 | 14.35 | 13.91 | 13.2 | 11.05 | 14.24 |
| Test cmpd, 0.1 mg/kg | 9.64 | 8.97 | 10.23 | 8.42 | 8.49 | 9.6 | 11.68 | 10.27 |
| Test cmpd, 1.0 mg/kg | 6.49 | 7.68 | 7.75 | 8.87 | 7.56 | 8.01 | 8.86 | 9.49 |

At a dose level of 0.1 mg/kg, (R)-3-amino-1-(3-((tetrahydro-2H-pyran-4-yl)methoxy)phenyl)-propan-1-ol (Example 1) inhibited A2E accumulation at 46.4% (sd 12.7) following daily oral administration for 91 days. This was a statistically significant difference, $P<0.001$, from the vehicle control group.

At a dose level of 1 mg/kg, (R)-3-amino-1-(3-((tetrahydro-2H-pyran-4-yl)methoxy)phenyl)-propan-1-ol (Example 1) inhibited A2E accumulation at 65.0% (sd 11.2) following daily oral administration for 91 days. This was a statistically significant difference, $P<0.001$, from the vehicle control group.

Conclusions (R)-3-amino-1-(3-((tetrahydro-2H-pyran-4-yl)methoxy)phenyl)-propan-1-ol (Example 1) had statistically significant inhibitory effects on the accumulation of A2E following 91 days of oral dosing at 0.1 mg/kg and 1.0 mg/kg. The vehicle control and the time zero A2E data were consistent with historical data for A2E accumulation in this assay.

Example 4

In Vivo Light Mouse Model

This Example describes the effect of a compound disclosed herein in an in vivo light damage mouse model.

Exposure of the eye to intense white light can cause photodamage to the retina. The extent of damage after light treatment can be evaluated by measuring cytoplasmic histoneassociated-DNA-fragment (mono- and oligonucleosomes) content in the eye (see, e.g., Wenzel et al., *Prog. Retin. Eye Res.* 24:275-306 (2005)).

Dark adapted male Balb/c (albino, 10/group) mice are gavaged with test compound at various doses (0.03, 0.1, 0.3, 1, and 3 mg/kg) or vehicle only is administered. Six hours after dosing, the animals are subjected to light treatment (8,000 lux of white light for 1 hour). Mice are sacrificed after 40 hours of recovery in dark, and retinas are dissected. A cell death detection ELISA assay is performed according to the manufacturer's instructions (ROCHE APPLIED SCIENCE, Cell Death Detection ELISA plus Kit). Contents of fragmented DNA in the retinas are measured to estimate the retinal-protective activity of the test compound.

Example 5

Electroretinographic (ERG) Study

ERG experiments are performed using 11-16 week old BALB/c mice of both genders (n=5). All studies involve the pharmacodynamic assessment of dark-adapted (scotopic, rod-dominated) and light-adapted (photopic, cone-dominated) ERG responses. Experiments are performed using test compound. All recording procedures are performed according to the same protocol and with the same equipment. Data are aggregated across individual studies to generate summary graphs.

Results from four independent studies are combined to build the dose-response function between administration of test compound and changes in the amplitude of the scotopic b-wave (0.01 cd·s/m$^2$), 4 hours after single oral administration of the test compound (dissolved in corn oil).

The effect on the cone system is estimated based on recording and measurement of the ERG b-wave intensity-response function under photopic conditions. In such studies, two parameters are typically evaluated: maximal response ($V_{max}$), measured in microvolts, and semi-saturation constant (k), measured in cd·s/m$^2$.

Results from three independent studies are combined to estimate the effect of single dosing of test compound on the photopic ERG (11-16 week old BALB/c mice of both genders, n=5).

III. Preparation of Dosage Forms

Example 1

Parenteral Composition

To prepare a parenteral pharmaceutical composition suitable for administration by injection, 100 mg of a water-soluble salt of a 3-phenylpropylamine derivative compound as described herein such as (R)-3-amino-1-(3-((tetrahydro-2H-pyran-4-yl)methoxy)phenyl)propan-1-ol (example 1) is dissolved in sterile water and then mixed with 10 mL of 0.9% sterile saline. The mixture is incorporated into a dosage unit form suitable for administration by injection.

Example 2

Oral Composition

To prepare a pharmaceutical composition for oral delivery, 100 mg of a 3-phenylpropylamine derivative compound as described herein such as (R)-3-amino-1-(3-((tetrahydro-2H-pyran-4-yl)methoxy)phenyl)propan-1-ol (example 1) is mixed with 750 mg of starch. The mixture is incorporated into an oral dosage unit, such as a hard gelatin capsule, which is suitable for oral administration.

Example 3

Ophthalmic Solution Composition

To prepare a pharmaceutical ophthalmic solution composition, 100 mg of a 3-phenylpropylamine derivative compound as described herein such as (R)-3-amino-1-(3-((tetrahydro-2H-pyran-4-yl)methoxy)phenyl)propan-1-ol (example 1) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

IV. Clinical Trial

Example 1

Phase 1A Study of Safety and Pharmacodynamics Effect

A single-center, randomized, double masked, placebo controlled, dose-escalating Phase 1A study to determine the safety and pharmacodynamic effect of single oral dose of a compound as described herein, such as (R)-3-amino-1-(3-((tetrahydro-2H-pyran-4-yl)methoxy)phenyl)propan-1-ol (example 1), measured by dark-adapted electroretinogram (ERG), is performed. Study participants are healthy volunteers of both genders, aged 55-80, weighing between 50 and 110 kg. Major exclusion criteria include other ocular conditions (e.g. cataracts, glaucoma, uveitis, diabetic retinopathy, active conjunctivitis), change in prescription chronic medications within the preceding 28 days, treatment with a retinoid compound within the last year, treatment with sildenafil citrate, tadalafil, or vardenafil citrate within the last week, or concomitant treatment with hypnotics, anti-depressants, psychoactive substances, digitalis glycosides, L-DOPA, chloroquine, hydroxychloroquine, systemic corticosteroids, topical anti-glaucoma medications, or medications for the treatment of wet AMD. Eight cohorts are randomized 5:1/drug:placebo and assigned to dosage cohorts of 2 mg, 7 mg, 10 mg, 20 mg, 40 mg, 60 mg, and 75 mg. Plasma concentration versus time is determined. Peak plasma concentrations ($C_{max}$), time of peak plasma concentration ($T_{max}$) and mean terminal elimination half-life ($t_{1/2}$) will be determined across all doses.

ERG studies are performed prior to dosing, 4-6 hours post-dose (Day 1 ERG), 24 hours post-dose (Day 2 ERG), Day 4, and on Day 7. For patients given placebo, the ERG readout will be monitored for a rapid rise in amplitude such that the response is 90% recovered by about 20 minutes. For patients given a test compound, such as (R)-3-amino-1-(3-((tetrahydro-2H-pyran-4-yl)methoxy)phenyl)propan-1-ol (example 1), the ERG readout will be monitored for a clear dose-related slowing of the rate of recovery; i.e. the slope of the recovery function became slower with increasing dose.

Example 2

Treatment of Dry-Form Age Related Macular Degeneration

An individual diagnosed with dry-form age related macular degeneration is treated with an oral dose of 5 mg of a compound as described herein, such as (R)-3-amino-1-(3-((tetrahydro-2H-pyran-4-yl)methoxy)phenyl)propan-1-ol (example 1). On days 2, 4, 6, 8, 12, 18, 24 and 30 the individual is subjected to an electroretinogram determination to evaluate treatment response and the individual is monitored for instances of delayed dark adaptation and achromatopsia, as well as systemic adverse effects.

When ranges are used herein for physical properties, such as molecular weight, or chemical properties, such as chemical formulae, all combinations and subcombinations of ranges and specific embodiments therein are intended to be included.

The various embodiments described herein can be combined to provide further embodiments. All U.S. patents, U.S. patent application publications, U.S. patent applications, foreign patents, foreign patent applications, and non-patent publications referred to in this specification and/or listed in the Application Data Sheet, are incorporated herein by reference in their entireties.

From the foregoing it will be appreciated that, although specific embodiments have been described herein for purposes of illustration, various modifications may be made. Those skilled in the art will recognize, or be able to ascertain, using no more than routine experimentation, many equivalents to the specific embodiments described herein. Such equivalents are intended to be encompassed by the following claims. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:
1. A compound of Formula (C), or a pharmaceutically acceptable salt thereof:

Formula (C)

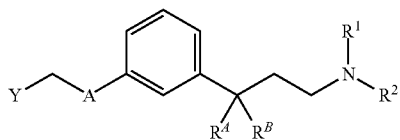

wherein,
A is selected from —O— or —CH$_2$—;
Y is

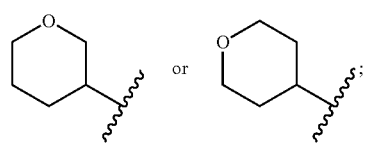 [SMILES: *C1CCCOC1 ; *C1CCOCC1]

$R^A$ is OH, $R^B$ is H; or optionally, $R^A$ and $R^B$ together form an oxo;
$R^1$ and $R^2$ are each independently selected from hydrogen, $C_1$-$C_4$ alkyl, —C(=O)R$^3$; and
$R^3$ is selected from alkyl, alkoxy, or —OCH$_2$OC(O)R$^4$, wherein $R^4$ is an alkyl or alkoxy.

2. The compound of claim 1, wherein A is —O—.
3. The compound of claim 1, wherein A is —CH$_2$—.
4. The compound of claim 1, wherein $R^A$ is OH and $R^B$ is H.
5. The compound of claim 1, wherein $R^1$ and $R^2$ are both hydrogen.
6. The compound of claim 1, wherein $R^1$ is hydrogen and $R^2$ is $C_1$-$C_4$ alkyl.
7. The compound of claim 1, wherein $R^1$ is hydrogen and $R^2$ is —C(=O)R$^3$.
8. The compound of claim 1, wherein Y is

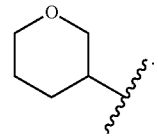

9. The compound of claim 1, wherein Y is

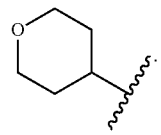

10. A compound, or a pharmaceutically acceptable salt thereof, selected from the group consisting of:
(R)-3-Amino-1-(3-((tetrahydro-2H-pyran-4-yl)methoxy)phenyl)propan-1-ol;
3-Amino-1-(3-((tetrahydro-2H-pyran-4-yl)methoxy)phenyl)propan-1-ol;
(1R)-3-Amino-1-(3-((tetrahydro-2H-pyran-3-yl)methoxy)phenyl)propan-1-ol;
(R)-3-Amino-1-(3-(pyridin-4-ylmethoxy)phenyl)propan-1-ol;
(R)-3-Amino-1-(3-(pyridin-3-ylmethoxy)phenyl)propan-1-ol;
(R)-3-Amino-1-(3-(pyridin-2-ylmethoxy)phenyl)propan-1-ol;
(1R)-3-amino-1-(3-((tetrahydro-2H-thiopyran-3-yl)methoxy)phenyl)propan-1-ol;
(R)-3-Amino-1-(3-((tetrahydro-2H-thiopyran-4-yl)methoxy)phenyl)propan-1-ol;
(R)-4-((3-(3-Amino-1-hydroxypropyl)phenoxy)methyl)tetrahydro-2H-thiopyran 1,1-dioxide;
3-((3-((R)-3-Amino-1-hydroxypropyl)phenoxy)methyl)tetrahydro-2H-thiopyran 1,1-dioxide;
(R)-1-(4-((3-(3-amino-1-hydroxypropyl)phenoxy)methyl)piperidin-1-yl)ethanone;
(R)-3-Amino-1-(3-((6-methylpyridin-2-yl)methoxy)phenyl)propan-1-ol;
(1R)-3-Amino-1-(3-((2,3-dihydrobenzofuran-2-yl)methoxy)phenyl)propan-1-ol;
(1R)-3-Amino-1-(3-((tetrahydrofuran-2-yl)methoxy)phenyl)propan-1-ol;
(R)-3-Amino-1-(3-(piperidin-4-ylmethoxy)phenyl)propan-1-ol;

(R)-3-Amino-1-(3-((1-methylpiperidin-4-yl)methoxy) phenyl)propan-1-ol;
(R)-Methyl 4-((3-(3-amino-1-hydroxypropyl)phenoxy) methyl)piperidine-1-carboxylate;
(R)-3-Amino-1-(3-(pyrimidin-5-ylmethoxy)phenyl)propan-1-ol;
(1R)-3-Amino-1-(3-(chroman-3-ylmethoxy)phenyl)propan-1-ol;
(R)-4-((3-(3-Amino-1-hydroxypropyl)phenoxy)methyl) tetrahydro-2H-thiopyran 1-oxide;
(R)-3-Amino-1-(3-(((S)-1-methylpyrrolidin-2-yl)methoxy)phenyl)propan-1-ol;
(R)-3-Amino-1-(3-((S)-pyrrolidin-2-ylmethoxy)phenyl) propan-1-ol;
(R)-3-Amino-1-(3-(((tetrahydro-2H-pyran-4-yl)methyl) amino)phenyl)propan-1-ol;
3-Amino-1-(3-(((1,1-dioxidotetrahydro-2H-thiopyran-4-yl)methyl)sulfonyl)-phenyl)propan-1-one;
3-Amino-1-(3-(((tetrahydro-2H-pyran-3-yl)methyl)sulfonyl)phenyl)propan-1-one;
3-Amino-1-(3-(((tetrahydro-2H-pyran-4-yl)methyl)sulfonyl)phenyl)propan-1-one;
3-((3-((R)-3-Amino-1-hydroxypropyl)phenoxy)methyl) piperidin-2-one;
(R)-3-Amino-1-(3-(thiophen-2-ylmethoxy)phenyl)propan-1-ol;
(R)-3-Amino-1-(3-(thiophen-3-ylmethoxy)phenyl)propan-1-ol;
(R)-tert-Butyl 4-((3-(3-amino-1-hydroxypropyl)phenoxy) methyl)piperidine-1-carboxylate;
(E)-3-(3-((Tetrahydro-2H-pyran-4-yl)methoxy)phenyl) prop-2-en-1-amine;
3-(3-((Tetrahydro-2H-pyran-4-yl)methoxy)phenyl)propan-1-amine;
(R)-3-(Methylamino)-1-(3-((tetrahydro-2H-pyran-4-yl) methoxy)phenyl)propan-1-ol;
1-((S)-2-((3-((R)-3-Amino-1-hydroxypropyl)phenoxy) methyl)pyrrolidin-1-yl)ethanone;
5-((3-((R)-3-Amino-1-hydroxypropyl)phenoxy)methyl) piperidin-2-one;
4-((3-((R)-3-Amino-1-hydroxypropyl)phenoxy)methyl) piperidin-2-one;
6-((3-((R)-3-Amino-1-hydroxypropyl)phenoxy)methyl)-1-methylpiperidin-2-one;
5-((3-((R)-3-Amino-1-hydroxypropyl)phenoxy)methyl) pyrrolidin-2-one;
5-((3-((R)-3-Amino-1-hydroxypropyl)phenoxy)methyl)-1-methylpyrrolidin-2-one;
N-(3-(3-Amino-1-hydroxypropyl)phenyl)-6-oxopiperidine-3-carboxamide;
3-((3-((R)-3-Amino-1-hydroxypropyl)phenoxy)methyl)-1,2-thiazinane 1,1-dioxide;
(R)-1-(3-((1H-Pyrrol-2-yl)methoxy)phenyl)-3-aminopropan-1-ol;
(R)-3-Amino-1-(3-(furan-2-ylmethoxy)phenyl)propan-1-ol;
(R)-3-Amino-1-(3-((1-(methylsulfonyl)piperidin-4-yl) methoxy)phenyl)propan-1-ol;
(R)-1-(3-(((1H-Indol-6-yl)methyl)amino)phenyl)-3-aminopropan-1-ol;
(R)-1-(3-((1H-Indol-6-yl)methoxy)phenyl)-3-aminopropan-1-ol;
(R)-3-Amino-1-(3-(benzofuran-2-ylmethoxy)phenyl)propan-1-ol;
3-(3-((Tetrahydro-2H-pyran-4-yl)methoxy)phenyl)prop-2-yn-1-amine;
3-Amino-1-(3-(((tetrahydro-2H-pyran-4-yl)methyl)thio) phenyl)propan-1-ol;
3-Amino-1-(3-(((tetrahydro-2H-pyran-4-yl)methyl)sulfonyl)phenyl)propan-1-ol;
3-Amino-1-(3-(2-(tetrahydro-2H-pyran-4-yl)ethyl)phenyl)propan-1-ol;
3-Amino-1-(3-(2-(pyridin-3-yl)ethyl)phenyl)propan-1-ol;
3-Amino-1-(3-(2-(thiophen-3-yl)ethyl)phenyl)propan-1-ol;
(E)-1-(3-(3-Amino-1-hydroxypropyl)styryl)pyrrolidin-2-one;
1-(3-(3-Amino-1-hydroxypropyl)phenethyl)pyrrolidin-2-one;
3-Amino-1-(3-(2-(pyrrolidin-1-yl)ethyl)phenyl)propan-1-ol;
(E)-1-(3-(2-(1H-Imidazol-1-yl)vinyl)phenyl)-3-aminopropan-1-ol;
1-(3-(2-(1H-Imidazol-1-yl)ethyl)phenyl)-3-aminopropan-1-ol;
(E)-3-Amino-1-(3-(2-(pyridin-2-yl)vinyl)phenyl)propan-1-ol;
3-Amino-1-(3-(2-(pyridin-2-yl)ethyl)phenyl)propan-1-ol;
(E)-3-Amino-1-(3-(2-(tetrahydro-2H-pyran-4-yl)vinyl) phenyl)propan-1-ol; and
3-Amino-1-(3-(2-(tetrahydro-2H-pyran-4-yl)ethyl)phenyl)propan-1-ol.

11. A pharmaceutical composition comprising a pharmaceutically acceptable carrier and a compound of Formula (C) as represented in claim 1, or a pharmaceutically acceptable salt thereof.

12. A pharmaceutical composition comprising a pharmaceutically acceptable carrier and a compound of claim 10, or a pharmaceutically acceptable salt thereof.

* * * * *